US012702658B2

(12) United States Patent
Abe et al.

(10) Patent No.: US 12,702,658 B2
(45) **Date of Patent: *Aug. 11, 2026**

(54) ANTICANCER COMBINATION THERAPY WITH N-(1-ACRYLOYL-AZETIDIN-3-YL)-2-((1H-INDAZOL-3-YL)AMINO)METHYL)-1H-IMIDAZOLE-5-CARBOXAMIDE INHIBITOR OF KRAS-G12C

(71) Applicants: TAIHO PHARMACEUTICAL CO., LTD., Tokyo (JP); Astex Therapeutics Ltd., Cambridge (GB)

(72) Inventors: Tetsuya Abe, Tsukuba (JP); Yoko Nakatsuru, Tsukuba (JP); Hiroshi Sootome, Tsukuba (JP)

(73) Assignees: TAIHO PHARMACEUTICAL CO., LTD., Tokyo (JP); ASTEX THERAPEUTICS LTD., Cambridge (GB)

( * ) Notice: Subject to any disclaimer, the term of this patent is extended or adjusted under 35 U.S.C. 154(b) by 759 days.

This patent is subject to a terminal disclaimer.

(21) Appl. No.: 17/920,870

(22) PCT Filed: Apr. 23, 2021

(86) PCT No.: PCT/JP2021/017606

§ 371 (c)(1),
(2) Date: Oct. 24, 2022

(87) PCT Pub. No.: WO2021/215545

PCT Pub. Date: Oct. 28, 2021

(65) Prior Publication Data

US 2023/0181536 A1 Jun. 15, 2023

Related U.S. Application Data

(60) Provisional application No. 63/015,031, filed on Apr. 24, 2020.

(51) Int. Cl.
*A61K 31/4178* (2006.01)
*A61K 31/166* (2006.01)
(Continued)

(52) U.S. Cl.
CPC ........ *A61K 31/4178* (2013.01); *A61K 31/166* (2013.01); *A61K 31/416* (2013.01);
(Continued)

(58) Field of Classification Search
CPC .............. A61K 31/4178; A61K 31/166; A61K 31/416; A61K 31/422; A61K 31/427;
(Continued)

(56) References Cited

U.S. PATENT DOCUMENTS 4,034,075 A 7/1977 Bays et al.
9,840,516 B2 12/2017 Li et al.
(Continued)

FOREIGN PATENT DOCUMENTS

CN 104011054 A 8/2014
CN 107556289 A 1/2018
(Continued)

OTHER PUBLICATIONS

Dear, R. F. et. al. Cochrane Database Syst. Rev. 2013(12). (Year: 2013).*

(Continued)

*Primary Examiner* — Clinton A Brooks
*Assistant Examiner* — Kendall Nicole Heitmeier
(74) *Attorney, Agent, or Firm* — Venable LLP

(57) ABSTRACT

A method of treating cancer comprises administering: (a) a therapeutically effective amount of a compound of Formula (I) or a pharmaceutically acceptable salt thereof; and (b) a therapeutically effective amount of an additional anti-cancer agent, to a subject in need of such treatment, the compound of Formula (I) being:

(Continued)

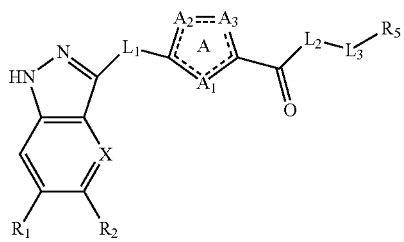

where X, $R_1$, $R_2$, ring A, $L_1$, $L_2$, $L_3$, and $R_5$ are as defined in this disclosure.

20 Claims, 4 Drawing Sheets

(51) Int. Cl.

| | |
|---|---|
| ***A61K 31/416*** | (2006.01) |
| ***A61K 31/422*** | (2006.01) |
| ***A61K 31/427*** | (2006.01) |
| ***A61K 31/4439*** | (2006.01) |
| ***A61K 31/454*** | (2006.01) |
| ***A61K 31/496*** | (2006.01) |
| ***A61K 31/506*** | (2006.01) |
| ***A61K 31/5365*** | (2006.01) |
| ***A61N 5/10*** | (2006.01) |
| ***A61P 1/00*** | (2006.01) |
| ***A61P 1/18*** | (2006.01) |
| ***A61P 11/00*** | (2006.01) |
| ***A61P 13/10*** | (2006.01) |
| ***A61P 35/00*** | (2006.01) |

(52) U.S. Cl.
CPC .......... *A61K 31/422* (2013.01); *A61K 31/427* (2013.01); *A61K 31/4439* (2013.01); *A61K 31/454* (2013.01); *A61K 31/496* (2013.01); *A61K 31/506* (2013.01); *A61K 31/5365* (2013.01); *A61N 5/10* (2013.01); *A61P 1/00* (2018.01); *A61P 1/18* (2018.01); *A61P 11/00* (2018.01); *A61P 13/10* (2018.01); *A61P 35/00* (2018.01)

(58) Field of Classification Search
CPC .............. A61K 31/4439; A61K 31/454; A61K 31/496; A61K 31/506; A61K 31/5365; A61N 5/10; A61P 1/00; A61P 1/18; A61P 11/00; A61P 13/10; A61P 35/00
See application file for complete search history.

(56) References Cited

U.S. PATENT DOCUMENTS

| | | | |
|---|---|---|---|
| 10,125,134 | B2 | 11/2018 | Blake et al. |
| 10,144,724 | B2 | 12/2018 | Li et al. |
| 10,556,906 | B2 | 2/2020 | Kuramoto et al. |
| 10,662,204 | B2 | 5/2020 | Planken et al. |
| 10,988,485 | B2 | 4/2021 | Minatti et al. |
| 11,045,484 | B2 | 6/2021 | Wurz et al. |
| 11,090,304 | B2 | 8/2021 | Allen et al. |
| 11,096,939 | B2 | 8/2021 | Booker et al. |
| 11,299,491 | B2 | 4/2022 | Parsons et al. |
| 11,453,683 | B1 | 9/2022 | Wang et al. |
| 11,459,327 | B1 | 10/2022 | Lv et al. |
| 11,530,218 | B2 | 12/2022 | Zhao et al. |
| 11,697,657 | B2 | 7/2023 | Bharathan et al. |
| 11,932,633 | B2 | 3/2024 | Marx et al. |
| 12,208,099 | B2 | 1/2025 | Aranda et al. |
| 2006/0135532 | A1 | 6/2006 | Bryant et al. |
| 2010/0331305 | A1 | 12/2010 | Bergeron et al. |
| 2014/0275070 | A1 | 9/2014 | Grembecka et al. |
| 2014/0288045 | A1 | 9/2014 | Ren et al. |
| 2014/0371203 | A1 | 12/2014 | Madge et al. |
| 2015/0176010 | A1 | 6/2015 | Wersinger |
| 2015/0239900 | A1 | 8/2015 | Li et al. |
| 2015/0246934 | A1 | 9/2015 | Bensen et al. |
| 2016/0046647 | A1 | 2/2016 | Grembecka et al. |
| 2016/0108019 | A1 | 4/2016 | Li et al. |
| 2016/0137665 | A1 | 5/2016 | Grembecka et al. |
| 2016/0152634 | A1 | 6/2016 | Madge et al. |
| 2016/0159738 | A1 | 6/2016 | Ren et al. |
| 2016/0297774 | A1 | 10/2016 | Li et al. |
| 2016/0318866 | A1 | 11/2016 | Becker-Pelster et al. |
| 2017/0131278 | A1 | 5/2017 | Patricelli et al. |
| 2017/0197945 | A1 | 7/2017 | Li et al. |
| 2017/0253611 | A1 | 9/2017 | Grembecka et al. |
| 2018/0072723 | A1 | 3/2018 | Blake et al. |
| 2018/0118757 | A1 | 5/2018 | Li et al. |
| 2018/0127396 | A1 | 5/2018 | Li et al. |
| 2018/0141927 | A1 | 5/2018 | Li et al. |
| 2018/0162812 | A1 | 6/2018 | Ren et al. |
| 2018/0177767 | A1 | 6/2018 | Lanman et al. |
| 2018/0334454 | A1 | 11/2018 | Lanman et al. |
| 2019/0062313 | A1 | 2/2019 | Li et al. |
| 2019/0062330 | A1 | 2/2019 | Blake et al. |
| 2019/0127336 | A1 | 5/2019 | Li et al. |
| 2019/0144444 | A1 | 5/2019 | Blake et al. |
| 2019/0233440 | A1 | 8/2019 | Planken et al. |
| 2019/0248767 | A1 | 8/2019 | Planken et al. |
| 2019/0270743 | A1 | 9/2019 | Marx et al. |
| 2019/0276432 | A1 | 9/2019 | Beaumont et al. |
| 2019/0284144 | A1 | 9/2019 | Li et al. |
| 2019/0292182 | A1 | 9/2019 | Kuramoto et al. |
| 2019/0343838 | A1 | 11/2019 | Allen et al. |
| 2019/0374542 | A1 | 12/2019 | Allen et al. |
| 2019/0375749 | A1 | 12/2019 | Chen et al. |
| 2020/0055845 | A1 | 2/2020 | Lanman et al. |
| 2020/0069657 | A1 | 3/2020 | Lanman et al. |
| 2020/0115363 | A1 | 4/2020 | Li et al. |
| 2020/0115375 | A1 | 4/2020 | Barda et al. |
| 2020/0140437 | A1 | 5/2020 | Kuramoto et al. |
| 2020/0165231 | A1 | 5/2020 | Shin et al. |
| 2020/0181118 | A1 | 6/2020 | Malhotra et al. |
| 2020/0237771 | A1 | 7/2020 | Hallur et al. |
| 2020/0262837 | A1 | 8/2020 | Marx et al. |
| 2020/0289503 | A1 | 9/2020 | Huang |
| 2020/0331911 | A1 | 10/2020 | Marx et al. |
| 2021/0009577 | A1 | 1/2021 | Lanman et al. |
| 2021/0024501 | A1 | 1/2021 | Li et al. |
| 2021/0040089 | A1 | 2/2021 | Gao et al. |
| 2021/0047297 | A1 | 2/2021 | Schulze et al. |
| 2021/0122764 | A1 | 4/2021 | Bharathan et al. |
| 2021/0395234 | A1 | 12/2021 | Sakamoto et al. |
| 2022/0064141 | A1 | 3/2022 | Fang et al. |
| 2022/0112204 | A1 | 4/2022 | Fan et al. |
| 2022/0298174 | A1 | 9/2022 | Guo et al. |
| 2022/0315597 | A1 | 10/2022 | Su et al. |
| 2022/0315598 | A1 | 10/2022 | Xu et al. |
| 2022/0370416 | A1 | 11/2022 | Chu et al. |
| 2022/0389029 | A1 | 12/2022 | Guo et al. |
| 2022/0402916 | A1 | 12/2022 | Hoover et al. |
| 2023/0023023 | A1 | 1/2023 | Shibata et al. |
| 2023/0049402 | A1 | 2/2023 | Sakamoto et al. |
| 2023/0174518 | A1 | 6/2023 | Kawai |
| 2023/0348495 | A1 | 11/2023 | Kawai et al. |
| 2023/0416266 | A1 | 12/2023 | Han et al. |
| 2024/0043448 | A1 | 2/2024 | Bharathan et al. |
| 2024/0083913 | A1 | 3/2024 | Bharathan et al. |
| 2024/0124478 | A1 | 4/2024 | Han et al. |
| 2024/0174691 | A1 | 5/2024 | Jiang et al. |
| 2024/0239788 | A1 | 7/2024 | Sloman et al. |
| 2024/0246968 | A1 | 7/2024 | Shibata et al. |
| 2024/0262842 | A1 | 8/2024 | Shibata et al. |
| 2024/0317759 | A1 | 9/2024 | Kobayakawa et al. |
| 2024/0376123 | A1 | 11/2024 | Zhou et al. |

(56) References Cited

U.S. PATENT DOCUMENTS

2024/0417408 A1 12/2024 Shibata et al.
2025/0136615 A1 5/2025 Kawamura et al.

FOREIGN PATENT DOCUMENTS

CN 109843856 A 6/2019
CN 112390788 A1 2/2021
CN 112430234 A 3/2021
CN 114615981 A 6/2022
EP 3871673 A1 9/2021
EP 4053120 A1 9/2022
EP 4397664 A1 10/2024
WO 03/037898 A1 5/2003
WO 2005/019177 A1 3/2005
WO 2009/114575 A1 9/2009
WO 2010/064705 A1 6/2010
WO 2013/072694 A1 5/2013
WO 2014/043272 A1 3/2014
WO 2014/143659 A1 9/2014
WO WO-2014152588 A1 * 9/2014 .......... C07D 285/16
WO 2014/164543 A1 10/2014
WO 2015/054572 A1 4/2015
WO 2015/091415 A1 6/2015
WO 2015/131005 A1 9/2015
WO 2016/029454 A1 3/2016
WO 2016/044772 A1 3/2016
WO 2016/049524 A1 3/2016
WO 2016/049565 A1 3/2016
WO 2016/049568 A1 3/2016
WO 2016/164675 A1 10/2016
WO 2016/168540 A1 10/2016
WO 2017/015562 A1 1/2017
WO 2017/058728 A1 4/2017
WO 2017/058768 A1 4/2017
WO 2017/058792 A1 4/2017
WO 2017/058805 A1 4/2017
WO 2017/058807 A1 4/2017
WO 2017/058902 A1 4/2017
WO 2017/058915 A1 4/2017
WO 2017/070256 A2 4/2017
WO 2017/087528 A1 5/2017
WO 2017/100546 A1 6/2017
WO 2017/172979 A1 10/2017
WO 2017/201161 A1 11/2017
WO 2018/022897 A1 2/2018
WO 2018/064510 A1 4/2018
WO 2018/068017 A1 4/2018
WO 2018/119183 A2 6/2018
WO 2018/140512 A1 8/2018
WO 2018/140513 A1 8/2018
WO 2018/140514 A1 8/2018
WO 2018/140598 A1 8/2018
WO 2018/140599 A1 8/2018
WO 2018/140600 A1 8/2018
WO 2018/143315 A1 8/2018
WO 2018/206539 A1 11/2018
WO 2018/217651 A1 11/2018
WO 2018/218069 A1 11/2018
WO 2018/218070 A2 11/2018
WO 2018/218071 A1 11/2018
WO 2019/051291 A1 3/2019
WO 2019/058132 A1 3/2019
WO 2019/058393 A1 3/2019
WO 2019/077631 A1 4/2019
WO 2019/099524 A1 5/2019
WO 2019/099703 A1 5/2019
WO 2019/110751 A1 6/2019
WO 2019/141250 A1 7/2019
WO 2019/155399 A1 8/2019
WO 2019/167000 A1 9/2019
WO 2019/185525 A1 10/2019
WO 2019/215203 A1 11/2019
WO 2019213526 A1 11/2019
WO 2019217307 A1 11/2019
WO 2019217691 A1 11/2019
WO 2019232419 A1 12/2019
WO 2020/035031 A1 2/2020
WO 2020/041331 A1 2/2020
WO 2020/050890 A2 3/2020
WO 2020047192 A1 3/2020
WO 2020055755 A1 3/2020
WO 2020055756 A1 3/2020
WO 2020055758 A1 3/2020
WO 2020055760 A1 3/2020
WO 2020055761 A1 3/2020
WO 2020/085493 A1 4/2020
WO 2020/097537 A2 5/2020
WO 2020/101736 A1 5/2020
WO 2020102730 A1 5/2020
WO 2020/113071 A1 6/2020
WO 2020118066 A1 6/2020
WO 2020/146613 A1 7/2020
WO 2020/156285 A1 8/2020
WO 2020/177629 A1 9/2020
WO 2020/178282 A1 9/2020
WO 2020/221239 A1 11/2020
WO 2020/233592 A1 11/2020
WO 2020/234103 A1 11/2020
WO 2020/236940 A1 11/2020
WO 2020/238791 A1 12/2020
WO 2020/239077 A1 12/2020
WO 2020/239123 A1 12/2020
WO 2020/244637 A1 12/2020
WO 2020/259432 A1 12/2020
WO 2020/259513 A1 12/2020
WO 2020/259573 A1 12/2020
WO 2021/000885 A1 1/2021
WO 2021/023154 A1 2/2021
WO 2021/027911 A1 2/2021
WO 2021/027943 A1 2/2021
WO 2021/031952 A1 2/2021
WO 2021/041671 A1 3/2021
WO 2021/043322 A1 3/2021
WO 2021/052499 A1 3/2021
WO 2021/055728 A1 3/2021
WO 2021/057832 A1 4/2021
WO 2021/058018 A1 4/2021
WO 2021/063346 A1 4/2021
WO 2021/078312 A1 4/2021
WO 2021/081212 A1 4/2021
WO 2021/083167 A1 5/2021
WO 2021/084765 A1 5/2021
WO 2021/085653 A1 5/2021
WO 2021/086833 A1 5/2021
WO 2021/088458 A1 5/2021
WO 2021/093758 A1 5/2021
WO 2021/098859 A1 5/2021
WO 2021/104431 A1 6/2021
WO 2021/106230 A1 6/2021
WO 2021/106231 A1 6/2021
WO 2021/107160 A1 6/2021
WO 2021/109737 A1 6/2021
WO 2021/113595 A1 6/2021
WO 2021/118877 A1 6/2021
WO 2021/121330 A1 6/2021
WO 2021/121367 A1 6/2021
WO 2021/121371 A1 6/2021
WO 2021/124222 A1 6/2021
WO 2021/127404 A1 6/2021
WO 2021/129824 A1 7/2021
WO 2021/147965 A1 7/2021
WO 2021/147967 A1 7/2021
WO 2021142252 A1 7/2021
WO 2021150613 A1 7/2021
WO 2021/215544 A1 10/2021
WO 2021211864 A1 10/2021
WO 2021/219072 A1 11/2021
WO 2022002102 A1 1/2022
WO 2022015375 A1 1/2022
WO 2022031678 A1 2/2022
WO 2022/066646 A1 3/2022
WO 2022042630 A1 3/2022
WO 2022047260 A1 3/2022
WO 2022061251 A1 3/2022

(56) References Cited

FOREIGN PATENT DOCUMENTS

| | | | |
|---|---|---|---|
| WO | 2022068921 | A1 | 4/2022 |
| WO | 2022083569 | A1 | 4/2022 |
| WO | 2022087371 | A1 | 4/2022 |
| WO | 2022087375 | A1 | 4/2022 |
| WO | 2022/105857 | A1 | 5/2022 |
| WO | 2022/109485 | A1 | 5/2022 |
| WO | 2022/109487 | A1 | 5/2022 |
| WO | 2022/132200 | A1 | 6/2022 |
| WO | 2022/133038 | A1 | 6/2022 |
| WO | 2022/148421 | A1 | 7/2022 |
| WO | 2022/148422 | A1 | 7/2022 |
| WO | 2022/173870 | A1 | 8/2022 |
| WO | 2022/177917 | A2 | 8/2022 |
| WO | 2022187688 | A1 | 9/2022 |
| WO | 2022/221739 | A1 | 10/2022 |
| WO | 2022/228568 | A1 | 11/2022 |
| WO | 2022/232318 | A1 | 11/2022 |
| WO | 2022/232320 | A1 | 11/2022 |
| WO | 2022/247760 | A1 | 12/2022 |
| WO | 2022/250170 | A1 | 12/2022 |
| WO | 2022/251576 | A1 | 12/2022 |
| WO | 2022/256459 | A1 | 12/2022 |
| WO | 2022/266206 | A1 | 12/2022 |
| WO | 2022248885 | A2 | 12/2022 |
| WO | 2022258974 | A1 | 12/2022 |
| WO | 2022261210 | A1 | 12/2022 |
| WO | 2022262686 | A1 | 12/2022 |
| WO | 2022266069 | A1 | 12/2022 |
| WO | 2022271658 | A1 | 12/2022 |
| WO | 2023018699 | A1 | 2/2023 |
| WO | 2023018809 | A1 | 2/2023 |
| WO | 2023018812 | A1 | 2/2023 |
| WO | 2023020518 | A1 | 2/2023 |
| WO | 2023020519 | A1 | 2/2023 |
| WO | 2023020521 | A1 | 2/2023 |
| WO | 2023020523 | A1 | 2/2023 |
| WO | 2023/046135 | A1 | 3/2023 |
| WO | 2023034290 | A1 | 3/2023 |
| WO | 2023049697 | A1 | 3/2023 |
| WO | 2023/059596 | A1 | 4/2023 |
| WO | 2023/059597 | A1 | 4/2023 |
| WO | 2023/059598 | A1 | 4/2023 |
| WO | 2023056421 | A1 | 4/2023 |
| WO | 2023056951 | A1 | 4/2023 |
| WO | 2023060253 | A1 | 4/2023 |
| WO | 2023061294 | A1 | 4/2023 |
| WO | 2023061463 | A1 | 4/2023 |
| WO | 2023064857 | A1 | 4/2023 |
| WO | 2023072188 | A1 | 5/2023 |
| WO | 2023/097227 | A1 | 6/2023 |
| WO | 2023/103523 | A1 | 6/2023 |
| WO | 2023098425 | A1 | 6/2023 |
| WO | 2023098426 | A1 | 6/2023 |
| WO | 2023098832 | A1 | 6/2023 |
| WO | 2023099592 | A1 | 6/2023 |
| WO | 2023099608 | A1 | 6/2023 |
| WO | 2023099612 | A1 | 6/2023 |
| WO | 2023099620 | A1 | 6/2023 |
| WO | 2023099623 | A1 | 6/2023 |
| WO | 2023099624 | A1 | 6/2023 |
| WO | 2023101928 | A1 | 6/2023 |
| WO | 2023103906 | A1 | 6/2023 |
| WO | 2023104018 | A1 | 6/2023 |
| WO | 2023105491 | A1 | 6/2023 |
| WO | 2023114733 | A1 | 6/2023 |
| WO | 2023117681 | A1 | 6/2023 |
| WO | 2023122154 | A1 | 6/2023 |
| WO | 2023125627 | A1 | 7/2023 |
| WO | 2023125989 | A1 | 7/2023 |
| WO | 2023133183 | A | 7/2023 |
| WO | 2023/150284 | A2 | 8/2023 |
| WO | 2023/159087 | A1 | 8/2023 |
| WO | 2023/173017 | A1 | 9/2023 |
| WO | 2023/179703 | A1 | 9/2023 |
| WO | 2023/244615 | A1 | 12/2023 |
| WO | 2024/009191 | A1 | 1/2024 |
| WO | 2024/015262 | A1 | 1/2024 |
| WO | 2024/032704 | A1 | 2/2024 |
| WO | 2024/041573 | A1 | 2/2024 |
| WO | 2024/044667 | A2 | 2/2024 |
| WO | 2024031088 | A1 | 2/2024 |
| WO | 2024/063578 | A1 | 3/2024 |
| WO | 2024/083168 | A1 | 4/2024 |
| WO | 2024/088069 | A1 | 5/2024 |
| WO | 2024/103010 | A1 | 5/2024 |
| WO | 2024/120433 | A1 | 6/2024 |
| WO | 2024/209339 | A1 | 10/2024 |
| WO | 2024/213979 | A1 | 10/2024 |
| WO | 2024/233776 | A1 | 11/2024 |
| WO | 2024/238343 | A1 | 11/2024 |
| WO | 2025/019819 | A1 | 1/2025 |
| WO | 2025/019823 | A1 | 1/2025 |
| WO | 2025/085748 | A1 | 4/2025 |
| WO | 2025/230961 | A1 | 11/2025 |
| WO | 2025/235740 | A1 | 11/2025 |
| WO | 2025/240740 | A1 | 11/2025 |
| WO | 2025/240742 | A1 | 11/2025 |

OTHER PUBLICATIONS

Canon, J. et. al. Nature, 2019, 575, 217-223. (Year: 2019).*

Wang, H. et al., "Annual review of KRAS inhibitors in 2022", European J. of Medicinal Chem., 249, p. 1-14 (2023).

International Search Report and Written Opinion in corresponding international application No. PCT/JP2021/017606 dated Aug. 24, 2021 (9 pages).

PubChem SID 469710826, available Jul. 28, 2022.

J.G. Kettle, et al., "Structure-Based Design and Pharmacokinetic Optimization of Covalent Allosteric Inhibitors of the Mutant GTPase KRAS G12C", J. Med. Chem., vol. 63, pp. 4468-4483 (2020).

Q. Zheng, et al., "Drugging the Next Undruggable KRAS Allele-Gly12Asp", J. Med. Chem, vol. 65, pp. 3119-3122 (2022).

D.S. Hong, et al., "KRASG12C Inhibition with Sotorasib in Advanced Solid Tumors", The New England Journal of Medicine, vol. 383 No. 13 pp. 1207-1217 (2020).

D. Gentile, et al., "Ras Binder Induces a Modified Switch-II Pocket in GTP and GDP States", Cell Chemical Biology, 24, pp. 1455-1466 (2017).

D. Kessler, et al., "Drugging an undruggable pocket on KRAS", Proceedings of the National Academy of Sciences (PNAS), vol. 116, No. 32, pp. 15823-15829 (2019).

Y. Mao, et al., "Design, synthesis and biological evaluation of novel pyrimidine, 3-cyanopyridine and m-amino-N-phenylbenzamide based monocyclic EGFR tyrosine kinase inhibitors", Bioorganic & Medicinal Chemistry, 21, pp. 3090-3104 (2013).

PubChem CID 10121096, PubChem release Jun. 18, 2019, modify date Nov. 21, 2020, retrieved on Feb. 10, 2021 (9 pages).

G. Palfy, et al., "1H, 15N backbone assignment and comparative analysis of the wild type and G12C, G12D, G12V mutants of K-Ras bound to GDP at physiological pH", Biomolecular NMR Assignment, vol. 14, No. 1, pp. 1-7 (2019).

M.R. Janes, et al., "Targeting KRAS Mutant Cancers with a Covalent G12C-Specific Inhibitor", Cell, 172, pp. 578-589 (2018).

M.P. Patricelli, et al., "Selective Inhibition of Oncogenic KRAS Output with Small Molecules Targeting the Inactive State", Cancer Discovery, 6(3), pp. 316-329 (2016).

H. Chuang, et al., "Pharmacological strategies to target oncogenic KRAS signaling in pancreatic cancer", Pharmacological Research, 117, pp. 370-376 (2017).

Lopez-Tapia, F., et al., "Linker Variation and Structure-Activity Relationship Analyses of Carboxylic Acid-based Small Molecule STAT3 Inhibitors", ACS Med. Chem. Lett. 2018, 9, 250-255.

R.B. Kargbo, "Small Molecule Inhibitors of KRAS G12C Mutant", Acs Med. Chem. Lett., vol. 12, pp. 1210-1211 (2021).

El-Meligie, Salwa E. M. et al., "New synthetic approaches to thieno[3,2-d]pyrimidine and thieno[3, 4-b]pyridine derivatives", Chemical Papers, vol. 74, pp. 2501-2514 (2020).

(56) References Cited

OTHER PUBLICATIONS

El-Kashef, H. et al., "Pyridine-Based Heterocycles. Synthesis of New Pyrido[4',3':4,5]thieno[2,3-d]pyrimidines and Related Heterocycles", Molecules, vol. 15, pp. 2651-2666 (2010).
Szanto, Get al., "New P2X3 receptor antagonists. Part 2: Identification and SAR of quinazolinones," Bioorganic and Medicinal Chemistry Letters, vol. 26, No. 16, pp. 3905-3912, abstract (2016).
Sanad, SMH et al., "Efficient Synthesis and Characterization of Novel Pyrido[3',2':4,5]thieno[3,2-d]pyrimidines and Their Fused [1,2,4]triazole Derivatives", Journal of Heterocyclic Chemistry, vol. 55, No. 12, pp. 2823-2833, abstract (2018).
Showalter, H.D. Hollis et al., "Tyrosine Kinase Inhibitors. 16. 6,5,6-Tricyclic Benzothieno[3,2-d]pyrimidines and Pyrimido[S,4-b]- and -[4,5-b]indoles as Potent Inhibitors of the Epidermal Growth Factor Receptor Tyrosine Kinase", Journal of Medicinal Chemistry, vol. 42, No. 26, pp. 5464-5474, abstract (1999).
Sanad, SMH et al., "New thieno[2,3-b ]pyridine-fused pyrimidin-4(3H)-ones as potential thymidylate synthase inhibitors: Synthesis, SAR, in vitro and in silica study", Journal of Molecular Structure, vol. 1282, (2023).
Hamarsheh S., et al., "Immune modulatory effects of oncogenic KRAS in cancer", Nature Commun., 11:5439 (2020).

* cited by examiner

ANTICANCER COMBINATION THERAPY WITH N-(1-ACRYLOYL-AZETIDIN-3-YL)-2-((1H-INDAZOL-3-YL)AMINO)METHYL)-1H-IMIDAZOLE-5-CARBOXAMIDE INHIBITOR OF KRAS-G12C

BACKGROUND OF THE INVENTION

RAS, which is a small monomeric GTP-binding protein having a molecular weight of about 21 kDa, acts as a molecular on/off switch. RAS can bind to GTP by binding to proteins of a guanine nucleotide exchange factor (GEF) (e.g., SOS1), which forces the release of a bound nucleotide, and releasing GDP. When RAS binds to GTP, it becomes activated (turned on) and recruits and activates proteins necessary for the propagation of other receptors' signals, such as c-Raf and PI 3-kinase. RAS also possesses enzymatic activity with which it cleaves the terminal phosphate of the nucleotide and converts it to GDP. The rate of conversion is usually slow, but can be dramatically sped up by a protein of the GTPase-activating protein (GAP) class, such as RasGAP. When GTP is converted into GDP, RAS is deactivated (turned off).

The mainly known members of the RAS subfamily include HRAS, KRAS, and NRAS. Of these, mutations of KRAS are observed in many malignant tumors: 95% of pancreatic cancers, 45% of colorectal cancers, and 35% of lung cancers. The mutations often occur in the glycine residue at position 12; in pulmonary adenocarcinoma, in particular, the mutation in the glycine residue at position 12 occurs in about 90% of the whole. Among such mutations, the most often occurring mutation (44%) has been reported to be a mutation into cysteine (Nature Reviews Drug Discovery 13 (11), 828-51, 2014).

A recent study has reported that ARS-853 binds to the cysteine of the G12C mutant of inactive KRAS (GDP), thus preventing conversion of inactive KRAS (GDP) to active KRAS (GTP), inhibiting downstream signaling, and inducing apoptosis in cancer cells with KRAS G12C mutation (WO 2014/152588 and Cancer Discov. 6 (3), 316-29, 2016). It has also been reported that ARS-1620 with a quinazoline backbone exerts antitumor action in tumor-bearing mice expressing KRAS G12C mutation by improving metabolic stability of ARS-853 mice (WO 2015/054572 and Cell. 172 (3), 578-89, 2018).

SUMMARY OF INVENTION

The disclosure is directed to a method of treating cancer comprising administering: (a) a compound of Formula (I) or a pharmaceutically acceptable salt thereof, and (b) an additional anti-cancer agent, to a subject in need of such treatment, the compound of Formula (I) being:

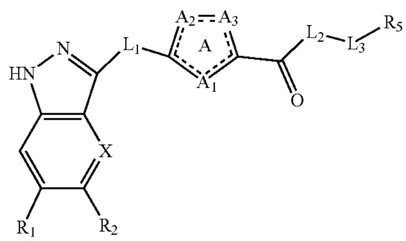

wherein

X is nitrogen or CH, $R_1$ is selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_4$-$C_{10}$ cycloalkyl, $C_6$-$C_{10}$ aromatic hydrocarbon, a 5- to 10-membered saturated heterocyclic group, and a 5- to 10-membered unsaturated heterocyclic group, $R_2$ is selected from the group consisting of hydrogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ cycloalkyl, $C_6$-$C_{10}$ aromatic hydrocarbon, a 5- to 10-membered saturated heterocyclic group, and a 5- to 10-membered unsaturated heterocyclic group, $L_1$ is —NH—C($R_a$)$_2$—, wherein $R_a$s are identical or different, and each is a hydrogen atom, a deuterium atom, or $C_1$-$C_6$ alkyl, ring A is a substituted or unsubstituted 5-membered unsaturated heterocyclic group, one of $A_1$, $A_2$, and $A_3$ is substituted or unsubstituted nitrogen or sulfur, and the rest of $A_1$, $A_2$, and $A_3$ are identical or different, and are substituted or unsubstituted carbon, substituted or unsubstituted nitrogen, sulfur, or oxygen, when $A_1$ is substituted carbon or substituted nitrogen, the substituent is at least one member selected from the group consisting of hydrogen, halogen, cyano, nitro, amino, hydroxy, carboxy, $C_1$-$C_6$ alkyl that may be substituted with $R_b$, $C_2$-$C_6$ alkenyl that may be substituted with $R_b$, $C_2$-$C_6$ alkynyl that may be substituted with $R_b$, $C_3$-$C_{10}$ cycloalkyl that may be substituted with $R_c$, $C_4$-$C_{10}$ cycloalkenyl that may be substituted with $R_c$, $C_6$-$C_{10}$ aromatic hydrocarbon that may be substituted with $R_c$, a 4- to 10-membered saturated heterocyclic group that may be substituted with $R_c$, and a 5- to 10-membered unsaturated heterocyclic group that may be substituted with $R_c$, $R_b$ is selected from the group consisting of halogen, cyano, nitro, amino, hydroxy, carboxy, $C_1$-$C_6$ alkoxy, $C_1$-$C_6$ alkylamino, $C_3$-$C_6$ cycloalkyl, substituted or unsubstituted $C_6$-$C_{10}$ aromatic hydrocarbon, and a substituted or unsubstituted 5- to 10-membered saturated heterocyclic group, $R_c$ is selected from the group consisting of halogen, cyano, nitro, amino, hydroxy, carboxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkylamino, $C_1$-$C_6$ alkylcarbonyl, $C_1$-$C_6$ alkoxy-$C_1$-$C_6$ alkyl, $C_7$-$C_{20}$ aralkyl, $C_1$-$C_6$ alkoxycarbonyl, $C_3$-$C_6$ cycloalkyl, $C_6$-$C_{10}$ aromatic hydrocarbon, a 5- to 10-membered saturated heterocyclic group, and a 5- to 10-membered unsaturated heterocyclic group, when two or more $R_b$s are present, the plurality of $R_b$s may be identical or different, when two or more $R_c$s are present, the plurality of $R_c$s may be identical or different, when $A_2$ is substituted carbon or substituted nitrogen, the substituent is at least one member selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, and substituted or unsubstituted $C_2$-$C_6$ alkynyl, when $A_3$ represents substituted carbon or substituted nitrogen, the substituent is at least one member selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, and substituted or unsubstituted $C_2$-$C_6$ alkynyl, $L_2$ is

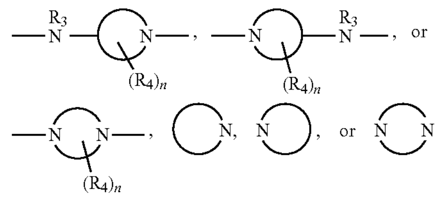

is a 4- to 8-membered saturated heterocyclic group that contains at least one nitrogen atom, and that may contain 1 or 2 heteroatoms selected from sulfur and oxygen, in which N represents nitrogen, $R_3$ is hydrogen or $C_1$-$C_6$ alkyl, $R_4$ is selected from the group consisting of halogen, cyano, nitro, amino, hydroxy, carboxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkylamino-$C_1$-$C_6$ alkyl, cyano-$C_1$-$C_6$ alkyl, $C_1$-$C_6$ alkoxy-$C_1$-$C_6$ alkyl, and $C_1$-$C_6$ hydroxyalkyl, when two or more $R_4$s are present, the plurality of $R_4$s may be identical or different, when two $R_4$s are attached to the same carbon atom, and these two $R_4$s each represent $C_1$-$C_6$ alkyl, then these two $R_4$s, taken together with the carbon atom to which these two $R_4$s are attached, may form a ring, and n is 0, 1, 2, or 3, $L_3$ is —C(═O)— or —S(═O)$_2$—, and $R_5$ is substituted or unsubstituted $C_2$-$C_6$ alkenyl or substituted or unsubstituted $C_2$-$C_6$ alkynyl.

The disclosure is further directed to a method of treating cancer comprising administering: (a) a compound of Formula (I) or a pharmaceutically acceptable salt thereof; and (b) radiation therapy, to a subject in need of such treatment.

BRIEF DESCRIPTION OF THE FIGURES

The disclosure may be better understood with reference to the figures.

DETAILED DESCRIPTION

Compound of Formula (I)

Figure 1A:
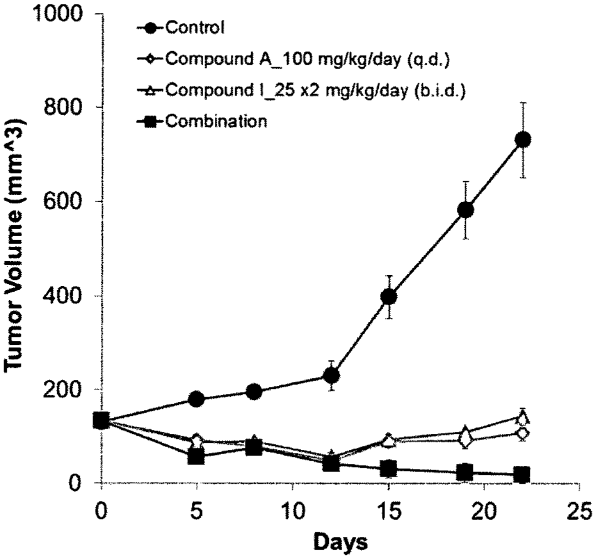
FIG. 1A shows the anti-tumor effects of Compound A of the present disclosure and SHP2 inhibitor Compound I used alone or concomitantly in an MIAPaCa-2 xenograft model.

The compound of Formula (I) is:

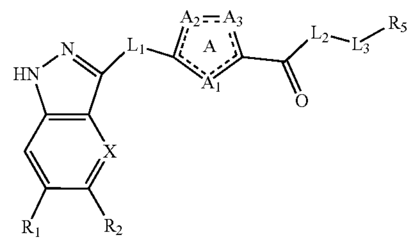

wherein

X is nitrogen or CH, $R_1$ is selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_4$-$C_{10}$ cycloalkyl, $C_6$-$C_{10}$ aromatic hydrocarbon, a 5- to 10-membered saturated heterocyclic group, and a 5- to 10-membered unsaturated heterocyclic group, $R_2$ is selected from the group consisting of hydrogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ cycloalkyl, $C_6$-$C_{10}$ aromatic hydrocarbon, a 5- to 10-membered saturated heterocyclic group, and a 5- to 10-membered unsaturated heterocyclic group, $L_1$ is —NH—C$(R_a)_2$—, wherein $R_a$s are identical or different, and each is a hydrogen atom, a deuterium atom, or $C_1$-$C_6$ alkyl, ring A is a substituted or unsubstituted 5-membered unsaturated heterocyclic group, one of $A_1$, $A_2$, and $A_3$ is substituted or unsubstituted nitrogen or sulfur, and the rest of $A_1$, $A_2$, and $A_3$ are identical or different, and are substituted or unsubstituted carbon, substituted or unsubstituted nitrogen, sulfur, or oxygen, when $A_1$ is substituted carbon or substituted nitrogen, the substituent is at least one member selected from the group consisting of hydrogen, halogen, cyano, nitro, amino, hydroxy, carboxy, $C_1$-$C_6$ alkyl that may be substituted with $R_b$, $C_2$-$C_6$ alkenyl that may be substituted with $R_b$, $C_2$-$C_6$ alkynyl that may be substituted with $R_b$, $C_3$-$C_{10}$ cycloalkyl that may be substituted with $R_c$, $C_4$-$C_{10}$ cycloalkenyl that may be substituted with $R_c$, $C_6$-$C_{10}$ aromatic hydrocarbon that may be substituted with $R_c$, a 4- to 10-membered saturated heterocyclic group that may be substituted with $R_c$, and a 5- to 10-membered unsaturated heterocyclic group that may be substituted with $R_c$, $R_b$ is selected from the group consisting of halogen, cyano, nitro, amino, hydroxy, carboxy, $C_1$-$C_6$ alkoxy, $C_1$-$C_6$ alkylamino, $C_3$-$C_6$ cycloalkyl, substituted or unsubstituted $C_6$-$C_{10}$ aromatic hydrocarbon, and a substituted or unsubstituted 5- to 10-membered saturated heterocyclic group, $R_c$ is selected from the group consisting of halogen, cyano, nitro, amino, hydroxy, carboxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkylamino, $C_1$-$C_6$ alkylcarbonyl, $C_1$-$C_6$ alkoxy-$C_1$-$C_6$ alkyl, $C_7$-$C_{20}$ aralkyl, $C_1$-$C_6$ alkoxycarbonyl, $C_3$-$C_6$ cycloalkyl, $C_6$-$C_{10}$ aromatic hydrocarbon, a 5- to 10-membered saturated heterocyclic group, and a 5- to 10-membered unsaturated heterocyclic group, when two or more $R_b$s are present, the plurality of $R_b$s may be identical or different, when two or more $R_c$s are present, the plurality of $R_c$s may be identical or different, when $A_2$ is substituted carbon or substituted nitrogen, the substituent is at least one member selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, and substituted or unsubstituted $C_2$-$C_6$ alkynyl, when $A_3$ represents substituted carbon or substituted nitrogen, the substituent is at least one member selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, and substituted or unsubstituted $C_2$-$C_6$ alkynyl, $L_2$ is

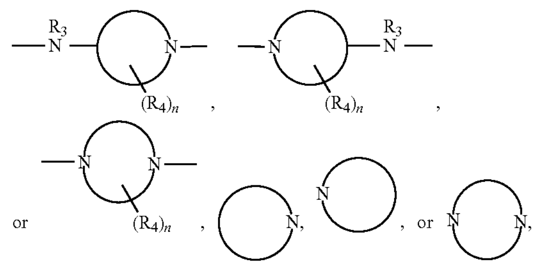

is a 4- to 8-membered saturated heterocyclic group that contains at least one nitrogen atom, and that may contain 1 or 2 heteroatoms selected from sulfur and oxygen, in which N represents nitrogen, $R_3$ is hydrogen or $C_1$-$C_6$ alkyl, $R_4$ is selected from the group consisting of halogen, cyano, nitro, amino, hydroxy, carboxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkylamino-$C_1$-$C_6$ alkyl, cyano-$C_1$-$C_6$ alkyl, $C_1$-$C_6$ alkoxy-$C_1$-$C_6$ alkyl, and $C_1$-$C_6$ hydroxyalkyl, when two or more $R_4$s are present, the plurality of $R_4$s may be identical or different, when two $R_4$s are attached to the same carbon atom, and these two $R_4$s each represent $C_1$-$C_6$ alkyl, then these two $R_4$s, taken together with the carbon atom to which these two $R_4$s are attached, may form a ring, and n is 0, 1, 2, or 3, $L_3$ is —C(═O)— or —S(═O)$_2$—, and $R_5$ is substituted or unsubstituted $C_2$-$C_6$ alkenyl or substituted or unsubstituted $C_2$-$C_6$ alkynyl.

As used throughout this disclosure, "a compound of Formula (I)" is to be understood to include "a compound of Formula (I) or a pharmaceutically acceptable salt thereof".

A compound represented by Formula (I) or a salt thereof impairs the KRAS function in KRAS G12C mutation-positive cancer cells, thereby showing antitumor action; therefore, an indazole compound represented by Formula (I) or a salt thereof can be used as an anti-cancer agent.

In this specification, the term "CA-CB" used in the description of a group indicates that the group has A to B number of carbon atoms. For example, "$C_1$-$C_6$ alkyl" refers to alkyl having 1 to 6 carbon atoms, and "$C_6$-$C_{14}$ aromatic hydrocarbon oxy" refers to oxy to which $C_6$-$C_{14}$ aromatic hydrocarbon is bonded. Further, the term "A- to B-membered" indicates that the number of atoms (number of ring members) that constitute a ring is A to B. More specifically, "4- to 10-membered saturated heterocyclic group" refers to a saturated heterocyclic group containing 4 to 10 ring members.

For the symbols as used herein, C denotes a carbon atom, N denotes a nitrogen atom, S denotes a sulfur atom, O denotes an oxygen atom, and H denotes a hydrogen atom. In the chemical formulas, a double line denotes a double bond, and a double line, one line of which is a dotted line, denotes a single bond or a double bond.

In this disclosure, unless otherwise specified, examples of the "substituent" include hydrogen, halogen, cyano, nitro, amino, hydroxy, oxo, carbonyl, carboxy, carbamoyl, alkyl, haloalkyl, hydroxyalkyl, cyanoalkyl, cycloalkyl, cycloalkenyl, cycloalkyl-alkyl, alkenyl, alkynyl, alkoxy, haloalkoxy, alkoxy-alkyl, cycloalkoxy, cycloalkyl-alkoxy, cycloalkyl-haloalkyl, alkylthio, cycloalkyl-alkylthio, mono- or dialkylamino, alkylaminoalkyl, cycloalkyl-alkylamino, aromatic hydrocarbon, aralkyl, aralkyloxy, acyl, alkylcarbonyl, arylcarbonyl, acyloxy, alkylcarbonyloxy, arylcarbonyloxy, alkoxycarbonyl, aralkyloxycarbonyl, saturated or unsaturated heterocyclic group, saturated heterocyclic oxy, and the like. Unless otherwise specified, when a substituent listed above is present, the number of them is typically one, two, or three, preferably one or two, and most preferably one.

In this specification, specific examples of the "halogen" include chlorine, bromine, fluorine, and iodine, with chlorine, fluorine, and bromine being preferable, and chlorine and fluorine being more preferable.

In this specification, the "alkyl" refers to a linear or branched saturated hydrocarbon group. Examples include $C_1$-$C_{10}$ alkyl, such as methyl, ethyl, n-propyl, isopropyl, n-butyl, isobutyl, sec-butyl, tert-butyl, n-pentyl, isopentyl, hexyl, and heptyl. The "alkyl" is preferably $C_1$-$C_6$ alkyl, such as methyl, ethyl, n-propyl, isopropyl, n-butyl, isobutyl, and tert-butyl, and more preferably methyl, ethyl, or tert-butyl.

In this specification, the "haloalkyl" refers to alkyl mentioned above having at least one halogen atom (preferably having 1 to 10, and more preferably 1 to 3 halogen atoms). Examples include $C_1$-$C_6$ haloalkyl, such as fluoromethyl, difluoromethyl, trifluoromethyl, trichloromethyl, 1-fluoroethyl, 1,1-difluoroethyl, 1,1,1-trifluoroethyl, 1-fluoro-n-propyl, 1,1,1-trifluoro-n-propyl, perfluoro-n-propyl, and perfluoroisopropyl, with trifluoromethyl, 1-fluoroethyl, 1,1-difluoroethyl, and 1,1,1-trifluoroethyl being preferable.

In this specification, the "hydroxyalkyl" refers to alkyl mentioned above having at least one hydroxy group (preferably having 1 to 10, and more preferably 1 to 2 hydroxy groups). Examples include $C_1$-$C_6$ hydroxyalkyl, such as hydroxymethyl, hydroxyethyl, 1-hydroxypropyl, and 2-hydroxybutyl.

In this specification, the "cyanoalkyl" refers to alkyl mentioned above having at least one cyano group (preferably having 1 to 10, and more preferably 1 to 2 cyano groups). Examples include $C_1$-$C_6$ cyanoalkyl, such as cyanomethyl, cyanoethyl, 1-cyanopropyl, and 2-cyanobutyl.

In this specification, the "cycloalkyl" refers to monocyclic, bridged cyclic, or polycyclic saturated hydrocarbon. Examples include $C_3$-$C_{10}$ cycloalkyl, such as cyclopropyl, cyclobutyl, cyclopentyl, cyclohexyl, cycloheptyl, and cyclodecyl, with cyclopropyl, cyclobutyl, and cyclopentyl being preferable, and cyclobutyl and cyclopentyl being particularly preferable.

In this specification, the "cycloalkenyl" refers to monocyclic, bridged cyclic, or polycyclic unsaturated hydrocarbon containing at least one carbon-carbon double bond (e.g., one to two carbon-carbon double bonds, and preferably one carbon-carbon double bond). Examples include $C_4$-$C_{10}$ cycloalkenyl, such as cyclobutenyl, cyclopentenyl, cyclohexenyl, cycloheptenyl, and cyclodecenyl, with cyclobutenyl, cyclopentenyl, and cyclohexenyl being preferable, and cyclobutenyl and cyclopentenyl being particularly preferable.

In this specification, the "cycloalkyl-alkyl" refers to alkyl mentioned above having at least one cycloalkyl group. Examples include $C_3$-$C_{10}$ cycloalkyl-$C_1$-$C_4$ alkyl, such as cyclopropylmethyl, cyclobutylmethyl, cyclopentylmethyl, cyclohexylmethyl, cyclohexylisopropyl, cyclohexyl 1-methyl-4-isopropyl, and cycloheptylmethyl, with cyclohexylmethyl being preferable.

In this specification, the "unsaturated hydrocarbon" refers to linear or branched unsaturated hydrocarbon containing at least one carbon-carbon double bond or triple bond. Examples include $C_2$-$C_{10}$ unsaturated hydrocarbon, such as vinyl, allyl, methylvinyl, 1-propenyl, butenyl, pentenyl, hexenyl, ethynyl, and 2-propynyl, with $C_{2-6}$ linear or branched hydrocarbon containing at least one carbon-carbon double bond or triple bond being preferable, vinyl, allyl, and 1-propenyl being more preferable, and vinyl being most preferable.

In this specification, the "alkenyl" refers to a linear or branched unsaturated hydrocarbon group containing at least one double bound (e.g., one to two double bonds, and preferably one double bond). Examples include $C_2$-$C_{10}$ alkenyl, such as vinyl, allyl, 1-propenyl, 2-methyl-2-propenyl, isopropenyl, 1-, 2-, or 3-butenyl, 2-, 3- or 4-pentenyl, 2-methyl-2-butenyl, 3-methyl-2-butenyl, and 5-hexenyl, with $C_2$-$C_6$ alkenyl, such as vinyl, allyl, 1-propenyl, and 2-methyl-2-propenyl being preferable, and vinyl being most preferable.

In this specification, the "alkynyl" refers to linear or branched unsaturated hydrocarbon containing at least one triple bond (e.g., one or two triple bonds, and preferably one triple bond). Examples include $C_2$-$C_{10}$ alkynyl, such as ethynyl, 1- or 2-propynyl, 1-, 2-, or 3-butynyl, and 1-methyl-2-propynyl, with $C_2$-$C_6$ alkynyl, such as ethynyl and 2-propynyl, being preferable, and 2-propynyl being most preferable.

In this specification, the "alkoxy" refers to oxy having alkyl mentioned above. Examples include $C_1$-$C_6$ alkoxy, such as methoxy, ethoxy, n-propoxy, isopropoxy, n-butoxy, isobutoxy, sec-butoxy, tert-butoxy, pentyloxy, isopentyloxy, and hexyloxy, with methoxy and ethoxy being preferable, and methoxy being more preferable.

In this specification, the "haloalkoxy" refers to alkoxy mentioned above having at least one halogen atom (preferably having 1 to 13, and more preferably 1 to 3 halogen atoms). Examples include $C_1$-$C_6$ haloalkoxy, such as fluoromethoxy, difluoromethoxy, trifluoromethoxy, trichloromethoxy, fluoroethoxy, 1,1-difluoroethoxy, 1,1,1-trifluoroethoxy, monofluoro-n-propoxy, perfluoro-n-propoxy, and perfluoro-isopropoxy, with fluoroethoxy, difluoromethoxy, and trifluoromethoxy being preferable.

In this specification, the "alkoxy-alkyl" refers to alkyl mentioned above having at least one alkoxy group mentioned above. Examples include $C_1$-$C_4$ alkoxy-$C_1$-$C_{10}$ alkyl, such as methoxymethyl, ethoxymethyl, methoxyethyl, ethoxyethyl, methoxypropyl, methoxy-n-, methoxypentyl, methoxyhexyl, methoxyheptyl, propoxyethyl, and butoxyethyl, with $C_1$-$C_2$ alkoxy-$C_1$-$C_3$ alkyl, such as methoxymethyl, ethoxymethyl, methoxyethyl, and ethoxyethyl being preferable, and methoxymethyl and methoxyethyl being more preferable.

In this specification, the "cycloalkoxy" refers to oxy having cycloalkyl mentioned above. Examples include $C_3$-$C_{10}$ cycloalkoxy, such as cyclopropoxy, cyclobutoxy, cyclopentyloxy, cyclohexyloxy, and cycloheptyloxy, with cyclobutoxy, cyclopentyloxy, and cyclohexyloxy being preferable.

In this specification, the "cycloalkyl-alkoxy" refers to alkoxy mentioned above having at least one cycloalkyl group mentioned above. Examples include $C_3$-$C_{10}$ cycloalkyl-$C_1$-$C_4$ alkoxy, such as cyclopropylmethoxy, cyclobutylmethoxy, cyclopentylmethoxy, cyclohexylmethoxy, and cycloheptylmethoxy, with cyclohexylmethoxy being preferable.

In this specification, the "cycloalkyl-haloalkyl" refers to haloalkyl mentioned above having at least one cycloalkyl group mentioned above. Examples include $C_3$-$C_{10}$ cycloalkyl-$C_1$-$C_4$ haloalkyl, such as cyclopropylfluoromethyl, cyclobutylfluoromethyl, cyclopentylfluoromethyl, cyclohexylfluoromethyl, and cycloheptylfluoromethyl, with cyclohexylfluoromethyl being preferable.

In this specification, the "alkylthio" refers to thioxy having alkyl mentioned above. Examples include $C_1$-$C_6$ alkylthio, such as methylthio, ethylthio, n-propylthio, isopropylthio, n-butylthio, isobutylthio, tert-butylthio, n-pentylthio, isopentylthio, and hexylthio, with methylthio and ethylthio being preferable.

In this specification, the "cycloalkyl-alkylthio" refers to alkylthio mentioned above having at least one cycloalkyl group mentioned above. Examples include $C_3$-$C_7$ cycloalkyl-$C_1$-$C_4$ alkylthio, such as cyclopropylmethylthio, cyclobutylmethylthio, cyclopentylmethylthio, cyclohexylmethylthio, and cycloheptylmethylthio, with cyclohexylmethylthio being preferable.

In this specification, the "alkylamino" refers to amino having one or two alkyl groups mentioned above. Specific examples include $C_1$-$C_6$ alkylamino, such as methylamino, ethylamino, dimethylamino, diethylamino, and ethylmethylamino, with methylamino, dimethylamino, and methylethylamino being preferable.

In this specification, the "monoalkylamino" refers to amino having one alkyl group mentioned above. Examples include $C_1$-$C_6$ monoalkylamino, such as methylamino, ethylamino, n-propylamino, isopropylamino, n-butylamino, isobutylamino, tert-butylamino, n-pentylamino, isopentylamino, and hexylamino, with methylamino being preferable.

In this specification, the "dialkylamino" refers to amino having two alkyl groups mentioned above. Examples include $C_2$-$C_{12}$ dialkylamino, such as dimethylamino, diethylamino, di(n-propyl)amino, diisopropylamino, di(n-butyl) amino, diisobutylamino, di(tert-butyl)amino, di(n-pentyl)

amino, diisopentylamino, dihexylamino, methylethylamino, and methylisopropylamino, with dimethylamino being preferable.

In this specification, the "alkylaminoalkyl" refers to alkyl mentioned above having at least one alkylamino group mentioned above. Examples include $C_1$-$C_6$ alkylamino-$C_1$-$C_6$ alkyl, such as methylaminomethyl, methylaminoethyl, ethylaminomethyl, and ethylaminopropyl, with dimethylaminomethyl and dimethylaminoethyl being preferable.

In this specification, the "cycloalkyl-alkylamino" refers to alkylamino mentioned above having cycloalkyl mentioned above in which cycloalkyl is attached to the alkyl moiety of alkylamino. Examples include $C_3$-$C_7$ cycloalkyl-$C_1$-$C_4$ alkylamino, such as cyclopropylmethylamino, cyclobutylmethylamino, cyclopentylmethylamino, cyclohexylmethylamino, and cycloheptylmethylamino, with cyclobutylmethylamino and cyclohexylmethylamino being preferable.

In this specification, the "aromatic hydrocarbon" refers to monocyclic or polycyclic aromatic hydrocarbon as being an unsaturated bond-containing ring substituent containing carbon and hydrogen, the monocyclic or polycyclic aromatic hydrocarbon containing 4e+2 number of electrons (e is an integer of 1 or more) in the cyclic $\pi$ electron system. Examples include phenyl, naphthyl, tetrahydronaphthyl, anthracenyl, and the like, with phenyl being preferable.

In this specification, the "aralkyl" refers to alkyl mentioned above substituted with aromatic hydrocarbon mentioned above. Examples include $C_7$-$C_{16}$ aralkyl, such as benzyl, phenylethyl, phenylpropyl, naphthylmethyl, and naphthylethyl, with benzyl being preferable.

In this specification, the "aralkyloxy" refers to oxy having aralkyl mentioned above. Examples include $C_7$-$C_{20}$ aralkyloxy, such as benzyloxy, phenethyloxy, naphthylmethyloxy, and fluorenylmethyloxy, with benzyloxy being preferable.

In this specification, the "acyl" refers to carbonyl having alkyl mentioned above or aryl. Examples include substituted $C_1$-$C_{16}$ carbonyl, such as methylcarbonyl, ethylcarbonyl, and phenylcarbonyl, with methylcarbonyl and ethylcarbonyl being preferable.

In this specification, the "alkylcarbonyl" refers to carbonyl having alkyl mentioned above and is also included in the synonym "acyl." Examples include $C_1$-$C_6$ alkylcarbonyl, such as methylcarbonyl, ethylcarbonyl, n-propylcarbonyl, isopropylcarbonyl, n-butylcarbonyl, isobutylcarbonyl, tert-butylcarbonyl, n-pentylcarbonyl, isopentylcarbonyl, and hexylcarbonyl, with methylcarbonyl being preferable. Further, in the disclosure, $C_1$-$C_6$ alkylcarbonyl refers to ($C_1$-$C_6$ alkyl)carbonyl.

In this specification, the "arylcarbonyl" refers to carbonyl having aromatic hydrocarbon mentioned above and is also included in the synonym "acyl." Examples include ($C_6$-$C_{20}$ aryl)carbonyl, such as phenylcarbonyl, naphthylcarbonyl, fluorenylcarbonyl, anthrylcarbonyl, biphenylylcarbonyl, tetrahydronaphthylcarbonyl, chromanylcarbonyl, 2,3-dihydro-1,4-dioxanaphthalenylcarbonyl, indanylcarbonyl, and phenanthrylcarbonyl.

In this specification, the "acyloxy" refers to oxy having $C_1$-$C_{16}$ acyl mentioned above. The acyloxy is preferably oxy binding to substituted $C_1$-$C_{16}$ acyl, such as acetoxy, ethylacyloxy, and phenylacyloxy, and more preferably acetoxy, tert-butylcarbonyloxy, or phenylcarbonyloxy.

In this specification, the "alkylcarbonyloxy" refers to oxy having alkylcarbonyl mentioned above and is included in the synonym "acyloxy." Examples include ($C_1$-$C_6$ alkyl)carbonyloxy, such as methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy, and hexylcarbonyloxy, with acetoxy and tert-butylcarbonyloxy being preferable.

In this specification, the "arylcarbonyloxy" refers to oxy having arylcarbonyl mentioned above and is included in the synonym "acyloxy." Examples include ($C_6$-$C_{14}$ aryl)carbonyloxy, such as phenylcarbonyloxy, naphthylcarbonyloxy, fluorenylcarbonyloxy, anthrylcarbonyloxy, biphenylylcarbonyloxy, tetrahydronaphthylcarbonyloxy, chromanylcarbonyloxy, 2,3-dihydro-1,4-dioxanaphthalenylcarbonyloxy, indanylcarbonyloxy, and phenanthrylcarbonyloxy, with phenylcarbonyloxy being preferable.

In this specification, the "alkoxycarbonyl" refers to carbonyl having alkoxy mentioned above. Examples include ($C_1$-$C_6$ alkoxy)carbonyl, such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, and hexyloxycarbonyl, with methoxycarbonyl, ethoxycarbonyl, and tert-butoxycarbonyl being preferable, and tert-butoxycarbonyl being more preferable.

In this specification, the "aralkyloxycarbonyl" refers to carbonyl having aralkyloxy mentioned above. Examples include ($C_6$-$C_{20}$ aralkyl)oxycarbonyl, such as benzyloxycarbonyl, phenethyloxycarbonyl, naphthylmethyloxycarbonyl, and fluorenylmethyloxycarbonyl, with benzyloxycarbonyl being preferable.

In this specification, the "saturated heterocyclic group" refers to a monocyclic or polycyclic saturated heterocyclic group containing at least one heteroatom (preferably having 1 to 5, and more preferably 1 to 3 heteroatoms) selected from nitrogen, oxygen, and sulfur. Examples include aziridinyl, azetidinyl, imidazolidinyl, morpholino, pyrrolidinyl, pyrazolidinyl, piperidinyl, piperazinyl, tetrahydrofuranyl, tetrahydropyranyl, tetrahydrothiophenyl, thiazolidinyl, thianyl, oxazolidinyl, morpholyl, and the like, with azetidinyl, pyrrolidinyl, and piperidinyl being preferable, and azetidinyl and pyrrolidinyl being more preferable.

In this specification, the "unsaturated heterocyclic group" refers to a monocyclic or polycyclic, completely or partially unsaturated heterocyclic group containing at least one heteroatom (preferably containing 1 to 5, and more preferably 1 to 3 heteroatoms) selected from nitrogen, oxygen, and sulfur. Examples include imidazolyl, thienyl, pyrrolyl, oxazolyl, isoxazolyl, thiazolyl, isothiazolyl, thiadiazolyl, oxadiazolyl, pyrazolyl, triazolyl, tetrazolyl, pyridyl, pyrazyl, pyrimidinyl, pyridazinyl, indolyl, isoindolyl, indazolyl, triazolopyridyl, benzoimidazolyl, benzoxazolyl, benzothiazolyl, benzothienyl, furanyl, benzofuranyl, purinyl, quinolyl, isoquinolyl, quinazolinyl, quinoxalyl, methylenedioxyphenyl, ethylenedioxyphenyl, dihydrobenzofuranyl, and the like, with imidazolyl, pyrazolyl, thiazolyl, isoxazolyl, oxazolyl, and furanyl being preferable, imidazolyl, pyrazolyl, and thiazolyl being more preferable, and imidazolyl being most preferable.

In this specification, the "saturated heterocyclic oxy" refers to oxy having a saturated heterocyclic group mentioned above. Examples include morpholinyloxy, 1-pyrrolidinyloxy, piperidinooxy, piperazinyloxy, 4-methyl-1-piperazinyloxy, tetrahydrofuranyloxy, tetrahydropyranyloxy, tetrahydrothiophenyloxy, thiazolidinyloxy, oxazolidinyloxy, and the like, with azetidinyloxy and pyrrolidinyloxy being preferable.

In the compound represented by Formula (I) of the disclosure, X represents nitrogen or CH, and preferably CH.

In the compound represented by Formula (I) of the disclosure, $R_1$ represents hydrogen, halogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ cycloalkyl, $C_6$-$C_{10}$ aromatic hydrocarbon, a 4- to 10-membered saturated heterocyclic group, or a 5- to 10-membered unsaturated heterocyclic group.

The "halogen" represented by $R_1$ is preferably fluorine, chlorine, or bromine, and more preferably chlorine.

The "$C_1$-$C_6$ alkyl" in the "substituted or unsubstituted $C_1$-$C_6$ alkyl" represented by $R_1$ is preferably methyl, ethyl, n-propyl, or isopropyl ($C_1$-$C_3$ alkyl), more preferably methyl or ethyl, and particularly preferably methyl.

The substituent in the "substituted or unsubstituted $C_1$-$C_6$ alkyl" represented by $R_1$ may be, for example, the substituents mentioned above, and is preferably, halogen, cyano, or hydroxy, and more preferably fluorine, chlorine, cyano, or hydroxy.

The "substituted or unsubstituted $C_1$-$C_6$ alkyl" represented by $R_1$ is preferably $C_1$-$C_6$ alkyl, more preferably methyl, ethyl, or tert-butyl, more preferably methyl or ethyl, and particularly preferably methyl.

The "$C_2$-$C_6$ alkenyl" in the "substituted or unsubstituted $C_2$-$C_6$ alkenyl" represented by $R_1$ is preferably vinyl, 1-propenyl, allyl, or isopropenyl, and more preferably 1-propenyl.

The substituent in the "substituted or unsubstituted $C_2$-$C_6$ alkenyl" represented by $R_1$ may be, for example, the substituents mentioned above, and is preferably halogen or hydroxy, and more preferably chlorine or fluorine.

The "substituted or unsubstituted $C_2$-$C_6$ alkenyl" represented by $R_1$ is preferably 1-propenyl or 2-methyl-2-propenyl.

The "$C_2$-$C_6$ alkynyl" in the "substituted or unsubstituted $C_2$-$C_6$ alkynyl" represented by $R_1$ is preferably ethynyl or 1-propynyl.

The substituent in the "substituted or unsubstituted $C_2$-$C_6$ alkynyl" represented by $R_1$ may be, for example, the substituents mentioned above, and is preferably halogen or hydroxy, and more preferably fluorine or chlorine.

The "substituted or unsubstituted $C_2$-$C_6$ alkynyl" represented by $R_1$ is preferably $C_2$-$C_6$ alkynyl, and more preferably ethynyl or 1-propynyl.

The "$C_3$-$C_{10}$ cycloalkyl" in the "substituted or unsubstituted $C_3$-$C_{10}$ cycloalkyl" represented by $R_1$ is preferably cyclobutyl, cyclopentyl, or cyclohexyl.

The substituent in the "substituted or unsubstituted $C_3$-$C_{10}$ cycloalkyl" represented by $R_1$ may be, for example, the substituents mentioned above, and is preferably halogen or $C_1$-$C_6$ alkyl, and more preferably methyl, ethyl, n-propyl, fluorine, or chlorine.

The "substituted or unsubstituted $C_3$-$C_{10}$ cycloalkyl" represented by $R_1$ is preferably $C_3$-$C_{10}$ cycloalkyl, and more preferably cyclobutyl, cyclopentyl, or cyclohexyl.

The "$C_6$-$C_{10}$ aromatic hydrocarbon" represented by $R_1$ is preferably phenyl.

The "4- to 10-membered saturated heterocyclic group" represented by $R_1$ is preferably a monocyclic or bicyclic 4- to 10-membered saturated heterocyclic group containing 1 to 5 heteroatoms selected from nitrogen, oxygen, and sulfur, more preferably a monocyclic 4- to 7-membered saturated heterocyclic group containing 1 to 3 heteroatoms selected from nitrogen, oxygen, and sulfur, and more preferably aziridinyl, pyrrolidinyl, or piperidinyl.

The "5- to 10-membered unsaturated heterocyclic group" represented by $R_1$ is preferably a monocyclic or bicyclic 5- to 10-membered unsaturated heterocyclic group containing 1 to 5 heteroatoms selected from nitrogen, oxygen, and sulfur, more preferably a monocyclic 5- to 7-membered unsaturated heterocyclic group containing 1 to 3 heteroatoms selected from nitrogen, oxygen, and sulfur, and more preferably pyridyl.

$R_1$ is preferably hydrogen, halogen, or a substituted or unsubstituted $C_1$-$C_6$ alkyl.

$R_1$ is more preferably hydrogen, halogen, or $C_1$-$C_6$alkyl.

$R_1$ is more preferably halogen or $C_1$-$C_6$ alkyl.

$R_1$ is more preferably halogen or methyl.

$R_1$ is more preferably chlorine or methyl.

$R_1$ is most preferably chlorine.

In the compound represented by Formula (I) of the disclosure, $R_2$ represents hydrogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ cycloalkyl, $C_6$-$C_{10}$ aromatic hydrocarbon, a 4- to 10-membered saturated heterocyclic group, or a 5- to 10-membered unsaturated heterocyclic group.

The "$C_1$-$C_6$ alkyl" in the "substituted or unsubstituted $C_1$-$C_6$ alkyl" represented by $R_2$ is preferably methyl, ethyl, n-propyl, isopropyl, n-butyl, tert-butyl, sec-butyl, isobutyl, or n-pentyl, more preferably methyl, ethyl, n-propyl, isopropyl, n-butyl, or tert-butyl, more preferably methyl, ethyl, or tert-butyl, and most preferably tert-butyl.

The substituent in the "substituted or unsubstituted $C_1$-$C_6$ alkyl" represented by $R_2$ may be, for example, the substituents mentioned above, and is preferably halogen, cyano, hydroxy, or $C_3$-$C_7$ cycloalkyl, and more preferably fluorine, chlorine, cyclopropyl, or cyclobutyl.

The "substituted or unsubstituted $C_1$-$C_6$ alkyl" represented by $R_2$ is preferably $C_1$-$C_6$ alkyl, such as methyl, ethyl, n-propyl, isopropyl, n-butyl, tert-butyl, sec-butyl, isobutyl, and n-pentyl, more preferably methyl, ethyl, isopropyl, and tert-butyl, still more preferably isopropyl or tert-butyl, and most preferably tert-butyl.

The "$C_2$-$C_6$ alkenyl" in the "substituted or unsubstituted $C_2$-$C_6$ alkenyl" represented by $R_2$ is preferably vinyl, 1-propenyl, allyl, or isopropenyl, and more preferably vinyl or isopropenyl.

The substituent in the "substituted or unsubstituted $C_2$-$C_6$ alkenyl" represented by $R_2$ may be, for example, the substituents mentioned above, and is preferably halogen, cyano, or hydroxy, more preferably chlorine or fluorine, and more preferably fluorine.

The "substituted or unsubstituted $C_2$-$C_6$ alkenyl" represented by $R_2$ is preferably $C_2$-$C_6$ alkenyl that may contain halogen, more preferably vinyl, 1-propenyl, 2-methyl-2-propenyl, or 1-(trifluoromethyl)vinyl, and more preferably vinyl or 1-(trifluoromethyl)vinyl.

The "$C_2$-$C_6$ alkynyl" in the "substituted or unsubstituted $C_2$-$C_6$ alkynyl" represented by $R_2$ is preferably ethynyl or 1-propynyl.

The substituent in the "substituted or unsubstituted $C_2$-$C_6$ alkynyl" represented by $R_2$ may be, for example, the substituents mentioned above, and is preferably halogen or hydroxy, more preferably fluorine or chlorine, and still more preferably fluorine.

The "substituted or unsubstituted $C_2$-$C_6$ alkynyl" represented by $R_2$ is preferably ethynyl or 1-propynyl.

The "$C_3$-$C_{10}$ cycloalkyl" in the "substituted or unsubstituted $C_3$-$C_{10}$ cycloalkyl" represented by $R_2$ is preferably cyclopropyl, cyclobutyl, cyclopentyl, or cyclohexyl, and more preferably cyclopropyl.

The substituent in the "substituted or unsubstituted $C_3$-$C_{10}$ cycloalkyl" represented by $R_2$ may be, for example, the substituents mentioned above, and is preferably halogen, $C_1$-$C_6$ alkyl, or $C_1$-$C_6$ haloalkyl, more preferably fluorine, chlorine, methyl, ethyl, n-propyl, fluoromethyl, difluoromethyl, or trifluoromethyl, and still more preferably fluorine, methyl, ethyl, or trifluoromethyl.

The "substituted or unsubstituted $C_3$-$C_{10}$ cycloalkyl" represented by $R_2$ is preferably $C_3$-$C_{10}$ cycloalkyl that may contain $C_1$-$C_6$haloalkyl, and more preferably cyclopropyl, cyclobutyl, cyclopentyl, cyclohexyl, or 1-(trifluoromethyl) cyclopropyl.

The "$C_6$-$C_{10}$ aromatic hydrocarbon" represented by $R_2$ is preferably phenyl.

The "4- to 10-membered saturated heterocyclic group" represented by $R_2$ is preferably a monocyclic or bicyclic 4- to 10-membered saturated heterocyclic group containing 1 to 5 heteroatoms selected from nitrogen, oxygen, and sulfur, and more preferably a monocyclic 4- to 7-membered saturated heterocyclic group containing 1 to 3 heteroatoms selected from nitrogen, oxygen, and sulfur, and more preferably aziridinyl, pyrrolidinyl, piperidinyl, or tetrahydropyranyl.

The "5- to 10-membered unsaturated heterocyclic group" represented by $R_2$ is preferably a monocyclic or bicyclic 5- to 10-membered unsaturated heterocyclic group containing 1 to 5 heteroatoms selected from nitrogen, oxygen, and sulfur, more preferably a monocyclic 5- to 7-membered unsaturated heterocyclic group containing 1 to 3 heteroatoms selected from nitrogen, oxygen, and sulfur, and more preferably pyridyl.

$R_2$ is preferably substituted or unsubstituted $C_1$-$C_6$ alkyl, substituted or unsubstituted $C_2$-$C_6$ alkenyl, or substituted or unsubstituted $C_3$-$C_{10}$ cycloalkyl.

$R_2$ is more preferably $C_1$-$C_6$ alkyl, $C_2$-$C_6$ alkenyl that may contain halogen, or $C_3$-$C_{10}$ cycloalkyl that may contain $C_1$-$C_6$ haloalkyl.

$R_2$ is more preferably $C_1$-$C_6$ alkyl, vinyl, 1-(trifluoromethyl)vinyl, or 1-(trifluoromethyl)cyclopropyl.

$R_2$ is more preferably $C_1$-$C_6$ alkyl.

$R_2$ is more preferably $C_3$-$C_6$ alkyl.

$R_2$ is most preferably tert-butyl.

In the compound represented by Formula (I) of the disclosure, Ras are identical or different, and each represents a hydrogen atom, a deuterium atom, or $C_1$-$C_6$ alkyl.

The "$C_1$-$C_6$ alkyl" represented by $R_a$ is preferably methyl or ethyl, and most preferably methyl.

$R_a$ is preferably a hydrogen atom, a deuterium atom, or methyl, and most preferably a hydrogen atom. In the compound represented by Formula (I) of the disclosure, $L_1$ repesents —NH—C$(R_a)_2$—. $L_1$ preferably represents —NH—C$(R_a)_2$, wherein one of the two Ras is a hydrogen atom while the other is a hydrogen atom, a deuterium atom, or methyl, and most preferably —NH—$CH_2$—.

In the compound represented by Formula (I) of the disclosure, ring A represents a substituted or unsubstituted 5-membered unsaturated heterocyclic group. Ring A typically represents a substituted or unsubstituted 5-membered unsaturated heterocyclic group containing two double bonds in the ring. In ring A, $A_1$, $A_2$, and $A_3$ are identical or different, and represent substituted or unsubstituted carbon, substituted or unsubstituted nitrogen, sulfur, or oxygen, and in ring A, one of $A_1$, $A_2$, and $A_3$ represents substituted or unsubstituted nitrogen or sulfur, and two of the rest of $A_1$, $A_2$, and $A_3$ are identical or different, and represent substituted or unsubstituted carbon, substituted or unsubstituted nitrogen, sulfur, or oxygen.

Ring A is preferably a substituted or unsubstituted group in which two hydrogen atoms are removed from imidazole, pyrazole, thiazole, or oxazol, more preferably a substituted or unsubstituted group in which two hydrogen atoms are removed from imidazole, pyrazole, or thiazole, and most preferably a substituted or unsubstituted group in which two hydrogen atoms are removed from imidazole.

The "5-membered unsaturated heterocyclic group" represented by ring A is preferably a group in which two hydrogen atoms are removed from imidazole, pyrazole, thiazole, or oxazol, more preferably a substituted or unsubstituted group in which two hydrogen atoms are removed from imidazole, pyrazole, or thiazole, and most preferably a group in which two hydrogen atoms are removed from imidazole.

The substituent in the "substituted or unsubstituted 5-membered unsaturated heterocyclic group" represented by ring A may be, for example, the substituents mentioned above, and is preferably hydrogen, halogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ cycloalkyl, substituted or unsubstituted $C_4$-$C_{10}$ cycloalkenyl, substituted or unsubstituted $C_6$-$C_{10}$ aromatic hydrocarbon, a substituted or unsubstituted 4- to 10-membered saturated heterocyclic group, or a substituted or unsubstituted 5- to 10-membered unsaturated heterocyclic group.

The "halogen" included in the substituents of ring A is preferably fluorine or chlorine.

The "$C_1$-$C_6$ alkyl" in the "substituted or unsubstituted $C_1$-$C_6$ alkyl" included in the substituents of ring A is preferably methyl, ethyl, n-propyl, isopropyl, n-butyl, sec-butyl, tert-butyl, isobutyl, or n-pentyl, and more preferably methyl or ethyl.

The substituent in the "substituted or unsubstituted $C_1$-$C_6$ alkyl" included in the substituents of ring A may be, for example, the substituents mentioned above, and is preferably halogen, substituted or unsubstituted $C_1$-$C_6$ alkoxy, substituted or unsubstituted $C_1$-$C_6$ alkylamino, substituted or unsubstituted $C_3$-$C_{10}$ cycloalkyl, substituted or unsubstituted $C_6$-$C_{10}$ aromatic hydrocarbon, or a substituted or unsubstituted 4- to 10-membered saturated heterocyclic group, more preferably halogen, $C_1$-$C_6$ alkoxy, $C_1$-$C_6$ alkylamino, $C_3$-$C_{10}$ cycloalkyl that may contain $C_1$-$C_6$ alkoxy, $C_6$-$C_{10}$ aromatic hydrocarbon, or a 4- to 10-membered saturated heterocyclic group that may contain $C_1$-$C_6$ alkyl, and more preferably halogen, $C_1$-$C_6$ alkoxy, $C_1$-$C_6$ alkylamino, $C_3$-$C_7$ cycloalkyl, phenyl, phenyl substituted with 1 to 3 $C_1$-$C_6$ alkoxy groups, or a 4- to 10-membered saturated heterocyclic group substituted with 1 to 3 $C_1$-$C_6$ alkyl groups, and more preferably fluorine, methoxy, dimethylamino, cyclopentyl, phenyl, 3,5-dimethoxyphenyl, or N-isopropyl-2-pyrrolidyl.

The "substituted or unsubstituted $C_1$-$C_6$ alkyl" included in the substituents of ring A is preferably $C_1$-$C_6$ alkyl substituted or unsubstituted with at least one substituent selected from the group consisting of halogen, substituted or unsubstituted $C_1$-$C_6$ alkoxy, substituted or unsubstituted $C_1$-$C_6$ alkylamino, substituted or unsubstituted $C_3$-$C_{10}$ cycloalkyl, substituted or unsubstituted $C_6$-$C_{10}$ aromatic hydrocarbon, and a substituted or unsubstituted 4- to 10-membered saturated heterocyclic group, more preferably $C_1$-$C_6$ alkyl substituted or unsubstituted with at least one substituent selected from the group consisting of halogen, $C_1$-$C_6$ alkoxy, $C_1$-$C_6$ alkylamino, $C_3$-$C_{10}$ cycloalkyl that may contain $C_1$-$C_6$ alkoxy, $C_6$-$C_{10}$ aromatic hydrocarbon, and a 4- to 10-membered saturated heterocyclic group that may contain $C_1$-$C_6$ alkyl, more preferably $C_1$-$C_6$ alkyl substituted or unsubstituted with at least one substituent selected from the group consisting of fluorine, methoxy, dimethylamino, cyclopentyl, phenyl, 3,5-dimethoxyphenyl, and N-isopropyl-2-pyrrolidylmethyl, and more preferably, methyl, ethyl, n-propyl, isopropyl, n-butyl, sec-butyl, tert-butyl, isobutyl, difluoromethyl, trifluoromethyl, 2,2-difluoroethyl, 2,2,2-trifluoroethyl, 2-methoxyethyl, 2-(dimethylamino)ethyl, cyclopentylmethyl, benzyl, 3,5-dimethoxyphenylmethyl, or N-isopropyl-2-pyrrolidylmethyl.

The "$C_2$-$C_6$ alkenyl" in the "substituted or unsubstituted $C_2$-$C_6$ alkenyl" included in the substituents of ring A is preferably vinyl or allyl.

The substituent in the "substituted or unsubstituted $C_2$-$C_6$ alkenyl" included in the substituents of ring A may be, for example, the substituents mentioned above, and is preferably halogen, and more preferably fluorine or chlorine.

The "substituted or unsubstituted $C_2$-$C_6$ alkenyl" included in the substituents of ring A is preferably vinyl or allyl.

The "$C_2$-$C_6$ alkynyl" in the "substituted or unsubstituted $C_2$-$C_6$ alkynyl" included in the substituents of ring A is preferably ethynyl or 1-propynyl.

The substituent in the "substituted or unsubstituted $C_2$-$C_6$ alkynyl" included in the substituents of ring A may be, for example, the substituents mentioned above, and is preferably halogen, and more preferably fluorine or chlorine.

The "substituted or unsubstituted $C_2$-$C_6$ alkynyl" included in the substituents of ring A is preferably ethynyl or 1-propynyl.

Examples of the "$C_3$-$C_{10}$ cycloalkyl" in the "substituted or unsubstituted $C_3$-$C_{10}$ cycloalkyl" included in the substituents of ring A include cyclopropyl, cyclobutyl, cyclopentyl, cyclohexyl, cycloheptyl, cyclodecyl, and the like, with $C_3$-$C_7$ cycloalkyl being preferable, and cyclopropyl, cyclopentyl, and cyclohexyl being more preferable.

The substituent in the "substituted or unsubstituted $C_3$-$C_{10}$ cycloalkyl" included in the substituents of ring A may be, for example, the substituents mentioned above, and is preferably hydroxy, substituted or unsubstituted $C_1$-$C_6$ alkyl, or substituted or unsubstituted $C_1$-$C_6$ alkoxy, more preferably hydroxy, $C_1$-$C_6$ alkyl, or $C_1$-$C_6$ alkoxy, and more preferably hydroxy, methyl, isopropyl, or methoxy.

The "substituted or unsubstituted $C_3$-$C_{10}$ cycloalkyl" included in the substituents of ring A is preferably $C_3$-$C_{10}$ cycloalkyl substituted or unsubstituted with a substituent selected from the group consisting of hydroxy, substituted or unsubstituted $C_1$-$C_6$ alkyl, and substituted or unsubstituted $C_1$-$C_6$ alkoxy, more preferably $C_3$-$C_{10}$ cycloalkyl substituted or unsubstituted with a substituent selected from the group consisting of hydroxy, $C_1$-$C_6$ alkyl, and $C_1$-$C_6$ alkoxy, more preferably $C_3$-$C_7$ cycloalkyl substituted or unsubstituted with a substituent selected from the group consisting of hydroxy, $C_1$-$C_6$ alkyl, and $C_1$-$C_6$ alkoxy, and more preferably cyclopropyl, cyclopentyl, cyclohexyl, 3,4-dihydroxycyclopentyl, 2-isopropyl-5-methyl-cyclohexyl, or 4-methoxycyclohexyl.

Examples of the "$C_4$-$C_{10}$ cycloalkenyl" in the "substituted or unsubstituted $C_4$-$C_{10}$ cycloalkenyl" included in the substituents of ring A include cyclobutenyl, cyclopentenyl, cyclohexenyl, cycloheptenyl, cyclodecenyl, and the like, with $C_4$-$C_7$ cycloalkenyl being preferable, and cyclopentenyl being more preferable.

The substituent in the "substituted or unsubstituted $C_4$-$C_{10}$ cycloalkenyl" included in the substituents of ring A may be, for example, the substituents mentioned above, and is preferably halogen, and more preferably fluorine or chlorine.

The "substituted or unsubstituted $C_4$-$C_{10}$ cycloalkenyl" included in the substituents of ring A is preferably $C_4$-$C_{10}$ cycloalkenyl, more preferably $C_4$-$C_7$ cycloalkenyl, and more preferably cyclopentenyl.

The "$C_6$-$C_{10}$ aromatic hydrocarbon" in the "substituted or unsubstituted $C_6$-$C_{10}$ aromatic hydrocarbon" included in the substituents of ring A is preferably phenyl, naphthyl, or tetrahydronaphthyl, and more preferably phenyl.

The substituent in the "substituted or unsubstituted $C_6$-$C_{10}$ aromatic hydrocarbon" included in the substituents of ring A may be, for example, the substituents mentioned above, and is preferably halogen, and more preferably fluorine or chlorine.

The "substituted or unsubstituted $C_6$-$C_{10}$ aromatic hydrocarbon" included in the substituents of ring A is preferably $C_6$-$C_{10}$ aromatic hydrocarbon, and more preferably phenyl.

The "4- to 10-membered saturated heterocyclic group" in the "substituted or unsubstituted 4- to 10-membered saturated heterocyclic group" included in the substituents of ring A is preferably a monocyclic or bicyclic 4- to 10-membered saturated heterocyclic group containing 1 to 5 heteroatoms selected from nitrogen, oxygen, and sulfur, more preferably a monocyclic 4- to 7-membered saturated heterocyclic group containing 1 to 3 heteroatoms selected from nitrogen, oxygen, and sulfur, and more preferably azetidinyl, pyrrolidinyl, or piperidinyl.

The "substituent" in the "substituted or unsubstituted 4- to 10-membered saturated heterocyclic group" included in the substituents of ring A may be, for example, the substituents mentioned above, and is preferably substituted or unsubstituted $C_1$-$C_6$ alkyl, $C_1$-$C_6$ alkenyl, ($C_1$-$C_6$ alkyl)carbonyl, ($C_1$-$C_6$ alkoxy)carbonyl, $C_3$-$C_{10}$ cycloalkyl, $C_6$-$C_{10}$ aromatic hydrocarbon, a 4- to 10-membered saturated heterocyclic group, or a 5- to 10-membered unsaturated heterocyclic group, more preferably $C_1$-$C_6$ alkyl, $C_1$-$C_6$ haloalkyl, $C_1$-$C_6$ alkoxy-$C_1$-$C_6$ alkyl, $C_7$-$C_{16}$ aralkyl, $C_1$-$C_6$ alkenyl, ($C_1$-$C_6$ alkyl)carbonyl, ($C_1$-$C_6$ alkoxy)carbonyl, $C_3$-$C_{10}$ cycloalkyl, a 4- to 10-membered saturated heterocyclic group, or a 5- to 10-membered unsaturated heterocyclic group, and more preferably methyl, ethyl, isopropyl, 2,2-difluoroethyl, 2-methoxyethyl, benzyl, allyl, acetyl, tert-butoxycarbonyl, cyclopropyl, oxetanyl, pyridyl, carboxylate, alkenyl, or benzyl, with methyl, ethyl, isopropyl, methylcarbonyl, tert-butoxycarbonyl, 2,2-difluoroethyl, 2-methoxyethyl, benzyl, and allyl being more preferable.

The "substituted or unsubstituted 4- to 10-membered saturated heterocyclic group" included in the substituents of ring A is preferably N-tert-butoxycarbonylazetidinyl, N-isopropylazetidinyl, N-acetylazetidinyl, N-methylpyrrolidinyl, N-ethylpyrrolidinyl, N-acetylpyrrolidinyl, N-isopropylpyrrolidinyl, N-pyridinepyrrolidinyl, N-2-methoxyethylpyrrolidinyl, N-cyclopropylpyrrolidinyl, N-oxetanylpyrrolidinyl, N-benzylpyrrolidinyl, N-carboxylateazetidinyl, N-difluoroethyl-pyrrolidinyl, N-prop-2-enyl-pyrrolidinyl, 1-(2,2-difluoroethyl)-2-methylpyrrolidinin-3-yl, 1-(2,2-difluoroethyl)-5-methylpyrrolidinin-3-yl, N-methyl piperazinyl, N-difluoroethyl piperazinyl, N-methyl piperidinyl, N-difluoroethyl piperidinyl, tetrahydropyranyl, or tetrahydrofuranyl.

The "5- to 10-membered unsaturated heterocyclic group" included in the substituents of ring A is preferably pyridinyl.

The substituent in the "substituted or unsubstituted 5- to 10-membered unsaturated heterocyclic group" included in the substituent of ring A may be, for example, the substituents mentioned above, and is preferably halogen, hydroxy, or $C_1$-$C_6$ alkyl, and more preferably methyl, ethyl, hydroxy, fluorine, or chlorine.

The "substituted or unsubstituted 5- to 10-membered unsaturated heterocyclic group" in the "substituted or unsubstituted 5- to 10-membered unsaturated heterocyclic group" included in the substituents of ring A is preferably a 5- to 10-membered unsaturated heterocyclic group, and more preferably pyridinyl or N-methylpyridinyl.

In Formula (I), $L_2$ represents

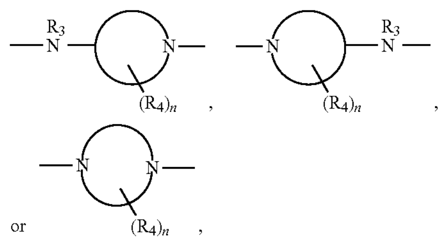

wherein

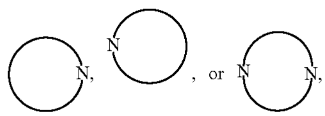

represents a 4- to 8-membered saturated heterocyclic group that may contain 1 or 2 heteroatoms selected from sulfur and oxygen, and that contains at least one, and preferably 1 or 2, nitrogen atoms, and $R_3$ represents hydrogen or $C_1$-$C_6$ alkyl.

$R_4$ represents halogen, cyano, nitro, amino, hydroxy, carboxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkylamino-$C_1$-$C_6$ alkyl, $C_1$-$C_6$ cyanoalkyl, $C_1$-$C_6$ alkoxy-$C_1$-$C_6$ alkyl, or $C_1$-$C_6$ hydroxyalkyl.

In $L_2$,

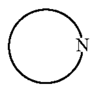

preferably represents a 4- to 8-membered saturated heterocyclic group that does not contain sulfur or oxygen, and contains at least one nitrogen atom (preferably one or two nitrogen atoms), and more preferably, azetidinyl, pyrrolidinyl, or piperidinyl.

In $L_2$,

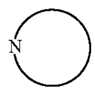

preferably represents a 4- to 8-membered saturated heterocyclic group that does not contain sulfur or oxygen, and contains at least one nitrogen atom (preferably one or two nitrogen atoms), and more preferably azetidinyl, pyrrolidinyl, or piperidinyl.

In $L_2$,

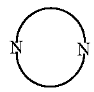

preferably represents a 4- to 8-membered saturated heterocyclic group that does not contain sulfur or oxygen, and contains at least two (preferably two or three) nitrogen atoms, and more preferably 1,3-diazetidinyl, imidazolidinyl, or piperazinyl.

The "$C_1$-$C_6$ alkyl" represented by $R_3$ is preferably methyl or ethyl, and more preferably methyl.

The "halogen" represented by $R_4$ is preferably fluorine.

The "$C_1$-$C_6$ alkyl" represented by $R_4$ is preferably methyl or ethyl.

The "$C_2$-$C_6$ alkenyl" represented by $R_4$ is preferably vinyl or allyl.

The "$C_2$-$C_6$ alkynyl" represented by $R_4$ is preferably ethynyl.

The "$C_1$-$C_6$ alkoxy" represented by $R_4$ is preferably methoxy.

The "$C_1$-$C_6$ haloalkyl" represented by $R_4$ is preferably fluoromethyl.

The "$C_1$-$C_6$ cyanoalkyl" represented by $R_4$ is preferably cyanomethyl.

The "$C_1$-$C_6$ alkylamino-$C_1$-$C_6$ alkyl" represented by $R_4$ is preferably N,N-dimethylaminomethyl.

The "$C_1$-$C_6$ alkoxy-$C_1$-$C_6$ alkyl" represented by $R_4$ is preferably methoxymethyl or methoxyethyl, and more preferably methoxymethyl.

The "$C_1$-$C_6$ hydroxyalkyl" represented by $R_4$ is preferably hydroxymethyl or 2-hydroxyethyl, and more preferably hydroxymethyl.

When two $R_4$s are attached to the same carbon atom, and these two $R_4$s each represent $C_1$-$C_6$ alkyl, these two $R_4$s, taken together with the carbon atom to which these groups are attached, may form a ring. Such a ring has a structure in which, for example, two hydrogen atoms that attach to the same carbon are removed from $C_3$-$C_6$ (preferably $C_3$-$C_4$, and more preferably $C_3$) cycloalkane.

n represents 0, 1, 2, or 3. n is preferably 0, 1, or 2, more preferably 0 or 1, and most preferably 0.

In Formula (I), it is more preferable that $L_2$ above represent a 4- to 6-membered saturated heterocyclic group containing 1 or 2 nitrogen atoms, $R_3$ represents hydrogen or methyl, and $R_4$ represents halogen, cyano, cyanomethyl, hydroxy, $C_1$-$C_2$ alkyl, methoxy, $C_1$-$C_2$ haloalkyl, $C_1$-$C_2$ hydroxyalkyl, dimethylaminomethyl, methoxymethyl, or ethoxymethyl. In this embodiment, when two $R_4$s are attached to the same carbon atom, and these two $R_4$s each represent $C_1$-$C_2$ alkyl, these two $R_4$s, taken together with the carbon atom to which these groups are attached, may form a structure in which two hydrogen atoms that attach to the same carbon are removed from $C_3$-$C_5$ (preferably $C_3$) cycloalkane.

In Formula (I), it is more preferable that $L_2$ represents

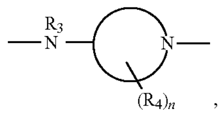

wherein

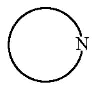

represents a 4- to 5-membered saturated heterocyclic group containing one N, $R_3$ represents hydrogen, n represents 0, 1, or 2, and $R_4$ represents halogen, methyl, ethyl, or methoxy.

In Formula (I), $L_3$ represents —C(═O)— or —S(═O)$_2$—, and preferably —C(═O)—.

In Formula (I), $R_5$ represents substituted or unsubstituted $C_2$-$C_6$ alkenyl or substituted or unsubstituted $C_2$-$C_6$ alkynyl. The compound or a salt thereof according to the disclosure has structural features as represented by Formula (I) above; in particular, due to the above structure of $R_5$, the compound or a salt thereof according to the disclosure can specifically bind to the cysteine residue of the G12C mutant of KRAS.

The "$C_2$-$C_6$ alkenyl" in the "substituted or unsubstituted $C_2$-$C_6$ alkenyl" represented by $R_5$ is preferably vinyl, 1-propenyl, allyl, or isopropenyl.

The "substituent" in the "substituted or unsubstituted $C_2$-$C_6$ alkenyl" represented by $R_5$ may be, for example, the substituents mentioned above, and is preferably halogen, $C_1$-$C_6$ alkylamino, $C_1$-$C_6$ alkoxy, or a 4- to 10-membered saturated heterocyclic group, and more preferably chlorine, methoxymethyl, dimethylamino, or piperidinyl.

The "substituted or unsubstituted $C_2$-$C_6$ alkenyl" represented by $R_5$ is preferably vinyl, 1-propenyl, 1-chlorovinyl, 2-chlorovinyl, 3-(dimethylamino)prop-1-en-1-yl, 3-(piperidin-1-yl)prop-1-en-1-yl, or 3-(methoxy)prop-1-en-1-yl.

The "$C_2$-$C_6$ alkynyl" in the "substituted or unsubstituted $C_2$-$C_6$ alkynyl" represented by $R_5$ is preferably ethynyl, 1-propynyl, or 2-propynyl.

The substituent in the "substituted or unsubstituted $C_2$-$C_6$ alkynyl" represented by $R_5$ may be, for example, the substituents mentioned above, and is preferably halogen, $C_1$-$C_6$ alkyl, or $C_1$-$C_6$ alkoxy, and more preferably fluorine, chlorine, methyl, or methoxy.

The "substituted or unsubstituted $C_2$-$C_6$ alkynyl" represented by $R_5$ is preferably ethynyl. $R_5$ is preferably substituted or unsubstituted $C_2$-$C_6$ alkenyl, more preferably substituted or unsubstituted $C_2$-$C_3$ alkenyl, and most preferably vinyl.

$R_5$ is preferably substituted or unsubstituted $C_2$-$C_6$ alkenyl or substituted or unsubstituted $C_2$-$C_6$ alkynyl (the substituent is selected from the group consisting of halogen, $C_1$-$C_6$ alkyl, $C_1$-$C_6$ alkylamino, $C_1$-$C_6$ alkoxy, and 4- to 10-membered saturated heterocyclic group), more preferably substituted or unsubstituted $C_2$-$C_6$ alkenyl (the substituent is selected from the group consisting of halogen, $C_1$-$C_6$ alkylamino, $C_1$-$C_6$ alkoxy, and 4- to 10-membered saturated heterocyclic group) or substituted or unsubstituted $C_2$-$C_6$ alkynyl (the substituent is selected from halogen, $C_1$-$C_6$ alkyl, and $C_1$-$C_6$ alkoxy), more preferably substituted or unsubstituted $C_2$-$C_3$ alkenyl (the substituent is selected from the group consisting of chlorine, methoxymethyl, dimethylamino, and piperidinyl), more preferably $C_2$-$C_3$ alkenyl, and most preferably vinyl.

In Formula (I), when ring A is substituted with alkyl, the alkyl is preferably not substituted with $C_6$-$C_{10}$ aromatic hydrocarbon, a 4- to 10-membered saturated heterocyclic group, or a 5- to 10-membered unsaturated heterocyclic group.

When $A_1$ represents substituted carbon or substituted nitrogen, the substituent is at least one member selected from the group consisting of hydrogen, halogen, cyano, nitro, amino, hydroxy, carboxy, $C_1$-$C_6$ alkyl that may have $R_b$, $C_2$-$C_6$ alkenyl that may have $R_b$, $C_2$-$C_6$ alkynyl that may have $R_b$, $C_3$-$C_{10}$ cycloalkyl that may have $R_c$, $C_3$-$C_{10}$ cycloalkenyl that may have $R_c$, $C_6$-$C_{10}$ aromatic hydrocarbon that may have $R_c$, a 4- to 10-membered saturated heterocyclic group that may have $R_c$, and a 4- to 10-membered unsaturated heterocyclic group that may have $R_c$.

In this embodiment, $R_b$ represents halogen, cyano, nitro, amino, hydroxy, carboxy, $C_1$-$C_6$ alkoxy, $C_1$-$C_6$ alkylamino, $C_3$-$C_6$ cycloalkyl, substituted or unsubstituted $C_6$-$C_{10}$ aromatic hydrocarbon, or a substituted or unsubstituted 4- to 10-membered saturated heterocyclic group, and $R_c$ represents halogen, cyano, nitro, amino, hydroxy, carboxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkylamino, $C_1$-$C_6$ alkylcarbonyl, $C_1$-$C_6$ alkoxy-$C_1$-$C_6$ alkyl, $C_7$-$C_{20}$ aralkyl, $C_1$-$C_6$ alkoxycarbonyl, $C_3$-$C_6$ cycloalkyl, $C_6$-$C_{10}$ aromatic hydrocarbon, a 4- to 10-membered saturated heterocyclic group, or a 5- to 10-membered unsaturated heterocyclic group, wherein when two or more $R_b$s are present, the plurality of $R_b$s may be identical or different, and when two or more $R_c$s are present, the plurality of $R_c$s may be identical or different.

$R_b$ is preferably halogen, $C_1$-$C_6$ alkoxy, $C_1$-$C_6$ alkylamino, $C_3$-$C_{10}$ cycloalkyl, substituted or unsubstituted $C_6$-$C_{10}$ aromatic hydrocarbon, or a substituted or unsubstituted 4- to 10-membered saturated heterocyclic group.

$R_b$ is more preferably halogen, $C_1$-$C_3$ alkoxy, $C_1$-$C_3$ alkylamino, $C_3$-$C_6$ cycloalkyl, substituted or unsubstituted phenyl, or a substituted or unsubstituted 4- to 5-membered saturated heterocyclic group.

$R_b$ is more preferably chlorine, fluorine, methoxy, cyclopentyl, phenyl, 2,4-dimethoxyphenyl, dimethylamino, or N-isopropyl-pyrrolidinyl.

$R_b$ is more preferably chlorine, methyl, ethyl, cyano, difluoromethyl, trifluoromethyl, or 2,4-dimethoxyphenyl.

$R_c$ is preferably halogen, hydroxy, $C_1$-$C_6$ alkyl, $C_2$-$C_6$ alkenyl, $C_1$-$C_6$ alkoxy, $C_1$-$C_6$ haloalkyl, $C_1$-$C_6$ alkylamino, $C_1$-$C_6$ alkylcarbonyl, $C_1$-$C_6$ alkoxy-$C_1$-$C_6$ alkyl, $C_3$-$C_6$ cycloalkyl, $C_1$-$C_6$ alkoxycarbonyl, $C_7$-$C_{20}$ aralkyl, a 4- to 10-membered saturated heterocyclic group, or a 5- to 10-membered unsaturated heterocyclic group.

$R_c$ is more preferably halogen, hydroxy, $C_1$-$C_3$ alkyl, $C_2$-$C_3$ alkenyl, $C_1$-$C_3$ alkoxy, $C_1$-$C_3$ haloalkyl, $C_1$-$C_3$ alkylamino, $C_1$-$C_3$ alkylcarbonyl, $C_1$-$C_3$ alkoxy $C_1$-$C_3$ alkyl, $C_3$-$C_6$ cycloalkyl, $C_1$-$C_3$ alkoxycarbonyl, benzyl, a 4- to 6-membered saturated heterocyclic group, or a 5- to 6-membered unsaturated heterocyclic group.

$R_c$ is still more preferably chlorine, fluorine, hydroxy, methyl, ethyl, isopropyl, acetyl, methoxy, vinyl, difluoromethyl, trifluoromethyl, 2,2-difluoroethyl, cyclopropyl, oxetanyl, benzyl, tert-butoxycarbonyl, methoxyethyl, or pyridinyl.

$A_1$ preferably represents substituted carbon or substituted nitrogen, and the substituent is preferably hydrogen, cyano, halogen, $C_1$-$C_6$ alkyl that may have $R_b$, $C_2$-$C_6$ alkenyl that may have $R_b$, $C_3$-$C_{10}$ cycloalkyl that may have $R_c$, $C_4$-$C_{10}$ cycloalkenyl that may have $R_c$, a 4- to 10-membered saturated heterocyclic group that may have $R_c$, or a 4- to 10-membered unsaturated heterocyclic group that may have $R_c$.

$A_1$ more preferably represents substituted nitrogen, and the substituent is hydrogen, halogen, $C_1$-$C_6$ alkyl (substituted or unsubstituted with a substituent selected from the group consisting of halogen, $C_1$-$C_6$ alkoxy, $C_1$-$C_6$ alkylamino, $C_3$-$C_{10}$ cycloalkyl, substituted or unsubstituted $C_6$-$C_{10}$ aromatic hydrocarbon, and a substituted or unsubstituted, 4- to 10-membered saturated heterocyclic group), $C_3$-$C_{10}$ cycloalkyl (substituted or unsubstituted with a substituent selected from the group consisting of hydroxy, $C_1$-$C_6$ alkyl, and $C_1$-$C_6$ alkoxy), $C_3$-$C_{10}$ cycloalkenyl, a 4- to 10-membered saturated heterocyclic group (substituted or unsubstituted with a substituent selected from the group consisting of $C_1$-$C_6$ alkyl, $C_1$-$C_6$ haloalkyl, $C_1$-$C_6$ alkoxy-$C_1$-$C_6$ alkyl, $C_7$-$C_{16}$ aralkyl, $C_1$-$C_6$ alkenyl, $C_1$-$C_6$ alkylcarbonyl, $C_1$-$C_6$ alkoxycarbonyl, $C_3$-$C_{10}$ cycloalkyl, a 4- to 10-membered saturated heterocyclic group, and a 5- to 10-membered unsaturated heterocyclic group), or a 4- to 10-membered unsaturated heterocyclic group.

$A_1$ more preferably represents substituted nitrogen, and the substituent is hydrogen, halogen, $C_1$-$C_6$ alkyl (substituted or unsubstituted with a substituent selected from the group consisting of halogen, $C_1$-$C_3$ alkoxy, $C_1$-$C_3$ alkylamino, $C_3$-$C_6$ cycloalkyl, substituted or unsubstituted phenyl, and a substituted or unsubstituted 4- to 5-membered saturated heterocyclic group), $C_3$-$C_6$ cycloalkyl (substituted or unsubstituted with a substituent selected from the group consisting of hydroxy, $C_1$-$C_3$ alkyl, and $C_1$-$C_3$ alkoxy), $C_3$-$C_6$ cycloalkenyl, a 4- to 5-membered saturated heterocyclic group (substituted or unsubstituted with a substituent selected from the group consisting of $C_1$-$C_3$ alkyl, $C_1$-$C_3$ haloalkyl, $C_1$-$C_3$ alkoxy-$C_1$-$C_3$ alkyl, benzyl, $C_1$-$C_3$ alkenyl, $C_1$-$C_3$ alkylcarbonyl, $C_1$-$C_3$ alkoxycarbonyl, $C_3$-$C_6$ cycloalkyl, a 4- to 6-membered saturated heterocyclic group, and a 5- to 6-membered unsaturated heterocyclic group), or a 4- to 6-membered unsaturated heterocyclic group.

$A_1$ still more preferably represents substituted nitrogen, and the substituent is hydrogen, chlorine, methyl, ethyl, n-propyl, isopropyl, n-butyl, isobutyl, tert-butyl, cyclopropyl, cyclopentyl, 3,4-dihydroxycyclopentyl, cyclohexyl, 2-isopropyl-5-methylcyclohexyl, 4-methoxycyclohexyl, cyclopentenyl, N-tert-butoxycarbonylaziridinyl, N-isopropylaziridinyl, N-methylcarbonylaziridinyl, N-methylpyrrolidinyl, N-ethylpyrrolidinyl, N-isopropylpyrrolidinyl, N-(2,2-difluoroethyl)pyrrolidinyl, N-methylcarbonylpyrrolidinyl, N-methoxyethylpyrrolidinyl, N-benzylpyrrolidinyl, N-oxetanepyrrolidinyl, N-methylpiperidinyl, N-(2,2-difluoroethyl)piperidinyl, tetrahydrofuranyl, tetrahydropyranyl, or pyridinyl.

$A_1$ still more preferably represents substituted nitrogen, and the substituent is hydrogen, chlorine, methyl, ethyl, n-propyl, isopropyl, n-butyl, isobutyl, tert-butyl, cyclopentyl, 4-methoxycyclohexyl, N-isopropylaziridinyl, N-methylpyrrolidinyl, N-isopropylpyrrolidinyl, N-(2,2-difluoroethyl)pyrrolidinyl, N-(2,2-difluoroethyl)piperidinyl, tetrahydrofuranyl, or tetrahydropyranyl.

$A_2$ preferably represents sulfur or substituted nitrogen, and the substituent is hydrogen, halogen, cyano, nitro, amino, hydroxy, carboxy, substituted or unsubstituted $C_1$-$C_6$ alkyl, substituted or unsubstituted $C_2$-$C_6$ alkenyl, or substituted or unsubstituted $C_2$-$C_6$ alkynyl.

$A_2$ still more preferably represents substituted nitrogen, and the substituent is hydrogen, halogen, cyano, hydroxy, or $C_1$-$C_6$ alkyl.

$A_2$ still more preferably represents substituted nitrogen, and the substituent is hydrogen, methyl, or ethyl.

The substituent of $A_2$ is most preferably nitrogen that is substituted with hydrogen.

$A_3$ preferably represents substituted carbon or substituted nitrogen, and the substituent is hydrogen, halogen, cyano, nitro, amino, hydroxy, carboxy, substituted or unsubstituted $C_1$-$C_6$ alkyl, substituted or unsubstituted $C_2$-$C_6$ alkenyl, or substituted or unsubstituted $C_2$-$C_6$ alkynyl.

$A_3$ more preferably represents substituted carbon or substituted nitrogen, and the substituent is hydrogen, halogen, cyano, nitro, amino, hydroxy, carboxy, $C_1$-$C_6$ alkyl, $C_1$-$C_6$ haloalkyl, $C_2$-$C_6$ alkenyl, or $C_2$-$C_6$ alkynyl.

$A_3$ still more preferably represents substituted carbon, and the substituent is hydrogen, halogen, cyano, $C_1$-$C_6$ alkyl, or $C_1$-$C_6$ haloalkyl.

$A_3$ most preferably represents substituted carbon, and the substituent is methyl, ethyl, difluoromethyl, chlorine, fluorine, or cyano.

A preferable combination of $A_1$, $A_2$, and $A_3$ is a combination of $A_1$ being substituted nitrogen, $A_2$ being nitrogen, and $A_3$ being substituted carbon;

a combination of $A_1$ being nitrogen, $A_2$ being sulfur, and $A_3$ being substituted carbon;

a combination of $A_1$ being substituted carbon, $A_2$ being nitrogen, and $A_3$ being substituted nitrogen; or a combination of $A_1$ being nitrogen, $A_2$ being sulfur, and $A_3$ being substituted carbon.

A more preferable combination of $A_1$, $A_2$, and $A_3$ is a combination of $A_1$ being substituted nitrogen, $A_2$ being nitrogen, and $A_3$ being substituted carbon; or a combination of $A_1$ being nitrogen, $A_2$ being sulfur, and $A_3$ being substituted carbon.

A most preferable combination of $A_1$, $A_2$, and $A_3$ is a combination of $A_1$ being substituted nitrogen, $A_2$ being nitrogen, and $A_3$ being substituted carbon.

The compound or a salt thereof of the disclosure is preferably a compound represented by Formula (I) or a salt thereof, wherein X represents nitrogen or CH, $R_1$ represents hydrogen, halogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ cycloalkyl, $C_6$-$C_{10}$ aromatic hydrocarbon, a 4- to 10-membered saturated heterocyclic group, or a 5- to 10-membered unsaturated heterocyclic group, $L_1$ represents —NH—C($R_a$)$_2$—, wherein Ras are identical or different, and each represents a hydrogen atom, a deuterium atom, or $C_1$-$C_6$ alkyl, ring A represents a substituted or unsubstituted, 5-membered unsaturated heterocyclic group, wherein one of $A_1$, $A_2$, and $A_3$ represents substituted or unsubstituted nitrogen or sulfur, and two of the rest of $A_1$, $A_2$, and $A_3$ are identical or different, and represent substituted or unsubstituted carbon, substituted or unsubstituted nitrogen, sulfur, or oxygen, the substituent of $A_1$ is preferably hydrogen, cyano, halogen, $C_1$-$C_6$ alkyl that may have $R_b$, $C_2$-$C_6$ alkenyl that may have $R_b$, $C_3$-$C_{10}$ cycloalkyl that may have $R_c$, $C_4$-$C_{10}$ cycloalkenyl that may have $R_c$, a 4- to 10-membered saturated heterocyclic group that may have $R_c$, or a 4- to 10-membered unsaturated heterocyclic group that may have $R_c$, wherein $R_b$ represents halogen, cyano, nitro, amino, hydroxy, carboxy, $C_1$-$C_6$ alkoxy, $C_1$-$C_6$ alkylamino, $C_3$-$C_6$ cycloalkyl, substituted or unsubstituted $C_6$-$C_{10}$ aromatic hydrocarbon, or a substituted or unsubstituted 4- to 10-membered saturated heterocyclic group, and $R_c$ represents halogen, cyano, nitro, amino, hydroxy, carboxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkylamino, $C_1$-$C_6$ alkylcarbonyl, $C_1$-$C_6$ alkoxy-$C_1$-$C_6$ alkyl, $C_7$-$C_{20}$ aralkyl, $C_1$-$C_6$ alkoxycarbonyl, $C_3$-$C_6$ cycloalkyl, $C_6$-$C_{10}$ aromatic hydrocarbon, a 4- to 10-membered saturated heterocyclic group, or a 5- to 10-membered unsaturated heterocyclic group, and wherein when two or more $R_b$s are present, the plurality of $R_b$s may be identical or different, and when two or more $R_c$s are present, the plurality of $R_c$s may be identical or different, the substituent of $A_2$ is hydrogen, halogen, cyano, nitro, amino, hydroxy, carboxy, substituted or unsubstituted $C_1$-$C_6$ alkyl, substituted or unsubstituted $C_2$-$C_6$ alkenyl, or substituted or unsubstituted $C_2$-$C_6$ alkynyl, the substituent of $A_3$ is hydrogen, halogen, cyano, nitro, amino, hydroxy, carboxy, substituted or unsubstituted $C_1$-$C_6$ alkyl, substituted or unsubstituted $C_2$-$C_6$ alkenyl, and substituted or unsubstituted $C_2$-$C_6$ alkynyl, and $L_2$ represents

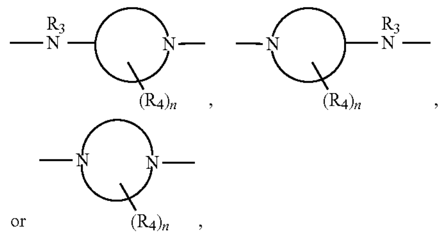

where

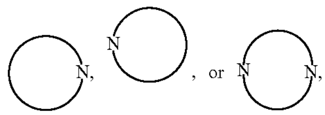

is a 4- to 8-membered saturated heterocyclic group that contains at least one nitrogen atom and contains 0 to 2 heteroatoms selected from sulfur and oxygen, $R_3$ represents hydrogen or $C_1$-$C_6$ alky, and $R_4$ represents halogen, cyano, nitro, amino, hydroxy, carboxy, $C_1$-$C_6$ alkyl, $C_2$-$C_6$ alkenyl, $C_2$-$C_6$ alkynyl, $C_3$-$C_6$ cycloalkyl, $C_1$-$C_6$ alkoxy, $C_1$-$C_6$ haloalkyl, $C_1$-$C_6$ alkylamino-$C_1$-$C_6$ alkyl, $C_1$-$C_6$ alkoxy-$C_1$-$C_6$ alkyl, or $C_1$-$C_6$ hydroxyalkyl, and $L_3$ represents —C(═O)— or —S(═O)$_2$—, and $R_5$ represents substituted or unsubstituted $C_2$-$C_6$ alkenyl or substituted or unsubstituted $C_2$-$C_6$ alkynyl.

The compound or a salt thereof of the disclosure is more preferably a compound represented by Formula (I) or a salt thereof, wherein X represents N or CH, $R_1$ represents halogen, substituted or unsubstituted $C_1$-$C_6$ alkyl, substituted or unsubstituted $C_2$-$C_6$ alkenyl, or substituted or unsubstituted $C_3$-$C_{10}$ cycloalkyl, $L_1$ represents —NH—C($R_a$)$_2$—, and one of the two Ras is a hydrogen atom while the other is a hydrogen atom, a deuterium atom, or methyl, wherein Ras are identical or different, and each represents a hydrogen atom, a deuterium atom, or methyl, ring A is a combination of $A_1$, $A_2$, and $A_3$, wherein $A_1$ is substituted nitrogen, $A_2$ is nitrogen, and $A_3$ is substituted carbon; $A_1$ is substituted nitrogen, $A_2$ is sulfur, and $A_3$ is substituted carbon; $A_1$ is substituted carbon, $A_2$ is nitrogen, and $A_3$ is substituted nitrogen; or $A_1$ is sulfur, $A_2$ is nitrogen, and $A_3$ is substituted carbon, the substituent of $A_1$ is hydrogen, halogen, $C_1$-$C_6$ alkyl (substituted or unsubstituted with a substituent selected from the group consisting of halogen, $C_1$-$C_6$ alkoxy, $C_1$-$C_6$ alkylamino, $C_3$-$C_{10}$ cycloalkyl, substituted or unsubstituted $C_6$-$C_{10}$ aromatic hydrocarbon, and a substituted or unsubstituted, 4- to 10-membered saturated heterocyclic group), $C_3$-$C_{10}$ cycloalkyl (substituted or unsubstituted with a substituent selected from the group consisting of hydroxy, $C_1$-$C_6$ alkyl, and $C_1$-$C_6$ alkoxy), $C_3$-$C_{10}$ cycloalkenyl, a 4- to 10-membered saturated heterocyclic group (substituted or unsubstituted with a substituent selected from the group consisting of $C_1$-$C_6$ alkyl, $C_1$-$C_6$ haloalkyl, $C_1$-$C_6$ alkoxy-$C_1$-$C_6$ alkyl, $C_7$-$C_{16}$ aralkyl, $C_1$-$C_6$ alkenyl, $C_1$-$C_6$ alkylcarbonyl, $C_1$-$C_6$ alkoxycarbonyl, $C_3$-$C_{10}$ cycloalkyl, a 4- to 10-membered saturated heterocyclic group, and a 5- to 10-membered unsaturated heterocyclic group), or a 4- to 10-membered unsaturated heterocyclic group, the substituent of $A_2$ is hydrogen, halogen, cyano, nitro, amino, hydroxy, carboxy, substituted or unsubstituted $C_1$-$C_6$ alkyl, substituted or unsubstituted $C_2$-$C_6$ alkenyl, or substituted or unsubstituted $C_2$-$C_6$ alkynyl, the substituent of $A_3$ is hydrogen, halogen, cyano, nitro, amino, hydroxy, carboxy, substituted or unsubstituted $C_1$-$C_6$ alkyl, substituted or unsubstituted $C_2$-$C_6$ alkenyl, or substituted or unsubstituted $C_2$-$C_6$ alkynyl, $L_2$ represents a 4- to 6-membered saturated heterocyclic group containing 1 or 2 Ns, $R_3$ represents hydrogen or methyl, $R_4$ wherein n=1 or 2 represents halogen, cyano, hydroxy, $C_1$-$C_2$ alkyl, methoxy, $C_1$-$C_2$ haloalkyl, dimethylaminomethyl, or ethoxymethyl, $L_3$ represents —C(═O), and $R_5$ represents substituted or unsubstituted $C_2$-$C_6$ alkenyl or substituted or unsubstituted $C_2$-$C_6$ alkynyl.

The compound or a salt thereof of the disclosure is still more preferably a compound represented by Formula (I) or a salt thereof, wherein X represents CH, $R_1$ represents halogen, substituted or unsubstituted $C_1$-$C_3$ alkyl, 1-propenyl, 2-methyl-2-propenyl, or 1-methylcyclopropyl, $L_1$ represents —NH—C($R_a$)$_2$—, and one of the two Ras is a hydrogen atom while the other is a hydrogen atom, a deuterium atom, or methyl, wherein Ras are identical or different, and each represents a hydrogen atom, a deuterium atom, or methyl, ring A is a combination of $A_1$, $A_2$, and $A_3$, wherein $A_1$ is substituted nitrogen, $A_2$ is nitrogen, and $A_3$ is substituted carbon; or $A_1$ is substituted nitrogen, $A_2$ is sulfur, and $A_3$ is substituted carbon;

the substituent of $A_1$ is hydrogen, halogen, $C_1$-$C_6$ alkyl (substituted or unsubstituted with a substituent selected from the group consisting of halogen, $C_1$-$C_3$ alkoxy, $C_1$-$C_3$ alkylamino, $C_3$-$C_6$ cycloalkyl, substituted or unsubstituted phenyl, and a substituted or unsubstituted 4- to 5-membered saturated heterocyclic group), $C_3$-$C_6$ cycloalkyl (substituted or unsubstituted with a substituent selected from the group consisting of hydroxy, $C_1$-$C_3$ alkyl, and $C_1$-$C_3$ alkoxy), $C_3$-$C_6$ cycloalkenyl, a 4- to 5-membered saturated heterocyclic group (substituted or unsubstituted with a substituent selected from the group consisting of $C_1$-$C_3$ alkyl, $C_1$-$C_3$ haloalkyl, $C_1$-$C_3$ alkoxy-$C_1$-$C_3$ alkyl, benzyl, $C_1$-$C_3$ alkenyl, $C_1$-$C_3$ alkylcarbonyl, $C_1$-$C_3$ alkoxycarbonyl, $C_3$-$C_6$ cycloalkyl, a 4- to 6-membered saturated heterocyclic group, and a 5- to 6-membered unsaturated heterocyclic group), or a 4- to 6-membered unsaturated heterocyclic group, the substituent of $A_2$ is hydrogen, halogen, cyano, hydroxy, or $C_1$-$C_6$ alkyl, the substituent of $A_3$ is hydrogen, halogen, cyano, nitro, amino, hydroxy, carboxy, $C_1$-$C_6$ alkyl, $C_1$-$C_6$ haloalkyl, $C_2$-$C_6$ alkenyl, or $C_2$-$C_6$ alkynyl, $L_2$ represents

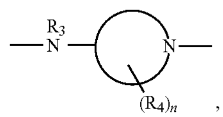

wherein

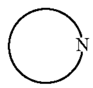

represents a 4- to 5-membered saturated heterocyclic group containing one N, $R_3$ represents hydrogen, and $R_4$ wherein n=1 or 2 represents halogen, methyl, ethyl, or methoxy, and $L_3$ represents —C(=O), and $R_5$ represents a substituted or unsubstituted $C_2$-$C_6$ alkenyl.

The compound or a salt thereof of the disclosure is still more preferably a compound represented by Formula (I) or a salt thereof, wherein X represents CH, $R_1$ represents chlorine or substituted $C_1$-$C_3$ alkyl, $L_1$ represents —NH—$CH_2$—, wherein Ras are identical or different, and each represents a hydrogen atom, a deuterium atom, or methyl, ring A is a combination of $A_1$, $A_2$, and $A_3$, wherein $A_1$ is substituted nitrogen, $A_2$ is nitrogen, and $A_3$ is substituted carbon; or $A_1$ is nitrogen, $A_2$ is sulfur, and $A_3$ is substituted carbon, the substituent of $A_1$ is hydrogen, chlorine, methyl, ethyl, n-propyl, isopropyl, n-butyl, isobutyl, tert-butyl, cyclopropyl, cyclopentyl, 3,4-dihydroxycyclopentyl, cyclohexyl, 2-isopropyl-5-methylcyclohexyl, 4-methoxycyclohexyl, cyclopentenyl, N-tert-butoxycarbonylaziridinyl, N-isopropylaziridinyl, N-methylcarbonylaziridinyl, N-methylpyrrolidinyl, N-ethylpyrrolidinyl, N-isopropylpyrrolidinyl, N-(2,2-difluoroethyl)pyrrolidinyl, N-methylcarbonylpyrrolidinyl, N-methoxyethylpyrrolidinyl, N-benzylpyrrolidinyl, N-oxetanepyrrolidinyl, N-methylpiperidinyl, N-(2,2-difluoroethyl)piperidinyl, tetrahydrofuranyl, tetrahydropyranyl, or pyridinyl, the substituent of $A_2$ is hydrogen, methyl, or ethyl, the substituent of $A_3$ is hydrogen, halogen, cyano, $C_1$-$C_6$ alkyl, or $C_1$-$C_6$ haloalkyl, $L_2$ represents

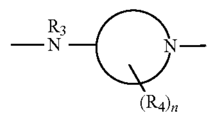

wherein

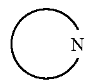

represents a 4- to 5-membered saturated heterocyclic group containing one N, $R_3$ represents hydrogen, $R_4$ represents halogen, methyl, ethyl, or methoxy, and n represents 0, 1, or 2, and $L_3$ represents —C(=O), and $R_5$ represents a substituted or unsubstituted $C_1$-$C_3$ alkenyl.

The compound or a salt thereof of the disclosure is most preferably a compound represented by Formula (I) or a salt thereof, wherein X represents CH, $R_1$ represents chlorine or tert-butyl, $L_1$ represents —NH—$CH_2$—, wherein Ras are identical or different, and each represents a hydrogen atom, a deuterium atom, or methyl, ring A is a combination of $A_1$, $A_2$, and $A_3$, wherein $A_1$ is substituted nitrogen, $A_2$ is nitrogen, and $A_3$ is substituted carbon, the substituent of $A_1$ is hydrogen, chlorine, methyl, ethyl, n-propyl, isopropyl, n-butyl, isobutyl, tert-butyl, cyclopentyl, 4-methoxycyclohexyl, N-isopropylaziridinyl, N-methylpyrrolidinyl, N-isopropylpyrrolidinyl, N-(2,2-difluoroethyl)pyrrolidinyl, N-(2,2-difluoroethyl)piperidinyl, tetrahydrofuranyl, or tetrahydropyranyl, the substituent of $A_2$ is nitrogen that is substituted with hydrogen, the substituent of $A_3$ is methyl, ethyl, difluoromethyl, chlorine, fluorine, or cyano, $L_2$ represents

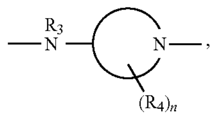

wherein

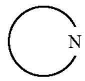

represents a 4- to 5-membered saturated heterocyclic group containing one N, $R_3$ represents hydrogen, $R_4$ represents halogen, methyl, ethyl, or methoxy, and n represents 0, 1, or 2, and $L_3$ represents —C(═O), and $R_5$ represents vinyl.

The compound or a salt thereof of the disclosure is preferably a compound represented by Formula (I) or a salt thereof, wherein X represents nitrogen or CH, $R_1$ represents hydrogen, halogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ cycloalkyl, $C_6$-$C_{10}$ aromatic hydrocarbon, a 4- to 10-membered saturated heterocyclic group, or a 5- to 10-membered unsaturated heterocyclic group, $L_1$ represents —NH—C($R_a$)$_2$—, wherein Ras are identical or different, and each represents a hydrogen atom, a deuterium atom, or $C_1$-$C_6$ alkyl, ring A represents a substituted or unsubstituted, 5-membered unsaturated heterocyclic group containing 1 to 2 heteroatoms selected from nitrogen, sulfur, and oxygen, $L_2$ is

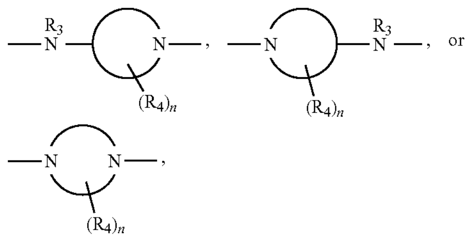

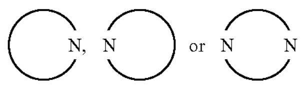

represent a 4- to 8-membered saturated heterocyclic group that contains at least one nitrogen atom and contains 0 to 2 heteroatoms selected from sulfur atom and oxygen, $R_3$ represents hydrogen or $C_1$-$C_6$ alkyl, and $R_4$ represents halogen, cyano, nitro, amino, hydroxy, carboxy, $C_1$-$C_6$ alkyl, $C_2$-$C_6$ alkenyl, $C_2$-$C_6$ alkynyl, $C_3$-$C_6$ cycloalkyl, $C_1$-$C_6$ alkoxy, $C_1$-$C_6$ haloalkyl, $C_1$-$C_6$ alkylamino-$C_1$-$C_6$ alkyl, $C_1$-$C_6$ alkoxy-$C_1$-$C_6$ alkyl, or $C_1$-$C_6$ hydroxyalkyl, and $L_3$ represents —C(═O)— or —S(═O)$_2$—, and $R_5$ represents substituted or unsubstituted $C_2$-$C_6$ alkenyl or substituted or unsubstituted $C_2$-$C_6$ alkynyl.

The compound or a salt thereof of the disclosure is more preferably a compound represented by Formula (I) or a salt thereof, wherein X represents N or CH, $R_1$ represents halogen, substituted or unsubstituted $C_1$-$C_6$ alkyl, substituted or unsubstituted $C_2$-$C_6$ alkenyl, or substituted or unsubstituted $C_3$-$C_{10}$ cycloalkyl, $L_1$ represents —NH—C($R_a$)$_2$—, wherein Ras are identical or different, and each represents a hydrogen atom, a deuterium atom, or methyl, ring A represents a substituted or unsubstituted group in which two hydrogen atoms are removed from imidazole, pyrazole, thiazole, or oxazol, $L_2$ represents a 4- to 6-membered saturated heterocyclic group containing 1 or 2 Ns, $R_3$ represents hydrogen or methyl, $R_4$ wherein n=1 or 2 represents halogen, cyano, hydroxy, $C_1$-$C_2$ alkyl, methoxy, $C_1$-$C_2$ haloalkyl, dimethylaminomethyl, or ethoxymethyl, $L_3$ represents —C(═O), and $R_5$ represents substituted or unsubstituted $C_2$-$C_6$ alkenyl or substituted or unsubstituted $C_2$-$C_6$ alkynyl.

The compound or a salt thereof of the disclosure is more preferably a compound represented by Formula (I) or a salt thereof, wherein X represents CH, $R_1$ represents halogen, substituted or unsubstituted $C_1$-$C_3$ alkyl, 1-propenyl, 2-methyl 2-propenyl, or 1-methylcyclopropyl, $L_1$ represents —NH—C($R_a$)$_2$—, wherein Ras are identical or different, and each represents a hydrogen atom, a deuterium atoms, or methyl, ring A represents a substituted or unsubstituted group in which two hydrogen atoms are removed from imidazole, pyrazole, or thiazole, $L_2$ represents

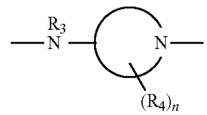

wherein

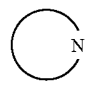

represents a 4- to 5-membered saturated heterocyclic group containing one N, $R_3$ represents hydrogen, $R_4$ wherein n=1 or 2 represents halogen, methyl, ethyl, or methoxy, $L_3$ represents —C(═O), and $R_5$ represents a substituted or unsubstituted $C_2$-$C_6$ alkenyl.

The compound or a salt thereof of the disclosure is still more preferably a compound represented by Formula (I) or a salt thereof, wherein X represents CH, $R_1$ represents chlorine or substituted $C_1$-$C_3$ alkyl, $L_1$ represents —NH—C$(R_a)_2$—, wherein Ras are identical or different, and each represents a hydrogen atom, a deuterium atom, or methyl, ring A represents a substituted or unsubstituted group in which two hydrogen atoms are removed from imidazole, pyrazole, or thiazole, $L_2$ represents

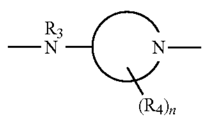

wherein

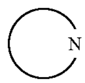

represents a 4- to 5-membered saturated heterocyclic group containing one N, $R_3$ represents hydrogen, $R_4$ represents halogen, methyl, ethyl, or methoxy, n represents 0, 1, or 2, $L_3$ represents —C(═O), and $R_5$ represents a substituted or unsubstituted $C_1$-$C_3$ alkenyl.

The compound or a salt thereof of the disclosure is most preferably a compound represented by Formula (I) or a salt thereof, wherein X represents CH, $R_1$ represents chlorine or tert-butyl, $L_1$ represents —NH—C$(R_a)_2$—, wherein Ras are identical or different, and each represents a hydrogen atom, a deuterium atom, or methyl, ring A represents a substituted or unsubstituted group in which two hydrogen atoms are removed from imidazole, $L_2$ represents

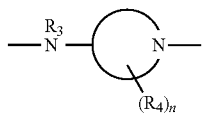

wherein

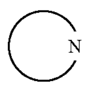

represents a 4- to 5-membered saturated heterocyclic group containing one N, $R_3$ represents hydrogen, $R_4$ represents halogen, methyl, ethyl, or methoxy, n is 0, 1, or 2, $L_3$ represents —C(═O), and $R_5$ represents vinyl.

Examples of specific compounds of the disclosure include, but are not limited to, the compounds produced in the Examples below.

Examples of preferable compounds of the disclosure include the following:

N-(1-acryloylazetidin-3-yl)-2-(((5-(tert-butyl)-6-chloro-1H-indazol-3-yl)amino)methyl)-1,4-dimethyl-1H-imidazole-5-carboxamide;

N-(1-acryloylazetidin-3-yl)-2-(((5-(tert-butyl)-6-chloro-1H-indazol-3-yl)amino)methyl)-1-isopropyl-4-methyl-1H-imidazole-5-carboxamide;

N-(1-acryloylazetidin-3-yl)-2-(((5-(tert-butyl)-6-chloro-1H-indazol-3-yl)amino)methyl)-4-chloro-1-methyl-1H-imidazole-5-carboxamide;

N-(1-acryloylazetidin-3-yl)-2-(((5-(tert-butyl)-6-chloro-1H-indazol-3-yl)amino)methyl)-4-(difluoromethyl)-1-isopropyl-1H-imidazole-5-carboxamide;

N-(1-acryloylazetidin-3-yl)-2-(((5-(tert-butyl)-6-chloro-1H-indazol-3-yl)amino)methyl)-4-chloro-1-isopropyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-1,4-dimethyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-4-fluoro-1-methyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-4-chloro-1-methyl-1H-imidazole-5-carboxamide;

N-((3R,4R)-1-acryloyl-4-methylpyrrolidin-3-yl)-2-(((5-(tert-butyl)-6-chloro-1H-indazol-3-yl)amino)methyl)-4-chloro-1-methyl-1H-imidazole-5-carboxamide;

N-(1-acryloylazetidin-3-yl)-2-(((5-(tert-butyl)-6-chloro-1H-indazol-3-yl)amino)methyl)-4-(difluoromethyl)-1-(1-isopropylpyrrolidin-3-yl)-1H-imidazole-5-carboxamide;

(S)-N-(1-acryloylazetidin-3-yl)-2-(((5-(tert-butyl)-6-chloro-1H-indazol-3-yl)amino)methyl)-4-chloro-1-(tetrahydrofuran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(tetrahydro-2H-pyran-4-yl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(tetrahydrofuran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(1-methylpiperidin-4-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(tetrahydro-2H-pyran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-cyclopentyl-1H-imidazole-5-carboxamide;

tert-butyl 3-(5-((1-acryloylazetidin-3-yl)carbamoyl)-2-(((5-(tert-butyl)-6-chloro-1H-indazol-3-yl)amino)methyl)-4-chloro-1H-imidazol-1-yl)azetidine-1-carboxylate;

N-(1-acryloylazetidin-3-yl)-2-(((5-(tert-butyl)-6-chloro-1H-indazol-3-yl)amino)methyl)-4-chloro-1-(1-isopropylazetidin-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(4-methoxycyclohexyl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-(2,2-difluoroethyl)pyrrolidin-3-yl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-isopropylpyrrolidin-3-yl)-1H-imidazole-5-carboxamide;

(S)-N-(1-acryloylazetidin-3-yl)-2-(((5-(tert-butyl)-6-chloro-1H-indazol-3-yl)amino)methyl)-4-chloro-1-(1-(2,2-difluoroethyl)pyrrolidin-3-yl)-1H-imidazole-5-carboxamide;

(R)-N-(1-acryloylazetidin-3-yl)-1-(1-allylpyrrolidin-3-yl)-2-(((5-(tert-butyl)-6-chloro-1H-indazol-3-yl)amino)methyl)-4-chloro-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-(pyridin-2-yl)pyrrolidin-3-yl)-1H-imidazole-5-carboxamide; and N-(1-acryloylazetidin-3-yl)-2-(((5-(tert-butyl)-6-chloro-1H-indazol-3-yl)amino)methyl)-4-chloro-1-((3R,5R)-1-(2,2-difluoroethyl)-5-methylpyrrolidin-3-yl)-1H-imidazole-5-carboxamide.

Method of Producing Compound of Formula (I)

The compound represented by Formula (I) of the disclosure can be produced, for example, through the following production methods or the methods described in the Examples. However, the production methods for the compound represented by Formula (I) of the disclosure are not limited to these reaction examples. The reaction product obtained in each step can be subjected to the subsequent step after, or without, isolation and purification by known separation and purification methods, such as concentration, vacuum concentration, crystallization, solvent extraction, reprecipitation, and chromatography.

To the reaction product obtained in each step and the starting material, a protecting group that can be easily converted to the functional group can be introduced if it is effective in each step, or so as to change the order of the steps. Examples of the protecting group used here may be the protecting groups etc. used in the method disclosed in the document "Protective Groups in Organic Synthesis," 5th edition, Greene and Wuts, John Wiley & Sons Inc., 2014. The protecting group may be appropriately selected according to the reaction conditions of each step. After introducing a protecting group and performing reaction, the protecting group is optionally removed to thus yield a desired compound.

General Production Method 1

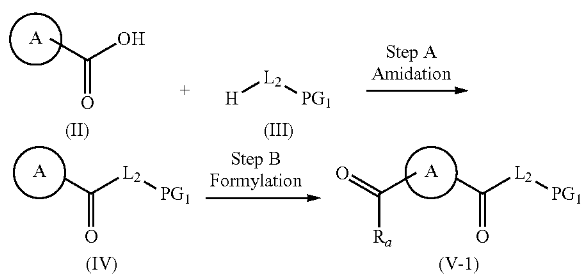

(II) (III) (IV) (V-1)

wherein $PG_1$ represents hydrogen, an amine protecting group, or $-L_3-R_5$, $R_a$ represents a hydrogen atom or a deuterium atom, and A, $L_2$, $L_3$, and $R_5$ are as defined above.

Compound (II) and compound (III) are subjected to amidation reaction of step A to obtain compound (IV), and compound (IV) is subjected to formylation reaction of step B to produce a compound represented by Formula (V-1).

In step A, compound (III) is used in an amount of 0.5 to 10 mol, and preferably 1 to 3 mol, per mol of compound (II). Step A is performed in a solvent inactive to the reaction by adding a condensation agent suitable as an amidation reagent, and stirring under cooling or heating, preferably at −20° C. to 80° C., usually for 1 minute to 1 week. Examples of the condensation agent used here include, but are not particularly limited to, N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris-(dimethylamino)phosphonium hexafluorophosphate, benzotriazol-1-yloxy-tris-pyrrolidinophosphonium hexafluorophosphate, bromotris-(dimethylamino)phosphonium hexafluorophosphate, diphenylphosphoryl azide, 1,1'-carbonyldiimidazole, and the like. Examples of the solvent used here include, but are not particularly limited to, toluene, methylene chloride, chloroform, THF, 1,4-dioxane, DMF, N,N-dimethylacetamide, NMP, 2-propanol, ethanol, methanol, water, and the like, and mixtures thereof. It is also possible to add additives, such as 1-hydroxybenzotriazole and a base, if necessary. Examples of the base include, but are not particularly limited to, inorganic bases, such as sodium carbonate, potassium carbonate, and sodium hydrogen carbonate; organic bases, such as triethylamine, N,N-diisopropylethylamine, and 4-dimethylaminopyridine; and mixtures thereof.

In step B, known reaction methods for introducing a formyl group may be used. For example, the following methods are applicable:

(1) a method in which a strong base is used to generate anions, followed by reaction with a formylating agent;

(2) a method in which formaldehyde etc. are used to perform hydroxymethylation, followed by conversion into a formyl group using an oxidizing agent, such as manganese dioxide;

(3) a method in which after halogenation, a halogen-metal conversion is performed using an alkyl metal reagent, followed by reaction with a formylating agent;

(4) a reaction in which after halogenation, a vinyl group is introduced by performing coupling reaction, and the vinyl group is oxidatively cleaved. The reaction can be performed, for example, in an appropriate solvent by adding a strong base, stirring the mixture at −78° C. to room temperature usually for 10 minutes to 12 hours to generate anions, and adding a formylating agent. The reaction solvent that can be used here is not particularly limited as long as it does not affect the reaction. Examples include ethers, such as tetrahydrofuran and 1,4-dioxane; hydrocarbons, such as benzene and toluene; and mixtures thereof. Examples of the strong base used here include, but are not particularly limited to, butyl lithium, lithium diisopropylamide, lithium 2,2,6,6-tetramethylpiperidide, 2,2,6,6-tetramethylpiperidinyl magnesium chloride-lithium chloride complex, and the like. Examples of the formylating reagent used here include, but are not particularly limited to, N,N-dimethylformamide, ethyl formate, and the like.

General Production Method 2

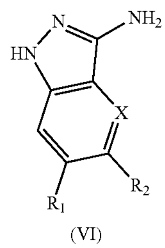

+

(VI)

-continued

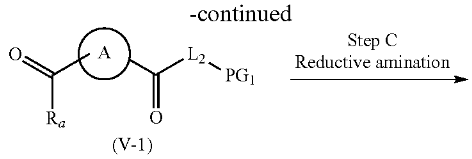

(V-1)

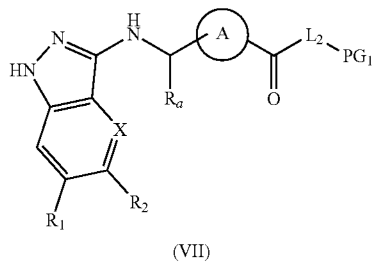

(VII)

wherein A, $L_2$, $PG_1$, $R_a$, $R_1$, $R_2$, and X are as defined above.

Compound (V-1) and compound (VI) are subjected to reductive amination reaction of step C to thus produce a compound represented by Formula (VII).

Step C is performed using compound (VI) in an amount of 0.5 to 10 mol, and preferably 0.5 to 2 mol, per mol of compound (V-1). Step C is performed in a solvent suitable for the reaction by using a reducing agent and optionally adding additives. Preferable examples of the solvent include toluene, methylene chloride, chloroform, ethyl acetate, THF, 1,4-dioxane, N,N-dimethylformamide, N-methylpyrrolidone, DMSO, methanol, ethanol, 2-propanol, tert-butylalcohol, and the like, and mixed solvents thereof. Examples of the reducing agent used here include, but are not particularly limited to, a metal hydride complex, etc. (e.g., 0.1 mol or a large excessive molar amount of sodium borohydride, sodium cyanoborohydride, or triacetoxyborohydride.) Example of the additives used here include, but are not particularly limited to, acids, bases, and inorganic salts or organic salts. Examples include 0.01 mol or a large excessive molar amount of trifluoroacetic acid, formic acid, acetic acid, hydrochloric acid, potassium carbonate, sodium hydroxide, lithium hydroxide, sodium sulfate, magnesium sulfate, titanium isopropoxide, and the like.

General Production Method 3

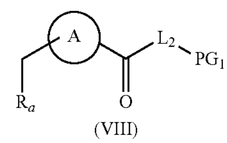

(VIII)

Step D
Halogenation

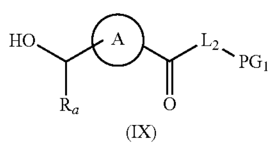

(IX)

Step E
Introduction of
leaving group

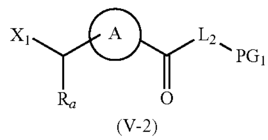

(V-2)

wherein $X_1$ represents a leaving group, and A, $L_2$, $PG_1$, and $R_a$ are as defined above.

Compound (VIII) is halogenated in step D, or a leaving group is introduced into compound (IX) in step E, to thus produce a compound represented by Formula (V-2).

Step D can be performed by using N-chlorosuccinimide, N-bromosuccinimide, N-iodosuccinimide, bromine, iodine, etc. The solvent is not particularly limited as long as it does not affect the reaction. For example, the reaction may be performed in an appropriate solvent that does not affect the invention, such as acetonitrile, ethyl acetate, THF, methanol, ethanol, DMF, N,N-dimethylacetamide, NMP, chloroform, and carbon tetrachloride. The reaction temperature is usually 0° C. to 100° C., and preferably room temperature to reflux temperature. The reaction time is usually 10 minutes to 3 days, and preferably 30 minutes to 24 hours.

The method for introducing a leaving group in step E is not particularly limited. For example, sulfonyl esterification may be performed under the conditions such that methanesulfonyl chloride, toluenesulfonyl chloride, etc. and an appropriate base are used. For example, halogenation may be performed under such conditions that a halogenating agent, such as carbon tetrachloride, carbon tetrabromide, or iodine, and triphenylphosphine etc. are used, or that a sulfonyl ester mentioned above is treated with lithium halide etc. and converted into a halogen group.

General Production Method 4

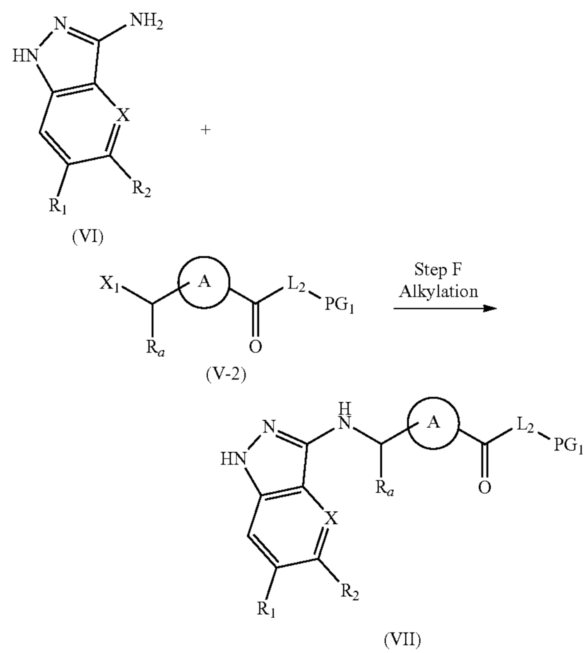

(VI) (V-2) (VII)

wherein A, $L_2$, $PG_1$, $R_a$, $R_1$, $R_2$, X, and $X_1$ are as defined above.

Compound (V-2) and compound (VI) are subjected to alkylation reaction of step F to thus produce a compound represented by Formula (VII).

In step F, compound (VI) is used in an amount of 0.5 to 10 mol, and preferably 1 to 3 mol, per mol of compound (V-2). Preferable examples of solvents include toluene, methylene chloride, chloroform, THF, 1,4-dioxane, DMF, N-methylpyrrolidone, DMSO, methanol, ethanol, isopropanol, tert-butyl alcohol, and the like, and mixed solvents thereof. Examples of the base used here include inorganic bases, such as sodium hydrogen carbonate, potassium carbonate, cesium carbonate, and potassium hydroxide; and organic bases, such as potassium-tert-butyrate, sodium-tert-butyrate, sodium methoxide, sodium ethoxide, lithium hexamethyldisilazide, sodium hexamethyldisilazide, potassium hexamethyldisilazide, triethylamine, and N,N-diisopropylethylamine.

General Production Method 5

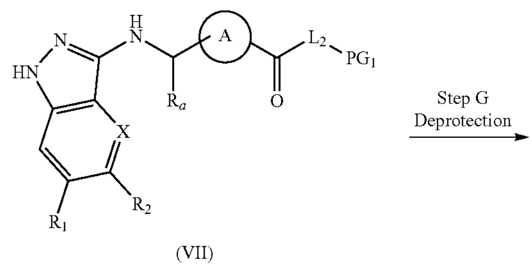

(VII)

-continued

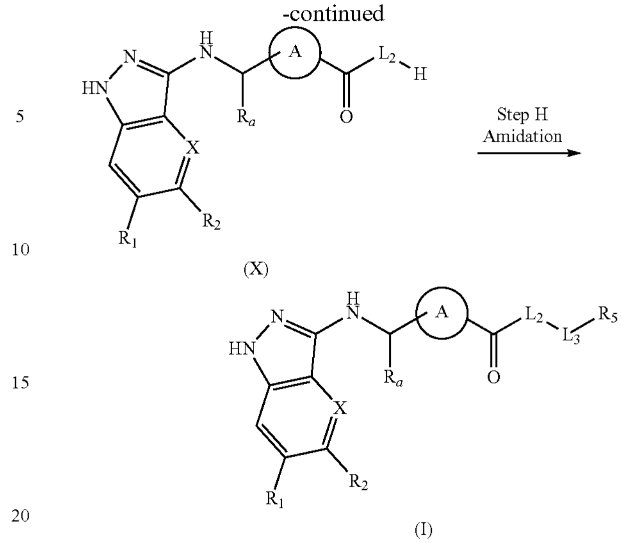

(X) (I)

wherein A, $L_2$, $L_3$, $PG_1$, $R_a$, $R_1$, $R_2$, $R_5$, and X are as defined above.

When $PG_1$ is an amine protecting group, compound (VII) is subjected to deprotection reaction of step G to obtain compound (X), and the obtained compound is subjected to amidation reaction of step H to thus produce a compound represented by Formula (I). When $PG_1$ is hydrogen, compound (VII) is subjected to amidation reaction of step H to produce a compound represented by Formula (I). The amine protecting group used here is not particularly limited. Examples include tert-butoxycarbonyl, benzyloxycarbonyl, and the like.

In step G, the following methods can be used, although it varies depending on the type of the protecting group: solvolysis using an acid or a base according to the method disclosed in the document "Protective Groups in Organic Synthesis," fifth edition, Green and Wuts, John Wiley & Sons Inc., 2014, or a similar method, i.e., a method comprising reacting with 0.01 mol or a large excessive molar amount of an acid, preferably trifluoroacetic acid, formic acid, or hydrochloric acid, or an equimolar to large excessive molar amount of a base, preferably sodium hydroxide, lithium hydroxide, etc.; chemical reduction using a metal hydride complex etc.; or catalytic reduction using a palladium-carbon catalyst, Raney nickel catalyst, etc.

In step H, an acylating reagent is used in an amount of 0.5 to 10 mol, per mol of compound (X) obtained in the previous step, and the mixture is stirred in a solvent inactive to the reaction in the presence of a base under cooling to heating, preferably at −20° C. to 80° C., usually for 3 days from the completion of the addition of the acylating reagent. Examples of the solvent used here include, but are not particularly limited to, ethers, such as THF, diethyl ether, 1,4-dioxane, and 1,2-dimethoxyethane; halogenated hydrocarbons, such as dichloromethane, 1,2-dichloroethane, and chloroform; alcohols, such as methanol and ethanol; aromatic hydrocarbons, such as benzene, toluene, and xylene; DMF, DMSO, ethyl acetate, acetonitrile, water, and mixtures thereof. Examples of the base used here include inorganic bases, such as sodium carbonate, potassium carbonate, and sodium hydrogen carbonate; organic bases, such as triethylamine and N,N-diisopropylethylamine; and mixtures thereof. Examples of the acylating reagent include acid halide compounds and acid anhydrides. Examples of acid halide compounds include acryloyl chloride and the like. It is also possible to use a method in which carboxylic acid is used in an amount of 0.5 to 10 mol, and preferably 1 to 3 mol, per mol of compound (X), and the mixture is stirred in a solvent inactive to the reaction in the presence of a condensation agent, and optionally in the presence of a base, under cooling to heating, preferably at −20° C. to 80° C., usually for 1 minute to 3 days. Examples of the condensation agent include, but are not particularly limited to, N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris-(dimethylamino)phosphonium hexafluorophosphate, benzotriazol-1-yloxy-tris-pyrrolidinophosphonium hexafluorophosphate, bromotris-(dimethylamino)phosphonium hexafluorophosphate, diphenylphosphoric acid azide, 1,1'-carbonyldiimidazole, and the like. Examples of the solvent used here include, but are not particularly limited to, toluene, methylene chloride, chloroform, THF, 1,4-dioxane, DMF, N,N-dimethylacetamide, NMP, 2-propanol, ethanol, methanol, water, and mixtures thereof. If necessary, additives, such as a base, can also be added. Examples of bases include, but are not particularly limited to, inorganic bases, such as sodium carbonate, potassium carbonate, and sodium hydrogen carbonate; organic bases, such as triethylamine, N,N-diisopropylethylamine, and 4-dimethylaminopyridine; and mixtures thereof.

General Production Method 6

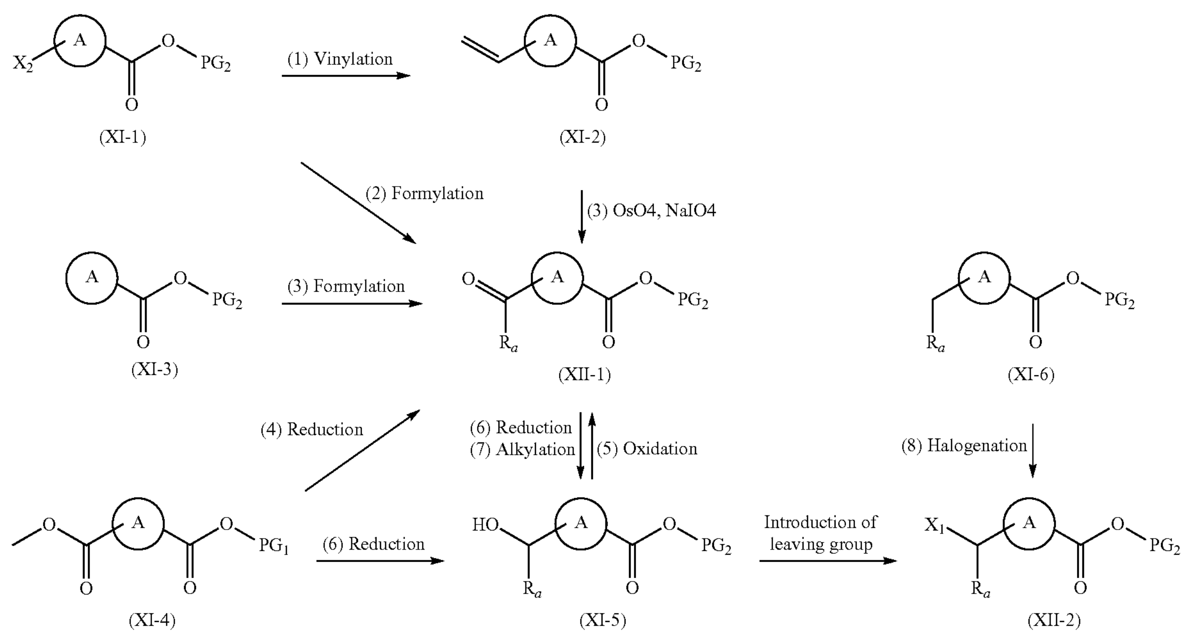

wherein $X_2$ represents halogen, $PG_2$ represents an ester protecting group, and A, $R_a$, and $X_1$ are as defined above.

A known reaction is used to produce a compound represented by Formula (XII-1) or Formula (XII-2) from a commercially available aromatic ring ester or from an aromatic ring ester that can be synthesized by known methods.

For example, the compound represented by Formula (XII-1) is obtained by the following methods:

(1) a method in which the halogen atom in Formula (XI-1) is subjected to cross-coupling reaction etc., for vinylation to obtain a compound represented by Formula (XI-2), and via the compound represented by Formula (XI-2), the double bond is cleaved by using both a catalytic amount of osmium tetroxide and a large excess of sodium periodate;

(2) a method in which the halogen atom in Formula (XI-1) is subjected to halogen-metal exchange using a Grignard reagent, butyl lithium, etc., followed by reaction with a formylating agent or an acylating agent;

(3) a method in which a strong base is used with a compound represented by Formula (XI-3) to generate anions, followed by reaction with a formylating agent or an acylating agent; or a method in which formylation is performed by Vilsmeier reaction;

(4) a method in which the ester in Formula (XI-4) is reduced;

(5) a method in which the hydroxymethyl group in Formula (XI-5) is oxidized; and the like. Further, the compound represented by Formula (XII-2) is obtained by the following methods:

(6) a method in which the ester of Formula (XI-4), or the ketone, aldehyde, etc. of Formula (XII-1) is reacted with a reducing agent, or (7) an alkyl metal reagent, such as a Grignard reagent, is used with the ketone, aldehyde, etc. of Formula (XII-1), to obtain the compound represented by Formula (XI-5), and via the compound represented by Formula (XI-5), introduction of a methanesulfonyl group is performed, or substitution with halogen atom is performed;

(8) a method in which methylene in Formula (XI-6) is halogenated with N-bromosuccinimide etc.; or the like.

General Production Method 7

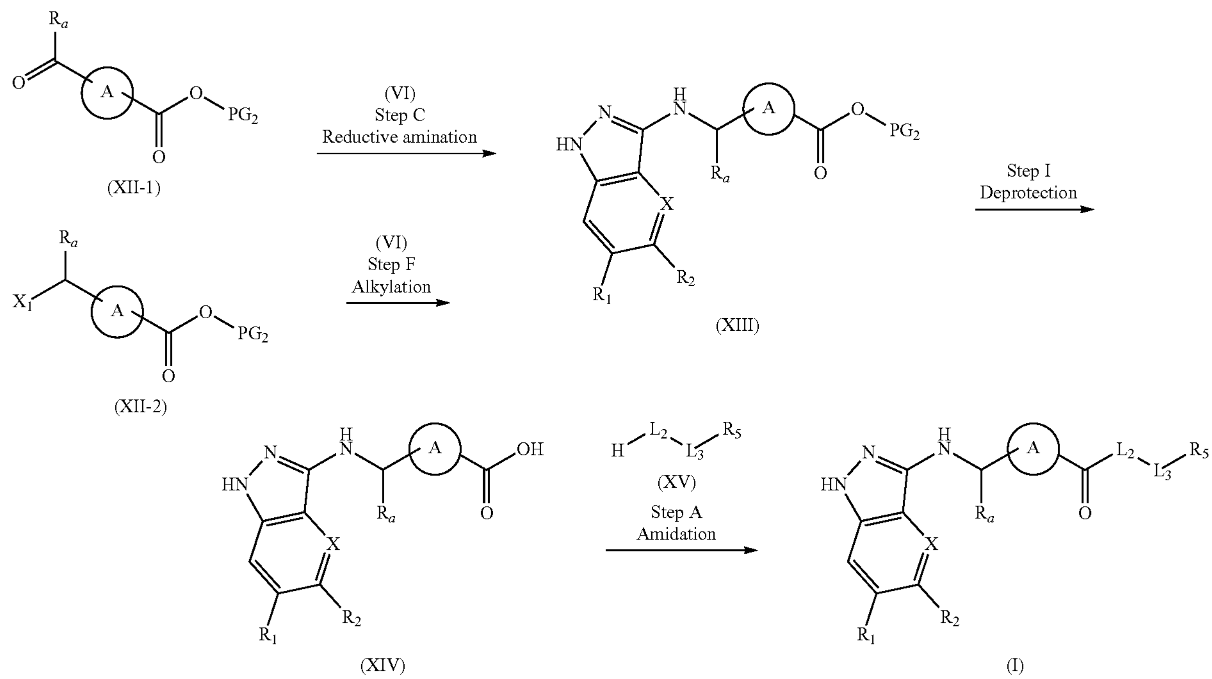

(XII-1)

(XII-2)

(XIII)

(XIV)

(I)

wherein A, $L_2$, $L_3$, $PG_2$, $R_a$, $R_1$, $R_2$, $R_5$, X, and $X_1$ are as defined above.

Compound (XII-1) is subjected to step C mentioned above, or compound (XII-2) is subjected to step F mentioned above to obtain compound (XIII), and then deprotection of step I is performed, and the resulting product is subjected to step A mentioned above to thus produce a compound represented by Formula (I).

In step I, reaction of carboxylic acid ester hydrolysis well known in the field of organic chemistry is applicable. This hydrolysis reaction is not particularly limited, and may be performed, for example, by solvolysis using an acid or a base, i.e., a method comprising reacting with 0.01 mol or a large excessive molar amount of an acid, preferably trifluoroacetic acid, formic acid, hydrochloric acid, or the like, or an equimolar to large excessive molar amount of a base, preferably sodium hydroxide, lithium hydroxide, or the like.

General Production Method 8

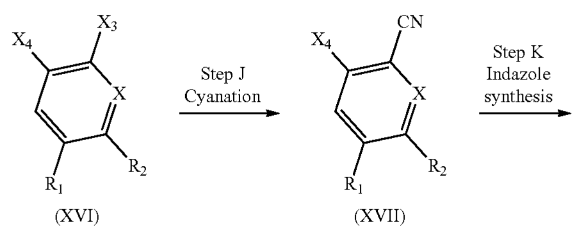

(XVI)

(XVII)

-continued

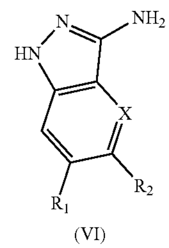

(VI)

In the scheme above, $X_3$ represents a substituent that is convertible into cyano or the like. Examples include halogen, amine, ester, amide, carboxylic acid, and the like. $X_4$ represents a substituent that is convertible into hydrazine or the like. Examples include a protector etc. for halogen, amine, and hydrazine. $R_1$, $R_2$, and X are as defined above.

Compound (XVI), which can be synthesized by known methods, is subjected to cyanation reaction of step J to obtain compound (XVII), and then the obtained compound is subjected to indazole cyclization reaction of step K to thus produce a compound represented by Formula (VI).

In step J, a method well known in the field of organic chemistry is used to introduce a cyano group. For example, when $X_3$ in Formula (XVI) is an amino group, a diazotization agent is used at −20° C. to room temperature in an appropriate solvent to prepare a diazonium salt, and the obtained diazonium salt is added at −20 to 100° C. to a solution of a base and a cyanating agent. Examples of usable reaction solvents include acidic solvents, such as hydrochloric acid, acetic acid, trifluoroacetic acid, and sulfuric acid; alcohols, such as methanol and ethanol; water; and mixtures thereof. Examples of the diazotization agent include sodium nitrite, isopentyl nitrite, and the like. Examples of the base include sodium hydroxide, sodium carbonate, sodium hydrogen carbonate, and the like. Examples of the cyanating agent include sodium cyanide, potassium cyanide, copper cyanide, zinc cyanide, and the like, and mixtures thereof. Further, for example, when $X_3$ in Formula (XVI) is halogen, the reaction may also be performed at room temperature to 200° C. using a cyanating agent in an appropriate solvent. In the reaction, a palladium catalyst etc. may be added as additives. Examples of the cyanating agent include sodium cyanide, potassium cyanide, copper cyanide, zinc cyanide, and the like, and mixtures thereof. The usable reaction solvent is not limited as long as it does not affect the reaction. Examples include ethers, such as THF and 1,4-dioxane; alcohols, such as methanol and ethanol; amides, such as DMF, N,N-dimethylacetamide, and N-methyl-2-pyrrolidone; hydrocarbons, such as toluene; acetonitrile; dimethylsulfoxide; water; and mixed solvents thereof.

In step K, for example, when $X_4$ in Formula (XVII) is halogen, hydrazine etc. may be reacted at 20 to 200° C. in an appropriate solvent. It is also possible to subject hydrazine etc. protected by a protecting group to cross-coupling reaction using a palladium catalyst, and thereafter remove the hydrazine protecting group. The reaction solvent usable here is not limited as long as it does not affect the reaction. Examples include ethers, such as THE and 1,4-dioxane; alcohols, such as methanol and ethanol; amides, such as DMF, N,N-dimethylacetamide, and N-methyl-2-pyrrolidone; hydrocarbons, such as toluene; acetonitrile; dimethylsulfoxide; water; and mixed solvents thereof. Examples of the palladium catalyst usable here include palladium acetate, palladium chloride, tetrakis(triphenylphosphine)palladium, dichlorobis(triphenylphosphine)palladium, dichloro(1,1'-bis(diphenylphosphino)ferrocene)palladium, dichlorobisacetonitrile palladium, and tris(dibenzylideneacetone) dipalladium (0). It is appropriate to use the palladium catalyst in an amount of 0.001 to 1 mol, per mol of the compound represented by formula (XVII). As a ligand of palladium, it is possible to use 1-1'-bis(diphenylphosphino)ferrocene, 4,5-bis(diphenylphosphino)-9,9'-dimethylxanthene, 2-dicyclohexylphosphino-2',4',6'-triisopropylbiphenyl, 2-dicyclohexylphosphino-2',6'-dimethoxybiphenyl, 2-di-tert-butylphosphino-3,4,5,6-tetramethyl-2',4',6'-triisopropylbiphenyl, and the like, if necessary. In this step, it is possible to use a base. Examples include organic bases, such as potassium-tert-butyrate, sodium-tert-butyrate, sodium methoxide, sodium ethoxide, lithium hexamethyldisilazide, sodium hexamethyldisilazide, and potassium hexamethyldisilazide; and inorganic bases, such as sodium carbonate, potassium carbonate, cesium carbonate, sodium hydroxide, sodium phosphate, and potassium phosphate. Although it varies depending on the reaction temperature, the reaction may be performed for 30 minutes to 24 hours. The hydrazine protecting group may be removed, for example, by the method disclosed in the document "Protective Groups in Organic Synthesis," fifth edition, Greene and Wuts, John Wiley & Sons Inc., 2014, or a similar method, although it varies depending on the type of the protecting group used.

When the compound of the disclosure has isomers such as optical isomers, stereoisomers, rotational isomers, and tautomers, any of the isomers and mixtures thereof are included within the scope of the compound of the disclosure unless otherwise specified. For example, when the compound of the disclosure has optical isomers, racemic mixtures and the optical isomers separated from a racemic mixture are also included within the scope of the compound of the disclosure unless otherwise specified.

The compound or a salt thereof of the disclosure may be in the form of amorphous or crystals. Single crystals and polymorphic mixtures are included within the scope of the compound or a salt thereof of the disclosure. Such crystals can be produced by crystallization according to a crystallization method known in the art. The compound or a salt thereof of the disclosure may be a solvate (e.g., a hydrate) or a non-solvate. Any of such forms are included within the scope of the compound or a salt thereof of the disclosure. Compounds labeled with an isotope (e.g., $^{2}H$, $^{3}H$, $^{13}C$, $^{14}C$, $^{35}S$, $^{125}I$) are also included within the scope of the compound or a salt thereof of the disclosure.

The salts of the compound of the disclosure refer to any pharmaceutically acceptable salts; examples include base addition salts and acid addition salts.

The compound or a salt thereof of the disclosure also encompass prodrugs thereof. A prodrug refers to a compound that can be converted to the compound or a salt thereof of the disclosure through a reaction with an enzyme, gastric acid, or the like under physiological conditions in vivo, i.e., a compound that can be converted to the compound or a salt thereof of the disclosure by enzymatic oxidation, reduction, hydrolysis, or the like; or a compound that can be converted to the compound or a salt thereof of the disclosure by hydrolysis or the like with gastric acid or the like. Further, the prodrug may be compounds that can be converted to the compound or a salt thereof of the disclosure under physiological conditions, such as those described in Iyakuhin no Kaihatsu, "Development of Pharmaceuticals," Vol. 7, Molecular Design, published in 1990 by Hirokawa Shoten Co., pp. 163-198.

When the compound or a salt thereof of the disclosure is used as a pharmaceutical preparation, a pharmaceutical carrier can be added, if required, thereby forming a suitable dosage form according to prevention and treatment purposes. Examples of the dosage form include oral preparations, injections, suppositories, ointments, inhalations, patches, and the like. Such dosage forms can be formed by methods conventionally known to a person skilled in the art.

As the pharmaceutical acceptable carrier, various conventional organic or inorganic carrier materials used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, pharmaceutical preparation additives, such as antiseptics, antioxidants, colorants, sweeteners, and stabilizers, may also be used, if required.

Oral solid preparations are prepared as follows. After an excipient is added optionally with a binder, disintegrant, lubricant, colorant, taste-masking or flavoring agent, etc. to the compound or a salt thereof of the disclosure, the resulting mixture is formulated into tablets, coated tablets, granules, powders, capsules, or the like by ordinary methods.

When an injection agent is prepared, a pH regulator, a buffer, a stabilizer, an isotonizing agent, a local anesthetic, and the like may be added to the compound of the disclosure; and the mixture may be formulated into a subcutaneous, intramuscular, or intravenous injection according to an ordinary method.

The amount of the compound of the disclosure to be incorporated in each of such dosage unit forms depends on the condition of the patient to whom the compound is administered, the dosage form, etc. In general, for an oral agent, the amount of the compound is preferably about 0.05 to 1000 mg per dosage unit form. For an injection, the amount of the compound is preferably about 0.01 to 500 mg per dosage unit form, and for a suppository, the amount of the compound is preferably about 1 to 1000 mg per dosage unit form.

Further, the daily dose of the medicine in such a dosage form varies depending on the condition, body weight, age, sex, etc. of the patient, and cannot be unconditionally determined. For example, the daily dose for an adult (body weight: 50 kg) of the compound of the disclosure may be generally about 0.05 to 5000 mg, and preferably 0.1 to 1000 mg.

The compound or a salt thereof of the disclosure has excellent KRAS inhibitory activity against KRAS G12C mutation-positive cancer cells, and also has excellent selectivity for wild-type KRAS normal cells. Therefore, the compound or a salt thereof of the disclosure is useful as an antitumor agent against KRAS G12C mutation-positive cancer cells, and has the advantage of fewer side effects.

Due to its excellent KRAS G12C inhibitory activity, the compound or a salt thereof of the disclosure inhibits the KRAS function and is useful as a pharmaceutical preparation for preventing and/or treating KRAS-associated signaling-related diseases.

According to one embodiment of the disclosure, an administration of the compound or a salt thereof of the disclosure, in combination with an effective amount of one or more other antitumor agents, can prevent and/or treat KRAS-associated signaling-related diseases (in particular, tumors).

In terms of RAS-associated signaling in the KRAS-associated signaling-related diseases, KRAS is involved in various signaling transduction as RAS-associated signaling; KRAS mainly activates, but is not limited to, RAF, PI3K, RAL-GEF, and the like. Examples of the diseases include diseases for which the incidence can be reduced, and for which symptoms can be remitted, relieved, and/or completely cured by deleting, suppressing, and/or inhibiting their functions. Examples of such diseases include, but are not limited to, cancer, autoimmune disease, macroglobulinemia, and the like.

Cancer, in accordance with the present disclosure includes, but is not limited to, glandular tumors, carcinoid tumors, undifferentiated carcinomas, angiosarcoma, adenocarcinoma, gastrointestinal cancers (e.g., colorectal cancers ("CRC") including colon cancer and rectal cancer, biliary cancers including gall bladder cancer and bile duct cancer, anal cancer, esophageal cancer, gastric (stomach) cancer, gastrointestinal carcinoid tumor(s), gastrointestinal stromal tumor(s) ("GIST"), liver cancer, duodenal cancer and small intestine cancer), lung cancers (e.g., non-small cell lung cancer ("NSCLC"), squamous-cell lung carcinoma, large-cell lung carcinoma, small cell lung carcinoma, mesothelioma and other lung cancers such as bronchial tumors and pleuropulmonary blastoma), urological cancers (e.g., kidney (renal) cancer, transitional cell cancer ("TCC") of kidney, TCC of the renal pelvis and ureter ("PDQ"), bladder cancer, urethral cancer and prostate cancer), head and neck cancers (e.g., eye cancer, retinoblastoma, intraocular melanoma, hypopharyngeal cancer, pharyngeal cancer, laryngeal cancer, laryngeal papillomatosis, metastatic squamous neck cancer with occult primary, oral (mouth) cancer, lip cancer, throat cancer, oropharyngeal cancer, esthesioneuroblastoma, nasal cavity and paranasal sinus cancer, nasopharyngeal cancer, and salivary gland cancer), endocrine cancers (e.g., thyroid cancer, parathyroid cancer, multiple endocrine neoplasia syndromes, thymoma and thymic carcinoma, pancreatic cancers including pancreatic ductal adenocarcinoma ("PDAC"), pancreatic neuroendocrine tumors and islet cell tumors), breast cancers (extrahepatic ductal carcinoma in situ ("DCIS"), lobular carcinoma in situ ("LCIS"), triple negative breast cancer, and inflammatory breast cancer), male and female reproductive cancers (e.g., cervical cancer, ovarian cancer, endometrial cancer, uterine sarcoma, uterine cancer, vaginal cancer, vulvar cancer, gestational trophoblastic tumor ("GTD"), extragonadal germ cell tumor, extracranial germ cell tumor, germ cell tumor, testicular cancer and penile cancer), brain and nervous system cancers (e.g., astrocytomas, brain stem glioma, brain tumor, craniopharyngioma, central nervous system ("CNS") cancer, chordomas, ependymoma, embryonal tumors, neuroblastoma, paraganglioma and atypical teratoid), skin cancers (e.g., basal cell carcinoma ("BCC"), squamous cell skin carcinoma ("SCC"), Merkel cell carcinoma and melanoma), tissue and bone cancers (e.g., soft-tissue sarcoma, rhabdomyosarcoma, fibrous histiocytoma of bone, Ewing sarcoma, malignant fibrous histiocytoma of bone ("MFH"), osteosarcoma and chondrosarcoma), cardiovascular cancers (e.g., heart cancer and cardiac tumors), appendix cancers, childhood and adolescent cancers (e.g., adrenocortical carcinoma childhood, midline tract carcinoma, hepatocellular carcinoma ("HCC"), hepatoblastoma and Wilms' tumor) and viral-induced cancers (e.g., HHV-8 related cancers (Kaposi sarcoma) and HIV/AIDS related cancers). In some embodiments, the cancer is lung cancer, pancreatic cancer, or colorectal cancer.

Cancer, in accordance with the present disclosure also includes, but is not limited to, hematological and plasma cell malignancies (e.g., cancers that affect blood, bone marrow and/or lymph nodes) such as multiple myeloma, leukemias and lymphomas, myelodysplastic syndromes and myeloproliferative disorders. Leukemias include, without limitation, acute lymphoblastic leukemia ("ALL"), acute myelogenous (myeloid) leukemia ("AML"), chronic lymphocytic leukemia ("CLL"), chronic myelogenous leukemia ("CML"), acute monocytic leukemia ("AMoL"), hairy cell leukemia, and/or other leukemias. Lymphomas include, without limitation, Hodgkin's lymphoma and non-Hodgkin's lymphoma ("NHL"). In some embodiments, NHL is B-cell lymphomas and/or T-cell lymphomas. In some embodiments, NHL includes, without limitation, diffuse large B-cell lymphoma ("DLBCL"), small lymphocytic lymphoma ("SLL"), chronic lymphocytic leukemia ("CLL"), mantle cell lymphoma ("MCL"), Burkitt's lymphoma, cutaneous T-cell lymphoma including mycosis fungoides and Sezary syndrome, AIDS-related lymphoma, follicular lymphoma, lymphoplasmacytic lymphoma (Waldenstrom's macroglobulinemia ("WM")), primary central nervous system (CNS) lymphoma and/or other lymphomas.

Combination Therapy

This disclosure provides a method of treating cancer comprising administering: (a) a compound of Formula (I) or a pharmaceutically acceptable salt thereof; and (b) an additional anti-cancer agent, to a subject in need of such treatment. A single compound of Formula (I) or more than one compound of Formula (I) may be used in combination with a single additional anti-cancer agent or more than one additional anti-cancer agents.

This disclosure also provides a method of treating cancer comprising administering: (a) a compound of Formula (I) or a pharmaceutically acceptable salt thereof; and (b) radiation therapy, to a subject in need of such treatment. A single compound of Formula (I) or more than one compound of Formula (I) may be used in combination with the radiation therapy.

As used herein, an "additional anti-cancer agent" can be any pharmaceutically active agent (or pharmaceutically acceptable salt thereof) that is active in the body against cancer and that is different from the compound of Formula (I). The additional anti-cancer agents include prodrugs, free-acid, free-base and pharmaceutically acceptable salts of the additional anti-cancer agents. Generally any suitable additional anti-cancer agent, including chemotherapeutic agents or therapeutic antibodies, may be used in any combination with a compound of Formula (I) in a single dosage formulation (e.g., a fixed dose drug combination) or in one or more separate dosage formulations which allow for concurrent or sequential administration of the pharmaceutically active agents (co-administration of the separate active agents) to subjects. In certain embodiments, a compound of Formula (I) and an additional active agent are administered a few minutes apart, or a few hours apart, or a few days apart. In addition, the compounds of Formula (I) can be administered in combination with radiation therapy, hormone therapy, surgery or immunotherapy. In one embodiment, one or more additional anti-cancer agents are included in a pharmaceutical preparation as described above.

As used herein, "treat" or "treatment" includes treating for the purpose of curing or ameliorating cancer, or for the purpose of suppressing the progression, occurrence, or recurrence of the cancer or alleviating symptoms.

As used herein, a "therapeutically effective amount" refers to an amount of a pharmaceutically active agent, e.g., a KRAS G12C inhibitor, that will elicit the biological or medical response of a tissue, system, animal or human that is being sought by a researcher, veterinarian, medical doctor or other clinician. In an embodiment, "therapeutically effective amount" means an amount of a pharmaceutically active agent that alleviates at least one clinical symptom in a human patient. In an embodiment, the "therapeutically effective amount" may also be a "prophylactically effective amount", i.e., an amount sufficient to prevent a cancer. In an embodiment, the "therapeutically effective amount" coincides with a daily dosage.

As used herein, "subject" includes animals, both mammals and nonmammals, and preferably humans. In an embodiment, the subject is a human patient and may be a human who has been diagnosed to need a treatment for a clinical symptom or medical state associated with cancer as disclosed herein. In an embodiment, the subject has been identified or diagnosed as having a cancer having a KRAS G12C mutation. In an embodiment, the subject has a tumor that is positive for a KRAS G12C mutation. The subject may be in need of, or desire, treatment for an existing cancer or may be in need of or desire prophylactic treatment to prevent or reduce the risk of occurrence of cancer. As used herein, a subject "in need" of treatment of an existing cancer or of prophylactic treatment encompasses both a determination of need by a medical professional as well as the desire of a patient for such treatment.

In an embodiment, the compound of Formula (I) used in combination with the additional anti-cancer agent and/or radiation therapy is selected from the group consisting of:

N-(1-acryloylazetidin-3-yl)-2-(((5-(tert-butyl)-6-chloro-1H-indazol-3-yl)amino)methyl)-1,4-dimethyl-1H-imidazole-5-carboxamide;

N-(1-acryloylazetidin-3-yl)-2-(((5-(tert-butyl)-6-chloro-1H-indazol-3-yl)amino)methyl)-1-isopropyl-4-methyl-1H-imidazole-5-carboxamide;

N-(1-acryloylazetidin-3-yl)-2-(((5-(tert-butyl)-6-chloro-1H-indazol-3-yl)amino)methyl)-4-chloro-1-methyl-1H-imidazole-5-carboxamide;

N-(1-acryloylazetidin-3-yl)-2-(((5-(tert-butyl)-6-chloro-1H-indazol-3-yl)amino)methyl)-4-(difluoromethyl)-1-isopropyl-1H-imidazole-5-carboxamide;

N-(1-acryloylazetidin-3-yl)-2-(((5-(tert-butyl)-6-chloro-1H-indazol-3-yl)amino)methyl)-4-chloro-1-isopropyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-1,4-dimethyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-4-fluoro-1-methyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-4-chloro-1-methyl-1H-imidazole-5-carboxamide;

N-((3R,4R)-1-acryloyl-4-methylpyrrolidin-3-yl)-2-(((5-(tert-butyl)-6-chloro-1H-indazol-3-yl)amino)methyl)-4-chloro-1-methyl-1H-imidazole-5-carboxamide;

N-(1-acryloylazetidin-3-yl)-2-(((5-(tert-butyl)-6-chloro-1H-indazol-3-yl)amino)methyl)-4-(difluoromethyl)-1-(1-isopropylpyrrolidin-3-yl)-1H-imidazole-5-carboxamide;

(S)-N-(1-acryloylazetidin-3-yl)-2-(((5-(tert-butyl)-6-chloro-1H-indazol-3-yl)amino)methyl)-4-chloro-1-(tetrahydrofuran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(tetrahydro-2H-pyran-4-yl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(tetrahydrofuran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(1-methylpiperidin-4-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(tetrahydro-2H-pyran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-cyclopentyl-1H-imidazole-5-carboxamide;

tert-butyl 3-(5-((1-acryloylazetidin-3-yl)carbamoyl)-2-(((5-(tert-butyl)-6-chloro-1H-indazol-3-yl)amino)methyl)-4-chloro-1H-imidazol-1-yl)azetidine-1-carboxylate;

N-(1-acryloylazetidin-3-yl)-2-(((5-(tert-butyl)-6-chloro-1H-indazol-3-yl)amino)methyl)-4-chloro-1-(1-isopropylazetidin-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(4-methoxycyclohexyl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-(2,2-difluoroethyl)pyrrolidin-3-yl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-isopropylpyrrolidin-3-yl)-1H-imidazole-5-carboxamide;

(S)-N-(1-acryloylazetidin-3-yl)-2-(((5-(tert-butyl)-6-chloro-1H-indazol-3-yl)amino)methyl)-4-chloro-1-(1-(2,2-difluoroethyl)pyrrolidin-3-yl)-1H-imidazole-5-carboxamide;

(R)-N-(1-acryloylazetidin-3-yl)-1-(1-allylpyrrolidin-3-yl)-2-(((5-(tert-butyl)-6-chloro-1H-indazol-3-yl)amino)methyl)-4-chloro-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-(pyridin-2-yl)pyrrolidin-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-((3R,5R)-1-(2,2-difluoroethyl)-5-methylpyrrolidin-3-yl)-1H-imidazole-5-carboxamide; and the pharmaceutically acceptable salts thereof.

In certain embodiments, the compound of Formula (I) is administered in a therapeutically effective amount. In an embodiment, the additional anti-cancer agent is administered in a therapeutically effective amount. In an embodiment, the compound of Formula (I) and the additional anti-cancer agent are administered simultaneously. In an embodiment, the compound of Formula (I) and the additional anti-cancer agent are administered separately. In an embodiment, the compound of Formula (I) and the additional anti-cancer agent are administered via a single pharmaceutical preparation further comprising at least one pharmaceutical acceptable carrier. In an embodiment, the compound of Formula (I) and the additional anti-cancer agent are administered sequentially. In an embodiment, the compound of Formula (I) is administered before the additional anti-cancer agent. In an embodiment, the compound of Formula (I) is administered after the additional anti-cancer agent. In an embodiment, the compound of Formula (I) and the radiation therapy are administered simultaneously. In an embodiment, the compound of Formula (I) and the radiation therapy are administered sequentially. In an embodiment, the compound of Formula (I) is administered before the radiation therapy. In an embodiment, the compound of Formula (I) is administered after the radiation therapy.

In an embodiment, the subject is a human. In an embodiment, the cancer to be treated is selected from the group consisting of glandular tumors, carcinoid tumors, undifferentiated carcinomas, angiosarcoma, adenocarcinoma, gastrointestinal cancers, lung cancers, urological cancers, head and neck cancers, endocrine cancers, breast cancers, male and female reproductive cancers, brain and nervous system cancers, skin cancers, tissue and bone cancers, cardiovascular cancers, appendix cancers, childhood and adolescent cancers, viral-induced cancers, multiple myeloma, leukemias, lymphomas, myelodysplastic syndromes and myeloproliferative disorders.

Examples of additional anti-cancer agents include chemotherapeutic agents (e.g., cytotoxic agents), immunotherapeutic agents, hormonal and anti-hormonal agents, targeted therapy agents, and anti-angiogenesis agents. Many anti-cancer agents can be classified within one or more of these groups. While certain anti-cancer agents have been categorized within a specific group(s) or subgroup(s) herein, many of these agents can also be listed within one or more other group(s) or subgroup(s), as would be presently understood in the art. It is to be understood that the classification herein of a particular agent into a particular group is not intended to be limiting. Many anti-cancer agents are presently known in the art and can be used in combination with the compounds of the present disclosure.

Further, an agent can be an agonist, antagonist, allosteric modulator, toxin or, more generally, may act to inhibit or stimulate its target (e.g., receptor or enzyme activation or inhibition). For example, suitable for use are one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

In an embodiment, the additional anti-cancer agent is a chemotherapeutic agent, an immunotherapeutic agent, a hormonal agent, an anti-hormonal agent, a targeted therapy agent, or an anti-angiogenesis agent (or angiogenesis inhibitor). In an embodiment, the additional anti-cancer agent is selected from the group consisting of a chemotherapeutic agent, a mitotic inhibitor, a plant alkaloid, an alkylating agent, an anti-metabolite, a platinum analog, an enzyme, a topoisomerase inhibitor, a retinoid, an aziridine, an antibiotic, a hormonal agent, an anti-hormonal agent, an anti-estrogen, an anti-androgen, an anti-adrenal, an androgen, a targeted therapy agent, an immunotherapeutic agent, a biological response modifier, a cytokine inhibitor, a tumor vaccine, a monoclonal antibody, an immune checkpoint inhibitor, an anti-PD-1 agent, an anti-PD-$L_1$ agent, a colony-stimulating factor, an immunomodulator, an immunomodulatory imide (IMiD), an anti-CTLA4 agent, an anti-LAG1 agent, an anti-OX40 agent, a GITR agonist, a CAR-T cell, a BiTE, a signal transduction inhibitor, a growth factor inhibitor, a tyrosine kinase inhibitor, an EGFR inhibitor, a histone deacetylase (HDAC) inhibitor, a proteasome inhibitor, a cell-cycle inhibitor, an anti-angiogenesis agent, a matrix-metalloproteinase (MMP) inhibitor, a hepatocyte growth factor inhibitor, a TOR inhibitor, a KDR inhibitor, a VEGF inhibitor, a HIF-1$\alpha$ inhibitor a HIF-2$\alpha$ inhibitor, a fibroblast growth factor (FGF) inhibitor, a RAF inhibitor, a MEK inhibitor, an ERK inhibitor, a PI3K inhibitor, an AKT inhibitor, an MCL-1 inhibitor, a BCL-2 inhibitor, an SHP2 inhibitor, a HER-2 inhibitor, a BRAF-inhibitor, a gene expression modulator, an autophagy inhibitor, an apoptosis inducer, an antiproliferative agent, and a glycolysis inhibitor. In an embodiment, the additional anti-cancer agent is an MEK inhibitor, an ERK inhibitor, an AKT inhibitor, or an SHP2 inhibitor.

In one embodiment, the additional anti-cancer agent(s) is a chemotherapeutic agent. Non-limiting examples of chemotherapeutic agents include mitotic inhibitors and plant alkaloids, alkylating agents, anti-metabolites, platinum analogs, enzymes, topoisomerase inhibitors, retinoids, aziridines, and antibiotics.

Non-limiting examples of mitotic inhibitors and plant alkaloids include taxanes such as cabazitaxel, docetaxel, larotaxel, ortataxel, paclitaxel, and tesetaxel; demecolcine; epothilone; eribulin; etoposide (VP-16); etoposide phosphate; navelbine; noscapine; teniposide; thaliblastine; vinblastine; vincristine; vindesine; vinflunine; and vinorelbine.

Non-limiting examples of alkylating agents include nitrogen mustards such as chlorambucil, chlornaphazine, cholophosphamide, cytophosphane, estramustine, ifosfamide, mannomustine, mechlorethamine, mechlorethamine oxide hydrochloride, melphalan, novembichin, phenesterine, prednimustine, tris(2-chloroethyl)amine, trofosfamide, and uracil mustard; alkyl sulfonates such as busulfan, improsulfan, and piposulfan; nitrosoureas such as carmustine, chlorozotocin, fotemustine, lomustine, nimustine, ranimustine, streptozotocin, and TA-07; ethylenimines and methylamelamines such as altretamine, thiotepa, triethylenemelamine, triethylenethiophosphaoramide, trietylenephosphoramide, and trimethylolomelamine; ambamustine; bendamustine; dacarbazine; etoglucid; irofulven; mafosfamide; mitobronitol; mitolactol; pipobroman; procarbazine; temozolomide; treosulfan; and triaziquone.

Non-limiting examples of anti-metabolites include folic acid analogues such as aminopterin, denopterin, edatrexate, methotrexate, pteropterin, raltitrexed, and trimetrexate; purine analogs such as 6-mercaptopurine, 6-thioguanine, fludarabine, forodesine, thiamiprine, and thioguanine;

pyrimidine analogs such as 5-fluorouracil (5-FU), 6-azauridine, ancitabine, azacytidine, capecitabine, carmofur, cytarabine, decitabine, dideoxyuridine, doxifiuridine, doxifluridine, enocitabine, floxuridine, galocitabine, gemcitabine, and sapacitabine; 3-aminopyridine-2-carboxaldehyde thiosemicarbazone; broxuridine; cladribine; cyclophosphamide; cytarabine; emitefur; hydroxyurea; mercaptopurine; nelarabine; pemetrexed; pentostatin; tegafur; and troxacitabine.

Non-limiting examples of platinum analogs include carboplatin, cisplatin, dicycloplatin, heptaplatin, lobaplatin, nedaplatin, oxaliplatin, satraplatin, and triplatin tetranitrate.

Non-limiting examples of enzymes include asparaginase and pegaspargase.

Non-limiting examples of topoisomerase inhibitors include acridine carboxamide, amonafide, amsacrine, belotecan, elliptinium acetate, exatecan, indolocarbazole, irinotecan, lurtotecan, mitoxantrone, razoxane, rubitecan, SN-38, sobuzoxane, and topotecan.

Non-limiting examples of retinoids include alitretinoin, bexarotene, fenretinide, isotretinoin, liarozole, RII retinamide, and tretinoin.

Non-limiting examples of aziridines include benzodopa, carboquone, meturedopa, and uredopa.

Non-limiting examples of antibiotics include intercalating antibiotics; anthracenediones; anthracycline antibiotics such as aclarubicin, amrubicin, daunomycin, daunorubicin, doxorubicin, epirubicin, idarubicin, menogaril, nogalamycin, pirarubicin, and valrubicin; 6-diazo-5-oxo-L-norleucine; aclacinomysins; actinomycin; authramycin; azaserine; bleomycins; cactinomycin; calicheamicin; carabicin; carminomycin; carzinophilin; chromomycins; dactinomycin; detorubicin; esorubicin; esperamicins; geldanamycin; marcellomycin; mitomycins; mitomycin C; mycophenolic acid; olivomycins; novantrone; peplomycin; porfiromycin; potfiromycin; puromycin; quelamycin; rebeccamycin; rodorubicin; streptonigrin; streptozocin; tanespimycin; tubercidin; ubenimex; zinostatin; zinostatin stimalamer; and zorubicin.

In one embodiment, the additional anti-cancer agent(s) is a hormonal and/or anti-hormonal agent (i.e., hormone therapy). Non-limiting examples of hormonal and anti-hormonal agents include anti-androgens such as abiraterone, apalutamide, bicalutamide, darolutamide, enzalutamide, flutamide, goserelin, leuprolide, and nilutamide; anti-estrogens such as 4-hydroxy tamoxifen, aromatase inhibiting 4(5)-imidazoles, EM-800, fosfestrol, fulvestrant, keoxifene, LY 117018, onapristone, raloxifene, tamoxifen, toremifene, and trioxifene; anti-adrenals such as aminoglutethimide, dexaminoglutethimide, mitotane, and trilostane; androgens such as calusterone, dromostanolone propionate, epitiostanol, mepitiostane, and testolactone; abarelix; anastrozole; cetrorelix; deslorelin; exemestane; fadrozole; finasteride; formestane; histrelin (RL 0903); human chorionic gonadotropin; lanreotide; LDI 200 (Milkhaus); letrozole; leuprorelin; mifepristone; nafarelin; nafoxidine; osaterone; prednisone; thyrotropin alfa; and triptorelin.

In one embodiment, the additional anti-cancer agent(s) is an immunotherapeutic agent (i.e., immunotherapy). Non-limiting examples of immunotherapeutic agents include biological response modifiers, cytokine inhibitors, tumor vaccines, monoclonal antibodies, immune checkpoint inhibitors, colony-stimulating factors, and immunomodulators.

Non-limiting examples of biological response modifiers, including cytokine inhibitors (cytokines) such as interferons and interleukins, include interferon alfa/interferon alpha such as interferon alfa-2, interferon alfa-2a, interferon alfa-2b, interferon alfa-nl, interferon alfa-n3, interferon alfacon-1, peginterferon alfa-2a, peginterferon alfa-2b, and leukocyte alpha interferon; interferon beta such as interferon beta-1a, and interferon beta-1b; interferon gamma such as natural interferon gamma-1a, and interferon gamma-1b; aldesleukin; interleukin-1 beta; interleukin-2; oprelvekin; sonermin; tasonermin; and virulizin.

Non-limiting examples of tumor vaccines include APC 8015, AVICINE, bladder cancer vaccine, cancer vaccine (Biomira), gastrin 17 immunogen, Maruyama vaccine, melanoma lysate vaccine, melanoma oncolysate vaccine (New York Medical College), melanoma vaccine (New York University), melanoma vaccine (Sloan Kettering Institute), TICE® BCG (Bacillus Calmette-Guerin), and viral melanoma cell lysates vaccine (Royal Newcastle Hospital).

Non-limiting examples of monoclonal antibodies include abagovomab, adecatumumab, aflibercept, alemtuzumab, blinatumomab, brentuximab vedotin, CA 125 MAb (Biomira), cancer MAb (Japan Pharmaceutical Development), daclizumab, daratumumab, denosumab, edrecolomab, gemtuzumab zogamicin, HER-2 and Fc MAb (Medarex), ibritumomab tiuxetan, idiotypic 105AD7 MAb (CRC Technology), idiotypic CEA MAb (Trilex), ipilimumab, lintuzumab, LYM-1-iodine 131 MAb (Techni clone), mitumomab, moxetumomab, ofatumumab, polymorphic epithelial mucin-yttrium 90 MAb (Antisoma), ranibizumab, rituximab, and trastuzumab.

Non-limiting examples of immune checkpoint inhibitors include anti-PD-1 agents or antibodies such as cemiplimab, nivolumab, and pembrolizumab; anti-PD-$L_1$ agents or antibodies such as atezolizumab, avelumab, and durvalumab; anti-CTLA-4 agents or antibodies such as ipilumumab; anti-LAG1 agents; and anti-OX40 agents.

Non-limiting examples of colony-stimulating factors include darbepoetin alfa, epoetin alfa, epoetin beta, filgrastim, granulocyte macrophage colony stimulating factor, lenograstim, leridistim, mirimostim, molgramostim, nartograstim, pegfilgrastim, and sargramostim.

Non-limiting examples of additional immunotherapeutic agents include BiTEs, CAR-T cells, GITR agonists, imiquimod, immunomodulatory imides (IMiDs), mismatched double stranded RNA (Ampligen), resiquimod, SRL 172, and thymalfasin.

In one embodiment, the additional anti-cancer agent(s) is a targeted therapy agent (i.e., targeted therapy). Targeted therapy agents include, for example, monoclonal antibodies and small molecule drugs. Non-limiting examples of targeted therapy agents include signal transduction inhibitors, growth factor inhibitors, tyrosine kinase inhibitors, EGFR inhibitors, histone deacetylase (HDAC) inhibitors, proteasome inhibitors, cell-cycle inhibitors, angiogenesis inhibitors, matrix-metalloproteinase (MMP) inhibitors, hepatocyte growth factor inhibitors, TOR inhibitors, KDR inhibitors, VEGF inhibitors, fibroblast growth factors (FGF) inhibitors, MEK inhibitors, ERK inhibitors, PI3K inhibitors, AKT inhibitors, MCL-1 inhibitors, BCL-2 inhibitors, SHP2 inhibitors, HER-2 inhibitors, BRAF-inhibitors, gene expression modulators, autophagy inhibitors, apoptosis inducers, antiproliferative agents, and glycolysis inhibitors.

Non-limiting examples of signal transduction inhibitors include tyrosine kinase inhibitors, multiple-kinase inhibitors, anlotinib, avapritinib, axitinib, dasatinib, dovitinib, imatinib, lenvatinib, lonidamine, nilotinib, nintedanib, pazopanib, pegvisomant, ponatinib, vandetanib, and EGFR inhibitory agents.

Non-limiting examples of EGFR inhibitory agents include small molecule antagonists of EGFR such as afatinib, brigatinib, erlotinib, gefitinib, lapatinib, and osimertinib; and antibody-based EGFR inhibitors, including any anti-EGFR antibody or antibody fragment that can partially or completely block EGFR activation by its natural ligand. Antibody-based EGFR inhibitory agents may include, for example, those described in Modjtahedi, H., et al., 1993, Br. J. Cancer 67:247-253; Teramoto, T., et al., 1996, Cancer 77:639-645; Goldstein et al, 1995, Clin. Cancer Res. 1: 1311-1318; Huang, S. M., et al., 1999, Cancer Res. 15:59(8): 1935-40; and Yang, X., et al., 1999, Cancer Res. 59: 1236-1243; monoclonal antibody Mab E7.6.3 (Yang, 1999 supra); Mab $C_{225}$ (ATCC Accession No. HB-8508), or an antibody or antibody fragment having the binding specificity thereof; specific antisense nucleotide or siRNA; afatinib, cetuximab; matuzumab; necitumumab; nimotuzumab; panitumumab; and zalutumumab.

Non-limiting examples of histone deacetylase (HDAC) inhibitors include belinostat, panobinostat, romidepsin, and vorinostat.

Non-limiting examples of proteasome inhibitors include bortezomib, carfilzomib, ixazomib, marizomib (salinosporamide a), and oprozomib.

Non-limiting examples of cell-cycle inhibitors, including CDK inhibitors, include abemaciclib, alvocidib, palbociclib, and ribociclib.

In one embodiment, the additional anti-cancer agent(s) is an anti-angiogenic agent (or angiogenesis inhibitor) including, but not limited to, matrix-metalloproteinase (MMP) inhibitors; VEGF inhibitors; EGFR inhibitors; TOR inhibitors such as everolimus and temsirolimus; PDGFR kinase inhibitory agents such as crenolanib; HIF-1α inhibitors such as PX 478; HIF-2α inhibitors such as belzutifan and the HIF-2α inhibitors described in WO 2015/035223; fibroblast growth factor (FGF) or FGFR inhibitory agents such as B-FGF and RG 13577; hepatocyte growth factor inhibitors; KDR inhibitors; anti-Ang1 and anti-Ang2 agents; anti-Tie2 kinase inhibitory agents; Tek antagonists (US 2003/0162712; U.S. Pat. No. 6,413,932); anti-TWEAK agents (U.S. Pat. No. 6,727,225); ADAM distintegrin domain to antagonize the binding of integrin to its ligands (US 2002/0042368); anti-eph receptor and/or anti-ephrin antibodies or antigen binding regions (U.S. Pat. Nos. 5,981,245; 5,728,813; 5,969,110; 6,596,852; 6,232,447; and 6,057,124); and anti-PDGF-BB antagonists as well as antibodies or antigen binding regions specifically binding to PDGF-BB ligands.

Non-limiting examples of matrix-metalloproteinase (MMP) inhibitors include MMP-2 (matrix-metalloproteinase 2) inhibitors, MMP-9 (matrix-metalloproteinase 9) inhibitors, prinomastat, RO 32-3555, and RS 13-0830. Examples of useful matrix metalloproteinase inhibitors are described, for example, in WO 96/33172, WO 96/27583, EP 1004578, WO 98/07697, WO 98/03516, WO 98/34918, WO 98/34915, WO 98/33768, WO 98/30566, EP 0606046, EP 0931788, WO 90/05719, WO 99/52910, WO 99/52889, WO 99/29667, WO 1999/007675, EP 1786785, EP 1181017, US 2009/0012085, U.S. Pat. Nos. 5,863,949, 5,861,510, and EP 0780386. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Non-limiting examples of VEGF and VEGFR inhibitory agents include bevacizumab, cediranib, CEP 7055, CP 547632, KRN 633, orantinib, pazopanib, pegaptanib, pegaptanib octasodium, semaxanib, sorafenib, sunitinib, VEGF antagonist (Borean, Denmark), and VEGF-TRAP™

The additional anti-cancer agent(s) may also be another anti-angiogenic agent including, but not limited to, 2-methoxyestradiol, AE 941, alemtuzumab, alpha-D148 Mab (Amgen, US), alphastatin, anecortave acetate, angiocidin, angiogenesis inhibitors, (SUGEN, US), angiostatin, anti-Vn Mab (Crucell, Netherlands), atiprimod, axitinib, AZD 9935, BAY RES 2690 (Bayer, Germany, BC 1 (Genoa Institute of Cancer Research, Italy), beloranib, benefin (Lane Labs, US), cabozantinib, CDP 791 (Celltech Group, UK), chondroitinase AC, cilengitide, combretastatin A4 prodrug, CP 564959 (OSI, US), CV247, CYC 381 (Harvard University, US), E 7820, EHT 0101, endostatin, enzastaurin hydrochloride, ER-68203-00 (IVAX, US), fibrinogen-E fragment, Flk-1 (ImClone Systems, US), forms of FLT 1 (VEGFR 1), FR-111142, GCS-100, GW 2286 (GlaxoSmithKline, UK), IL-8, ilomastat, IM-862, irsogladine, KM-2550 (Kyowa Hakko, Japan), lenalidomide, lenvatinib, MAb alpha5beta3 integrin, second generation (Applied Molecular Evolution, USA and Medlmmune, US), MAb VEGF (Xenova, UK), marimastat, maspin (Sosei, Japan), metastatin, motuporamine C, M-PGA, ombrabulin, OXI4503, PI 88, platelet factor 4, PPI 2458, ramucirumab, rBPI 21 and BPI-derived antiangiogenic (XOMA, US), regorafenib, SC-236, SD-7784 (Pfizer, US), SDX 103 (University of California at San Diego, US), SG 292 (Telios, US), SU-0879 (Pfizer, US), TAN-1120, TBC-1635, tesevatinib, tetrathiomolybdate, thalidomide, thrombospondin 1 inhibitor, Tie-2 ligands (Regeneron, US), tissue factor pathway inhibitors (EntreMed, US), tumor necrosis factor-alpha inhibitors, tumstatin, TZ 93, urokinase plasminogen activator inhibitors, vadimezan, vandetanib, vasostatin, vatalanib, VE-cadherin-2 antagonists, xanthorrhizol, XL 784 (Exelixis, US), ziv-aflibercept, and ZD 6126.

In embodiments, the additional anti-cancer agent(s) is an additional active agent that disrupts or inhibits RAS-RAF-ERK or PI3K-AKT-TOR signaling pathways or is a PD-1 and/or PD-$L_1$ antagonist. In embodiments, the additional anti-cancer agent(s) is a RAF inhibitor, EGFR inhibitor, MEK inhibitor, ERK inhibitor, PI3K inhibitor, AKT inhibitor, TOR inhibitor, MCL-1 inhibitor, BCL-2 inhibitor, SHP2 inhibitor, proteasome inhibitor, or immune therapy, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

Non-limiting examples of RAF inhibitors include dabrafenib, encorafenib, regorafenib, sorafenib, and vemurafenib.

Non-limiting examples of MEK inhibitors include binimetinib, CI-1040, cobimetinib, PD318088, PD325901, PD334581, PD98059, refametinib, selumetinib, and trametinib.

Non-limiting examples of ERK inhibitors include LY3214996, LTT462, MK-8353, SCH772984, ravoxertinib, ulixertinib, and an ERKi as described in WO 2017/068412.

Non-limiting examples of PI3K inhibitors include 17-hydroxywortmannin analogs (e.g., WO 06/044453); AEZS-136; alpelisib; AS-252424; buparlisib; CAL263; copanlisib; CUDC-907; dactolisib (WO 06/122806); demethoxyviridin; duvelisib; GNE-477; GSK1059615; IC87114; idelalisib; INK1117; LY294002; Palomid 529; paxalisib; perifosine; PI-103; PI-103 hydrochloride; pictilisib (e.g., WO 09/036,082; WO 09/055,730); PIK 90; PWT33597; SF1126; sonolisib; TGI00-115; TGX-221; XL147; XL-765; wortmannin; and ZSTK474.

Non-limiting examples of AKT inhibitors include Akt-1-1 (inhibits Aktl) (Barnett et al. (2005) Biochem. J., 385 (Pt. 2), 399-408); Akt-1-1,2 (Barnett et al. (2005) Biochem. J. 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and $L_1$ (2004) JNutr. 134(12 Suppl), 3493S-3498S); perifosine, Dasmahapatra et al. (2004) Clin. Cancer Res. 10(15), 5242-52, 2004); phosphatidylinositol ether lipid analogues (e.g., Gills and Dennis (2004) Expert. Opin. Investig. Drugs 13, 787-97); triciribine (Yang et al. (2004) Cancer Res. 64, 4394-9); imidazooxazone compounds including trans-3-amino-1-methyl-3-[4-(3-phenyl-5H-imidazo[1,2-c]pyrido [3,4-e][1,3]oxazin-2-yl)phenyl]-cyclobutanol hydrochloride (WO 2012/137870); afuresertib; capivasertib; MK2206; and patasertib.

Non-limiting examples of TOR inhibitors include deforolimus; ATP-competitive TORC1/TORC2 inhibitors, including PI-103, PP242, PP30, and Torin 1; TOR inhibitors in FKBP12 enhancer, rapamycins and derivatives thereof, including temsirolimus, everolimus, WO 9409010; rapalogs, e.g. as disclosed in WO 98/02441 and WO 01/14387, e.g. AP23573, AP23464, or AP23841; 40-(2-hydroxyethyl) rapamycin, 40-[3-hydroxy(hydroxymethyl)methylpropanoate]-rapamycin; 40-epi-(tetrazolyl)-rapamycin (also called ABT578); 32-deoxorapamycin; 16-pentynyloxy-32(S)-dihydrorapanycin, and other derivatives disclosed in WO 05/005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; and phosphorus-containing rapamycin derivatives (e.g., WO 05/016252).

Non-limiting examples of MCL-1 inhibitors include AMG-176, MIK665, and S63845.

Non-limiting examples of SHP2 inhibitors include SHP2 inhibitors described in WO 2019/167000 and WO 2020/022323.

Additional non-limiting examples of anti-cancer agents that are suitable for use include 2-ethylhydrazide, 2,2',2"-trichlorotriethylamine, ABVD, aceglatone, acemannan, aldophosphamide glycoside, alpharadin, amifostine, aminolevulinic acid, anagrelide, ANCER, ancestim, anti-CD22 immunotoxins, antitumorigenic herbs, apaziquone, arglabin, arsenic trioxide, azathioprine, BAM 002 (Novelos), bcl-2 (Genta), bestrabucil, biricodar, bisantrene, bromocriptine, brostallicin, bryostatin, buthionine sulfoximine, calyculin, cell-cycle nonspecific antineoplastic agents, celmoleukin, clodronate, clotrimazole, cytarabine ocfosfate, DA 3030 (Dong-A), defofamine, denileukin diftitox, dexrazoxane, diaziquone, dichloroacetic acid, dilazep, discodermolide, docosanol, doxercalciferol, edelfosine, eflornithine, EL532 (Elan), elfomithine, elsamitrucin, eniluracil, etanidazole, exisulind, ferruginol, folic acid replenisher such as frolinic acid, gacytosine, gallium nitrate, gimeracil/oteracil/tegafur combination (S-1), glycopine, histamine dihydrochloride, HIT diclofenac, HLA-B7 gene therapy (Vical), human fetal alpha fetoprotein, ibandronate, ibandronic acid, ICE chemotherapy regimen, imexon, iobenguane, IT-101 (CRLX101), laniquidar, LC 9018 (Yakult), leflunomide, lentinan, levamisole+fluorouracil, lovastatin, lucanthone, masoprocol, melarsoprol, metoclopramide, miltefosine, miproxifene, mitoguazone, mitozolomide, mopidamol, motexafin gadolinium, MX6 (Galderma), naloxone+pentazocine, nitracrine, nolatrexed, NSC 631570 octreotide (Ukrain), olaparib, P-30 protein, PAC-1, palifermin, pamidronate, pamidronic acid, pentosan polysulfate sodium, phenamet, picibanil, pixantrone, platinum, podophyllinic acid, porfimer sodium, PSK (Polysaccharide-K), rabbit antithymocyte polyclonal antibody, rasburiembodiment, retinoic acid, rhenium Re 186 etidronate, romurtide, samarium (153 Sm) lexidronam, sizofiran, sodium phenylacetate, sparfosic acid, spirogermanium, strontium-89 chloride, suramin, swainsonine, talaporfin, tariquidar, tazarotene, tegafur-uracil, temoporfin, tenuazonic acid, tetrachlorodecaoxide, thrombopoietin, tin ethyl etiopurpurin, tirapazamine, TLC ELL-12, tositumomab-iodine 131, trifluridine and tipiracil combination, troponin I (Harvard University, US), urethan, valspodar, verteporfin, zoledronic acid, and zosuquidar.

The present disclosure further provides a method for using the compounds of Formula (I) or pharmaceutical compositions provided herein, in combination with radiation therapy to treat cancer. Techniques for administering radiation therapy are known in the art, and these techniques can be used in the combination therapy described herein. The administration of the compound of Formula (I) in this combination therapy can be determined as described herein.

Radiation therapy can be administered through one of several methods, or a combination of methods, including, without limitation, external-beam therapy, internal radiation therapy, implant radiation, stereotactic radiosurgery, systemic radiation therapy, radiotherapy and permanent or temporary interstitial brachy therapy. The term "brachytherapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive microspheres.

The present application also provides methods for combination therapies in which the additional active agent is known to modulate other pathways, or other components of the same pathway, or even overlapping sets of target enzymes which are used in combination with a compound of Formula (I), or a pharmaceutically acceptable salt thereof. In one embodiment, such therapy includes, but is not limited to, the combination of one or more compounds of Formula (I) with chemotherapeutic agents, immunotherapeutic agents, hormonal therapy agents, therapeutic antibodies, targeted therapy agents, and radiation treatment, to provide a synergistic or additive therapeutic effect.

The present disclosure also provides a compound of Formula (I) or a pharmaceutically acceptable salt thereof and an additional anti-cancer agent for use in the treatment of cancer, or use of the compound of Formula (I) or the pharmaceutically acceptable salt thereof and the additional anti-cancer agent for the treatment of cancer. The present disclosure also provides for a pharmaceutical preparation comprising (a) a compound of Formula (I) or a pharmaceutically acceptable salt thereof and (b) an additional anti-cancer agent for use in the treatment of cancer, or use of a pharmaceutical preparation comprising (a) and (b) in the treatment of cancer. The present disclosure also provides for a compound of Formula (I) or a pharmaceutically acceptable salt thereof and radiation therapy for use in the treatment of cancer, or use of the compound of Formula (I) or the pharmaceutically acceptable salt thereof and the radiation therapy in the treatment of cancer.

The present disclosure also provides for a compound of Formula (I) or a pharmaceutically acceptable salt thereof and an additional anti-cancer agent for use in the preparation of a medicament for the treatment of the cancer.

EXAMPLES

The following describes the disclosure in more detail, showing Examples and Test Examples. However, the disclosure is not limited to these Examples.

The reagents used in the Examples are commercially available products unless indicated otherwise. Prepacked columns manufactured by Shoko Scientific Co., Ltd., or Biotage were used in silica gel column chromatography and basic silica gel column chromatography. An AL400 spectrometer (400 MHz; JEOL Ltd. (JEOL)) or Mercury 400 (400 MHz; Varian) spectrometer was used for NMR spectra. For a deuterated solvent containing tetramethylsilane, tetramethylsilane was used as the internal reference. In other cases, measurement was performed using an NMR solvent as the internal reference. All S values are indicated in ppm. Microwave reaction was performed using an Initiator (trademark) manufactured by Biotage.

The following describes the meanings of the abbreviations.

s: singlet
d: doublet
t: triplet
q: quartet
sep: septet
dd: double doublet
dt: double triplet
td: triple doublet
tt: triple triplet
ddd: double double doublet
ddt: double double triplet
dtd: double triple doublet
tdd: triple double doublet
m: multiplet
br: broad
brs: broad singlet
tert: tertiary
DMSO-d 6: deuterated dimethyl sulfoxide
CDCl 3: deuterated chloroform
CD3OD: deuterated methanol
THF: tetrahydrofuran
DMF: N,N-dimethylformamide
NMP: 1-methyl-2-pyrrolidinone
DMSO: dimethyl sulfoxide
WSC: 1-(3-dimethylaminopropyl)-3-ethylcarbodiimide
HATU: 1-[bis(dimethylamino)methylene]-1H-1,2,3-triazole[4,5-b]pyridinium-3-oxidehexafluorophosphate
Boc: tert-butoxycarbonyl group

Production Example 1

5-(Tert-butyl)-6-chloro-1H-indazole-3-amine

Step 1: After nitric acid (1.40) (23 mL) was slowly added to concentrated sulfuric acid (32 mL) at ice cooling temperature, 1-bromo-4-tert-butylbenzene (60 g) was added thereto at an internal temperature of 25° C. or below. The mixture was stirred at room temperature for 3 hours, and then poured onto ice, followed by extraction with diethyl ether. The organic layer was washed with a sodium hydrogen carbonate aqueous solution and a saturated sodium chloride solution and dried over sodium sulfate. The solution was evaporated under reduced pressure, thereby obtaining crude 1-bromo-4-(tert-butyl)-2-nitrobenzene (72.1 g).

Step 2: A suspension of crude 1-bromo-4-(tert-butyl)-2-nitrobenzene (72.1 g) obtained in step 1, iron powder (50 g), and ammonium chloride (50 g) in ethanol (400 mL) and water (100 mL) was stirred at 70° C. for 90 minutes. After ethanol was evaporated under reduced pressure, water and ethyl acetate were added thereto, followed by filtrating off the insoluble matter. The organic layer was separated and washed with a saturated sodium chloride solution, followed by drying over sodium sulfate. The solvent was evaporated under reduced pressure, and then ethyl acetate (200 mL) and acetic anhydride (30 mL) were added thereto. The solvent was evaporated under reduced pressure, and hexane (300 mL) was added, followed by collecting the precipitated solid, thereby obtaining N-(2-bromo-5-(tert-butyl)phenyl)acetamide (40.6 g).

Step 3: N-chlorosuccinimide (4.00 g) was added to a solution of N-(2-bromo-5-(tert-butyl)phenyl)acetamide (5.40 g) obtained in step 2, (D)-(+)-10-camphorsulfonic acid (2.40 g), and 1,3-dimethyl imidazolium chloride (264 mg) in 1,4-dioxane (54 mL), and the mixture was stirred at room temperature overnight. A sodium hydrogen carbonate aqueous solution and sodium thiosulfate were added to the reaction mixture, and the mixture was extracted with ethyl acetate, followed by washing the organic layer with a saturated sodium chloride solution. After the washed organic layer was dried over sodium sulfate, the solvent was evaporated under reduced pressure, followed by collecting the solid, thereby obtaining N-(2-bromo-5-(tert-butyl)-4-chlorophenyl)acetamide (5.40 g).

Step 4: A 5N sodium hydroxide aqueous solution (100 mL) was added to a solution of N-(2-bromo-5-(tert-butyl)-4-chlorophenyl)acetamide (17.1 g) obtained in step 3 in ethanol (100 mL), and the mixture was stirred at 90° C. for 5 hours. After the ethanol in the reaction mixture was evaporated under reduced pressure, the mixture was extracted with 2-methyltetrahydrofuran, followed by washing the organic layer with a saturated sodium chloride solution. The washed organic layer was dried over sodium sulfate, and the solvent was evaporated under reduced pressure, thereby obtaining 2-bromo-5-(tert-butyl)-4-chloroaniline (14.8 g).

Step 5: 2-Bromo-5-(tert-butyl)-4-chloroaniline (81.1 g) obtained in step 4 was cooled to an internal temperature of 0° C., and 3N hydrochloric acid (566 mL) was added thereto. Sodium nitrite (24.3 g) was added little by little, and the mixture was stirred at an internal temperature of 0° C. for 1 hour to prepare a diazonium salt suspension. The diazonium salt suspension was added to a suspension of copper(I) cyanide (27.7 g), sodium cyanide (30.3 g), and sodium hydrogen carbonate (145 g) in water (570 mL) at ice cooling temperature, and the mixture was stirred at 0° C. for 1 hour. After stirring, the mixture was heated to room temperature, and ethyl acetate was added thereto, followed by celite filtration. The filtrate was partitioned, and the organic layer was washed with a 20% sodium chloride solution, followed by drying over magnesium sulfate. The solvent was evaporated under reduced pressure, and the obtained residue was purified by column chromatography (hexane:ethyl acetate), thereby obtaining 2-bromo-5-(tert-butyl)-4-chlorobenzonitrile (61.1 g).

Step 6: Palladium acetate (2.5 g) was added to a suspension of 2-bromo-5-(tert-butyl)-4-chlorobenzonitrile (61.1 g) obtained in step 5, benzophenone hydrazone (51.9 g), rac-2,2'-bis(diphenylphosphino)-1,1'-binaphthyl (7.7 g), and cesium carbonate (102 g) in toluene (470 mL). The mixture was heated at an internal temperature of 101° C. in a nitrogen atmosphere for 1.5 hours. The mixture was then cooled to room temperature, and ethyl acetate and water were added thereto, followed by celite filtration and separating the organic layer. The organic layer was dried over sodium sulfate, and the solvent was evaporated under reduced pressure. The residue was purified by column chromatography (hexane:dichloromethane), thereby obtaining 5-(tert-butyl)-4-chloro-2-(2-(diphenylmethylene)hydrazinyl) benzonitrile (52.8 g).

Step 7: p-toluenesulfonic acid monohydrate (51.8 g) was added to a solution of 5-(tert-butyl)-4-chloro-2-(2-(diphenylmethylene)hydrazinyl) benzonitrile (52.8 g) obtained in step 6 in methanol (375 mL), and the mixture was heated at an internal temperature of 63° C. for 1.5 hours. The reaction mixture was cooled to room temperature and washed with hexane. The hexane layer was then extracted with methanol, and the solvent was evaporated under reduced pressure. The residue was dissolved in ethyl acetate and washed with a mixture solution of a saturated sodium hydrogen carbonate aqueous solution (375 mL) and a 5N sodium hydroxide aqueous solution. The aqueous layer was extracted with ethyl acetate, and the organic layer was washed with a saturated sodium hydrogen carbonate aqueous solution. The washed organic layer was dried over magnesium sulfate, and the solvent was evaporated under reduced pressure. The obtained residue was purified by column chromatography (hexane:ethyl acetate), thereby obtaining the title compound (29.0 g).

Production Example 2

6-Chloro-5-vinyl-1H-indazole-3-amine

Step 1: Pyridine (100 mL) and acetic anhydride (30 mL) were added to 3-amino-6-chloro-1H-indazole (15.1 g), and the mixture was stirred at room temperature over 3 days. The reaction mixture was concentrated, and methanol (300 mL) and a 5N sodium hydroxide aqueous solution (70 mL) were added thereto, followed by stirring for 1 hour. The reaction mixture was concentrated and neutralized with a 10% phosphoric acid aqueous solution. The obtained solid was collected and washed with water. After the collected solid was dried, N-(6-chloro-1H-indazol-3-yl)acetamide (15.1 g) was obtained.

Step 2: N-bromosuccinimide (3.90 g) was added to a solution of N-(6-chloro-1H-indazol-3-yl)acetamide (4.20 g) obtained in step 1 in THE (20 mL) and DMF (10 mL), followed by stirring for 1 hour. Water was added to the reaction mixture, and THE was evaporated, followed by collecting the solid. The solid was dried at 50° C. under reduced pressure, thereby obtaining N-(5-bromo-6-chloro-1H-indazol-3-yl)acetamide (4.76 g).

Step 3: Concentrated hydrochloric acid (10 mL) was added to a suspension of N-(5-bromo-6-chloro-1H-indazol-3-yl)acetamide (4.76 g) obtained in step 2 in methanol (100 mL), followed by stirring at 70° C. for 2 hours. The reaction mixture was concentrated, and water was added to the obtained residue, followed by collecting the obtained solid. The solid was then dried at 70° C. under reduced pressure, thereby obtaining 5-bromo-6-chloro-1H-indazole-3-amine hydrochloride (4.06 g).

Step 4: A suspension of 5-bromo-6-chloro-1H-indazole-3-amine hydrochloride (282 mg) obtained in step 3, 4,4,5,5-tetramethyl-2-vinyl-1,3,2-dioxaborolane (300 μL), tetrakistriphenylphosphine palladium(0) (120 mg), and a 2M sodium carbonate aqueous solution (1.5 mL) in 1,4-dioxane (4.5 mL) was stirred at 100° C. for 13 hours. Ethyl acetate and water were added to the reaction mixture to separate the organic layer, and the organic layer was washed with a saturated sodium chloride solution. The washed organic layer was dried over sodium sulfate, and the solvent was evaporated under reduced pressure, followed by purifying the obtained residue by column chromatography (chloroform:ethanol), thereby obtaining the title compound (164 mg).

Production Example 3

6-Chloro-5-ethyl-1H-indazole-3-amine

Rhodium carbon (Rh 5%) (100 mg) was added to a solution of 6-chloro-5-vinyl-1H-indazole-3-amine (135 mg) obtained in Production Example 2 in THE (1.0 mL) and ethanol (1.0 mL) in a nitrogen atmosphere, and the reaction system was subjected to hydrogen replacement, followed by stirring for 5 days. The reaction system was then subjected to nitrogen replacement, and the reaction mixture was filtered. The solvent was concentrated under reduced pressure, and the obtained residue was purified by column chromatography (ethyl acetate:ethanol), thereby obtaining the title compound (31 mg).

Production Example 4

5-(Tert-butyl)-6-chloro-1H-pyrazolo[4,3-b]pyridine-3-amine

Step 1: N-chlorosuccinimide (620 mg) and chloroform (5.0 mL) were added to 6-(tert-butyl)pyridin-2-ol (291 mg), and the mixture was stirred at room temperature for 1 hour. Acetic acid (5.0 mL) was added to the reaction mixture, followed by stirring at 50° C. overnight. The reaction mixture was concentrated, and the obtained residue was purified by column chromatography (hexane:ethyl acetate), thereby obtaining 6-(tert-butyl)-3,5-dichloropyridin-2-ol (386 mg).

Step 2: Toluene (10 mL), phosphorus oxybromide (400 mg), and DMF (12 μL) were added to 6-(tert-butyl)-3,5-dichloropyridin-2-ol (386 mg) obtained in step 1, and the mixture was stirred at 100° C. for 18 hours. DMF (30 μL) was added thereto, followed by stirring at 120° C. for 9 hours. Ethyl acetate, water, and a sodium hydrogen carbonate aqueous solution were added to the reaction mixture to separate the organic layer. The organic layer was washed with a saturated sodium chloride solution and dried over sodium sulfate. The solvent was evaporated under reduced pressure, and the obtained residue was purified by column chromatography (hexane:ethyl acetate), thereby obtaining 2-bromo-6-(tert-butyl)-3,5-dichloropyridine (155 mg).

Step 3: A suspension of 2-bromo-6-(tert-butyl)-3,5-dichloropyridine (155 mg) obtained in step 2 and copper(I) cyanide (100 mg) in NMP (2 mL) was stirred at 120° C. for 2 hours. The reaction mixture was cooled to room temperature, and ethyl acetate and concentrated ammonia water were added to the reaction mixture to separate the organic layer. The organic layer was washed with water and a saturated sodium chloride solution and dried over sodium sulfate. The solvent was evaporated under reduced pressure, and the obtained residue was purified by column chromatography (hexane:ethyl acetate), thereby obtaining 6-(tert-butyl)-3,5-dichloropicolinonitrile (111 mg).

Step 4: Hydrazine monohydrate (300 μL) was added to a solution of 6-(tert-butyl)-3,5-dichloropicolinonitrile (105 mg) obtained in step 3 in 2-propanol (1.5 mL), and the mixture was allowed to react at 120° C. for 12 hours in a microwave reactor. Hydrazine monohydrate (300 μL) was further added, and the reaction allowed to further proceed at 130° C. for 6 hours. The reaction mixture was purified by column chromatography (chloroform:ethanol), thereby obtaining the title compound (42 mg).

Production Example 5

6-Chloro-5-methyl-1H-indazole-3-amine

Step 1: A sodium hydrogen carbonate aqueous solution was added to 5-bromo-6-chloro-1H-indazole-3-amine hydrochloride (110 mg) obtained in Production Example 2 (step 3), and the mixture was extracted with ethyl acetate. The organic layer was washed with a saturated sodium chloride solution and dried over sodium sulfate, followed by evaporating the solvent under reduced pressure, thereby obtaining 5-bromo-6-chloro-1H-indazole-3-amine (63.9 mg).

Step 2: 5-Bromo-6-chloro-1H-indazole-3-amine (37 mg) obtained in step 1, methylboronic acid (30 mg), a (1,1'-bis(diphenylphosphino)ferrocene)palladium(II) dichloride dichloromethane adduct (12 mg), a 0.5M tripotassium phosphate aqueous solution (1.0 mL), and 1,4-dioxane (1.0 mL) were placed in a reactor and stirred at 100° C. overnight. Methylboronic acid (30 mg) and a 0.5M tripotassium phosphate aqueous solution (1.0 mL) were further added, followed by further stirring overnight. Ethyl acetate and water were added to the reaction mixture to partition the mixture. The organic layer was washed with a saturated sodium chloride solution. The washed organic water was dried over sodium sulfate, and the solvent was evaporated under reduced pressure, followed by purifying the obtained residue by column chromatography (chloroform:ethanol), thereby obtaining the title compound (10.8 mg).

Production Example 6

5-(Tert-butyl)-6-methyl-1H-indazole-3-amine

Step 1: Acetic anhydride (7.0 mL) was added to a solution of 3-tert-butylaniline (10 g) in ethyl acetate (100 mL), and the mixture was concentrated under reduced pressure. 1,4-Dioxane (150 mL), 1,3-di(1-adamantyl)-1H-imidazolium tetrafluoroborate (500 mg), D-(+)-10-camphorsulfonic acid (7.80 g), and N-chlorosuccinimide (9.50 g) were added to the obtained residue, and the mixture was stirred at room temperature for 8 hours. The reaction mixture was concentrated, and ethyl acetate and a saturated sodium hydrogen carbonate aqueous solution were added to the obtained residue to separate the organic layer. The organic layer was washed with a saturated sodium chloride solution and dried over sodium sulfate, followed by evaporating the solvent under reduced pressure. The obtained residue was purified by column chromatography (hexane:ethyl acetate), thereby obtaining N-(3-(tert-butyl)-4-chlorophenyl)acetamide (9.19 g) and N-(5-(tert-butyl)-2-chlorophenyl)acetamide (4.14 g).

Step 2: A solution of N-(5-(tert-butyl)-2-chlorophenyl)acetamide (1.13 g) obtained in step 1, N-bromosuccinimide (1.00 g), and acetic acid (10 mL) was stirred at 60° C. overnight. N-bromosuccinimide (800 mg) was further added, followed by further stirring at 60° C. for 5 hours. The reaction mixture was concentrated under reduced pressure, and a sodium hydrogen carbonate aqueous solution and sodium thiosulfate were added to the residue, followed by extraction with ethyl acetate. The organic layer was washed with a saturated sodium chloride solution. The washed organic layer was dried over sodium sulfate, and the solvent was evaporated under reduced pressure, followed by purifying the obtained residue by column chromatography (hexane:ethyl acetate), thereby obtaining N-(4-bromo-5-(tert-butyl)-2-chlorophenyl)acetamide (1.11 g).

Step 3: A (1,1'-bis(diphenylphosphino)ferrocene)palladium(II) dichloride dichloromethane adduct (200 mg), 1,4-dioxane (12 mL), and dimethyl zinc (a 2M toluene solution, 3.50 mL) were added to N-(4-bromo-5-(tert-butyl)-2-chlorophenyl)acetamide (966 mg) obtained in step 2, followed by stirring at 100° C. for 90 minutes. The reaction mixture was cooled to room temperature, and water and a 10% phosphoric acid aqueous solution were added thereto, followed by extraction with ethyl acetate. The organic layer was washed with a saturated sodium chloride solution. The washed organic layer was dried over sodium sulfate, and the solvent was evaporated under reduced pressure, followed by purifying the obtained residue by column chromatography (hexane:ethyl acetate), thereby obtaining N-(5-(tert-butyl)-2-chloro-4-methylphenyl)acetamide (954 mg).

Step 4: The procedure of Production Example 1 (steps 4 and 5) was performed except that N-(5-(tert-butyl)-2-chloro-4-methylphenyl)acetamide (954 mg) obtained in step 3 was used instead of N-(2-bromo-5-(tert-butyl)-4-chlorophenyl)acetamide used in Production Example 1 (step 4), thereby obtaining 5-(tert-butyl)-2-chloro-4-methylbenzonitrile (517 mg).

Step 5: Anhydrous hydrazine (400 μL) was added to a solution of 5-(tert-butyl)-2-chloro-4-methylbenzonitrile (517 mg) obtained in step 4 in N-methylpyrrolidone (4.00 mL), and the mixture was allowed to react in a microwave reactor at 130° C. for 2 hours, followed by subsequent reaction at 140° C. for 6 hours. Water was added to the reaction mixture, and the mixture was extracted with ethyl acetate. The organic layer was washed with water and a saturated sodium chloride solution. The washed organic layer was dried over sodium sulfate, and the solvent was evaporated under reduced pressure. The obtained residue was purified by column chromatography (chloroform:ethanol), thereby obtaining the title compound (88 mg).

Production Example 7

5-(Tert-butyl)-1H-indazole-3-amine 5-(Tert-butyl)-6-chloro-1H-indazole-3-amine (99.9 mg) obtained in Production Example 1 was dissolved in methanol (10 mL), and a solution of 7.5% palladium carbon (19.6 mg) and hydrogen chloride in methanol (1 mL) was added thereto, followed by intense stirring at room temperature in a hydrogen atmosphere for 5 days. The insoluble matter was filtered off through celite, and the filtrate was concentrated, thereby obtaining the title compound (84 mg).

Production Example 8

6-Chloro-5-(3,3,3-trifluoroprop-1-en-2-yl)-1H-indazole-3-amine

Step 1: 5-Bromo-6-chloro-1H-indazole-3-amine hydrochloride (800 mg) obtained in Production Example 2 (step 3)

and 4-dimethylaminopyridine (18 mg) were dissolved in dichloromethane (10 mL). N,N-diisopropylethylamine (2 mL) and di-tert-butyl dicarbonate (1.2 g) were added thereto. After the mixture was stirred at room temperature overnight, a saturated ammonium chloride aqueous solution was added thereto, and the mixture was extracted with chloroform. The organic layer was washed with a saturated sodium chloride solution and dried over sodium sulfate, followed by evaporating the solvent under reduced pressure. Dichloromethane (10 mL), 4-dimethylaminopyridine (18 mg), N,N-diisopropylethylamine (2 mL), and di-tert-butyl dicarbonate (2.4 g) were added to the obtained mono Boc form, followed by stirring at room temperature for 1 hour. A saturated ammonium chloride aqueous solution was added to the reaction mixture, and the mixture was extracted with chloroform. The organic layer was washed with a saturated sodium chloride solution and dried over ammonium sulfate. The solvent was evaporated under reduced pressure, and the obtained residue was purified by column chromatography (hexane:ethyl acetate), thereby obtaining tert-butyl 3-(bis(tert-butoxycarbonyl)amino)-5-bromo-6-chloro-indazole-1-carboxylate (1.2 g).

Step 2: 4,4,6-Trimethyl-2-(3,3,3-trifluoroprop-1-en-2-yl)-1,3,2-dioxaborinan (200 mg), a 0.5M potassium phosphate aqueous solution (2.7 mL), and a 1,1'-bis(diphenylphosphino)ferrocene-palladium(II) dichloride-dichloromethane complex were added to a solution of tert-butyl 3-(bis(tert-butoxycarbonyl)amino)-5-bromo-6-chloro-indazole-1-carboxylate (250 mg) obtained in step 1 in 1,4-dioxane (7 mL). The mixture was stirred at 100° C. for 2 hours. The reaction mixture was cooled to room temperature, and water was added thereto, followed by extraction with ethyl acetate. The organic layer was washed with a saturated sodium chloride solution and dried over ammonium sulfate. The solvent was evaporated under reduced pressure, and the obtained residue was purified by column chromatography (hexane:ethyl acetate), thereby obtaining tert-butyl 3-(bis(tert-butoxycarbonyl)amino)-6-chloro-5-(3,3,3-trifluoroprop-1-en-2-yl)-indazole-1-carboxylate (62 mg).

Step 3: Trifluoroacetic acid (1 mL) was added to a solution of tert-butyl 3-(bis(tert-butoxycarbonyl)amino)-6-chloro-5-(3,3,3-trifluoroprop-1-en-2-yl)-indazole-1-carboxylate (62 mg) obtained in step 2 in dichloromethane (2 mL), followed by stirring at room temperature for 1 hour. The solvent was evaporated under reduced pressure, and the obtained residue was purified by column chromatography (hexane:ethyl acetate), thereby obtaining the title compound (14 mg).

Production Example 9

6-Chloro-5-(1-(trifluoromethyl)cyclopropyl)-1H-indazole-3-amine

Step 1: A potassium hydroxide (800 mg) aqueous solution (4 mL) was added to a solution of N-methyl-N-nitrosourea (265 mg) in diethyl ether (15 mL) at ice cooling temperature, followed by stirring for 15 minutes ("solution A"). Solution A was added dropwise to a solution of tert-butyl 3-(bis(tert-butoxycarbonyl)amino)-6-chloro-5-(3,3,3-trifluoroprop-1-en-2-yl)-indazole-1-carboxylate (73 mg) obtained in Production Example 8 (step 2) in diethyl ether (30 mL) at ice cooling temperature over 30 minutes, followed by stirring at room temperature overnight. After acetic acid was added, the solvent was evaporated under reduced pressure, and the obtained residue was purified by column chromatography (hexane:ethyl acetate), thereby obtaining tert-butyl 3-(bis(tert-butoxycarbonyl)amino)-6-chloro-5-(5-(trifluoromethyl)-3,4-dihydropyrazol-5-yl)-indazole-1-carboxylate (64 mg).

Step 2: A solution of tert-butyl 3-(bis(tert-butoxycarbonyl)amino)-6-chloro-5-(5-(trifluoromethyl)-3,4-dihydropyrazol-5-yl)-indazole-1-carboxylate (64 mg) obtained in step 1 in xylene (3 mL) was stirred at 140° C. overnight, and the solvent was evaporated under reduced pressure. The obtained residue was purified by column chromatography (hexane:ethyl acetate), thereby obtaining tert-butyl 3-(bis(tert-butoxycarbonyl)amino)-6-chloro-5-(1-(trifluoromethyl)cyclopropyl)-indazole-1-carboxylate (52 mg).

Step 3: Trifluoroacetic acid (1 mL) was added to a solution of tert-butyl 3-(bis(tert-butoxycarbonyl)amino)-6-chloro-5-(1-(trifluoromethyl)cyclopropyl)-indazole-1-carboxylate (52 mg) obtained in step 2 in dichloromethane (2 mL), followed by stirring at room temperature for 1 hour. The solvent was evaporated under reduced pressure, and the obtained residue was purified by column chromatography (hexane:ethyl acetate), thereby obtaining the title compound (14 mg).

Production Example 10

6-Chloro-5-isopropyl-1H-indazole-3-amine

Step 1: Acetic anhydride (1.54 mL) was added to a solution of 3-isopropyl aniline (2.00 g) in ethyl acetate (20 mL). After 20 minutes, the mixture was concentrated under reduced pressure. 1,4-Dioxane (20 mL), 1,3-di(1-adamantyl)-1H-imidazolium tetrafluoroborate (61.7 mg), D-(+)-10-camphorsulfonic acid (1.72 g), and N-chlorosuccinimide (1.97 g) were added to the residue, followed by stirring at room temperature for 13 hours. The reaction mixture was concentrated, and ethyl acetate and a saturated sodium hydrogen carbonate aqueous solution were added to the obtained residue to separate the organic layer. The organic layer was washed with a saturated sodium chloride solution, and the solvent was evaporated under reduced pressure. The obtained residue was purified by column chromatography (hexane:ethyl acetate=88:12 to 0:100), thereby obtaining N-(4-chloro-3-isopropyl-phenyl)acetamide (2.52 g) and N-(2-chloro-5-isopropylphenyl)acetamide (0.729 g).

Step 2: A solution of N-(4-chloro-3-isopropylphenyl)acetamide (2.52 g) obtained in step 1, N-bromosuccinimide (2.33 g), and acetic acid (15 mL) was stirred at 60° C. for 3 hours. The reaction mixture was concentrated under reduced pressure, and water was added to the residue, followed by extraction with ethyl acetate. The organic layer was washed with a saturated sodium chloride solution. The solvent was evaporated under reduced pressure, and the obtained residue was purified by column chromatography (hexane:ethyl acetate=62:38), thereby obtaining N-(2-bromo-4-chloro-5-isopropyl-phenyl)acetamide (2.82 g).

Step 3: The procedure of Production Example 1 (steps 4 and 5) was performed except that N-(2-bromo-4-chloro-5-isopropyl-phenyl)acetamide (2.82 g) obtained in step 2 was used instead of N-(2-bromo-5-(tert-butyl)-4-chlorophenyl) acetamide used in Production Example 1 (step 4), thereby obtaining 2-bromo-4-chloro-5-isopropyl-benzonitrile (1.82 g).

Step 4: The procedure of Production Example 1 (steps 6 and 7) was performed except that 2-bromo-4-chloro-5-isopropyl-benzonitrile (763 mg) obtained in step 3 was used instead of 2-bromo-5-(tert-butyl)-4-chlorobenzonitrile used in Production Example 1 (step 6), thereby obtaining the title compound (333 mg).

Production Example 11

Methyl 4-fluoro-1H-imidazole-5-carboxylate

Step 1: Methanesulfonic acid (90 mL) was added to a solution of 4-amino-1H-imidazole-5-carboxamide (52 g) in methanol (300 mL), followed by stirring at 110° C. for 3 days. The solution was concentrated under reduced pressure, and a 5N sodium hydroxide aqueous solution was added thereto. The mixture was extracted with ethyl acetate, and the organic layer was washed with a saturated sodium chloride solution. The washed organic layer was dried over sodium sulfate, and the solvent was evaporated under reduced pressure, thereby obtaining crude methyl 4-amino-1H-imidazole-5-carboxylate (33 g).

Step 2: A sodium nitrite (5.4 g) aqueous solution (3 mL) was added dropwise to a 42% tetrafluoroboric acid (40 mL) solution of methyl 4-amino-1H-imidazole-5-carboxylate (5.5 g) obtained in step 1 at ice cooling temperature, followed by stirring for 15 minutes. The reaction solution was spread on a glass plate, and irradiated with UV light at 302 nm with wattage of 6 W from a distance of 3 cm overnight. A 5N sodium hydroxide aqueous solution was added thereto at ice cooling temperature, and the mixture was extracted with ethyl acetate, followed by washing the organic layer with a saturated sodium chloride solution. The washed organic layer was dried over sodium sulfate, and the solvent was evaporated under reduced pressure. The obtained residue was purified by column chromatography (hexane:ethyl acetate), thereby obtaining the title compound (1.1 g).

Production Example 12

Methyl 4-chloro-1H-imidazole-5-carboxylate

Concentrated hydrochloric acid (20 mL) was added to methyl 4-amino-1H-imidazole-5-carboxylate (4.5 g) obtained in Production Example 11 (step 1), and a sodium nitrite (3.3 g) aqueous solution (1.5 mL) was added dropwise thereto at ice cooling temperature, followed by stirring at the same temperature for 15 minutes. The reaction solution was spread on a glass plate, and irradiated with UV light at 302 nm from a distance of 3 cm overnight. A 5N sodium hydroxide aqueous solution was added at ice cooling temperature, and the precipitated solid was collected, followed by drying by heating overnight, thereby obtaining the title compound (2.6 g).

Production Example 13

4-Chloro-1-methyl-1H-imidazole-5-carboxylic acid

Step 1: Methanol (150 μL), triphenylphosphine (1.2 g), and DIAD (880 μL) were added to a solution of methyl 4-chloro-1H-imidazole-5-carboxylate (600 mg) obtained in Production Example 12 in THF (7 mL), followed by stirring at room temperature for 30 minutes. The solvent was evaporated under reduced pressure, and the obtained residue was purified by column chromatography (hexane:ethyl acetate), thereby obtaining methyl 4-chloro-1-methyl-1H-imidazole-5-carboxylate (360 mg).

Step 2: A 5N sodium hydroxide aqueous solution (1 mL) was added to a solution of methyl 4-chloro-1-methyl-1H-imidazole-5-carboxylate (360 mg) obtained in step 1 in ethanol (2 mL), followed by stirring at room temperature for 1 hour. After the solvent was evaporated under reduced pressure, 5N hydrochloric acid was added thereto, and the mixture was extracted with ethyl acetate. The organic layer was washed with a saturated sodium chloride solution and dried over sodium sulfate. The solvent was evaporated under reduced pressure, thereby obtaining the title compound (285 mg).

Production Example 14

2-(Ethoxycarbonyl)thiazole-4-carboxylic acid

3-Bromopyruvic acid (1.29 g) was added to a solution of ethyl thiooxamate (1.02 g) in THF (20 mL), followed by stirring at 50° C. overnight. The reaction mixture was cooled to room temperature, and ethyl acetate (5 mL) was added thereto, followed by collecting the obtained solid, thereby obtaining the title compound (911 mg).

Production Example 15

3-(Ethoxycarbonyl)-1-methyl-1H-pyrazole-5-carboxylic acid

Potassium carbonate (850 mg) and methyl iodide (380 μL) were added to a solution of diethyl 3,5-pyrazoledicarboxylate (637 mg) in acetone (10 mL), followed by stirring at room temperature overnight. Water and a 10% phosphoric acid aqueous solution were added to the reaction mixture, and the mixture was extracted with ethyl acetate, followed by washing the organic layer with a saturated sodium chloride solution. The washed organic layer was dried over sodium sulfate, and the solvent was evaporated under reduced pressure. Ethanol (10 mL) and a 2N potassium hydroxide aqueous solution (1.65 mL) were added to the obtained residue, and the mixture was stirred at room temperature for 3 hours. Water was added to the reaction mixture, and ethanol was evaporated under reduced pressure. A 10% phosphoric acid aqueous solution was added thereto, and the mixture was extracted with ethyl acetate, followed by washing the organic layer with a saturated sodium chloride solution. The washed organic layer was dried over sodium sulfate, and the solvent was evaporated under reduced pressure. The obtained solid was collected, thereby obtaining the title compound (520 mg).

Production Example 16

2-(Diethoxymethyl)-1-methyl-4-(trifluoromethyl)-1H-imidazole-5-carboxylic acid

Step 1: 1-Methyl-4-trifluoromethylimidazole (334 mg) was dissolved in THF (4.0 mL), and the mixture was cooled to −78° C. After butyllithium (a 1.55M hexane solution, 1.60 mL) was slowly added to the reaction mixture, a solution of DMF (250 μL) in THF (1.0 mL) was added thereto. The mixture was stirred at −78° C. for 1 hour, and heated to 0° C., followed by stirring for 30 minutes. Water was added to the obtained mixture, and the mixture was extracted with ethyl acetate, followed by washing with a 20% sodium chloride solution. After the organic layer was dried over sodium sulfate, the solvent was evaporated under reduced pressure, followed by purifying the obtained residue by column chromatography (hexane:ethyl acetate=90:10 to 50:50), thereby obtaining 1-methyl-4-trifluoromethylimidazole-2-carbaldehyde (354 mg).

Step 2: 1-Methyl-4-trifluoromethylimidazole-2-carbaldehyde (350 mg) obtained in step 1 was dissolved in ethanol (7.0 mL), and concentrated sulfuric acid (0.1 mL) was added thereto. After stirring at room temperature for 6 hours, ethyl acetate was added thereto. The obtained mixture was then poured into saturated sodium bicarbonate water containing a 2N sodium hydroxide aqueous solution (1.8 mL). The organic layer was separated and dried over sodium sulfate, followed by concentrating the residue under reduced pressure, thereby obtaining 2-(diethoxymethyl)-1-methyl-4-(trifluoromethyl)-1H-imidazole (480 mg).

Step 3: 2-(Diethoxymethyl)-1-methyl-4-(trifluoromethyl)-1H-imidazole (45 mg) obtained in step 2 was dissolved in acetonitrile (0.45 mL), and N-bromosuccinimide (50 mg) was added thereto, followed by stirring overnight. The reaction mixture was concentrated, and water was added thereto, followed by extraction with a mixture solvent of hexane-ethyl acetate (3:1). The organic layer was separated and dried over sodium sulfate, followed by concentrating the residue under reduced pressure. The obtained residue was purified by column chromatography (hexane:ethyl acetate=80:20 to 20:80), thereby obtaining 5-bromo-2-(diethoxymethyl)-1-methyl-4-(trifluoromethyl)-1H-imidazole (15 mg).

Step 4: After THF (4.0 mL) was cooled to −78° C., butyllithium (a 1.55M hexane solution, 0.8 mL) was added thereto. A solution of 5-bromo-2-(diethoxymethyl)-1-methyl-4-(trifluoromethyl)-1H-imidazole (200 mg) obtained in step 3 in THE (1.5 mL) was added dropwise to the obtained mixture over 5 minutes. After the obtained mixture was stirred at −78° C. for 5 minutes, dry ice was added thereto. After the reaction mixture was heated to room temperature, a saturated ammonium chloride aqueous solution containing 2N hydrochloric acid (0.63 mL) was added thereto. The obtained mixture was extracted with ethyl acetate, thereby obtaining the title compound (220 mg).

Production Example 17

1-Isopropyl-4-(trifluoromethyl)-2-vinyl-1H-imidazole-5-carboxylic acid

Step 1: DIAD (0.086 mL) was added to a mixture of ethyl 2-bromo-5-(trifluoromethyl)-1H-imidazole-4-carboxylate (107 mg), THE (2.0 mL), 2-propanol (0.04 mL), and triphenylphosphine (0.123 g). After stirring at room temperature for 50 minutes, the reaction mixture was concentrated, followed by purifying the obtained residue by column chromatography (hexane:ethyl acetate=100:0 to 70:30), thereby obtaining ethyl 2-bromo-1-isopropyl-4-(trifluoromethyl)-1H-imidazole-5-carboxylate (89 mg).

Step 2: A mixture of ethyl 2-bromo-1-isopropyl-4-(trifluoromethyl)-1H-imidazole-5-carboxylate (413 mg) obtained in step 1, potassium vinyltrifluoroborate (0.185 g), a (1,1'-bis(diphenylphosphino)ferrocene)palladium(II) dichloride dichloromethane adduct (0.051 g), 1,4-dioxane (4 mL), and a 2N sodium carbonate aqueous solution (1.6 mL) was stirred at 90° C. for 7 hours. The reaction mixture was extracted with ethyl acetate, and the organic layer was washed with water and a 20% sodium chloride solution and dried over sodium sulfate. After the insoluble matter was filtered off, the filtrate was concentrated, and the obtained residue was purified by column chromatography (hexane: ethyl acetate=100:0 to 70:30), thereby obtaining ethyl 1-isopropyl-4-(trifluoromethyl)-2-vinyl-1H-imidazole-5-carboxylate (252 mg) as a colorless oily substance.

Step 3: ethyl 1-isopropyl-4-(trifluoromethyl)-2-vinyl-1H-imidazole-5-carboxylate (252 mg) obtained in step 2 was dissolved in THE (3 mL), and methanol (2.0 mL) and a 1N sodium hydroxide aqueous solution (2 mL) were added thereto. After the obtained mixture was stirred at room temperature for 40 minutes, 5N hydrochloric acid (0.4 mL) was added, and the mixture was extracted with ethyl acetate. The organic layer was washed with water and a 20% sodium chloride solution and dried over sodium sulfate. The insoluble matter was filtered off, and the filtrate was concentrated under reduced pressure, thereby obtaining the title compound (224 mg).

Production Example 18

4-Bromo-1-methyl-2-vinyl-1H-imidazole-5-carboxylic acid

Step 1: N-bromosuccinimide (8.5 g) was added to a solution of methyl 1H-imidazole-5-carboxylate (3 g) in acetonitrile (20 mL), followed by stirring at room temperature for 30 minutes. The solvent was evaporated under reduced pressure, and the obtained residue was purified by column chromatography (hexane:ethyl acetate), thereby obtaining methyl 2,4-dibromo-1H-imidazole-5-carboxylate (3.7 g).

Step 2: Methanol (300 μL), triphenylphosphine (2.2 g), and DIAD (1.6 mL) were added to a solution of methyl 2,4-dibromo-1H-imidazole-5-carboxylate (2 g) obtained in step 1 in THE (30 mL), and the mixture was stirred at room temperature for 30 minutes. The solvent was evaporated under reduced pressure, and the obtained residue was purified by column chromatography (hexane:ethyl acetate), thereby obtaining methyl 2,4-dibromo-1-methyl-1H-imidazole-5-carboxylate (1.6 g).

Step 3: Tetrakistriphenylphosphine palladium(0) (380 mg) and tributylvinyltin (1.9 mL) were added to a solution of methyl 2,4-dibromo-1-methyl-1H-imidazole-5-carboxylate (1.6 g) obtained in step 2 in 1,4-dioxane (20 mL), followed by stirring at 110° C. overnight. The solvent was evaporated under reduced pressure, and the obtained residue was purified by column chromatography (hexane:ethyl acetate), thereby obtaining methyl 4-bromo-1-methyl-2-vinyl-1H-imidazole-5-carboxylate (900 mg).

Step 4: A 5N sodium hydroxide aqueous solution (4.5 mL) was added to a solution of methyl 4-bromo-1-methyl-2-vinyl-1H-imidazole-5-carboxylate (900 mg) obtained in step 3 in ethanol (9 mL), followed by stirring at room temperature for 1 hour. The solvent was evaporated under reduced pressure, and 5N hydrochloric acid was added thereto, followed by extraction with ethyl acetate. The organic layer was washed with a saturated sodium chloride solution and dried over sodium sulfate. The solvent was evaporated under reduced pressure, thereby obtaining the title compound (840 mg).

Production Example 19

4-Cyano-1-methyl-1H-imidazole-5-carboxylic acid

Step 1: Concentrated sulfuric acid (0.88 mL) was slowly added to a solution of 4,5-dicyanoimidazole (4.00 g) in ethanol (20 mL), and the mixture was heated under reflux for 4 days. Ethyl acetate and water were added to the reaction mixture to partition the reaction mixture, and the organic layer was washed with a saturated sodium hydrogen carbonate aqueous solution and a saturated sodium chloride solution. The washed layer was dried over sodium sulfate, and the solvent was evaporated under reduced pressure. Chloroform was added to the obtained residue, and the obtained solid was collected, thereby obtaining a mixture of the starting material and ethyl 4-cyano-1H-imidazole-5-carboxylate in a ratio of about 2:3 (4.14 g).

Step 2: Potassium carbonate (1.26 g) and methyl iodide (565 μL) were added to a solution of the mixture of ethyl 4-cyano-1H-imidazole-5-carboxylate obtained in step 1 (1.00 g) in DMF (10 mL), followed by stirring at room temperature for 2 hours. Diethyl ether and water were added to the reaction mixture to partition the reaction mixture, followed by washing the organic layer with water and a saturated sodium chloride solution. The washed organic layer was dried over sodium sulfate, and the solvent was evaporated under reduced pressure, followed by purifying the obtained residue by column chromatography (hexane: ethyl acetate), thereby obtaining a mixture of ethyl 4-cyano-1-methyl-1H-imidazole-5-carboxylate and 1-methyl-1H-imidazole-4,5-dicarbonitrile in a ratio of about 3:2 (531 mg).

Step 3: Water (2.00 mL) and a 40% aqueous solution of benzyltrimethylammonium hydroxide (850 μL) were added to the mixture of ethyl 4-cyano-1-methyl-1H-imidazole-5-carboxylate (531 mg) obtained in step 2. After stirring at room temperature for 40 minutes, a 10% phosphoric acid aqueous solution and ethyl acetate were added to the reaction mixture, followed by collecting the obtained solid, thereby obtaining the title compound (252 mg).

Production Example 20

1-Cyclopropyl-4-methyl-1H-imidazole-5-carboxylic acid

Synthesis was performed with reference to Eur. J. Org. Chem. 2010, 4312-4320.

Step 1: Ethyl 2-chloroacetoacetate (919 mg) was added to a solution of methyl hydrazinocarboxylate (501 mg) in THE (10 mL), and the mixture was stirred at room temperature for 4 hours. An oily substance obtained by concentrating the reaction mixture and purifying the obtained residue by column chromatography (hexane:ethyl acetate=90:10 to 50:50) was formed into a powder with hexane and ethyl acetate to filter it, thereby obtaining ethyl (3E)-2-chloro-3-(methoxycarbonylhydrazono)butanoate (980 mg).

Step 2: Triethylamine (205 μL) was added to a solution of ethyl (3E)-2-chloro-3-(methoxycarbonylhydrazono)butanoate (350 mg) obtained in step 1 in acetonitrile (4 mL), followed by stirring at room temperature for 45 minutes. Cyclopropylamine (89.0 mg) and paraformaldehyde (92.9 mg) were further added, and the mixture was allowed to react at 150° C. for 20 minutes in a microwave reactor. The reaction mixture was concentrated, and the obtained residue was purified by column chromatography (hexane:ethyl acetate=35:65 to 10:90), thereby obtaining ethyl 1-cyclopropyl-4-methyl-1H-imidazole-5-carboxylate (240 mg).

Step 3: Ethyl 1-cyclopropyl-4-methyl-1H-imidazole-5-carboxylate (328 mg) obtained in step 2 was dissolved in methanol (5 mL), and a 4N sodium hydroxide aqueous solution (633 μL) was added thereto, followed by stirring at 100° C. for 2 hours. 6N hydrochloric acid (430 μL) was added to the reaction mixture for drying and solidifying the mixture, thereby obtaining the title compound.

Production Example 21

1-(Tert-butyl)-4-methyl-1H-imidazole-5-carboxylic acid

The procedure of Production Example 20 (step 2) was performed except that tert-butyl amine was used instead of cyclopropylamine used in Production Example 20 (step 2), thereby obtaining the title compound.

Production Example 22

2-(Hydroxymethy)-4-methyl-1-(2,2,2-trifluoroethyl)-1H-imidazole-5-carboxylic acid Step 1: The procedure of Production Example 20 (step 2) was performed except that 2,2,2-trifluoroethylamine was used instead of cyclopropylamine used in Production Example 20 (step 2), and that (tert-butyldimethylsiloxy) acetaldehyde was used instead of paraformaldehyde, thereby obtaining ethyl 2-(((tert-butyldimethylsilyl)oxy)methyl)-4-methyl-1-(2,2,2-trifluoroethyl)-1H-imidazole-5-carboxylate (260 mg).

Step 2: A 4N sodium hydroxide aqueous solution (512 μL) was added to a solution of ethyl 2-(((tert-butyldimethylsilyl)oxy)methyl)-4-methyl-1-(2,2,2-trifluoroethyl)-1H-imidazole-5-carboxylate (260 mg) obtained in step 1 in ethanol (5 mL), followed by stirring at 100° C. for 2 hours and 30 minutes. The reaction mixture was cooled to room temperature, and 6N hydrochloric acid was added to the reaction mixture to dry and solidify the mixture, thereby obtaining the title compound.

Production Example 23

Methyl (R)-1-(1-(tert-butoxycarbonyl)pyrrolidin-3-yl)-4-chloro-1H-imidazole-5-carboxylate The procedure of Production Example 13 (step 1) was performed except that (S)-1-(tert-butoxycarbonyl)-3-pyrrolidinol was used instead of methanol used in Production Example 13 (step 1), thereby obtaining the title compound (10.61 g, >99% ee).

Production Example 24

Methyl (S)-1-(1-(tert-butoxycarbonyl)pyrrolidin-3-yl)-4-chloro-1H-imidazole-5-carboxylate The procedure of Production Example 13 (step 1) was performed except that (R)-1-(tert-butoxycarbonyl)-3-pyrrolidinol was used instead of methanol used in Production Example 13 (step 1), thereby obtaining the title compound (659 mg, >99% ee).

Production Example 25

Methyl (R)-1-(1-(tert-butoxycarbonyl)pyrrolidin-3-yl)-4-chloro-2-formyl-1H-imidazole-5-carboxylate THE (70 mL) and DMF (3.18 mL) were added to (R)-1-(1-(tert-butoxycarbonyl)pyrrolidin-3-yl)-4-chloro-1H-imidazole-5-carboxylate (3.29 g) obtained in Production Example 23, followed by cooling in an ice-methanol bath. 2,2,6,6-Tetramethylpiperidinyl magnesium chloride and a lithium chloride complex (a 1M THF/toluene solution, 40 mL) were added thereto, and the mixture was stirred for 30 minutes. Water and a 10% phosphoric acid aqueous solution were added to the reaction mixture, and the mixture was extracted with ethyl acetate. The organic layer was washed with a saturated sodium chloride solution and dried over sodium sulfate, followed by evaporating the solvent under reduced pressure. The obtained residue was purified by column chromatography (hexane:ethyl acetate) and concentrated, followed by adding hexane to collect the precipitated solid, thereby obtaining the title compound (2.29 g).

Production Example 26

Methyl 2-formyl-4-iodo-1-methyl-1H-imidazole-5-carboxylate

Step 1: 1-Methyl-1H-imidazole-5-carboxylic acid methyl ester (0.51 g) was dissolved in acetonitrile (25 mL), and N-iodosuccinimide (1.8 g) was added thereto, followed by stirring at 85° C. for 22 hours. N-iodosuccinimide (0.91 g) was further added, and the obtained mixture was heated under reflux for 24 hours. N-iodosuccinimide (1.8 g) was further added, and the mixture was heated under reflux for 6 days, followed by adding ethyl acetate at room temperature. After the obtained mixture was washed with water, a saturated sodium sulfite aqueous solution, and a 20% sodium chloride solution, the organic layer was dried over sodium sulfate. The insoluble matter was filtered off, and the filtrate was concentrated under reduced pressure, followed by purifying the obtained residue by column chromatography (hexane:ethyl acetate=90:10 to 70:30), thereby obtaining 2,5-diiodo-3-methylimidazole-4-carboxylic acid methyl ester (229 mg).

Step 2: A mixture of 2,5-diiodo-3-methylimidazole-4-carboxylic acid methyl ester (102 mg) obtained in step 1, potassium vinyltrifluoroborate (0.035 g), a (1,1'-bis(diphenylphosphino)ferrocene)palladium(II) dichloride dichloromethane adduct (0.013 g), 1,4-dioxane (2 mL), and a 2N sodium carbonate aqueous solution (0.3 mL) was stirred at 90° C. for 2 hours. Potassium vinyltrifluoroborate (0.014 g) and a 2N sodium carbonate aqueous solution (0.1 mL) were further added, and the mixture was stirred at 90° C. for 1 hour, followed by adding water at room temperature. After the mixture was extracted with ethyl acetate, the organic layer was dried over sodium sulfate and concentrated. The obtained residue was purified by column chromatography (hexane:ethyl acetate=90:10 to 30:70), thereby obtaining 5-iodo-3-methyl-2-vinylimidazole-4-carboxylic acid methyl ester (43 mg).

Step 3: A mixture of 5-iodo-3-methyl-2-vinylimidazole-4-carboxylic acid methyl ester (62 mg) obtained in step 2, 1,4-dioxane (1 mL), water (0.2 mL), 2,6-lutidine (0.045 mL), an osmium tetroxide aqueous solution (0.15M, 0.031 mL), and sodium periodate (0.16 g) was stirred at room temperature for 17 hours. The reaction mixture was extracted with ethyl acetate and washed with water and a 20% sodium chloride solution, followed by drying over sodium sulfate. The insoluble matter was filtered off, and the filtrate was concentrated under reduced pressure. The obtained residue was purified by column chromatography (hexane:ethyl acetate=90:10 to 40:60), thereby obtaining the title compound (47 mg).

Production Example 27

1-(3-Aminoazetidin-1-yl)prop-2-en-1-one hydrochloride

Step 1: 3-Boc-aminoazetidine hydrochloride (10 g) was suspended in acetonitrile (120 mL), and a 1M sodium hydrogen carbonate aqueous solution (96 mL) was added thereto at room temperature. A solution of acryloyl chloride (4.7 mL) in acetonitrile (10 mL) was added thereto at ice cooling temperature, and the mixture was stirred at ice cooling temperature for 30 minutes. Water and ethyl acetate were added, and the insoluble matter was removed by filtration. The aqueous layer was separated, and the mixture was extracted with ethyl acetate. The organic layer was dried over sodium sulfate, and the solvent was evaporated. The residue was suspended in a mixture solution of tert-butyl methyl ether (20 mL) and hexane (20 mL), followed by stirring at room temperature for 1 hour. The precipitate was collected by filtration, washed with hexane (80 mL), and dried, thereby obtaining tert-butyl N-(1-prop-2-enoylazetidin-3-yl)carbamate (10.2 g).

Step 2: Tert-butyl N-(1-prop-2-enoylazetidin-3-yl)carbamate (10.2 g) was suspended in acetonitrile (10 mL) and 5N hydrochloric acid (25 mL), followed by stirring at room temperature for 3 hours. After the solution was concentrated, a mixture solution (55 mL, acetone:methanol=10:1) was added, followed by stirring at room temperature for 1 hour. The precipitate was collected by filtration, washed with a mixture solution (50 mL, acetone:methanol=10:1), and dried, thereby obtaining the title compound (5.7 g).

Production Example 28

1-(4-amino-3,3-difluoropyrrolidin-1-yl)prop-2-en-1-one trifluoroacetate

Step 1: Tert-butyl N-(4,4-difluoropyrrolidin-3-yl)carbamate (100 mg) was suspended in THE (2 mL), and N,N-diisopropylethylamine (0.16 mL) was added at room temperature, followed by adding diacrylic anhydride (0.052 mL) at ice cooling temperature. After stirring at ice cooling temperature for 45 minutes, ethyl acetate, water, and a saturated sodium hydrogen carbonate aqueous solution were added thereto to separate the aqueous layer, followed by extraction with ethyl acetate. The organic layer was washed with water and a saturated sodium chloride solution and dried over sodium sulfate, followed by evaporating the solvent. The obtained residue was purified by column chromatography (chloroform:methanol), thereby obtaining tert-butyl N-(4,4-difluoro-1-prop-2-enoyl-pyrrolidin-3-yl)carbamate (121 mg).

Step 2: Tert-butyl N-(4,4-difluoro-1-prop-2-enoyl-pyrrolidin-3-yl)carbamate (26 mg) was dissolved in chloroform (1 mL), and trifluoroacetic acid (0.5 mL) was added at room temperature, followed by stirring at room temperature for 1 hour. After the solution was concentrated, chloroform was added to concentrate the solution again, followed by adding THE to evaporate the solvent, thereby obtaining the title compound (26.8 mg).

Production Example 29

(R)-1-(7-Amino-5-azaspiro[2.4]heptan-5-yl)prop-2-en-1-one trifluoroacetate

Step 1: Tert-butyl N-((7R)-5-azaspiro[2.4]heptan-7-yl)carbamate (100 mg) was dissolved in THE (1 mL), and N,N-diisopropylethylamine (0.16 mL) was added at room temperature, followed by adding diacrylic anhydride (0.054 mL) at ice cooling temperature. After stirring at ice cooling temperature for 10 minutes, ethyl acetate and water were added to separate the aqueous layer, followed by extraction with ethyl acetate. The organic layer was washed with a saturated sodium chloride solution and dried over sodium sulfate, followed by evaporating the solvent. The obtained residue was purified by column chromatography (chloroform:methanol), thereby obtaining tert-butyl N-((7R)-5-prop-2-enoyl-5-azaspiro[2.4]heptan-7-yl)carbamate (108 mg).

Step 2: Tert-butyl N-[(7R)-5-prop-2-enoyl-5-azaspiro[2.4]heptan-7-yl]carbamate (19 mg) was dissolved in chloroform (1 mL), and trifluoroacetic acid (0.5 mL) was added thereto at room temperature, followed by stirring at room temperature for 1 hour and 20 minutes. After the solution was concentrated, chloroform was added to concentrate the solution again, followed by adding THE to evaporate the solvent, thereby obtaining the title compound (19 mg).

Production Example 30

1-((3R,4R)-3-amino-4-methylpyrrolidin-1-yl)prop-2-en-1-one trifluoroacetate

Step 1: Tert-butyl N-((3R,4R)-4-methylpyrrolidin-3-yl) carbamate (100 mg) was dissolved in THE (1 mL), and N,N-diisopropylethylamine (0.17 mL) was added thereto at room temperature, followed by adding diacrylic anhydride (0.058 mL) at ice cooling temperature. After stirring at ice cooling temperature for 10 minutes, ethyl acetate, water, and a saturated sodium hydrogen carbonate aqueous solution were added to separate the aqueous layer, followed by extraction with ethyl acetate. The organic layer was washed with a saturated sodium chloride solution and dried over sodium sulfate, followed by evaporating the solvent. The obtained residue was purified by column chromatography (chloroform:methanol), thereby obtaining tert-butyl N-((3R,4R)-4-methyl-1-prop-2-enoyl-pyrrolidin-3-yl)carbamate (111 mg).

Step 2: Tert-butyl N-[(3R,4R)-4-methyl-1-prop-2-enoyl-pyrrolidin-3-yl]carbamate (35 mg) was dissolved in chloroform (1 mL), and trifluoroacetic acid (0.5 mL) was added at room temperature, followed by stirring at room temperature for 45 minutes. After the solution was concentrated, chloroform was added to concentrate the solution again, followed by adding THF to evaporate the solvent, thereby obtaining the title compound (35 mg).

Production Example 31

Tert-butyl (3R,4R)-3-amino-4-(cyanomethyl)pyrrolidine-1-carboxylate

Step 1: Tert-butyl (3S,4S)-3-hydroxy-4-(hydroxymethyl) pyrrolidine-1-carboxylate (700 mg) was dissolved in dichloromethane (7 mL), and N,N-diisopropylethylamine (1.12 mL) was added thereto at room temperature, followed by adding methanesulfonyl chloride (0.25 mL) at ice cooling temperature. After stirring at ice cooling temperature for 2 hours, chloroform and water were added, and the aqueous layer was separated, followed by extraction with chloroform. The organic layer was washed with a saturated sodium chloride solution and dried over sodium sulfate, followed by evaporating the solvent. The obtained residue was purified by column chromatography (chloroform:methanol), thereby obtaining tert-butyl (3 S,4S)-3-hydroxy-4-(methylsulfonyloxymethyl)pyrrolidine-1-carboxylate (776 mg).

Step 2: Tert-butyl (3S,4S)-3-hydroxy-4-(methylsulfonyloxymethyl)pyrrolidine-1-carboxylate (400 mg) was dissolved in DMSO (4 mL), and sodium cyanide (334 mg) was added thereto at room temperature, followed by stirring at room temperature for 1 hour and 30 minutes. DMSO (4 mL) was further added, and the mixture was stirred at room temperature for 1 hour, followed by stirring at 50° C. overnight. Ethyl acetate, water, and a saturated sodium hydrogen carbonate aqueous solution were added to the reaction solution at room temperature, and the aqueous layer was separated, followed by extraction with ethyl acetate. The organic layer was washed with a saturated sodium chloride solution and dried over sodium sulfate, followed by evaporating the solvent. The obtained residue was purified by column chromatography (chloroform:methanol), thereby obtaining tert-butyl (3R,4S)-3-(cyanomethyl)-4-hydroxypyrrolidine-1-carboxylate (386 mg, 74 wt %).

Step 3: Tert-butyl (3R,4S)-3-(cyanomethyl)-4-hydroxypyrrolidine-1-carboxylate (200 mg) was dissolved in dichloromethane (2 mL), and triethylamine (0.14 mL) was added thereto at room temperature, followed by adding methanesulfonyl chloride (0.056 mL) at ice cooling temperature. After stirring at ice cooling temperature for 20 minutes, chloroform and water were added, and the aqueous layer was separated, followed by extraction with chloroform. The organic layer was washed with a saturated sodium chloride solution and dried over sodium sulfate, followed by evaporating the solvent, thereby obtaining tert-butyl (3R,4S)-3-(cyanomethyl)-4-methylsulfonyloxy-pyrrolidine-1-carboxylate (203 mg).

Step 4: Tert-butyl (3R,4S)-3-(cyanomethyl)-4-methylsulfonyloxy-pyrrolidine-1-carboxylate (199 mg) was dissolved in acetonitrile (2 mL), and tetra-N-butylammonium azido (279 mg) was added thereto at room temperature, followed by stirring at room temperature for 10 minutes, and stirring at 50° C. for 1 hour. The reaction mixture was heated to 80° C. and stirred for 3 hours, and then stirred at 85° C. for 2 hours and 30 minutes, followed by stirring at 90° C. for 1 hour and 30 minutes. After the reaction solution was concentrated, the obtained residue was purified by column chromatography (ethyl acetate:hexane), thereby obtaining tert-butyl (3R,4R)-3-azido-4-(cyanomethyl)pyrrolidine-1-carboxylate (137 mg).

Step 5: Tert-butyl (3R,4R)-3-azido-4-(cyanomethyl)pyrrolidine-1-carboxylate (135 mg) was dissolved in methanol (1 mL) and placed in a nitrogen atmosphere. 10% palladium carbon (23 mg) was added thereto at room temperature, followed by stirring at room temperature in a hydrogen atmosphere for 2 hours. The reaction solution was filtered through celite and washed with methanol, followed by evaporating the solvent, thereby obtaining the title compound (116 mg).

Production Example 32

Tert-butyl (3R,4R)-3-amino-4-(fluoromethyl)pyrrolidine-1-carboxylate

Step 1: Tert-butyl (3S,4S)-3-hydroxy-4-(methylsulfonyloxymethyl)pyrrolidine-1-carboxylate (180 mg) obtained in Production Example 31 (step 1) was dissolved in THE (2 mL), and a solution of 1M tetrabutylammonium fluoride in THE (1.83 mL) was added thereto at room temperature. The mixture was stirred at room temperature for 40 minutes, and then stirred at 50° C. for 30 minutes, followed by stirring at 65° C. overnight. A solution of 1M tetrabutylammonium fluoride in THE (1.83 mL) was further added at room temperature, and the mixture was stirred at 65° C. for 3 hours, followed by adding ethyl acetate and water to the reaction solution at room temperature. The organic layer was washed with water and a saturated sodium chloride solution.

The washed layer was dried over sodium sulfate, and the solvent was evaporated, followed by purifying the obtained residue by column chromatography (chloroform:methanol), thereby obtaining tert-butyl (3R,4S)-3-(fluoromethyl)-4-hydroxy-pyrrolidine-1-carboxylate (62 mg).

Step 2: Tert-butyl (3R,4S)-3-(fluoromethyl)-4-hydroxy-pyrrolidine-1-carboxylate (62 mg) was dissolved in dichloromethane (1.5 mL), and triethylamine (0.059 mL) was added thereto at room temperature, followed by adding methanesulfonyl chloride (0.024 mL) at ice cooling temperature. After stirring at ice cooling temperature for 20 minutes, ethyl acetate and water were added thereto, and the aqueous layer was separated, followed by extraction with ethyl acetate. The organic layer was washed with a saturated sodium hydrogen carbonate aqueous solution and a saturated sodium chloride solution, and dried over sodium sulfate, followed by evaporating the solvent, thereby obtaining tert-butyl (3R,4S)-3-(fluoromethyl)-4-methylsulfonyloxy-pyrrolidine-1-carboxylate (78 mg).

Step 3: Tert-butyl (3R,4S)-3-(fluoromethyl)-4-methylsulfonyloxy-pyrrolidine-1-carboxylate (78 mg) was dissolved in acetonitrile (1.5 mL), and tetra-N-butylammonium azido (112 mg) was added at room temperature, followed by stirring at 80° C. for 3 hours. After a solution of tetra-N-butylammonium azido (75 mg) in acetonitrile (0.5 mL) was further added thereto at room temperature, the mixture was stirred at 80° C. for 1 hour, followed by stirring at 90° C. for 2 hours. Ethyl acetate, water, and a saturated sodium chloride solution were added to the reaction solution at room temperature, and the organic layer was washed with a saturated sodium chloride solution. The washed organic layer was dried over sodium sulfate, and the solvent was evaporated. The obtained residue was purified by column chromatography (ethyl acetate:hexane), thereby obtaining tert-butyl (3R,4R)-3-azido-4-(fluoromethyl)pyrrolidine-1-carboxylate (58 mg).

Step 4: Tert-butyl (3R,4R)-3-azido-4-(fluoromethyl)pyrrolidine-1-carboxylate (58 mg) was dissolved in methanol (1 mL), and placed in a nitrogen atmosphere, followed by adding 10% palladium carbon (13 mg) at room temperature. The mixture was stirred at room temperature in a hydrogen atmosphere for 1 hour and 30 minutes. The reaction solution was filtered through celite and washed with chloroform and methanol, followed by evaporating the solvent. The obtained residue was purified by basic silica gel column chromatography (ethyl acetate:hexane), thereby obtaining the title compound (45 mg).

Production Example 33

Tert-butyl (3R,4R)-3-amino-4-(methoxymethyl) pyrrolidine-1-carboxylate

Step 1: Tert-butyl (3S,4S)-3-hydroxy-4-(methylsulfonyloxymethyl)pyrrolidine-1-carboxylate (200 mg) obtained in Production Example 31 (step 1) was dissolved in methanol (2 mL), and a solution of 25% sodium methoxide in methanol (0.16 mL) was added thereto at room temperature. After the mixture was stirred at room temperature for 40 minutes, the mixture was further stirred at 50° C. for 1 hour and 40 minutes, followed by further adding a solution of 25% sodium methoxide in methanol (0.16 mL) at 50° C. The mixture was stirred at 50° C. for 1 hour for 40 minutes, and then stirred at 65° C. for 2 days. A solution of 25% sodium methoxide in methanol (0.16 mL) was further added at room temperature, and the mixture was stirred at 65° C. for 8 hours. Ethyl acetate and water were added to the reaction solution at room temperature, and the organic layer was separated, followed by extracting the aqueous layer with ethyl acetate. The organic layer was washed with a saturated sodium chloride solution. After the washed organic layer was dried over sodium sulfate, the solvent was evaporated under reduced pressure, followed by purifying the obtained residue by column chromatography (ethyl acetate:hexane), thereby obtaining tert-butyl (3S,4S)-3-hydroxy-4-(methoxymethyl)pyrrolidine-1-carboxylate (81 mg).

Step 2: Tert-butyl (3 S,4S)-3-hydroxy-4-(methoxymethyl) pyrrolidine-1-carboxylate (81 mg) was dissolved in dichloromethane (1.5 mL), and triethylamine (0.073 mL) was added thereto at room temperature, followed by adding methanesulfonyl chloride (0.030 mL) at ice cooling temperature. After stirring at ice cooling temperature for 20 minutes, ethyl acetate and water were added thereto, and the aqueous layer was separated, followed by extraction with ethyl acetate. The organic layer was washed with a saturated sodium chloride solution and dried over sodium sulfate, followed by evaporating the solvent, thereby obtaining tert-butyl (3S,4S)-3-(methoxymethyl)-4-methylsulfonyloxy-pyrrolidine-1-carboxylate (107 mg).

Step 3: Tert-butyl (3S,4S)-3-(methoxymethyl)-4-methylsulfonyloxy-pyrrolidine-1-carboxylate (107 mg) was dissolved in DMF (1.5 mL), and sodium azide (42 mg) was added thereto at room temperature, followed by stirring at 80° C. for 6 hours and 30 minutes, then stirring at room temperature overnight. The reaction solution was again stirred at 80° C. for 5 hours and 20 minutes, and sodium azide (44 mg) was further added thereto at room temperature, followed by stirring at 80° C. for 10 hours, and then stirring at room temperature overnight. Ethyl acetate and water were added to the reaction solution at room temperature, and the aqueous layer was separated, followed by extraction with ethyl acetate. The organic layer was washed with a saturated sodium chloride solution and dried over sodium sulfate, followed by evaporating the solvent. The obtained residue was purified by column chromatography (ethyl acetate:hexane), thereby obtaining tert-butyl (3R,4R)-3-azido-4-(methoxymethyl)pyrrolidine-1-carboxylate (83 mg).

Step 4: Tert-butyl (3R,4R)-3-azido-4-(methoxymethyl) pyrrolidine-1-carboxylate (83 mg) was dissolved in methanol (1 mL), and placed in a nitrogen atmosphere. 10% palladium carbon (13 mg) was added thereto at room temperature, and the mixture was stirred at room temperature in a hydrogen atmosphere for 2 hours. The reaction solution was filtered through celite, and the filtrate was washed with chloroform and methanol, followed by evaporating the solvent. The obtained residue was purified by basic silica gel column chromatography (ethyl acetate: hexane), thereby obtaining the title compound (72 mg).

Production Example 34

Tert-butyl (3R,4R)-3-amino-4-((dimethylamino) methyl)pyrrolidine-1-carboxylate

Step 1: Tert-butyl (3S,4S)-3-hydroxy-4-(hydroxymethyl) pyrrolidine-1-carboxylate (300 mg) was dissolved in DMF (3 mL), and a solution of imidazole (122 mg) and tert-butyldimethylchlorosilane (208 mg) in DMF (0.5 mL) was added thereto at room temperature, followed by stirring at room temperature for 30 minutes. Ethyl acetate and water were added to the reaction solution, and the aqueous layer was separated, followed by extraction with ethyl acetate. The organic layer was washed with a saturated sodium chloride solution and dried over sodium sulfate, followed by evaporating the solvent. The obtained residue was purified by column chromatography (hexane:ethyl acetate, chloroform:methanol), thereby obtaining tert-butyl (3S,4S)-3-((tert-butyl(dimethyl)silyl)oxymethyl)-4-hydroxy-pyrrolidine-1-carboxylate (307 mg).

Step 2: Tert-butyl (3S,4S)-3-((tert-butyl(dimethyl)silyl)oxymethyl)-4-hydroxy-pyrrolidine-1-carboxylate (295 mg) was dissolved in dichloromethane (3 mL), and triethylamine (0.19 mL) was added thereto at room temperature, followed by adding methanesulfonyl chloride (0.078 mL) at ice cooling temperature. After stirring at ice cooling temperature for 10 minutes, ethyl acetate and water were added thereto, and the organic layer was washed with a saturated sodium chloride solution. The washed organic layer was dried over sodium sulfate, and the solvent was evaporated, thereby obtaining tert-butyl (3S,4S)-3-((tert-butyl(dimethyl)silyl)oxymethyl)-4-methylsulfonyloxy-pyrrolidine-1-carboxylate (368 mg).

Step 3: Tert-butyl (3S,4S)-3-((tert-butyl(dimethyl)silyl)oxymethyl)-4-methylsulfonyloxy-pyrrolidine-1-carboxylate (365 mg) was dissolved in DMF (3 mL), and sodium azide (95 mg) was added thereto at room temperature, followed by stirring at 80° C. overnight. Sodium azide (96 mg) was further added thereto at room temperature, followed by stirring at 80° C. overnight. Ethyl acetate and water were added to the reaction solution at room temperature, and the aqueous layer was separated, followed by extraction with ethyl acetate. After the organic layer was washed with a saturated sodium chloride solution, the organic layer was dried over sodium sulfate, and the solvent was evaporated, thereby obtaining tert-butyl (3R,4R)-3-azido-4-((tert-butyl(dimethyl)silyl)oxymethyl)pyrrolidine-1-carboxylate (410 mg).

Step 4: Tert-butyl (3R,4R)-3-azido-4-((tert-butyl(dimethyl)silyl)oxymethyl)pyrrolidine-1-carboxylate (317 mg) was dissolved in THE (2 mL), and a solution of 1M tetrabutylammonium fluoride in THE (0.98 mL) was added thereto at room temperature, followed by stirring at room temperature for 1 hour. Ethyl acetate, water, and a saturated sodium chloride solution were added to the reaction solution at room temperature, and the aqueous layer was separated, followed by extraction with ethyl acetate. The organic layer was washed with a saturated sodium chloride solution and dried over sodium sulfate, followed by evaporating the solvent under reduced pressure. The obtained residue was purified by column chromatography (ethyl acetate:hexane), thereby obtaining tert-butyl (3R,4R)-3-azido-4-(hydroxymethyl)pyrrolidine-1-carboxylate (221 mg).

Step 5: Tert-butyl (3R,4R)-3-azido-4-(hydroxymethyl)pyrrolidine-1-carboxylate (100 mg) was dissolved in dichloromethane (2 mL), and triethylamine (0.086 mL) was added thereto at room temperature, followed by adding methanesulfonyl chloride (0.035 mL) at ice cooling temperature. After stirring at ice cooling temperature for 15 minutes, ethyl acetate and water were added thereto, and the organic layer was washed with a saturated sodium chloride solution. The washed organic layer was dried over sodium sulfate, and the solvent was evaporated, thereby obtaining tert-butyl (3R,4R)-3-azido-4-(methylsulfonyloxymethyl)pyrrolidine-1-carboxylate (133 mg).

Step 6: Tert-butyl (3R,4R)-3-azido-4-(methylsulfonyloxymethyl)pyrrolidine-1-carboxylate (63 mg) was dissolved in DMF (1 mL), and a solution of sodium iodide (8 mg) and 2M dimethylamine in THE (1.03 mL) was added thereto at room temperature. After the mixture was allowed to react at 80° C. for 12 hours in a microwave reactor, DMF (1 mL) and a solution of 2M dimethylamine in THE (0.52 mL) were added thereto, followed by reaction at 80° C. for 6 hours in a microwave reactor. Sodium iodide (8 mg) and a solution of 2M dimethylamine in THE (1.03 mL) were further added thereto, and the resulting product was allowed to react at 80° C. for 12 hours in a microwave reactor, followed by stirring at 80° C. for 9 hours. Ethyl acetate and water were added to the reaction solution at room temperature, and the organic layer was washed with a saturated sodium chloride solution. The washed layer was dried over sodium sulfate, and the solvent was then evaporated, followed by purifying the obtained residue by basic silica gel column chromatography (ethyl acetate:hexane), thereby obtaining tert-butyl (3R,4R)-3-azido-4-((dimethylamino)methyl)pyrrolidine-1-carboxylate (41 mg).

Step 7: Tert-butyl (3R,4R)-3-azido-4-((dimethylamino)methyl)pyrrolidine-1-carboxylate (40 mg) was dissolved in methanol (1 mL), and placed in a nitrogen atmosphere, followed by adding 10% palladium carbon (12 mg) at room temperature. In a hydrogen atmosphere, the mixture was stirred at room temperature for 2 hours. The reaction solution was filtered through celite, and washed with methanol and chloroform, followed by evaporating the solvent. The obtained residue was purified by basic silica gel column chromatography (ethyl acetate:hexane), thereby obtaining the title compound (11 mg).

Production Example 35

N-(1-acryloylazetidin-3-yl)-2-formyl-1-methyl-1H-imidazole-5-carboxamide

Step 1: A mixture of methyl 1-methyl-1H-imidazole-5-carboxylate (0.5 g) and a formaldehyde aqueous solution (37%, 2 mL) was stirred at 140° C. for 2 hours under microwave irradiation. 0.2 g of NaCl was added to the obtained mixture, and the mixture was extracted with ethyl acetate. After the organic layer was concentrated, the obtained residue was purified by column chromatography (ethyl acetate:methanol=99:1 to 90:10), thereby obtaining methyl 2-(hydroxymethyl)-3-methylimidazole-4-carboxylate (0.38 g).

Step 2: Methyl 2-(hydroxymethyl)-3-methylimidazole-4-carboxylate (0.38 g) obtained in step 1 was dissolved in chloroform (8 mL), and manganese dioxide (1.0 g) was added thereto, followed by heating under reflux for 2 hours. After the resulting product was cooled to room temperature, the insoluble matter was filtered off through celite, followed by concentrating the filtrate. The obtained residue was purified by column chromatography (hexane:ethyl acetate=90:10 to 50:50), thereby obtaining methyl 2-formyl-3-methylimidazole-4-carboxylate (0.27 g).

Step 3: Methyl 2-formyl-3-methylimidazole-4-carboxylate (0.32 g) obtained in step 2 was dissolved in THE (1.5 mL), and methanol (1.5 mL) and a 2N sodium hydroxide aqueous solution (2.0 mL) were added thereto. The reaction mixture was stirred at room temperature overnight and concentrated, thereby obtaining a crude product of sodium 2-formyl-3-methylimidazole-4-carboxylate (0.29 g).

Step 4: The crude product of sodium 2-formyl-3-methylimidazole-4-carboxylate obtained in step 3 (0.29 g) was dissolved in DMF (2.0 mL), and 1-(3-aminoazetidin-1-yl)prop-2-en-1-one hydrochloride (0.37 g) obtained in Production Example 27, diisopropylethylamine (0.97 mL), and HATU (0.87 g) were added thereto. After the reaction mixture was stirred at room temperature for 1 hour, water was added thereto, followed by extraction with a mixture solvent of chloroform and methanol (chloroform:methanol=9:1). The organic layer was concentrated, and the obtained residue was purified by column chromatography (chloroform:methanol=96:4 to 90:10), thereby obtaining a purified crude product. The purified crude product was suspended and washed with ethyl acetate, thereby obtaining the title compound (0.25 g).

Production Example 36

Tert-butyl 3-(2-formyl-1,4-dimethyl-1H-imidazole-5-carboxamide)azetidine-1-carboxylate Step 1: N,N-diisopropylethylamine (4.00 mL) and HATU (3.53 g) were added to a solution of 1,4-dimethyl-1H-imidazole-5-carboxylic acid (1.00 g) and 1-Boc-3-aminoazetidine (1.34 mL) in DMF (14 mL), followed by stirring for 100 minutes. Ethyl acetate, water, and a 10% phosphoric acid aqueous solution were added to the reaction mixture to partition the mixture, and the organic layer was washed with water and a saturated sodium chloride solution. The washed layer was dried over sodium sulfate, and the solvent was evaporated under reduced pressure, followed by purifying the obtained residue by column chromatography (hexane:ethyl acetate). After concentration, diisopropyl ether was added thereto, and the obtained solid was collected, thereby obtaining tert-butyl 3-(1,4-dimethyl-1H-imidazole-5-carboxamide)azetidine-1-carboxylate (1.97 g).

Step 2: THE (15.0 mL) and 2,2,6,6-tetramethylpiperidine (1.44 mL) were added to tert-butyl 3-(1,4-dimethyl-1H-imidazole-5-carboxamide)azetidine-1-carboxylate (500 mg) obtained in step 1, followed by cooling with a dry ice-acetone bath. Butyllithium (a 2.6M hexane solution, 4.00 mL) was then added over 15 minutes. While being cooled in a dry ice-acetone bath, the mixture was stirred for 1 hour, and DMF (1.32 mL) was then added thereto, followed by stirring for another 30 minutes. A saturated ammonium chloride aqueous solution was added, and the mixture was heated to room temperature. After extraction with ethyl acetate, the organic layer was washed with a saturated sodium chloride solution and dried over sodium sulfate, followed by evaporating the solvent under reduced pressure. The obtained residue was purified by column chromatography (hexane:ethyl acetate), thereby obtaining the title compound (294 mg).

Production Example 37

Tert-butyl 3-(2-formyl-1-isopropyl-4-methyl-1H-imidazole-5-carboxamide)azetidine-1-carboxylate Step 1: Triphenylphosphine (1.02 g), 2-propanol (237 mg), and DIAD (772 μL) were added to a suspension of ethyl 4-methylimidazole-5-carboxylate (506 mg) in THE (10 mL), and the mixture was stirred at room temperature for 30 minutes. The solution was concentrated under reduced pressure, and the obtained residue was purified by column chromatography (hexane:ethyl acetate=33:67 to 10:90), thereby obtaining ethyl 1-isopropyl-4-methyl-1H-imidazole-5-carboxylate (517 mg).

Step 2: A 4N sodium hydroxide aqueous solution (988 μL) was added to a solution of ethyl 1-isopropyl-4-methyl-1H-imidazole-5-carboxylate (517 mg) obtained in step 1 in ethanol (5 mL), followed by stirring at 85° C. for 1 hour. 6N hydrochloric acid (660 μL) was added to the reaction mixture to dry and solidify it. Dichloromethane (5.0 mL), 1-hydroxybenzotriazole monohydrate (408 mg), 1-Boc-3-aminoazetidine (452 mg), diisopropylethylamine (1.34 mL), and WSC hydrochloride (768 mg) were added thereto, followed by stirring at room temperature for 3 days. Water was added to the reaction mixture, and the mixture was extracted with ethyl acetate, followed by washing the organic layer with a saturated sodium chloride solution. The washed layer was dried over sodium sulfate, and the solvent was evaporated under reduced pressure, followed by purifying the obtained residue by column chromatography (chloroform:methanol=100:0 to 25:1), thereby obtaining tert-butyl 3-(1-isopropyl-4-methyl-1H-imidazole-5-carboxamide)azetidine-1-carboxylate (673 mg).

Step 3: A solution of tert-butyl 3-(1-isopropyl-4-methyl-1H-imidazole-5-carboxamide)azetidine-1-carboxylate (673 mg) obtained in step 2 in THE (15 mL) was cooled in a dry ice-ethanol bath, and butyllithium (a 2.76M hexane solution, 4.5 mL) was added thereto over 15 minutes. While being cooled in a dry ice-ethanol bath, the mixture was stirred for 2 hours, and DMF (1.1 mL) was added thereto, followed by stirring for another 5 minutes. A saturated ammonium chloride aqueous solution was added, and the mixture was heated to room temperature. The mixture was then extracted with ethyl acetate, and the solvent was evaporated under reduced pressure. The obtained residue was purified by column chromatography (hexane:ethyl acetate=20:80 to 0:100-ethyl acetate:methanol=90/10), thereby obtaining the title compound (465 mg).

Production Example 38

Tert-butyl 3-(4-chloro-2-formyl-1-isopropyl-1H-imidazole-5-carboxamide)azetidine-1-carboxylate Step 1: 2-Propanol (800 μL), triphenylphosphine (3.1 g), and DIAD (2.4 mL) were added to a solution of methyl 4-chloro-1H-imidazole-5-carboxylate (1.6 g) obtained in Production Example 12 in THE (30 mL), followed by stirring at room temperature for 30 minutes. The solvent was evaporated under reduced pressure, and the obtained residue was purified by column chromatography (hexane:ethyl acetate), thereby obtaining methyl 4-chloro-1-isopropyl-1H-imidazole-5-carboxylate (1.9 g).

Step 2: A 5N sodium hydroxide aqueous solution (9 mL) was added to a solution of methyl 4-chloro-1-isopropyl-1H-imidazole-5-carboxylate (1.9 g) obtained in step 1 in ethanol (9 mL), followed by stirring at room temperature for 1 hour. After the solvent was evaporated under reduced pressure, 5N hydrochloric acid was added thereto, followed by extraction with ethyl acetate. The organic layer was washed with a saturated sodium chloride solution and dried over sodium sulfate. The solvent was evaporated under reduced pressure, thereby obtaining crude 4-chloro-1-isopropyl-1H-imidazole-5-carboxylic acid (1.8 g).

Step 3: 1-Boc-3-aminoazetidine (1.4 g), N,N-diisopropylethylamine (2.4 mL), and HATU (3.0 g) were added to a solution of 4-chloro-1-isopropyl-1H-imidazole-5-carboxylic acid (1.8 g) obtained in step 2 in DMF (12 mL), followed by stirring at room temperature for 30 minutes. Water was added to the reaction mixture, and the mixture was extracted with ethyl acetate. The organic layer was washed with 1N hydrochloric acid and a saturated sodium chloride solution and dried over sodium sulfate. The solvent was evaporated under reduced pressure, and the obtained residue was purified by column chromatography (chloroform:ethanol), thereby obtaining tert-butyl 3-(4-chloro-1-isopropyl-1H-imidazole-5-carboxamide)azetidine-1-carboxylate (1.8 g).

Step 4: 2,2,6,6-Tetramethylpiperidine (1.03 mL) was added to a solution of tert-butyl 3-(4-chloro-1-isopropyl-1H-imidazole-5-carboxamide)azetidine-1-carboxylate (510 mg) obtained in step 3 in THE (13 mL) in a nitrogen atmosphere, and the mixture was cooled to −78° C. Butyllithium (a 1.55M hexane solution, 3.45 mL) was added dropwise to the reaction mixture, and the mixture was stirred at the same temperature for 1 hour. DMF was added, followed by stirring at −78° C. for another 1 hour. Water and a 10% phosphoric acid aqueous solution were added to the reaction mixture, and the mixture was extracted with ethyl acetate. The organic layer was washed with a saturated sodium chloride solution and dried over sodium sulfate. The solvent was evaporated under reduced pressure, and the obtained residue was purified by column chromatography (hexane: ethyl acetate=100:0 to 0:100), thereby obtaining the title compound (240 mg).

Production Example 39

Tert-butyl 3-(2-formyl-1-methyl-4-phenyl-1H-imidazole-5-carboxamide)azetidine-1-carboxylate Step 1: 1-Boc-3-aminoazetidine (760 mg), N,N-diisopropylethylamine (1.25 mL), WSC hydrochloride (1.06 g), and 1-hydroxybenzotriazole (745 mg) were added to a solution of 4-bromo-1-methyl-2-vinyl-1H-imidazole-5-carboxylic acid (840 mg) obtained in Production Example 18 in dichloromethane (9 mL), followed by stirring at room temperature for 30 minutes. A sodium hydrogen carbonate aqueous solution was added thereto, and the mixture was extracted with chloroform. The organic layer was washed with a saturated sodium chloride solution and dried over sodium sulfate. The solvent was evaporated under reduced pressure, and the obtained residue was purified by column chromatography (hexane:ethyl acetate), thereby obtaining tert-butyl 3-(4-bromo-1-methyl-2-vinyl-1H-imidazole-5-carboxamide)azetidine-1-carboxylate (1.38 g).

Step 2: Water (6.45 mL), sodium periodate (3.06 g), 2,6-lutidine (830 μL), and a 0.15M osmium tetroxide aqueous solution (480 μL) were added to a solution of tert-butyl 3-(4-bromo-1-methyl-2-vinyl-1H-imidazole-5-carboxamide)azetidine-1-carboxylate (1.38 g) obtained in step 1 in 1,4-dioxane (40 mL), followed by stirring at room temperature overnight. Water was added thereto, and the mixture was extracted with ethyl acetate. The organic layer was then washed with a sodium thiosulfate aqueous solution and a saturated sodium chloride solution and dried over sodium sulfate. The solvent was evaporated under reduced pressure, and the obtained residue was purified by column chromatography (hexane:ethyl acetate), thereby obtaining tert-butyl 3-(4-bromo-2-formyl-1-methyl-1H-imidazole-5-carboxamide)azetidine-1-carboxylate (760 mg).

Step 3: A solution of tert-butyl 3-(4-bromo-2-formyl-1-methyl-1H-imidazole-5-carboxamide)azetidine-1-carboxylate (110 mg) obtained in step 2 in 1,4-dioxane (3 mL) was mixed with phenylboronic acid (35 mg), a 2M sodium carbonate aqueous solution (425 L), and a 1,1'-bis(diphenylphosphino) ferrocene-palladium(II) dichloride-dichloromethane complex (23 mg), followed by stirring at 90° C. for 3 hours under microwave irradiation.

Water was added to the reaction mixture, and the mixture was extracted with ethyl acetate.

The organic layer was washed with a saturated sodium chloride solution and dried over sodium sulfate. The solvent was evaporated under reduced pressure, and the obtained residue was purified by column chromatography (hexane: ethyl acetate), thereby obtaining the title compound (84 mg).

Production Example 40

Tert-butyl 3-(4-ethyl-2-formyl-1-methyl-1H-imidazole-5-carboxamide)azetidine-1-carboxylate Step 1: Methyl 2-chloro-3-oxovalerate (840 mg) was added to a solution of methyl hydrazinocarboxylate (482 mg) in THE (10 mL), followed by stirring at room temperature for 19 hours. The reaction mixture was concentrated, and the obtained residue was purified by column chromatography (hexane:ethyl acetate=90:10 to 50:50), thereby obtaining methyl (3E)-2-chloro-3-(methoxycarbonylhydrazono)pentanoate (1.13 g).

Step 2: Triethylamine (291 μL) was added to a solution of methyl (3E)-2-chloro-3-(methoxycarbonylhydrazono)pentanoate (496 mg) obtained in step 1 in acetonitrile (10 mL), followed by stirring at room temperature for 20 minutes. A solution of methylamine in THE (7%, 1.3 mL) and (tert-butyldimethylsilyloxy) acetaldehyde (799 μL) were further added thereto, followed by reaction in a microwave reactor at 150° C. for 20 minutes. The reaction mixture was concentrated, and the obtained residue was purified by column chromatography (hexane:ethyl acetate=80:20 to 50:50), thereby obtaining methyl 2-((tert-butyldimethylsilyl)oxymethyl)-4-ethyl-1-methyl-1H-imidazole-5-carboxylate (587 mg).

Step 3: A 4N sodium hydroxide aqueous solution (1.17 mL) was added to a solution of methyl 2-((tert-butyldimethylsilyl)oxymethyl)-4-ethyl-1-methyl-1H-imidazole-5-carboxylate (587 mg) obtained in step 2 in methanol (5 mL), followed by stirring at 100° C. for 1 hour. 6N hydrochloric acid (790 μL) was added to the reaction mixture, and the mixture was dried and solidified, thereby obtaining 5-ethyl-2-(hydroxymethyl)-3-methyl-imidazole-4-carboxylic acid. This obtained substance was suspended in DMF (2 mL), and 1-hydroxybenzotriazole monohydrate (288 mg), 1-Boc-3-aminoazetidine (320 mg), diisopropylethylamine (958 μL), and WSC hydrochloride (541 mg) were added thereto, followed by stirring at room temperature for 16 hours. Water was added to the reaction mixture, and the mixture was extracted with ethyl acetate. The solvent was evaporated under reduced pressure, and the obtained residue was purified by column chromatography (chloroform:methanol=100:00 to 90:10), thereby obtaining tert-butyl 3-(4-ethyl-2-(hydroxymethyl)-1-methyl-1H-imidazole-5-carboxylate (326 mg).

Step 4: Tert-butyl 3-(4-ethyl-2-(hydroxymethyl)-1-methyl-1H-imidazole-5-carboxylate (62.7 mg) obtained in step 3 was dissolved in ethyl acetate (3 mL), and manganese dioxide (187 mg) was added thereto, followed by heating with stirring at 100° C. for 50 minutes. The insoluble matter was filtered off through celite, and the filtrate was concentrated, thereby obtaining the title compound (55.4 mg).

Production Example 41

Methyl 2-(1-((5-(tert-butyl)-6-chloro-1H-indazol-3-yl)amino)ethyl)-1-methyl-1H-imidazole-5-carboxylate Step 1: Methyl 3-methylimidazole-4-carboxylate (1.0 g) was dissolved in dichloromethane (32 mL), and the solution was cooled to 0° C. Triethylamine (4.4 mL) and acetyl chloride (1.6 mL) were added thereto, followed by stirring for 30 minutes. Water was added to the reaction mixture, and the organic layer was separated, followed by drying over magnesium sulfate and concentrating the dried product. The obtained residue was purified by column chromatography (hexane:ethyl acetate=50:50 to 0:100), thereby obtaining methyl 2-(1-acetoxyvinyl)-1-methyl-1H imidazole-5-carboxylate (0.40 g).

Step 2: Methyl 2-(1-acetoxyvinyl)-1-methyl-1H imidazole-5-carboxylate (0.40 g) obtained in step 1 was dissolved in methanol (3 mL), and an ammonia aqueous solution (28%, 1 mL) was added thereto. The reaction mixture was stirred at room temperature for 30 minutes and concentrated, followed by adding water and ethyl acetate. After the organic layer was separated and concentrated, the obtained residue was purified by column chromatography (hexane: ethyl acetate=80:20 to 30:70), thereby obtaining methyl 2-acetyl-3-methylimidazole-4-carboxylate (0.19 g).

Step 3: Methyl 2-acetyl-3-methylimidazole-4-carboxylate (0.13 g) obtained in step 2 was dissolved in methanol (3.0 mL), and sodium borohydride (0.1 g) was added thereto, followed by stirring at room temperature for 15 minutes. After acetone (1.0 mL) was added to the reaction mixture, the mixture was concentrated. Water was added to the obtained residue, and the mixture was extracted with ethyl acetate. The organic layer was separated, dried over sodium sulfate, and concentrated, thereby obtaining methyl 2-(1-hydroxyethyl)-3-methylimidazole-4-carboxylate.

Step 4: Methyl 2-(1-hydroxyethyl)-3-methylimidazole-4-carboxylate obtained in step 3 was dissolved in dichloromethane (3.0 mL), and thionyl chloride (0.1 mL) was added thereto, followed by stirring at room temperature for 30 minutes. The reaction mixture was poured into saturated sodium bicarbonate water, and the obtained mixture was extracted with chloroform. After the organic layer was dried over sodium sulfate and concentrated, the obtained residue was subjected to column purification (hexane:ethyl acetate=90:10 to 40:60), thereby obtaining methyl 2-(1-chloroethyl)-3-methylimidazole-4-carboxylate (0.12 g).

Step 5: 5-(Tert-butyl)-6-chloro-1H-indazole-3-amine (0.03 g) obtained in Production Example 1 and potassium carbonate (0.05 g) were added to a solution of methyl 2-(1-chloroethyl)-3-methylimidazole-4-carboxylate (0.03 g) obtained in step 4 in DMF (0.2 mL), followed by stirring at room temperature for 2 days. The reaction mixture was diluted with ethyl acetate, and then washed with water. The organic layer was dried over sodium sulfate and concentrated, and the obtained residue was purified by column chromatography (hexane:ethyl acetate=50:50 to 10:90), thereby obtaining the title compound (0.027 g).

Production Example 42

Ethyl 3-(((5-(tert-butyl)-6-chloro-1H-indazol-3-yl)amino)methyl)-4-chloro-1-methyl-1H-pyrazole-5-carboxylate Step 1: N-chlorosuccinimide (0.20 g) was added to a solution of ethyl 1,3-dimethyl-1H-pyrazole-5-carboxylate (0.20 g) in DMF (2.0 mL), followed by stirring at room temperature for 2 hours. The reaction mixture was diluted with ethyl acetate and washed with water. The organic layer was separated, dried over sodium sulfate, and concentrated, thereby obtaining a crude product of ethyl 4-chloro-2,5-dimethyl-pyrazole-3-carboxylate (0.24 g).

Step 2: The crude product of ethyl 4-chloro-2,5-dimethyl-pyrazole-3-carboxylate (0.24 g) obtained in step 1 was dissolved in carbon tetrachloride (5 mL), and N-bromosuccinimide (0.63 g) and 2,2'-azobis(isobutyronitrile) (0.02 g) were added thereto, followed by heating under reflux for 3 hours. After the reaction mixture was cooled to room temperature, the mixture was diluted with ethyl acetate, followed by washing with water and a sodium sulfite aqueous solution. After the organic layer was dried over sodium sulfate, the obtained residue was purified by column chromatography (hexane:ethyl acetate=97:3 to 75:25), thereby obtaining ethyl 5-(bromomethyl)-4-chloro-2-methylpyrazole-3-carboxylate (0.10 g).

Step 3: 5-(Tert-butyl)-6-chloro-1H-indazole-3-amine (0.023 g) obtained in Production Example 1 and potassium carbonate (0.05 g) were added to a solution of ethyl 5-(bromomethyl)-4-chloro-2-methylpyrazole-3-carboxylate (0.10 g) obtained in step 2 in acetonitrile (0.50 mL), followed by stirring at room temperature for 1 day. The reaction mixture was diluted with ethyl acetate, and the insoluble matter was filtered off. After the filtrate was concentrated, the obtained residue was purified by column chromatography (hexane: ethyl acetate=97:3 to 40:60), thereby obtaining the title compound (0.013 g).

Production Example 43

3-(((5-(Tert-butyl)-6-chloro-1H-indazol-3-yl)amino)methyl)-1,4-dimethyl-1H-pyrazole-5-carboxylic acid In Production Example 42 (step 1), N-bromosuccinimide was used instead of N-chlorosuccinimide. Thereafter, Production Example 42 (steps 2 and 3) was performed, and the synthesized ethyl 3-(((5-(tert-butyl)-6-chloro-1H-indazol-3-yl)amino)methyl)-4-bromo-1-methyl-1H-pyrazole-5-carboxylate (0.23 g) was dissolved in 1,4-dioxane (1.0 mL). Methyl boric acid (0.046 g), a potassium phosphate aqueous solution (2N, 0.10 mL), and a (1,1'-bis(diphenylphosphino)ferrocene)palladium(II) dichloride dichloromethane adduct (0.004 g) were added thereto. After the reaction mixture was stirred at 110° C. for 15 hours, methyl boric acid (0.032 g), a potassium phosphate aqueous solution (2N, 0.60 mL), and a (1,1'-bis(diphenylphosphino)ferrocene)palladium(II) dichloride dichloromethane adduct (0.003 g) were added thereto, followed by stirring at 110° C. for another 24 hours. After the reaction mixture was cooled to room temperature, hydrochloric acid (1N) was added thereto to adjust the pH to 2. The obtained mixture was extracted with ethyl acetate, and the organic layer was separated. The separated organic layer was then dried over sodium sulfate and concentrated. The obtained residue was purified by preparative reversed-phase HPLC (water:acetonitrile (0.1% formic acid)), thereby obtaining the title compound (2.1 mg).

Production Example 44

2-(((5-(Tert-butyl)-6-chloro-1H-indazol-3-yl)amino)methyl)-1,4-dimethyl-1H-imidazole-5-carboxylic acid Step 1: O-tert-butyl-N,N'-diisopropylisourea (15.0 g) was added to a solution of 1,4-dimethyl-1H-imidazole-5-carboxylic acid (3.0 g) in dichloromethane (80 mL), followed by stirring at 45° C. overnight. O-tert-butyl-N,N'-diisopropylisourea (700 mg) was further added to the reaction mixture, followed by stirring at 45° C. for 9 hours. The insoluble matter was filtered off, and the solid was washed with hexane/ethyl acetate (2/1) (300 mL). The filtrate was concentrated, and hexane/ethyl acetate (2/1) (90 mL) were added thereto, followed by filtering the precipitated solid.

The filtrate was concentrated, and the obtained residue was purified by column chromatography (hexane:ethyl acetate), thereby obtaining tert-butyl 1,4-dimethyl-1H-imidazole-5-carboxylate (3.5 g).

Step 2: 2,2,6,6-Tetramethylpiperidine (0.65 mL) was added to a solution of tert-butyl 1,4-dimethyl-1H-imidazole-5-carboxylate (500 mg) obtained in step 1 in THE (5.0 mL) in a nitrogen atmosphere, followed by cooling to −78° C. Butyllithium (a 1.55M hexane solution, 3.30 mL) was added dropwise to the reaction mixture, and the mixture was stirred at the same temperature for 3 hours. DMF (0.59 mL) was added thereto, followed by stirring at −78° C. for another 1 hour. Water was added to the reaction mixture, and the mixture was heated to room temperature. A saturated ammonium chloride aqueous solution was added thereto, and the mixture was extracted with ethyl acetate. The organic layer was washed with a saturated sodium chloride solution and dried over sodium sulfate. The solvent was evaporated under reduced pressure, and the obtained residue was purified by column chromatography (hexane:ethyl acetate=100:0 to 80:20), thereby obtaining tert-butyl 2-formyl-1,4-dimethyl-1H-imidazole-5-carboxylate (246 mg).

Step 3: Tert-butyl 2-formyl-1,4-dimethyl-1H-imidazole-5-carboxylate (246 mg) obtained in step 2 was dissolved in dichloromethane (3 mL), and this solution was mixed with 5-(tert-butyl)-6-chloro-1H-indazole-3-amine (245 mg) obtained in Production Example 1, trifluoroacetic acid (168 μL), and sodium triacetoxyborohydride (560 mg), followed by stirring at room temperature for 1 hour. Water and saturated sodium hydrogen carbonate were added to the reaction mixture, and the mixture was extracted with ethyl acetate. The solvent was evaporated under reduced pressure, and the obtained residue was purified by column chromatography (ethyl acetate:methanol=100:0 to 90:10), thereby obtaining tert-butyl 2-(((5-(tert-butyl)-6-chloro-1H-indazol-3-yl)amino)methyl)-1,4-dimethyl-1H-imidazole-5-carboxylate (355 mg).

Step 4: Tert-butyl 2-(((5-(tert-butyl)-6-chloro-1H-indazol-3-yl)amino)methyl)-1,4-dimethyl-1H-imidazole-5-carboxylate (257 mg) obtained in step 3 was dissolved in trifluoroacetic acid (2.0 mL). After 1 hour, the reaction mixture was concentrated under reduced pressure, and ethyl acetate, water, and a 1N sodium hydroxide aqueous solution (595 μL) were added thereto, followed by separating the organic layer. The solvent was evaporated under reduced pressure, thereby obtaining the title compound (223 mg).

Production Example 45

2-(((5-(Tert-butyl)-6-chloro-1H-indazol-3-yl)amino)methyl)-4-(difluoromethyl)-1-methyl-1H-imidazole-5-carboxylic acid Step 1: Dimethyl 2-bromo-1H-imidazole-4,5-dicarboxylate (2.1 g) was dissolved in THE (13 mL), and methanol (0.65 mL) and triphenylphosphine (2.3 g) were added thereto. The obtained mixture was cooled in a water bath, and DIAD (1.7 mL) was slowly added thereto. After the reaction mixture was stirred at room temperature for 20 minutes, water was added, followed by concentrating the reaction mixture. The obtained residue was subjected to column purification (hexane:ethyl acetate=95:5 to 30:70), thereby obtaining dimethyl 2-bromo-1-methylimidazole-4,5-dicarboxylate (2.1 g).

Step 2: Dimethyl 2-bromo-1-methylimidazole-4,5-dicarboxylate (2.1 g) obtained in step 1 was dissolved in THE (25 mL), and diisobutylaluminium hydride (a 1M toluene solution, 10.5 mL) was added at −78° C., followed by stirring for 30 minutes. A potassium sodium tartrate aqueous solution (30%, 50 mL) was added to the reaction mixture, followed by stirring at room temperature for 14 hours. The reaction mixture was extracted with ethyl acetate, and the organic layer was dried over sodium sulfate and then concentrated. The obtained residue was purified by column chromatography (hexane:ethyl acetate=70:30 to 20:80), thereby obtaining methyl 2-bromo-5-formyl-3-methylimidazole-4-carboxylate (1.2 g).

Step 3: Methyl 2-bromo-5-formyl-3-methylimidazole-4-carboxylate (1.2 g) obtained in step 2 was dissolved in dichloromethane (12 mL), and bis(2-methoxyethyl)aminosulfur trifluoride (3.6 mL) was added at room temperature. The reaction mixture was stirred at room temperature for 3 hours, and then cooled in an ice bath. The reaction mixture was cooled to 0° C., and water was added, followed by extraction with chloroform. After the organic layer was dried over sodium sulfate and concentrated, the obtained residue was purified by column chromatography (hexane:ethyl acetate=100:0 to 40:60), thereby obtaining methyl 2-bromo-5-(difluoromethyl)-3-methylimidazole-4-carboxylate (1.1 g).

Step 4: A solution of methyl 2-bromo-5-(difluoromethyl)-3-methylimidazole-4-carboxylate (0.79 g) obtained in step 3 in THE (15 mL) was cooled to −78° C., and isopropyl magnesium chloride (a 2M THE solution, 0.75 mL) was added thereto over 5 minutes. After the reaction mixture was stirred at −78° C. for 40 minutes, DMF (1.2 mL) was added, and the mixture was slowly heated to 0° C. A mixture of 2N hydrochloric acid (3.5 mL) and a saturated ammonium chloride aqueous solution (30 mL) was added to the reaction mixture, and the mixture was extracted with ethyl acetate. After the organic layer was separated, the layer was dried over sodium sulfate, followed by purifying the obtained residue by column chromatography (hexane:ethyl acetate=100:0 to 50:50), thereby obtaining methyl 5-(difluoromethyl)-2-formyl-3-methylimidazole-4-carboxylate (0.50 g).

Step 5: Methyl 5-(difluoromethyl)-2-formyl-3-methylimidazole-4-carboxylate (45 mg) obtained in step 4 and 5-(tert-butyl)-6-chloro-1H-indazole-3-amine (49 mg) obtained in Production Example 1 were dissolved in dichloromethane (1 mL), and TFA (0.032 mL) was added thereto, followed by stirring for 5 minutes. Sodium triacetoxyborohydride (84 mg) was added to the generated suspension, followed by stirring for 30 minutes. The reaction mixture was diluted with ethyl acetate, and then washed with a saturated sodium hydrogen carbonate aqueous solution and water. After the organic layer was separated, the organic layer was dried over sodium sulfate and concentrated. The obtained residue was purified by column chromatography (hexane:ethyl acetate=70:30 to 0:100), thereby obtaining methyl 2-(((5-(tert-butyl)-6-chloro-1H-indazol-3-yl)amino)methyl)-4-(difluoromethyl)-1-methyl-1H-imidazole-5-carboxylate (60 mg).

Step 6: A mixture of methyl 2-(((5-(tert-butyl)-6-chloro-1H-indazol-3-yl)amino)methyl)-4-(difluoromethyl)-1-methyl-1H-imidazole-5-carboxylate (244 mg) obtained in step 5, THE (5 mL), methanol (2.0 mL), and a 2N sodium hydroxide aqueous solution (1.0 mL) was stirred at room temperature for 30 minutes, and 2N hydrochloric acid (1.1 mL) was added thereto. The obtained mixture was extracted with ethyl acetate, and the organic layer was washed with a sodium chloride solution (20%). The washed layer was then dried over sodium sulfate, and the solvent was concentrated under reduced pressure, thereby obtaining a crude product of the title compound (251 mg).

Production Example 46

Tert-butyl 2-(((5-(tert-butyl)-6-chloro-1H-indazol-3-yl)amino)methyl)-4-fluoro-1-methyl-1H-imidazole-5-carboxylate Step 1: Methanol (120 μL), triphenylphosphine (870 mg), and DIAD (660 μL) were added to a solution of methyl 4-fluoro-1H-imidazole-5-carboxylate (400 mg) obtained in Production Example 11 in THE (5 mL), followed by stirring at room temperature for 30 minutes. The solvent was evaporated under reduced pressure, and the obtained residue was purified by column chromatography (hexane:ethyl acetate), thereby obtaining methyl 4-fluoro-1-methyl-1H-imidazole-5-carboxylate (280 mg).

Step 2: A 5N sodium hydroxide aqueous solution (1 mL) was added to a solution of methyl 4-fluoro-1-methyl-1H-imidazole-5-carboxylate (280 mg) obtained in step 1 in ethanol (2 mL), followed by stirring at room temperature for 1 hour. After the solution was evaporated under reduced pressure, 5N hydrochloric acid was added thereto, and the mixture was extracted with ethyl acetate. The organic layer was washed with a saturated sodium chloride solution and dried over sodium sulfate. The solution was evaporated under reduced pressure, thereby obtaining crude 4-fluoro-1-methyl-1H-imidazole-5-carboxylic acid (237 mg).

Step 3: A solution of 4-fluoro-1-methyl-1H-imidazole-5-carboxylic acid (237 mg) obtained in step 2 in THE (10 mL) was mixed with 4-dimethylaminopyridine (400 mg) and di-tert-butyl dicarbonate (720 mg), followed by stirring at 50° C. for 4 hours. Water was added to the reaction mixture, and the mixture was extracted with ethyl acetate. The organic layer was washed with 1N hydrochloric acid, a 0.5N sodium hydroxide aqueous solution, and a saturated sodium chloride solution, and dried over sodium sulfate. The solvent was evaporated under reduced pressure, and the obtained residue was purified by column chromatography (hexane: ethyl acetate), thereby obtaining tert-butyl 4-fluoro-1-methyl-1H-imidazole-5-carboxylate (233 mg).

Step 4: 2,2,6,6-Tetramethylpiperidine (0.811 mL) was added to a solution of tert-butyl 4-fluoro-1-methyl-1H-imidazole-5-carboxylate (233 mg) obtained in step 3 in THE (12 mL) in a nitrogen atmosphere, followed by cooling to −78° C. Butyllithium (a 1.55M hexane solution, 3.78 mL) was added dropwise to the reaction mixture, followed by stirring at the same temperature for 1 hour. DMF (0.47 mL) was added thereto, followed by stirring for another 1 hour at −78° C. Water and a 10% phosphoric acid aqueous solution were added to the reaction mixture, and the mixture was extracted with ethyl acetate. The organic layer was washed with a saturated sodium chloride solution and dried over sodium sulfate. The solvent was evaporated under reduced pressure, and the obtained residue was purified by column chromatography (hexane:ethyl acetate), thereby obtaining tert-butyl 4-fluoro-2-formyl-1-methyl-1H-imidazole-5-carboxylate (84 mg).

Step 5: A solution of tert-butyl 4-fluoro-2-formyl-1-methyl-1H-imidazole-5-carboxylate (84 mg) obtained in step 4 in dichloromethane (1 mL) was mixed with 5-(tert-butyl)-6-chloro-1H-indazole-3-amine (75 mg) obtained in Production Example 1, trifluoroacetic acid (170 μL), and sodium triacetoxyborohydride (142 mg), followed by stirring at room temperature for 15 minutes. A sodium hydrogen carbonate aqueous solution was added to the reaction mixture, and the mixture was extracted with ethyl acetate. The organic layer was washed with a saturated sodium chloride solution and dried over sodium sulfate. The solvent was evaporated under reduced pressure, and the obtained residue was purified by column chromatography (hexane:ethyl acetate), thereby obtaining the title compound (103 mg).

Production Example 47

2-(((5-(Tert-butyl)-6-chloro-1H-indazol-3-yl)amino)methyl)-4-chloro-1-methyl-1H-imidazole-5-carboxylic acid Step 1: A solution of methyl 4-chloro-1-methyl-1H-imidazole-5-carboxylate (1 g) obtained in Production Example 13 (step 1) in carbon tetrachloride (20 mL) was mixed with N-bromosuccinimide (1.3 g) and azobisisobutyronitrile (120 mg) in a nitrogen atmosphere, followed by stirring at 95° C. overnight. After the reaction mixture was filtered, the solution was evaporated under reduced pressure, followed by subjecting the crude product to column purification (hexane: ethyl acetate), thereby obtaining methyl 2-bromo-4-chloro-1-methyl-1H-imidazole-5-carboxylate (930 mg).

Step 2: A solution of 2M isopropyl magnesium chloride in tetrahydrofuran (3.5 mL) was added dropwise to a solution of methyl 2-bromo-4-chloro-1-methyl-1H-imidazole-5-carboxylate (730 mg) obtained in step 1 in tetrahydrofuran (26 mL) at −78° C., followed by stirring at the same temperature for 1 hour. After N,N-dimethylformamide was added dropwise to the reaction mixture, the mixture was heated to −20° C., followed by stirring for another 1 hour. 1N hydrochloric acid was added to the reaction mixture, and the mixture was extracted with ethyl acetate. The organic layer was washed with a saturated sodium chloride solution and dried over sodium sulfate. The solution was evaporated under reduced pressure, and the crude product was subjected to column purification (hexane:ethyl acetate), thereby obtaining methyl 4-chloro-2-formyl-1-methyl-1H-imidazole-5-carboxylate (460 mg).

Step 3: A solution of methyl 4-chloro-2-formyl-1-methyl-1H-imidazole-5-carboxylate (290 mg) obtained in step 2 in dichloromethane (6 mL) was mixed with 5-(tert-butyl)-6-chloro-1H-indazole-3-amine (290 mg) obtained in Production Example 1, trifluoroacetic acid (220 μL), and sodium triacetoxyborohydride (550 mg), followed by stirring at room temperature for 15 minutes. A sodium hydrogen carbonate aqueous solution was added to the reaction mixture, and the mixture was extracted with ethyl acetate. The organic layer was washed with a saturated sodium chloride solution and dried over sodium sulfate. The solvent was evaporated under reduced pressure, and the obtained residue was purified by column chromatography (hexane:ethyl acetate), thereby obtaining methyl 2-(((5-(tert-butyl)-6-chloro-1H-indazol-3-yl)amino)methyl)-4-chloro-1-methyl-1H-imidazole-5-carboxylate (430 mg).

Step 4: A 5N sodium hydroxide aqueous solution (1 mL) was added to a solution of methyl 2-(((5-(tert-butyl)-6-chloro-1H-indazol-3-yl)amino)methyl)-4-chloro-1-methyl-1H-imidazole-5-carboxylate (85 mg) obtained in step 3 in ethanol (1 mL), followed by stirring at room temperature for 1 hour. The reaction mixture was evaporated under reduced pressure, and 5N hydrochloric acid was added thereto, followed by extraction with ethyl acetate. The organic layer was washed with a saturated sodium chloride solution and dried over sodium sulfate. The solution was evaporated under reduced pressure, thereby obtaining the title compound (70 mg).

Production Example 48

Tert-butyl 3-(2-(((5-(tert-butyl)-6-chloro-1H-indazol-3-yl)amino)methyl)-1-isopropyl-4-methyl-1H-imidazole-5-carboxamide)azetidine-1-carboxylate A solution of tert-butyl 3-(2-formyl-1-isopropyl-4-methyl-1H-imidazole-5-carboxamide)azetidine-1-carboxylate (148 mg) obtained in Production Example 37 in dichloromethane (3.0 mL) was mixed with 5-(tert-butyl)-6-chloro-1H-indazole-3-amine (86 mg) obtained in Production Example 1, trifluoroacetic acid (59 μL), and sodium triacetoxyborohydride (246 mg), followed by stirring at room temperature for 1 hour. Water was added to the reaction mixture, and the mixture was extracted with ethyl acetate. The solvent was evaporated under reduced pressure, and the obtained residue was purified by column chromatography (ethyl acetate:methanol=100:0 to 80:20), thereby obtaining the title compound (140 mg).

Production Example 49

Tert-butyl 3-(2-(((5-(tert-butyl)-6-chloro-1H-indazol-3-yl)amino)methyl)-1,4-dimethyl-1H-imidazole-5-carboxamide)azetidine-1-carboxylate Dichloromethane (4.0 mL) and trifluoroacetic acid (40 μL) were added to tert-butyl 3-(2-formyl-1,4-dimethyl-1H-imidazole-5-carboxamide)azetidine-1-carboxylate (55.5 mg) obtained in Production Example 36 and 5-(tert-butyl)-6-chloro-1H-indazole-3-amine (33 mg) obtained in Production Example 1, followed by adding sodium triacetoxyborohydride (60 mg). After stirring at room temperature for 35 minutes, a saturated sodium hydrogen carbonate aqueous solution and ethyl acetate were added to the reaction mixture. The organic layer was separated and dried over sodium sulfate. The solvent was evaporated under reduced pressure, and the obtained residue was purified by column chromatography (hexane:ethyl acetate), thereby obtaining the title compound (71.3 mg).

Production Example 50

Tert-butyl 3-(2-(((5-(tert-butyl)-6-chloro-1H-indazol-3-yl)amino)methyl)-4-(difluoromethyl)-1-isopropyl-1H-imidazole-5-carboxamide)azetidine-1-carboxylate Step 1: Potassium carbonate (20.3 g) and 2-iodopropane (24.9 g) were added to a solution of dimethyl 1H-imidazole-4,5-dicarboxylate (13.5 g) in DMF (135 mL), followed by stirring at 50° C. for 9 hours. Saturated ammonium chloride and water were added to the reaction mixture, and the mixture was extracted with ethyl acetate. The organic layer was washed with a saturated sodium chloride solution. The washed organic layer was dried over sodium sulfate, and the solvent was evaporated under reduced pressure, followed by purifying the obtained residue by column chromatography (hexane:ethyl acetate), thereby obtaining dimethyl 1-isopropyl-1H-imidazole-4,5-dicarboxylate (16.3 g).

Step 2: A solution of dimethyl 1-isopropyl-1H-imidazole-4,5-dicarboxylate (16.3 g) obtained in step 1 in THE (200 mL) was cooled in a dry ice-acetone bath, and a solution of 1M diisobutylaluminium hydride in toluene (79.3 mL) was added thereto. After the reaction, an aqueous solution (200 g) of Rochelle salt (100 g) was added thereto, followed by stirring for 1 hour. The organic layer was separated, and the aqueous layer was extracted with ethyl acetate. The organic layer was dried over sodium sulfate and filtered, followed by evaporating the solvent, thereby obtaining methyl 5-formyl-3-isopropylimidazole-4-carboxylate (14.1 g).

Step 3: Bis(2-methoxyethyl)aminosulfur trifluoride (53.0 mL) was added to a solution of methyl 5-formyl-3-isopropylimidazole-4-carboxylate (12.5 g) obtained in step 2 in dichloromethane (140 mL), followed by stirring at 45° C. for 100 minutes. The reaction mixture was cooled in an ice bath, and water was slowly added thereto. The mixture was extracted with chloroform, and the extract was dried over sodium sulfate. The solvent was evaporated under reduced pressure, and the obtained residue was purified by column chromatography (hexane:ethyl acetate), thereby obtaining methyl 4-(difluoromethyl)-1-isopropyl-1H-imidazole-5-carboxylate (10.3 g).

Step 4: A 5N sodium hydroxide aqueous solution (52 mL) was added to a solution of methyl 4-(difluoromethyl)-1-isopropyl-1H-imidazole-5-carboxylate (10.3 g) obtained in step 3 in ethanol (150 mL), followed by stirring at room temperature for 30 minutes. The reaction mixture was cooled in an ice bath, and 5N hydrochloric acid (80 mL) was added thereto. The mixture was extracted with ethyl acetate, and the organic layer was washed with a saturated sodium chloride solution. The washed layer was dried over sodium sulfate, and the solvent was evaporated under reduced pressure, thereby obtaining 4-(difluoromethyl)-1-isopropyl-1H-imidazole-5-carboxylic acid (9.64 g).

Step 5: 1-Hydroxybenzotriazole monohydrate (8.49 g), 1-Boc-3-aminoazetidine (8.35 mL), diisopropylethylamine (23.2 mL), and WSC hydrochloride (10.2 g) were added to a solution of 4-(difluoromethyl)-1-isopropyl-1H-imidazole-5-carboxylic acid (9.64 g) obtained in step 4 in DMF (90 mL). A reaction was performed at 45° C. for 9 hours. Water was added to the reaction mixture, and the mixture was extracted with ethyl acetate, followed by washing the organic layer with a saturated sodium chloride solution. The washed layer was dried over sodium sulfate, and the solvent was evaporated under reduced pressure. The obtained residue was purified by column chromatography (hexane:ethyl acetate), thereby obtaining tert-butyl 3-(4-(difluoromethyl)-1-isopropyl-1H-imidazole-5-carboxamide)azetidine-1-carboxylate (15.9 g).

Step 6: THE (100 mL) and 2,2,6,6-tetramethylpiperidine (11.9 mL) were added to tert-butyl 3-(4-(difluoromethyl)-1-isopropyl-1H-imidazole-5-carboxamide)azetidine-1-carboxylate (5.0 g) obtained in step 5, followed by cooling in a dry ice-acetone bath. Butyllithium (a 2.6M hexane solution, 33.0 mL) was added dropwise thereto over 15 minutes. While being cooled in a dry ice-acetone bath, the mixture was stirred for 1 hour, and DMF (1.32 mL) was added thereto, followed by further stirring for 30 minutes. A saturated ammonium chloride aqueous solution was added, and the mixture was heated to room temperature. The mixture was extracted with ethyl acetate, and the organic layer was washed with a saturated sodium chloride solution and dried over sodium sulfate, followed by evaporating the solvent under reduced pressure. The obtained residue was purified by column chromatography (hexane:ethyl acetate), thereby obtaining tert-butyl 3-(4-(difluoromethyl)-2-formyl-1-isopropyl-1H-imidazole-5-carboxamide)azetidine-1-carboxylate (3.55 g).

Step 7: Trifluoroacetic acid (396 μL) was added to a solution of tert-butyl 3-(4-(difluoromethyl)-2-formyl-1-isopropyl-1H-imidazole-5-carboxamide)azetidine-1-carboxylate (1.00 g) obtained in step 6 and 5-(tert-butyl)-6-chloro-1H-indazole-3-amine (608 mg) obtained in Production Example 1 in THF (10 mL), followed by stirring at room temperature for 30 minutes. Sodium triacetoxyborohydride (274 mg) was added every 20 minutes 3 times. Thereafter, the mixture was stirred at room temperature for 1 hour. The reaction mixture was cooled in an ice bath, and ethyl acetate and a saturated sodium hydrogen carbonate aqueous solution were added thereto. The organic layer was separated and dried over sodium sulfate. The solvent was evaporated under reduced pressure, and the obtained residue was purified by column chromatography (hexane:ethyl acetate), thereby obtaining the title compound (1.48 g).

Production Example 51

Methyl (R)-1-(1-(tert-butoxycarbonyl)pyrrolidin-3-yl)-2-(((5-(tert-butyl)-6-chloro-1H-indazol-3-yl)amino)methyl)-4-chloro-1H-imidazole-5-carboxylate Trifluoroacetic acid (1.00 mL) was added to a solution of methyl (R)-1-(1-(tert-butoxycarbonyl)pyrrolidin-3-yl)-4-chloro-2-formyl-1H-imidazole-5-carboxylate (2.16 g) obtained in Production Example 25 and 5-(tert-butyl)-6-chloro-1H-indazole-3-amine (1.34 g) obtained in Production Example 1 in THE (30 mL), followed by stirring at room temperature for 30 minutes. Sodium triacetoxyborohydride (600 mg) was added every 60 minutes 5 times. Thereafter, the mixture was stirred at room temperature for 80 minutes. Ethyl acetate and a saturated sodium hydrogen carbonate aqueous solution were added to the reaction mixture, and the organic layer was separated. The separated organic layer was washed with a saturated sodium chloride solution and then dried over sodium sulfate. The solvent was evaporated under reduced pressure, and the obtained residue was purified by column chromatography (chloroform:ethanol), followed by concentrating the resulting product. The obtained solid was collected, thereby obtaining the title compound (2.81 g).

TABLE 1

| | |
|---|---|
| 1 | 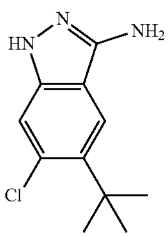 |
| 2 | 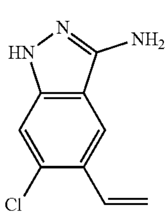 |

TABLE 1-continued

| | |
|---|---|
| 3 | 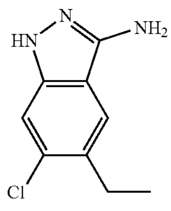 |
| 4 | 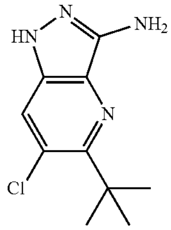 |
| 5 | 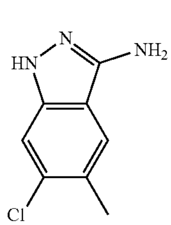 |
| 6 | 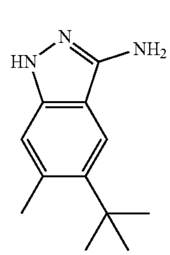 |
| 7 | 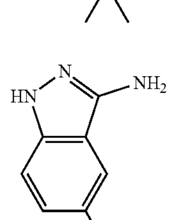 |
| 8 | 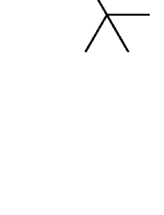 |

TABLE 1-continued
9
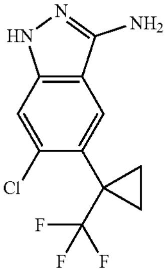 [SMILES: Nc1n[nH]c2cc(Cl)c(C3(C(F)(F)F)CC3)cc12]
10
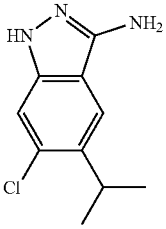
11
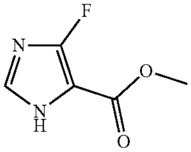
12
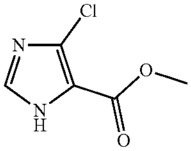
13
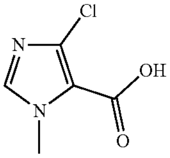
14
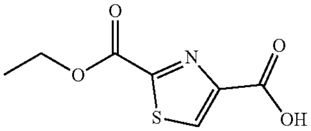
15
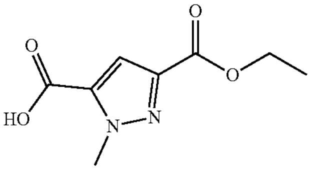
16
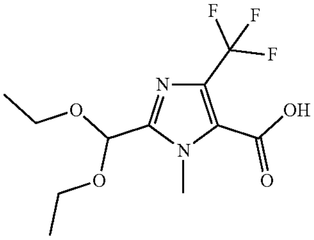 [SMILES: CCOC(OCC)c1nc(C(F)(F)F)c(C(=O)O)n1C]
TABLE 1-continued
17
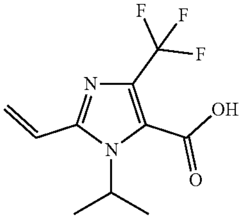 [SMILES: C=Cc1nc(C(F)(F)F)c(C(=O)O)n1C(C)C]
18
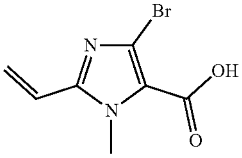
19
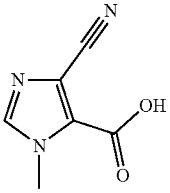
20
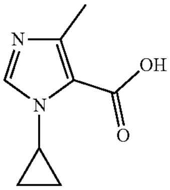
21
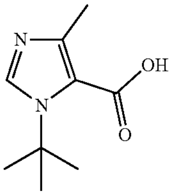
22
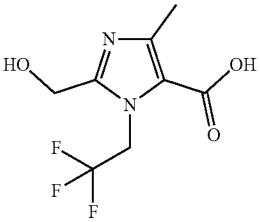 [SMILES: Cc1nc(CO)n(CC(F)(F)F)c1C(=O)O]
23
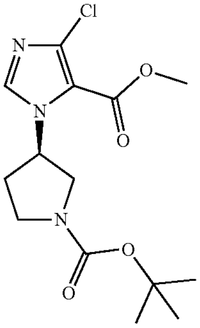 [SMILES: COC(=O)c1c(Cl)ncn1[C@@H]1CCN(C(=O)OC(C)(C)C)C1]

TABLE 1-continued
| | |
|---|---|
| 24 | 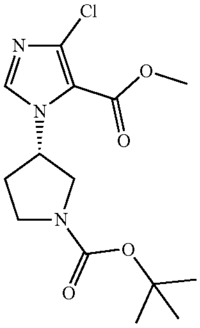 [SMILES: COC(=O)c1c(Cl)ncn1[C@H]1CCN(C(=O)OC(C)(C)C)C1] |
| 25 | 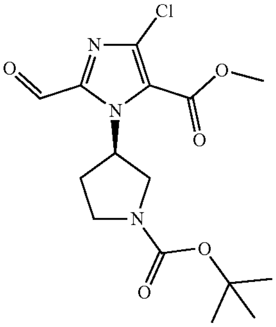 [SMILES: COC(=O)c1c(Cl)nc(C=O)n1[C@@H]1CCN(C(=O)OC(C)(C)C)C1] |
| 26 | 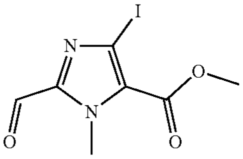 |
| 27 | 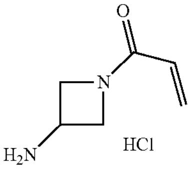 |
TABLE 2
| Pro Ex. | Structure |
|---|---|
| 28 | 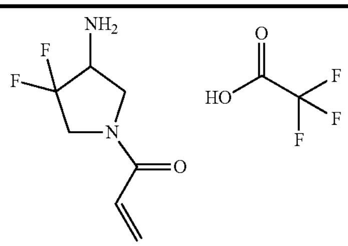 |
TABLE 2-continued
| Pro Ex. | Structure |
|---|---|
| 23 | Chiral<br>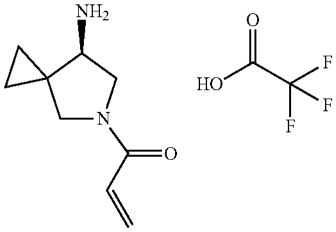 |
| 30 | Chiral<br>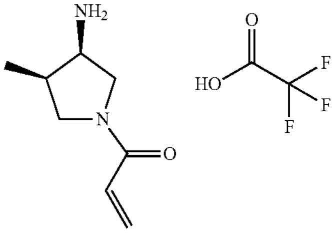 |
| 31 | Chiral<br>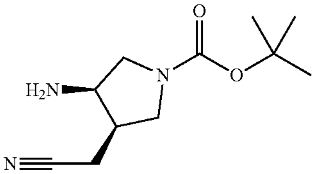 |
| 32 | Chiral<br>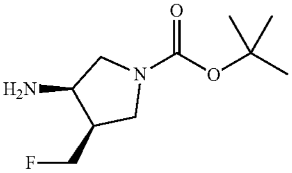 |
| 33 | Chiral<br>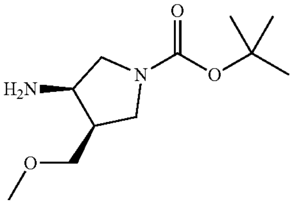 |
| 34 | Chiral<br>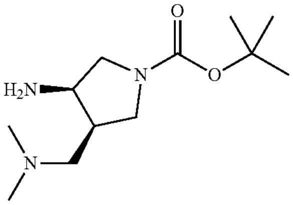 |

TABLE 2-continued
| Pro Ex. | Structure |
|---|---|
| 35 | 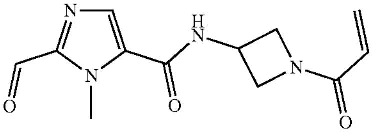 [SMILES: C=CC(=O)N1CC(NC(=O)c2cnc(C=O)n2C)C1] |
| 36 | 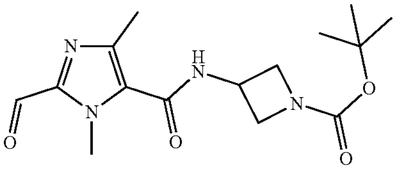 [SMILES: Cc1nc(C=O)n(C)c1C(=O)NC1CN(C(=O)OC(C)(C)C)C1] |
| 37 | 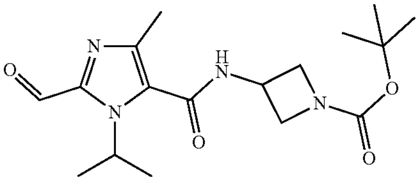 [SMILES: Cc1nc(C=O)n(C(C)C)c1C(=O)NC1CN(C(=O)OC(C)(C)C)C1] |
| 38 | 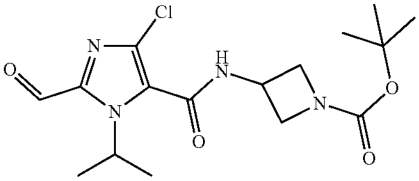 [SMILES: CC(C)n1c(C=O)nc(Cl)c1C(=O)NC1CN(C(=O)OC(C)(C)C)C1] |
| 39 | 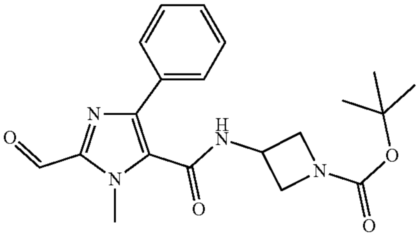 [SMILES: Cn1c(C=O)nc(-c2ccccc2)c1C(=O)NC1CN(C(=O)OC(C)(C)C)C1] |
| 40 | 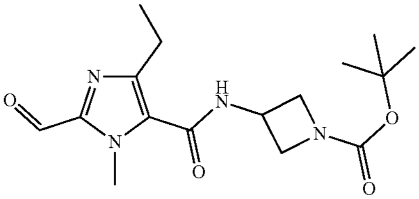 [SMILES: CCc1nc(C=O)n(C)c1C(=O)NC1CN(C(=O)OC(C)(C)C)C1] |
| 41 | 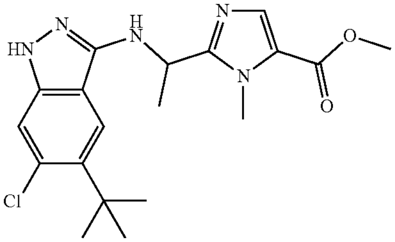 [SMILES: COC(=O)c1cnc(C(C)Nc2n[nH]c3cc(Cl)c(C(C)(C)C)cc23)n1C] |
TABLE 2-continued
| Pro Ex. | Structure |
|---|---|
| 42 | 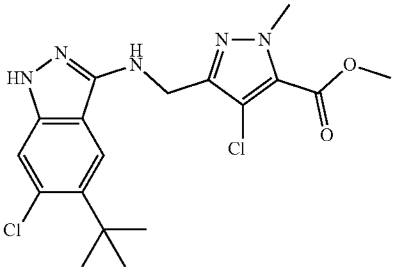 [SMILES: COC(=O)c1c(Cl)c(CNc2n[nH]c3cc(Cl)c(C(C)(C)C)cc23)nn1C] |
| 43 | 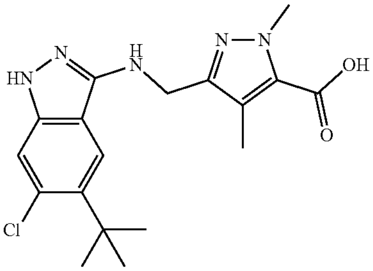 [SMILES: Cc1c(CNc2n[nH]c3cc(Cl)c(C(C)(C)C)cc23)nn(C)c1C(=O)O] |
| 44 | 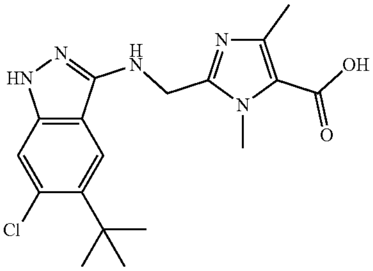 [SMILES: Cc1nc(CNc2n[nH]c3cc(Cl)c(C(C)(C)C)cc23)n(C)c1C(=O)O] |
| 45 | 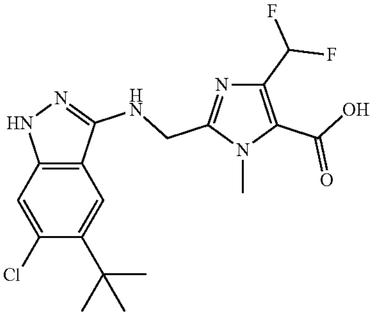 [SMILES: Cn1c(CNc2n[nH]c3cc(Cl)c(C(C)(C)C)cc23)nc(C(F)F)c1C(=O)O] |
| 46 | 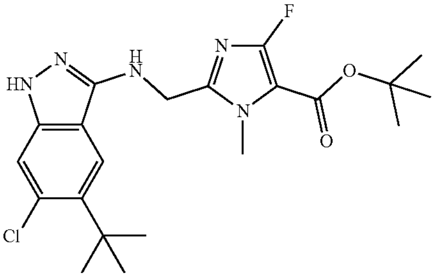 [SMILES: Cn1c(CNc2n[nH]c3cc(Cl)c(C(C)(C)C)cc23)nc(F)c1C(=O)OC(C)(C)C] |

TABLE 2-continued

| Pro Ex. | Structure |
|---|---|
| 47 | 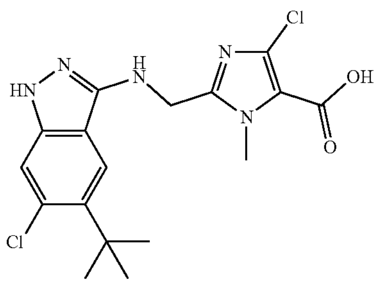 [SMILES: Cn1c(CNc2n[nH]c3cc(Cl)c(C(C)(C)C)cc23)nc(Cl)c1C(=O)O] |
| 48 | 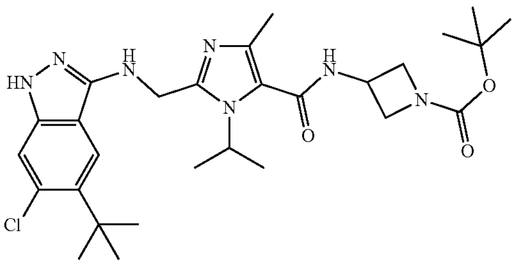 [SMILES: Cc1nc(CNc2n[nH]c3cc(Cl)c(C(C)(C)C)cc23)n(C(C)C)c1C(=O)NC1CN(C(=O)OC(C)(C)C)C1] |
| 49 | 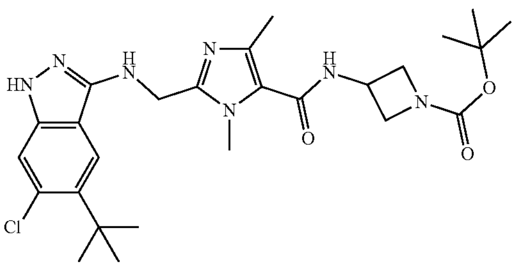 [SMILES: Cc1nc(CNc2n[nH]c3cc(Cl)c(C(C)(C)C)cc23)n(C)c1C(=O)NC1CN(C(=O)OC(C)(C)C)C1] |
| 50 | 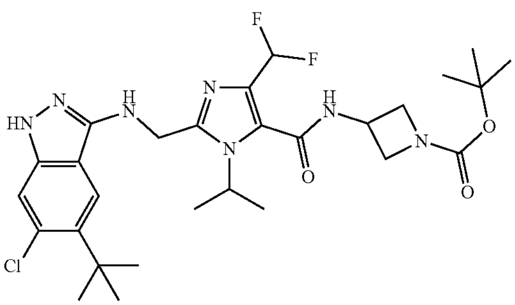 [SMILES: CC(C)n1c(CNc2n[nH]c3cc(Cl)c(C(C)(C)C)cc23)nc(C(F)F)c1C(=O)NC1CN(C(=O)OC(C)(C)C)C1] |
| 51 | 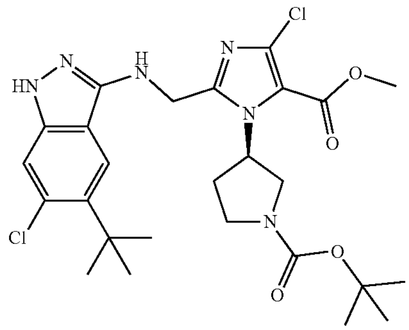 [SMILES: COC(=O)c1c(Cl)nc(CNc2n[nH]c3cc(Cl)c(C(C)(C)C)cc23)n1[C@@H]1CCN(C(=O)OC(C)(C)C)C1] |

(Note that "Pro Ex." means Production Example).

Example 1

N-(1-acryloylazetidin-3-yl)-2-(((5-(tert-butyl)-6-chloro-1H-indazol-3-yl)amino)methyl)-1-methyl-1H-imidazole-5-carboxamide Trifluoroacetic acid (10 μL) was added to a solution of 5-(tert-butyl)-6-chloro-1H-indazole-3-amine (18.3 mg) obtained in Production Example 1 and N-(1-acryloylazetidin-3-yl)-2-formyl-1-methyl-1H-imidazole-5-carboxamide (26.0 mg) obtained in Production Example 35 in dichloromethane (2.00 mL), followed by adding sodium triacetoxyborohydride (30 mg). After stirring at room temperature for 1 hour, a saturated sodium hydrogen carbonate aqueous solution and ethyl acetate were added to the reaction mixture. The organic layer was separated and washed with a saturated sodium chloride solution, followed by drying over sodium sulfate. The solvent was evaporated under reduced pressure, and the obtained residue was purified by column chromatography (chloroform:ethanol), thereby obtaining the title compound (25.2 mg).

Example 2

N-(1-acryloylazetidin-3-yl)-2-(((5-(tert-butyl)-6-chloro-1H-indazol-3-yl)amino)methyl)-4-methylthiazole-5-carboxamide Step 1: N,N-diisopropylethylamine (1.0 mL) and HATU (900 mg) were added to a solution of 2-bromo-4-methylthiazole-5-carboxylic acid (500 mg) and 1-Boc-3-aminoazetidine (344 mg) in DMF (6.0 mL). After stirring at room temperature for 3 hours and 30 minutes, water and a 10% phosphoric acid aqueous solution were added thereto, and the mixture was extracted with ethyl acetate. The organic layer was washed with water and a saturated sodium chloride solution and dried over sodium sulfate. The solvent was evaporated under reduced pressure, and the obtained residue was purified by column chromatography (hexane:ethyl acetate), thereby obtaining tert-butyl 3-(2-bromo-4-methylthiazole-5-carboxamide)azetidine-1-carboxylate (642 mg).

Step 2: A solution of tert-butyl 3-(2-bromo-4-methylthiazole-5-carboxamide)azetidine-1-carboxylate (642 mg) obtained in step 1, tributylvinyltin (600 μL), and tetrakis (triphenylphosphine) palladium(0) (60 mg) in 1,4-dioxane (10 mL) was stirred at 100° C. overnight. After the reaction mixture was concentrated, the obtained residue was purified by column chromatography (hexane:ethyl acetate), thereby obtaining tert-butyl 3-(4-methyl-2-vinylthiazole-5-carboxamide)azetidine-1-carboxylate (516 mg).

Step 3: 2,6-lutidine (372 μL) and sodium periodate (1.37 g) were added to a solution of tert-butyl 3-(4-methyl-2-vinylthiazole-5-carboxamide)azetidine-1-carboxylate (516 mg) obtained in step 2 in 1,4-dioxane (12 mL) and water (3.0 mL). Subsequently, a 1% osmium tetroxide aqueous solution (820 μL) was added thereto. After stirring at room temperature for 4 hours, a sodium thiosulfate aqueous solution was added thereto, and the mixture was extracted with ethyl acetate, followed by washing the organic layer with a saturated sodium chloride solution. The washed organic layer was dried over sodium sulfate, and the solvent was evaporated under reduced pressure. The obtained residue was purified by column chromatography (chloroform:ethanol), thereby obtaining tert-butyl 3-(2-formyl-4-methylthiazole-5-carboxamide)azetidine-1-carboxylate (336 mg).

Step 4: Trifluoroacetic acid (10 μL) was added to a solution of tert-butyl 3-(2-formyl-4-methylthiazole-5-carboxamide)azetidine-1-carboxylate obtained in step 3 and 5-(tert-butyl)-6-chloro-1H-indazole-3-amine (22 mg) obtained in Production Example 1 in dichloromethane (2.00 mL), followed by adding sodium triacetoxyborohydride (30 mg).

After stirring at room temperature for 2 hours, a saturated sodium hydrogen carbonate aqueous solution and ethyl acetate were added to the reaction mixture. The organic layer was separated and washed with a saturated sodium chloride solution, followed by drying over sodium sulfate. The solvent was evaporated under reduced pressure, and the obtained residue was purified by column chromatography (hexane:ethyl acetate), thereby obtaining tert-butyl 3-(2-(((5-(tert-butyl)-6-chloro-1H-indazol-3-yl)amino)methyl)-4-methylthiazole-5-carboxamide)aminoazetidine-1-carboxylate.

Step 5: Trifluoroacetic acid (1 mL) was added to tert-butyl 3-(2-(((5-(tert-butyl)-6-chloro-1H-indazol-3-yl)amino) methyl)-4-methylthiazole-5-carboxamide)aminoazetidine-1-carboxylate obtained in step 4. After trifluoroacetic acid was evaporated off, a solution of THE (4.0 mL), N,N-diisopropylethylamine (500 μL), and 1M acryloyl chloride in acetonitrile (80 μL) was added thereto. A saturated sodium hydrogen carbonate aqueous solution and ethyl acetate were added to the reaction mixture. The organic layer was washed with a saturated sodium chloride solution and dried over sodium sulfate. The solvent was evaporated under reduced pressure, and the obtained residue was purified by column chromatography (chloroform:ethanol), thereby obtaining the title compound (12.5 mg).

Example 3

N-(1-acryloylazetidin-3-yl)-2-(((5-(tert-butyl)-6-chloro-1H-indazol-3-yl)amino)methyl)-1,4-dimethyl-1H-imidazole-5-carboxamide The procedure of Example 2 (steps 4 and 5) was performed except that tert-butyl 3-(2-formyl-1,4-dimethyl-1H-imidazole-5-carboxamide)azetidine-1-carboxylate obtained in Production Example 36 was used instead of tert-butyl 3-(2-formyl-4-methylthiazole-5-carboxamide)azetidine-1-carboxylate used in Example 2 (step 4), thereby obtaining the title compound (45.8 mg).

Example 4

N-(1-acryloylazetidin-3-yl)-2-(1-((5-(tert-butyl)-6-chloro-1H-indazol-3-yl)amino)ethyl)-1-methyl-1H-imidazole-5-carboxamide Step 1: A 2N sodium hydroxide aqueous solution (0.5 mL) was added to a solution of methyl 2-(1-((5-(tert-butyl)-6-chloro-1H-indazol-3-yl)amino)ethyl)-1-methyl-1H-imidazole-5-carboxylate (27 mg) obtained in Production Example 41 in methanol (1.0 mL), followed by stirring at room temperature for 20 minutes. 5N hydrochloric acid (0.2 mL) was added to the reaction mixture, and the solvent was concentrated, thereby obtaining crude 2-[1-[(5-tert-butyl-6-chloro-1H-indazol-3-yl)amino]ethyl]-3-methyl-imidazole-4-carboxylic acid.

Step 2: 1-(3-Aminoazetidin-1-yl)prop-2-en-1-one hydrochloride (13.5 mg) obtained in Production Example 27 and DMF (2.0 mL) were added to crude 2-[1-[(5-tert-butyl-6-chloro-1H-indazol-3-yl)amino]ethyl]-3-methyl-imidazole-4-carboxylic acid obtained in step 1, followed by further adding N,N-diisopropylethylamine (56 μL) and HATU (32 mg). The resulting product was purified by preparative reversed-phase HPLC (water:acetonitrile (0.1% formic acid)), thereby obtaining the title compound (14 mg).

Example 5

N-(1-acryloylazetidin-3-yl)-2-(((5-(tert-butyl)-6-chloro-1H-indazol-3-yl)amino)methyl-d2)-1,4-dimethyl-1H-imidazole-5-carboxamide Step 1: The procedure of Production Example 36 (step 2) was performed except that DMF-d7 was used instead of DMF used in Production Example 36 (step 2), thereby obtaining tert-butyl 3-(2-(formyl-d)-1,4-dimethyl-1H-imidazole-5-carboxamide)azetidine-1-carboxylate (72.5 mg).

Step 2: Dichloromethane (4.0 mL) and trifluoroacetic acid (30 μL) were added to tert-butyl 3-(2-(formyl-d)-1,4-dimethyl-1H-imidazole-5-carboxamide)azetidine-1-carboxylate (36 mg) obtained in step 1 and 5-(tert-butyl)-6-chloro-1H-indazole-3-amine (22 mg) obtained in Production Example 1, followed by adding sodium cyanoborodeuteride (24 mg). After stirring at room temperature for 70 minutes, a saturated sodium hydrogen carbonate aqueous solution and ethyl acetate were added to the reaction mixture. The organic layer was separated, washed with a saturated sodium chloride solution, and dried over sodium sulfate. The solvent was evaporated under reduced pressure, and the obtained residue was purified by column chromatography (chloroform:ethanol), thereby obtaining tert-butyl 3-(2-(((5-(tert-butyl)-6-chloro-1H-indazol-3-yl)amino)methyl-d2)-1,4-dimethyl-1H-imidazole-5-carboxamide)aminoazetidine-1-1-carboxylate (33.9 mg).

Step 3: The procedure of Example 2 (step 5) was performed except that tert-butyl 3-(2-(((5-(tert-butyl)-6-chloro-1H-indazol-3-yl)amino)methyl-d2)-1,4-dimethyl-1H-imidazole-5-carboxamide)aminoazetidine-1-1-carboxylate (33.9 mg) obtained in step 2 was used instead of tert-butyl 3-(2-(((5-(tert-butyl)-6-chloro-1H-indazol-3-yl)amino) methyl)-4-methylthiazole-5-carboxamide)aminoazetidine-1-carboxylate used in Example 2 (step 5), thereby obtaining the title compound (24.2 mg)(deuteration rate: 75%).

Example 6

N-(1-acryloylazetidin-3-yl)-3-(((5-(tert-butyl)-6-chloro-1H-indazol-3-yl)amino)methyl)-4-chloro-1-methyl-1H-pyrazole-5-carboxamide The procedure of Example 4 (steps 1 and 2) was performed except that ethyl 3-(((5-(tert-butyl)-6-chloro-1H-indazol-3-yl)amino)methyl)-4-chloro-1-methyl-1H-pyrazole-5-carboxylate (12.6 mg) obtained in Production Example 42 was used instead of methyl 2-(1-((5-(tert-butyl)-6-chloro-1H-indazol-3-yl)amino)ethyl)-1-methyl-1H-imidazole-5-carboxylate used in Example 4 (step 1), thereby obtaining the title compound (7.7 mg).

Example 7

N-(1-acryloylazetidin-3-yl)-2-(((5-(tert-butyl)-6-chloro-1H-indazol-3-yl)amino)methyl)thiazole-4-carboxamide Step 1: N,N-diisopropylethylamine (672 μL) and HATU (599 mg) were added to a solution of 2-ethoxycarbonylthiazole-4-carboxylic acid (319 mg) obtained in Production Example 14 and 1-Boc-3-aminoazetidine (253 mg) in DMF (2.0 mL). After stirring at room temperature for 30 minutes, water and ethyl acetate were added thereto, and the organic layer was separated. The organic layer was washed with water and a saturated sodium chloride solution and dried over sodium sulfate. The solvent was evaporated under reduced pressure, and the obtained residue was purified by column chromatography (hexane:ethyl acetate), thereby obtaining ethyl 4-((1-tert-butoxycarbonylazetidin-3-yl)carbamoyl)thiazole-2-carboxylate (319 mg).

Step 2: Sodium borohydride (71.2 mg) was added to a solution of ethyl 4-((1-tert-butoxycarbonylazetidin-3-yl)carbamoyl)thiazole-2-carboxylate (319 mg) obtained in step 1 in ethanol (5.0 mL), followed by stirring at room temperature for 1 hour. 2N hydrochloric acid was added to the reaction mixture, and the reaction mixture was concentrated, followed by adding ethyl acetate and a saturated sodium hydrogen carbonate aqueous solution to the obtained residue. The organic layer was separated and dried over sodium sulfate. The solvent was evaporated under reduced pressure, and the obtained residue was purified by column chromatography (ethyl acetate), thereby obtaining tert-butyl 3-((2-(hydroxymethyl)thiazole-4-carbonyl)amino)azetidine-1-carboxylate (260 mg).

Step 3: Manganese dioxide (405 mg) was added to a solution of tert-butyl 3-((2-(hydroxymethyl)thiazole-4-carbonyl)amino)azetidine-1-carboxylate (130 mg) obtained in step 2 in ethyl acetate (10 mL), followed by stirring at 100° C. for 2 hours. The reaction mixture was filtered through celite, and the filtrate was concentrated, thereby obtaining tert-butyl 3-((2-formylthiazole-4-carbonyl)amino)azetidine-1-carboxylate (114 mg).

Step 4: The procedure of Example 2 (steps 4 and 5) was performed except that tert-butyl 3-[(2-formylthiazole-4-carbonyl)amino]azetidine-1-carboxylate (40.2 mg) obtained in step 3 was used instead of tert-butyl 3-(2-formyl-4-methylthiazole-5-carboxamide)azetidine-1-carboxylate used in Example 2 (step 4), thereby obtaining the title compound (26.6 mg).

Example 8

N-(1-acryloylazetidin-3-yl)-2-(((5-(tert-butyl)-6-chloro-1H-indazol-3-yl)amino)methyl)thiazole-5-carboxamide The procedure of Example 2 (steps 1 to 5) was performed except that 2-bromothiazole-5-carboxylic acid was used instead of 2-bromo-4-methylthiazole-5-carboxylic acid used in Example 2 (step 1), thereby obtaining the title compound (4.90 mg).

Example 9

N-(1-acryloylazetidin-3-yl)-3-(((5-(tert-butyl)-6-chloro-1H-indazol-3-yl)amino)methyl)-1-methyl-1H-pyrazole-5-carboxamide Step 1: 1-Hydroxybenzotriazole hydrate (140 mg), triethylamine (400 μL), and WSC hydrochloride (300 mg) were added to a solution of 3-(ethoxycarbonyl)-1-methyl-1H-pyrazole-5-carboxylic acid (150 mg) obtained in Production Example 15 and 1-Boc-3-aminoazetidine (165 mg) in DMF (4.0 mL). After stirring at room temperature overnight, water and ethyl acetate were added thereto. The organic layer was separated and washed with a saturated sodium chloride solution. The washed organic layer was dried over sodium sulfate, and the solvent was evaporated under reduced pressure, followed by purifying the obtained residue by column chromatography (hexane:ethyl acetate), thereby obtaining ethyl 5-((1-(tert-butoxycarbonyl)azetidin-3-yl)carbamoyl)-1-methyl-1H-pyrazole-3-carboxylate (205 mg).

Step 2: A solution of 1M lithium borohydride in THE (600 μL) was added to a solution of ethyl 5-((1-(tert-butoxycarbonyl)azetidin-3-yl)carbamoyl)-1-methyl-1H-pyrazole-3-carboxylate (205 mg) obtained in step 1 in THE (3.0 mL), followed by stirring at 60° C. for 90 minutes. The reaction mixture was cooled to room temperature, and a saturated ammonium chloride aqueous solution and ethyl acetate were added thereto. The organic layer was separated and washed with a saturated sodium chloride solution. The washed organic layer was dried over sodium sulfate, and the solvent was evaporated under reduced pressure, followed by purifying the obtained residue by column chromatography (ethyl acetate:ethanol), thereby obtaining tert-butyl 3-(3-(hydroxymethyl)-1-methyl-1H-pyrazole-5-carboxamide)azetidine-1-carboxylate (167 mg).

Step 3: The procedure of Example 7 (step 3) was performed except that tert-butyl 3-(3-(hydroxymethyl)-1-methyl-1H-pyrazole-5-carboxamide)azetidine-1-carboxylate (167 mg) obtained in step 2 was used instead of tert-butyl 3-((2-(hydroxymethyl)thiazole-4-carbonyl)amino)azetidine-1-carboxylate used in Example 7 (step 3), thereby obtaining tert-butyl 3-(3-formyl-1-methyl-1H-pyrazole-5-carboxamide)azetidine-1-carboxylate (110 mg).

Step 4: The procedure of Example 2 (steps 4 and 5) was performed except that tert-butyl 3-(3-formyl-1-methyl-1H-pyrazole-5-carboxamide)azetidine-1-carboxylate (28 mg) obtained in step 3 was used instead of tert-butyl 3-(2-formyl-4-methylthiazole-5-carboxamide)azetidine-1-carboxylate used in Example 2 (step 4), thereby obtaining the title compound (17.2 mg).

Example 10

N-(1-acryloylazetidin-3-yl)-3-(((5-(tert-butyl)-6-chloro-1H-indazol-3-yl)amino)methyl)-1,4-dimethyl-1H-pyrazole-5-carboxamide The procedure of Example 4 (step 2) was performed except that 3-(((5-(tert-butyl)-6-chloro-1H-indazol-3-yl)amino)methyl)-1,4-dimethyl-1H-pyrazole-5-carboxylic acid obtained in Production Example 43 was used instead of 2-[1-[(5-tert-butyl-6-chloro-1H-indazol-3-yl)amino]ethyl]-3-methyl-imidazole-4-carboxylic acid used in Example 4 (step 2), thereby obtaining the title compound (1.29 mg).

Example 11

N-(1-acryloylazetidin-3-yl)-2-(((5-(tert-butyl)-6-chloro-1H-indazol-3-yl)amino)methyl)-4-methyloxazole-5-carboxamide Step 1: The procedure of Example 2 (step 1) was performed except that 4-methyloxazole-5-carboxylic acid (1.00 g) was used instead of 2-bromo-4-methylthiazole-5-carboxylic acid used in Example 2 (step 1), thereby obtaining tert-butyl 3-(4-methyloxazole-5-carboxamide)azetidine-1-carboxylate (1.64 g).

Step 2: Diisopropylamine (200 μL) was added to a solution of tert-butyl 3-(4-methyloxazole-5-carboxamide)azetidine-1-carboxylate (76 mg) obtained in step 1 in THE (5.0 mL), and the mixture was cooled in a dry ice-acetone bath. Butyllithium (a 1.55M hexane solution, 0.60 mL) was added thereto, followed by stirring for 1 hour. The mixture was heated to an internal temperature of −16° C., and DMF (200 μL) was added thereto. The reaction mixture was then heated to room temperature and stirred overnight. Water and a 10% phosphoric acid aqueous solution were added to the reaction mixture, and the mixture was extracted with ethyl acetate. The organic layer was washed with water and a saturated sodium chloride solution and dried over sodium sulfate. The solvent was evaporated under reduced pressure, and the obtained residue was purified by column chromatography (hexane:ethyl acetate), thereby obtaining tert-butyl 3-(2-formyl-4-methyloxazole-5-carboxamide)azetidine-1-carboxylate (42.2 mg).

Step 3: The procedure of Example 2 (steps 4 and 5) was performed except that tert-butyl 3-(2-formyl-4-methyloxazole-5-carboxamide)azetidine-1-carboxylate (42.2 mg) obtained in step 2 was used instead of tert-butyl 3-(2-formyl-4-methylthiazole-5-carboxamide)azetidine-1-carboxylate used in Example 2 (step 4), thereby obtaining the title compound (41.5 mg).

Example 12

N-(1-acryloylazetidin-3-yl)-2-(((5-(tert-butyl)-6-chloro-1H-indazol-3-yl)amino)methyl)-1-ethyl-4-methyl-1H-imidazole-5-carboxamide Step 1: The procedure of Production Example 37 (steps 1 to 3) was performed except that ethanol was used instead of 2-propanol used in Production Example 37 (step 1), thereby obtaining tert-butyl 3-(2-formyl-1-ethyl-4-methyl-1H-imidazole-5-carboxamide)azetidine-1-carboxylate (428 mg).

Step 2: The procedure of Example 2 (steps 4 and 5) was performed except that tert-butyl 3-(2-formyl-1-ethyl-4-methyl-1H-imidazole-5-carboxamide)azetidine-1-carboxylate (30.9 mg) obtained in step 1 was used instead of tert-butyl 3-(2-formyl-4-methylthiazole-5-carboxamide)azetidine-1-carboxylate used in Example 2 (step 4), thereby obtaining the title compound (18.0 mg).

Example 13

N-(1-acryloylazetidin-3-yl)-2-(((5-(tert-butyl)-6-chloro-1H-indazol-3-yl)amino)methyl)-1-isopropyl-4-methyl-1H-imidazole-5-carboxamide The procedure of Example 2 (steps 4 and 5) was performed except that tert-butyl 3-(2-formyl-1-isopropyl-4-methyl-1H-imidazole-5-carboxamide)azetidine-1-carboxylate (91.0 mg) obtained in Production Example 37 was used instead of tert-butyl 3-(2-formyl-4-methylthiazole-5-carboxamide)azetidine-1-carboxylate used in Example 2 (step 4), thereby obtaining the title compound (31.0 mg).

Example 14

N-(1-acryloylazetidin-3-yl)-2-(((5-(tert-butyl)-6-chloro-1H-indazol-3-yl)amino)methyl)-1-(2-methoxyethyl)-4-methyl-1H-imidazole-5-carboxamide The procedure of Production Example 37 (steps 1 to 3), and then the procedure of Example 2 (steps 4 and 5) were performed except that 2-methoxyethanol was used instead of 2-propanol used in Production Example 37 (step 1), thereby obtaining the title compound (20.7 mg).

Example 15

N-(1-acryloylazetidin-3-yl)-1-benzyl-2-(((5-(tert-butyl)-6-chloro-1H-indazol-3-yl)amino)methyl)-4-methyl-JH-imidazole-5-carboxamide The procedure of Production Example 37 (steps 1 to 3), and then the procedure of Example 2 (steps 4 and 5) were performed except that benzyl alcohol was used instead of 2-propanol used in Production Example 37 (step 1), thereby obtaining the title compound (30.2 mg).

Example 16

N-(1-acryloylazetidin-3-yl)-2-(((5-(tert-butyl)-6-chloro-1H-indazol-3-yl)amino)methyl)-1-(2-(dimethylamino)ethyl)-4-methyl-JH-imidazole-5-carboxamide The procedure of Production Example 37 (steps 1 to 3), and then the procedure of Example 2 (steps 4 and 5) were performed except that N,N-dimethylethanolamine was used instead of 2-propanol used in Production Example 37 (step 1), thereby obtaining the title compound (9.0 mg).

Example 17

N-(1-acryloylazetidin-3-yl)-2-(((5-(tert-butyl)-6-chloro-1H-indazol-3-yl)amino)methyl)-1-cyclopentyl-4-methyl-JH-imidazole-5-carboxamide The procedure of Production Example 37 (steps 1 to 3) and then the procedure of Example 2 (steps 4 and 5) were performed except that cyclopentanol was used instead of 2-propanol used in Production Example 37 (step 1), thereby obtaining the title compound (20.5 mg).

Example 18

N-(1-acryloylazetidin-3-yl)-1-butyl 2-(((5-(tert-butyl)-6-chloro-JH-indazol-3-yl)amino)methyl)-4-methyl-JH-imidazole-5-carboxamide The procedure of Production Example 37 (steps 1 to 3) and then the procedure of Example 2 (steps 4 and 5) were performed except that 1-butanol was used instead of 2-propanol used in Production Example 37 (step 1), thereby obtaining the title compound (18.3 mg).

Example 19

N-(1-acryloylazetidin-3-yl)-2-(((5-(tert-butyl)-6-chloro-1H-indazol-3-yl)amino)methyl)-4-methyl-1-propyl-1H-imidazole-5-carboxamide The procedure of Production Example 37 (steps 1 to 3) and then the procedure of Example 2 (steps 4 and 5) were performed except that 1-propanol was used instead of 2-propanol used in Production Example 37 (step 1), thereby obtaining the title compound (20.5 mg).

Example 20

N-(1-acryloylazetidin-3-yl)-1-(sec-butyl)-2-(((5-(tert-butyl)-6-chloro-1H-indazol-3-yl)amino)methyl)-4-methyl-1H-imidazole-5-carboxamide The procedure of Production Example 37 (steps 1 to 3) and then the procedure of Example 2 (steps 4 and 5) were performed except that 2-butanol was used instead of 2-propanol used in Production Example 37 (step 1), thereby obtaining the title compound (26.3 mg).

Example 21

N-(1-acryloylazetidin-3-yl)-2-(((5-(tert-butyl)-6-chloro-1H-indazol-3-yl)amino)methyl)-1-(difluoromethyl)-4-methyl-1H-imidazole-5-carboxamide Step 1: A suspension of ethyl 4-methyl-1H-imidazole-5-carboxylate (2.0 g) and sodium chlorodifluoroacetate (2.98 g) in 2-propanol was heated to 150° C. with a microwave reactor. After 45 minutes, because the reactor was stopped due to increased internal pressure, the reactor was gradually opened to reduce the pressure. The suspension was again allowed to react at 150° C. for 16 hours. The insoluble matter was filtered off, and the filtrate was concentrated under reduced pressure, followed by purifying the obtained residue by column chromatography (hexane:ethyl acetate), thereby obtaining ethyl 1-(difluoromethyl)-4-methyl-1H-imidazole-5-carboxylate (290 mg).

Step 2: Paraformaldehyde (735 mg) was added to a solution of ethyl 1-(difluoromethyl)-4-methyl-1H-imidazole-5-carboxylate (328 mg) obtained in step 1 in ethanol (5.0 mL), and the mixture was allowed to react at 160° C. for 20 hours with a microwave reactor. The reaction mixture was concentrated, and the obtained residue was purified by column chromatography (hexane:ethyl acetate:methanol), thereby obtaining ethyl 1-(difluoromethyl)-2-(hydroxymethyl)-4-methyl-1H-imidazole-5-carboxylate (55.7 mg).

Step 3: A 4N sodium hydroxide aqueous solution (90 μL) was added to a solution of ethyl 1-(difluoromethyl)-2-(hydroxymethyl)-4-methyl-1H-imidazole-5-carboxylate (55.7 mg) obtained in step 2 in ethanol (2.0 mL), followed by stirring at room temperature overnight. 6N hydrochloric acid (60 μL) was added to the reaction mixture, and the solvent was concentrated, thereby obtaining crude 1-(difluoromethyl)-2-(hydroxymethyl)-4-methyl-1H-imidazole-5-carboxylic acid.

Step 4: 1-Boc-3-aminoazetidine (62 mg), 1-hydroxybenzotriazole hydrate (36.6 mg), DMF (1.0 mL), N,N-diisopropylethylamine (121 μL), and WSC hydrochloride (96.0 mg) were added to crude 1-(difluoromethyl)-2-(hydroxymethyl)-4-methyl-1H-imidazole-5-carboxylic acid obtained in step 3. After stirring at room temperature for 3 days, water and ethyl acetate were added thereto. The organic layer was separated, and the solvent was evaporated under reduced pressure, followed by purifying the obtained residue by column chromatography (chloroform:methanol), thereby obtaining tert-butyl 3-(1-(difluoromethyl)-2-(hydroxymethyl)-4-methyl-1H-imidazole-5-carboxamide)azetidine-1-carboxylate (80.0 mg).

Step 5: The procedure of Example 7 (step 3) was performed except that tert-butyl 3-(1-(difluoromethyl)-2-(hydroxymethyl)-4-methyl-1H-imidazole-5-carboxamide)azetidine-1-carboxylate (23.0 mg) obtained in step 4 was used instead of tert-butyl 3-((2-(hydroxymethyl)thiazole-4-carbonyl)amino)azetidine-1-carboxylate used in Example 7 (step 3), thereby obtaining tert-butyl 3-(1-(difluoromethyl)-2-formyl-4-methyl-1H-imidazole-5-carboxamide)azetidine-1-carboxylate (20.3 mg).

Step 6: The procedure of Example 2 (steps 4 and 5) was performed except that tert-butyl 3-(1-(difluoromethyl)-2-formyl-4-methyl-1H-imidazole-5-carboxamide)azetidine-1-carboxylate (20.3 mg) obtained in step 5 was used instead of tert-butyl 3-(2-formyl-4-methylthiazole-5-carboxamide)azetidine-1-carboxylate used in Example 2 (step 4), thereby obtaining the title compound (3.2 mg).

Example 22

N-(1-acryloylazetidin-3-yl)-2-(((5-(tert-butyl)-6-chloro-1H-indazol-3-yl)amino)methyl)-4-methyl-1-(2,2,2-trifluoroethyl)-1H-imidazole-5-carboxamide The procedure of Example 21 (steps 4 to 6) was performed except that 2-(hydroxymethyl)-4-methyl-1-(2,2,2-trifluoroethyl)-1H-imidazole-5-carboxylic acid (162 mg) obtained in Production Example 22 was used instead of 1-(difluoromethyl)-2-(hydroxymethyl)-4-methyl-1H-imidazole-5-carboxylic acid used in Example 21 (step 4), thereby obtaining the title compound (25.7 mg).

Example 23

N-(1-acryloylazetidin-3-yl)-2-(((5-(tert-butyl)-6-chloro-1H-indazol-3-yl)amino)methyl)-1-cyclopropyl-4-methyl-1H-imidazole-5-carboxamide The procedure of Production Example 36 (steps 1 and 2), and then the procedure of Example 2 (steps 4 and 5), were performed except that 1-cyclopropyl-4-methyl-1H-imidazole-5-carboxylic acid obtained in Production Example 20 was used instead of 1,4-dimethyl-1H-imidazole-5-carboxylic acid used in Production Example 36 (step 1), thereby obtaining the title compound (12.2 mg).

Example 24

N-(1-acryloylazetidin-3-yl)-1-(tert-butyl)-2-(((5-(tert-butyl)-6-chloro-1H-indazol-3-yl)amino)methyl)-4-methyl-1H-imidazole-5-carboxamide The procedure of Production Example 36 (steps 1 and 2), and then the procedure of Example 2 (steps 4 and 5), were performed except that 1-(tert-butyl)-4-methyl-1H-imidazole-5-carboxylic acid obtained in Production Example 21 was used instead of 1,4-dimethyl-1H-imidazole-5-carboxylic acid used in Production Example 36 (step 1), thereby obtaining the title compound (35.0 mg).

Example 25

N-(1-acryloylazetidin-3-yl)-2-(((5-(tert-butyl)-6-chloro-1H-indazol-3-yl)amino)methyl)-1-methyl-4-(trifluoromethyl)-1H-imidazole-5-carboxamide Step 1: 2-(Diethoxymethyl)-1-methyl-4-(trifluoromethyl)-1H-imidazole-5-carboxylic acid (220 mg) obtained in Production Example 16, 1-(3-aminoazetidin-1-yl)prop-2-en-1-one hydrochloride (240 mg) obtained in Production Example 27, and DMF (2.0 mL) were mixed, followed by further adding N,N-diisopropylethylamine (770 μL) and HATU (570 mg). After stirring at room temperature for 1 hour, water (1 mL) was added, and the solvent was evaporated. Water and ethyl acetate were added to the obtained residue. The organic layer was separated and washed with a saturated sodium chloride solution. The washed organic layer was dried over sodium sulfate, and the solvent was evaporated under reduced pressure, followed by purifying the obtained residue by column chromatography (hexane:ethyl acetate), thereby obtaining N-(1-acryloylazetidin-3- yl)-2-(diethoxymethyl)-1-methyl-4-(trifluoromethyl)-1H-imidazole-5-carboxamide (190 mg).

Step 2: THE (5.5 mL), water (3.9 mL), and trifluoroacetic acid (560 μL) were added to N-(1-acryloylazetidin-3-yl)-2-(diethoxymethyl)-1-methyl-4-(trifluoromethyl)-1H-imidazole-5-carboxamide (180 mg) obtained in step 1, followed by stirring at 45° C. for 4 hours. Ethyl acetate was added to the reaction mixture. The organic layer was separated and washed with a saturated sodium hydrogen carbonate aqueous solution and a saturated sodium chloride solution. The washed organic layer was dried over sodium sulfate, and the solvent was evaporated under reduced pressure, thereby obtaining N-(1-acryloylazetidin-3-yl)-2-formyl-1-methyl-4-(trifluoromethyl)-1H-imidazole-5-carboxamide (170 mg).

Step 3: The procedure of Example 1 was performed except that N-(1-acryloylazetidin-3-yl)-2-formyl-1-methyl-4-(trifluoromethyl)-1H-imidazole-5-carboxamide (40 mg) obtained in step 2 was used instead of N-(1-acryloylazetidin-3-yl)-2-formyl-1-methyl-1H-imidazole-5-carboxamide used in Example 1, thereby obtaining the title compound (20.6 mg).

Example 26

N-(1-acryloylazetidin-3-yl)-2-(((5-(tert-butyl)-6-chloro-1H-indazol-3-yl)amino)methyl)-4-iodo-1-methyl-1H-imidazole-5-carboxamide Step 1: Trifluoroacetic acid (30 μL) was added to a solution of 5-(tert-butyl)-6-chloro-1H-indazole-3-amine (35.8 mg) obtained in Production Example 1 and methyl 2-formyl-4-iodo-1-methyl-1H-imidazole-5-carboxylate (47 mg) obtained in Production Example 26 in dichloromethane (1.00 mL), followed by adding sodium triacetoxyborohydride (35 mg) thereto. After stirring at room temperature for 1 hour, water was added to the reaction mixture, and the solvent was evaporated under reduced pressure, followed by purifying the obtained residue by column chromatography (hexane:ethyl acetate), thereby obtaining methyl 2-(((5-(tert-butyl)-6-chloro-1H-indazol-3-yl)amino)methyl)-4-iodo-1-methyl-1H-imidazole-5-carboxylate (23 mg).

Step 2: The procedure of Example 4 (steps 1 and 2) was performed except that methyl 2-(((5-(tert-butyl)-6-chloro-1H-indazol-3-yl)amino)methyl)-4-iodo-1-methyl-1H-imidazole-5-carboxylate (23 mg) obtained in step 1 was used instead of methyl 2-(1-((5-(tert-butyl)-6-chloro-1H-indazol-3-yl)amino)ethyl)-1-methyl-1H-imidazole-5-carboxylate used in Example 4 (step 1), thereby obtaining the title compound (8.2 mg).

Example 27

N-(1-acryloylazetidin-3-yl)-4-bromo-2-(((5-(tert-butyl)-6-chloro-1H-indazol-3-yl)amino)methyl)-1-methyl-1H-imidazole-5-carboxamide Step 1: 1-Hydroxybenzotriazole hydrate (744 mg), N,N-diisopropylethylamine (1.25 mL), and WSC hydrochloride (1.06 g) were added to a solution of 4-bromo-1-methyl-2-vinyl-1H-imidazole-5-carboxylic acid (840 mg) obtained in Production Example 18 and 1-Boc-3-aminoazetidine (759 mg) in dichloromethane (9.0 mL). After stirring at room temperature for 1 hour, water and ethyl acetate were added thereto. The organic layer was separated and washed with a saturated sodium chloride solution. The washed organic layer was dried over sodium sulfate, and the solvent was evaporated under reduced pressure, followed by purifying the obtained residue by column chromatography (hexane:ethyl acetate), thereby obtaining tert-butyl 3-(4-bromo-1-methyl-2-vinyl-1H-imidazole-5-carboxamide)azetidine-1-carboxylate (1.38 g).

Step 2: The procedure of Example 2 (steps 3 to 5) was performed except that tert-butyl 3-(4-bromo-1-methyl-2-vinyl-1H-imidazole-5-carboxamide)azetidine-1-carboxylate (35 mg) obtained in step 1 was used instead of tert-butyl 3-(4-methyl-2-vinylthiazole-5-carboxamide)azetidine-1-carboxylate used in Example 2 (step 3), thereby obtaining the title compound (8.0 mg).

Example 28

N-(1-acryloylazetidin-3-yl)-2-(((5-(tert-butyl)-6-chloro-1H-indazol-3-yl)amino)methyl)-4-cyano-1-methyl-1H-imidazole-5-carboxamide Step 1: 4-Cyano-1-methyl-1H-imidazole-5-carboxylic acid (252 mg) obtained in Production Example 19, 1-Boc-3-aminoazetidine (400 mg), and DMF (3.0 mL) were mixed. N,N-diisopropylethylamine (750 μL) and HATU (750 mg) were further added thereto, followed by stirring at room temperature for 1 hour. Water and ethyl acetate were added to the reaction mixture, and the organic layer was separated and washed with a saturated sodium chloride solution. The washed organic layer was dried over sodium sulfate, and the solvent was evaporated under reduced pressure, followed by purifying the obtained residue by column chromatography (hexane:ethyl acetate), thereby obtaining tert-butyl 3-(4-cyano-1-methyl-1H-imidazole-5-carboxamide)azetidine-1-carboxylate (263 mg).

Step 2: Tert-butyl 3-(4-cyano-1-methyl-1H-imidazole-5-carboxamide)azetidine-1-carboxylate (263 mg) obtained in step 1, THE (7.0 mL), and 2,2,6,6-tetramethylpiperidine (600 μL) were cooled in a dry ice-acetone bath, followed by adding butyllithium (a 1.55M hexane solution, 2.0 mL) thereto over 15 minutes. While being cooled in a dry ice-acetone bath, the mixture was stirred for 2 hours. DMF (350 μL) was then added thereto, followed by stirring for another 1 hour. Water and a 10% phosphoric acid aqueous solution were added, and the mixture was heated to room temperature. The mixture was extracted with ethyl acetate, and the organic layer was washed with a saturated sodium chloride solution and dried over sodium sulfate, followed by evaporating the solvent under reduced pressure. The obtained residue was purified by column chromatography (chloroform:ethanol), thereby obtaining tert-butyl 3-(4-cyano-2-formyl-1-methyl-1H-imidazole-5-carboxamide)azetidine-1-carboxylate (199 mg).

Step 3: The procedure of Example 2 (steps 4 and 5) was performed except that tert-butyl 3-(4-cyano-2-formyl-1-methyl-1H-imidazole-5-carboxamide)azetidine-1-carboxylate (54 mg) obtained in step 2 was used instead of tert-butyl 3-(2-formyl-4-methylthiazole-5-carboxamide)azetidine-1-carboxylate used in Example 2 (step 4), thereby obtaining the title compound (27.3 mg).

Example 29

N-(1-acryloylazetidin-3-yl)-2-(((5-(tert-butyl)-6-chloro-1H-indazol-3-yl)amino)methyl)-4-chloro-1-methyl-1H-imidazole-5-carboxamide Step 1: Sodium chlorite (380 mg) was added to a mixture solution of 2,4-dichloro-1-methyl-1H-imidazole-5-carbaldehyde (500 mg) and amidosulfuric acid (542 mg) in 1,4-dioxane (20 mL) and water (20 mL), followed by stirring at room temperature for 30 minutes. A 10% phosphoric acid aqueous solution and ethyl acetate were added thereto, and the organic layer was separated and washed with a saturated sodium chloride solution. The washed organic layer was dried over sodium sulfate, and the solvent was evaporated under reduced pressure, thereby obtaining 2,4-dichloro-1-methyl-1H-imidazole-5-carboxylic acid (536 mg).

Step 2: The procedure of Example 2 (steps 1 to 5) was performed except that 2,4-dichloro-1-methyl-1H-imidazole-5-carboxylic acid (536 mg) obtained in step 1 was used instead of 2-bromo-4-methylthiazole-5-carboxylic acid used in Example 2 (step 1), thereby obtaining the title compound (63 mg).

Example 30

N-(1-acryloylazetidin-3-yl)-2-(((5-(tert-butyl)-6-chloro-1H-indazol-3-yl)amino)methyl)-4-fluoro-1-methyl-1H-imidazole-5-carboxamide Step 1: The procedure of Production Example 38 (steps 1 to 4) was performed except that methyl 4-fluoro-1H-imidazole-5-carboxylate obtained in Production Example 11 was used instead of methyl 4-chloro-1H-imidazole-5-carboxylate used in Production Example 38 (step 1), and that methanol was used instead of 2-propanol used in Production Example 38 (step 1), thereby obtaining tert-butyl 3-(4-fluoro-2-formyl-1-methyl-1H-imidazole-5-carboxamide) azetidine-1-carboxylate (150 mg).

Step 2: The procedure of Example 2 (steps 4 and 5) was performed except that tert-butyl 3-(4-fluoro-2-formyl-1-methyl-1H-imidazole-5-carboxamide)azetidine-1-carboxylate (75 mg) obtained in step 1 was used instead of tert-butyl 3-(2-formyl-4-methylthiazole-5-carboxamide)azetidine-1-carboxylate used in Example 2 (step 4), thereby obtaining the title compound (55.0 mg).

Example 31

N-(1-acryloylazetidin-3-yl)-2-(((5-(tert-butyl)-6-chloro-1H-indazol-3-yl)amino)methyl)-4-ethyl-1-methyl-1H-imidazole-5-carboxamide The procedure of Example 2 (steps 4 and 5) was performed except that tert-butyl 3-(4-ethyl-2-formyl-1-methyl-1H-imidazole-5-carboxamide)azetidine-1-carboxylate (55.4 mg) obtained in Production Example 40 was used instead of tert-butyl 3-(2-formyl-4-methylthiazole-5-carboxamide) azetidine-1-carboxylate used in Example 2 (step 4), thereby obtaining the title compound (30.5 mg).

Example 32

N-(1-acryloylazetidin-3-yl)-2-(((5-(tert-butyl)-6-chloro-1H-indazol-3-yl)amino)methyl)-1-isopropyl-4-(trifluoromethyl)-1H-imidazole-5-carboxamide Step 1: N,N-diisopropylethylamine (190 μL) and HATU (380 mg) were added to a solution of 1-isopropyl-4-(trifluoromethyl)-2-vinyl-1H-imidazole-5-carboxylic acid (224 mg) obtained in Production Example 17 and 1-Boc-3-aminoazetidine (190 mg) in DMF (3.0 mL). After stirring at room temperature for 1 hour, water and ethyl acetate were added thereto, and the organic layer was separated. The organic layer was washed with water and a saturated sodium chloride solution and dried over sodium sulfate. The solvent was evaporated under reduced pressure, and the obtained residue was purified by column chromatography (hexane: ethyl acetate), thereby obtaining tert-butyl 3-(1-isopropyl-4-(trifluoromethyl)-2-vinyl-1H-imidazole-5-carboxamide) azetidine-1-carboxylate (359 mg).

Step 2: The procedure of Example 2 (steps 3 to 5) was performed except that tert-butyl 3-(1-isopropyl-4-(trifluoromethyl)-2-vinyl-1H-imidazole-5-carboxamide)azetidine-1-carboxylate (49.5 mg) obtained in step 1 was used instead of tert-butyl 3-(4-methyl-2-vinylthiazole-5-carboxamide) azetidine-1-carboxylate used in Example 2 (step 3), thereby obtaining the title compound (28.8 mg).

Example 33

N-(1-acryloylazetidin-3-yl)-2-(((5-(tert-butyl)-6-chloro-1H-indazol-3-yl)amino)methyl)-4-(difluoromethyl)-1-isopropyl-1H-imidazole-5-carboxamide The procedure of Example 2 (step 5) was performed except that tert-butyl 3-(2-(((5-(tert-butyl)-6-chloro-1H-indazol-3-yl)amino)methyl)-4-(difluoromethyl)-1-isopropyl-1H-imidazole-5-carboxamide)azetidine-1-carboxylate (1.48 g) obtained in Production Example 50 was used instead of tert-butyl 3-(2-(((5-(tert-butyl)-6-chloro-1H-indazol-3-yl) amino)methyl)-4-methylthiazole-5-carboxamide)aminoazetidine-1-carboxylate used in Example 2 (step 5), thereby obtaining the title compound (503 mg).

Example 34

N-(1-acryloylazetidin-3-yl)-2-(((5-(tert-butyl)-6-chloro-1H-indazol-3-yl)amino)methyl)-4-fluoro-1-isopropyl-1H-imidazole-5-carboxamide Step 1: The procedure of Production Example 38 (steps 1 to 4) was performed except that methyl 4-fluoro-1H-imidazole-5-carboxylate obtained in Production Example 11 was used instead of methyl 4-chloro-1H-imidazole-5-carboxylate used in Production Example 38 (step 1), thereby obtaining tert-butyl 3-(4-fluoro-2-formyl-1-isopropyl-1H-imidazole-5-carboxamide)azetidine-1-carboxylate (150 mg).

Step 2: The procedure of Example 2 (steps 4 and 5) was performed except that tert-butyl 3-(4-fluoro-2-formyl-1-isopropyl-1H-imidazole-5-carboxamide)azetidine-1-carboxylate (107 mg) obtained in step 1 was used instead of tert-butyl 3-(2-formyl-4-methylthiazole-5-carboxamide) azetidine-1-carboxylate used in Example 2 (step 4), thereby obtaining the title compound (65 mg).

Example 35

N-(1-acryloylazetidin-3-yl)-2-(((5-(tert-butyl)-6-chloro-1H-indazol-3-yl)amino)methyl)-4-chloro-1-isopropyl-1H-imidazole-5-carboxamide The procedure of Example 2 (steps 4 and 5) was performed except that tert-butyl 3-(4-chloro-2-formyl-1-isopropyl-1H-imidazole-5-carboxamide)azetidine-1-carboxylate (111 mg) obtained in Production Example 38 was used instead of tert-butyl 3-(2-formyl-4-methylthiazole-5-carboxamide)azetidine-1-carboxylate used in Example 2 (step 4), thereby obtaining the title compound (64 mg).

Example 36

N-(1-acryloylazetidin-3-yl)-2-(((5-(tert-butyl)-6-chloro-1H-indazol-3-yl)amino)methyl-d2)-4-(difluoromethyl)-1-isopropyl-1H-imidazole-5-carboxamide Step 1: The procedure of Production Example 50 (step 6) was performed except that DMF-d7 was used instead of DMF used in Production Example 50 (step 6), thereby obtaining tert-butyl 3-(4-(difluoromethyl)-2-(formyl-d)-1-isopropyl-1H-imidazole-5-carboxamide)azetidine-1-carboxylate (165 mg).

Step 2: Methanol-d4 (1 mL) was added to tert-butyl 3-(4-(difluoromethyl)-2-(formyl-d)-1-isopropyl-1H-imidazole-5-carboxamide)azetidine-1-carboxylate (77 mg) obtained in step 1 and 5-(tert-butyl)-6-chloro-1H-indazole-3-amine (35 mg) obtained in Production Example 1 to dissolve them. The solvent was then evaporated under reduced pressure. Methanol-d4 (1 mL) was added to the obtained residue again to dissolve the residue, followed by evaporating the solvent under reduced pressure. Dichloromethane (3.0 mL) and trifluoroacetic acid-d (40 μL) were added to the obtained residue, and sodium cyanoborodeuteride (22 mg) was added thereto. After stirring at room temperature for 50 minutes, a saturated sodium hydrogen carbonate aqueous solution and ethyl acetate were added to the reaction mixture. The organic layer was separated and washed with a saturated sodium chloride solution and dried over sodium sulfate. The solvent was evaporated under reduced pressure, and the obtained residue was purified by column chromatography (chloroform:ethanol), thereby obtaining tert-butyl 3-(2-(((5-(tert-butyl)-6-chloro-1H-indazol-3-yl)amino)methyl-d2)-4-(difluoromethyl)-1-isopropyl-1H-imidazole-5-carboxamide)azetidine-1-carboxylate (67.8 mg).

Step 3: The procedure of Example 2 (step 5) was performed except that tert-butyl 3-(2-(((5-(tert-butyl)-6-chloro-1H-indazol-3-yl)amino)methyl-d2)-4-(difluoromethyl)-1-isopropyl-1H-imidazole-5-carboxamide)azetidine-1-carboxylate (67.8 mg) obtained in step 2 was used instead of tert-butyl 3-(2-(((5-(tert-butyl)-6-chloro-1H-indazol-3-yl)amino)methyl)-4-methylthiazole-5-carboxamide)aminoazetidine-1-carboxylate used in Example 2 (step 5), thereby obtaining the title compound (45.0 mg)(Deuteration Rate>95%).

Example 37

N-(1-acryloylazetidin-3-yl)-2-(((6-chloro-5-methyl-1H-indazol-3-yl)amino)methyl)-1-methyl-1H-imidazole-5-carboxamide The procedure of Example 1 was performed except that 6-chloro-5-methyl-1H-indazole-3-amine obtained in Production Example 5 was used instead of 5-(tert-butyl)-6-chloro-1H-indazole-3-amine used in Example 1, thereby obtaining the title compound (15.9 mg).

Example 38

N-(1-acryloylazetidin-3-yl)-2-(((6-chloro-5-vinyl 1H-indazol-3-yl)amino)methyl)-1-methyl-1H-imidazole-5-carboxamide The procedure of Example 1 was performed except that 6-chloro-5-vinyl-1H-indazole-3-amine obtained in Production Example 2 was used instead of 5-(tert-butyl)-6-chloro-1H-indazole-3-amine used in Example 1, thereby obtaining the title compound (14.8 mg).

Example 39

N-(1-acryloylazetidin-3-yl)-2-(((6-chloro-5-ethyl-1H-indazol-3-yl)amino)methyl)-1-methyl-1H-imidazole-5-carboxamide The procedure of Example 1 was performed except that 6-chloro-5-ethyl-1H-indazole-3-amine obtained in Production Example 3 was used instead of 5-(tert-butyl)-6-chloro-1H-indazole-3-amine used in Example 1, thereby obtaining the title compound (35.2 mg).

Example 40

N-(1-acryloylazetidin-3-yl)-2-(((5-(tert-butyl)-6-chloro-1H-pyrazolo[4,3-b]pyridin-3-yl)amino)methyl)-1-methyl-1H-imidazole-5-carboxamide The procedure of Example 1 was performed except that 5-(tert-butyl)-6-chloro-1H-pyrazolo[4,3-b]pyridine-3-amine obtained in Production Example 4 was used instead of 5-(tert-butyl)-6-chloro-1H-indazole-3-amine used in Example 1, thereby obtaining the title compound (21.4 mg).

Example 41

N-(1-acryloylazetidin-3-yl)-2-(((5-(tert-butyl)-6-methyl-1H-indazol-3-yl)amino)methyl)-1,4-dimethyl-1H-imidazole-5-carboxamide The procedure of Example 2 (steps 4 and 5) was performed except that 5-(tert-butyl)-6-methyl-1H-indazole-3-amine obtained in Production Example 6 was used instead of 5-(tert-butyl)-6-chloro-1H-indazole-3-amine used in Example 2 (step 4), and that tert-butyl 3-(2-formyl-1,4-dimethyl-1H-imidazole-5-carboxamide)azetidine-1-carboxylate obtained in Production Example 36 was used instead of tert-butyl 3-(2-formyl-4-methylthiazole-5-carboxamide)azetidine-1-carboxylate used in Example 2 (step 4), thereby obtaining the title compound (18.6 mg).

Example 42

N-(1-acryloylazetidin-3-yl)-2-(((5-(tert-butyl)-1H-indazol-3-yl)amino)methyl)-1-isopropyl-4-methyl-1H-imidazole-5-carboxamide The procedure of Example 2 (steps 4 and 5) was performed except that 5-(tert-butyl)-1H-indazole-3-amine obtained in Production Example 7 was used instead of 5-(tert-butyl)-6-chloro-1H-indazole-3-amine used in Example 2 (step 4), and that tert-butyl 3-(2-formyl-1-isopropyl-4-methyl-1H-imidazole-5-carboxamide)azetidine-1-carboxylate obtained in Production Example 37 was used instead of tert-butyl 3-(2-formyl-4-methylthiazole-5-carboxamide)azetidine-1-carboxylate used in Example 2 (step 4), thereby obtaining the title compound (29.1 mg).

Example 43

N-(1-acryloylazetidin-3-yl)-4-chloro-2-(((6-chloro-5-(3,3,3-trifluoroprop-1-en-2-yl)-1H-indazol-3-yl)amino)methyl)-1-isopropyl-1H-imidazole-5-carboxamide The procedure of Example 2 (steps 4 and 5) was performed except that 6-chloro-5-(3,3,3-trifluoroprop-1-en-2- yl)-1H-indazole-3-amine obtained in Production Example 8 was used instead of 5-(tert-butyl)-6-chloro-1H-indazole-3-amine used in Example 2 (step 4), and that tert-butyl 3-(4-chloro-2-formyl-1-isopropyl-1H-imidazole-5-carboxamide)azetidine-1-carboxylate obtained in Production Example 38 was used instead of tert-butyl 3-(2-formyl-4-methylthiazole-5-carboxamide)azetidine-1-carboxylate used in Example 2 (step 4), thereby obtaining the title compound (8.0 mg).

Example 44

N-(1-acryloylazetidin-3-yl)-4-chloro-2-(((6-chloro-5-(-(trifluoromethyl)cyclopropyl)-1H-indazol-3-yl)amino)methyl)-1-isopropyl-1H-imidazole-5-carboxamide The procedure of Example 2 (steps 4 and 5) was performed except that 6-chloro-5-(1-(trifluoromethyl)cyclopropyl)-1H-indazole-3-amine obtained in Production Example 9 was used instead of 5-(tert-butyl)-6-chloro-1H-indazole-3-amine used in Example 2 (step 4), and that tert-butyl 3-(4-chloro-2-formyl-1-isopropyl-1H-imidazole-5-carboxamide)azetidine-1-carboxylate obtained in Production Example 38 was used instead of tert-butyl 3-(2-formyl-4-methylthiazole-5-carboxamide)azetidine-1-carboxylate used in Example 2 (step 4), thereby obtaining the title compound (10.0 mg).

Example 45

N-(1-acryloylazetidin-3-yl)-4-chloro-2-(((6-chloro-5-isopropyl-1H-indazol-3-yl)amino)methyl)-1-isopropyl-1H-imidazole-5-carboxamide The procedure of Example 2 (steps 4 and 5) was performed except that 6-chloro-5-isopropyl-1H-indazole-3-amine obtained in Production Example 10 was used instead of 5-(tert-butyl)-6-chloro-1H-indazole-3-amine used in Example 2 (step 4), and that tert-butyl 3-(4-chloro-2-formyl-1-isopropyl-1H-imidazole-5-carboxamide)azetidine-1-carboxylate obtained in Production Example 38 was used instead of tert-butyl 3-(2-formyl-4-methylthiazole-5-carboxamide)azetidine-1-carboxylate used in Example 2 (step 4), thereby obtaining the title compound (23.3 mg).

Example 46

N-(1-(2-(((5-(tert-butyl)-6-chloro-1H-indazol-3-yl)amino)methyl)-1,4-dimethyl-1H-imidazole-5-carbonyl)azetidin-3-yl) acrylamide Step 1: 1-Hydroxybenzotriazole hydrate (10.0 mg), N,N-diisopropylethylamine (42.7 μL), and WSC hydrochloride (21.6 mg) were added to a solution of 2-(((5-(tert-butyl)-6-chloro-1H-indazol-3-yl)amino)methyl)-1,4-dimethyl-1H-imidazole-5-carboxylic acid (18.9 mg) obtained in Production Example 44 and 3-N-BOC-aminoazetidine (22.9 mg) in DMF (1.5 mL). After stirring at room temperature overnight, water and ethyl acetate were added thereto. The organic layer was separated and washed with a saturated sodium chloride solution. The washed organic layer was dried over sodium sulfate, and the solvent was evaporated under reduced pressure, followed by purifying the obtained residue by column chromatography (ethyl acetate:methanol), thereby obtaining tert-butyl (1-(2-(((5-(tert-butyl)-6-chloro-1H-indazol-3-yl)amino)methyl)-1,4-dimethyl-1H-imidazole-5-carbonyl)azetidin-3-yl)carbamate (24.8 mg).

Step 2: Trifluoroacetic acid (1.5 mL) was added to tert-butyl (1-(2-(((5-(tert-butyl)-6-chloro-1H-indazol-3-yl)amino)methyl)-1,4-dimethyl-1H-imidazole-5-carbonyl)azetidin-3-yl)carbamate (24.8 mg) obtained in step 1. After stirring at room temperature for 10 minutes, the reaction mixture was concentrated. THE (2.0 mL) and N,N-diisopropylethylamine (159 μL) were added to the obtained residue, and subsequently, an acetonitrile solution (100 μL) containing acryloyl chloride (3.78 μL) was added thereto. After stirring at room temperature for 15 minutes, methanol (2.0 mL) was added to the reaction mixture, and the reaction mixture was concentrated. The obtained residue was purified by column chromatography (ethyl acetate:methanol), thereby obtaining the title compound (10.4 mg).

Example 47

N-(1-acryloylpiperidin-4-yl)-2-(((5-(tert-butyl)-6-chloro-1H-indazol-3-yl)amino)methyl)-1,4-dimethyl-1H-imidazole-5-carboxamide The procedure of Example 46 (step 1) was performed except that 1-(4-aminopiperidin-1-yl)prop-2-en-1-one hydrochloride (9.7 mg) was used instead of 3-N-BOC-aminoazetidine used in Example 46 (step 1), thereby obtaining the title compound (21.4 mg).

Example 48

N-(1-acryloylpyrrolidin-3-yl)-2-(((5-(tert-butyl)-6-chloro-1H-indazol-3-yl)amino)methyl)-1,4-dimethyl-1H-imidazole-5-carboxamide Step 1: The procedure of Example 46 (step 1) was performed except that tert-butyl 3-aminopyrrolidine-1-carboxylate (9.5 mg) was used instead of 3-N-BOC-aminoazetidine used in Example 46 (step 1), thereby obtaining tert-butyl 3-(2-(((5-(tert-butyl)-6-chloro-1H-indazol-3-yl)amino)methyl)-1,4-dimethyl-1H-imidazole-5-carboxamide)pyrrolidine-1-carboxylate (27.5 mg).

Step 2: Chloroform (1.0 mL) and trifluoroacetic acid (0.5 mL) were added to tert-butyl 3-(2-(((5-(tert-butyl)-6-chloro-1H-indazol-3-yl)amino)methyl)-1,4-dimethyl-1H-imidazole-5-carboxamide)pyrrolidine-1-carboxylate (27.5 mg) obtained in step 1. After stirring at room temperature for 30 minutes, the reaction mixture was concentrated. THF (1.0 mL) and N,N-diisopropylethylamine (129 μL) were added to the obtained residue, and the reaction mixture was cooled in an ice bath, followed by adding anhydrous acryloyl (5.4 L). After stirring for 15 minutes, water and ethyl acetate were added to the reaction mixture, and the organic layer was separated. The organic layer was washed with a saturated sodium chloride solution and dried over sodium sulfate, followed by evaporating the solvent under reduced pressure. The obtained residue was purified by column chromatography (chloroform:methanol), thereby obtaining the title compound (16.6 mg).

Example 49

N-(1-acryloylazetidin-3-yl)-2-(((5-(tert-butyl)-6-chloro-1H-indazol-3-yl)amino)methyl)-N,1,4-trimethyl-1H-imidazole-5-carboxamide The procedure of Example 46 (steps 1 and 2) was performed except that tert-butyl 3-(methylamino)azetidine-1- carboxylate (9.5 mg) was used instead of 3-N-BOC-aminoazetidine used in Example 46 (step 1), thereby obtaining the title compound (15.0 mg).

Example 50

1-(4-(2-(((5-(Tert-butyl)-6-chloro-1H-indazol-3-yl)amino)methyl)-1,4-dimethyl-1H-imidazole-5-carbonyl)piperazin-1-yl)prop-2-en-1-one The procedure of Example 46 (steps 1 and 2) was performed except that tert-butyl piperazine-1-carboxylate (17.3 mg) was used instead of 3-N-BOC-aminoazetidine used in Example 46 (step 1), thereby obtaining the title compound (16.4 mg).

Example 51

N-(1-(2-(((5-(tert-butyl)-6-chloro-1H-indazol-3-yl)amino)methyl)-1,4-dimethyl-1H-imidazole-5-carbonyl)azetidin-3-yl)-N-methylacrylamide The procedure of Example 46 (steps 1 and 2) was performed except that tert-butyl N-(azetidin-3-yl)-N-methyl carbamate hydrochloride (23.7 mg) was used instead of 3-N-BOC-aminoazetidine used in Example 46 (step 1), thereby obtaining the title compound (19.9 mg).

Example 52

N-((2R*,3R*)-1-acryloyl-2-methylazetidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that cis-tert-butyl 3-amino-2-methylazetidine-1-carboxylate (17.3 mg) was used instead of 3-N-BOC-aminoazetidine used in Example 46 (step 1), thereby obtaining the title compound (18.0 mg).

Example 53

N-(1-acryloyl-4,4-difluoropyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (step 1) was performed except that 1-(4-amino-3,3-difluoropyrrolidin-1-yl)prop-2-en-1-one trifluoroacetate (26.9 mg) obtained in Production Example 28 was used instead of 3-N-BOC-aminoazetidine used in Example 46 (step 1), thereby obtaining the title compound (7.7 mg).

Example 54

(R)-N-(5-acryloyl-5-azaspiro[2.4]heptan-7-yl)-2-(((5-(tert-butyl)-6-chloro-1H-indazol-3-yl)amino)methyl)-1,4-dimethyl-1H-imidazole-5-carboxamide The procedure of Example 46 (step 1) was performed except that (R)-1-(7-amino-5-azaspiro[2.4]heptan-5-yl)prop-2-en-1-one trifluoroacetate (38.9 mg) obtained in Production Example 29 was used instead of 3-N-BOC-aminoazetidine used in Example 46 (step 1), thereby obtaining the title compound (22.3 mg).

Example 55

N-((3R,4R)-1-acryloyl-4-methylpyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (step 1) was performed except that 1-((3R,4R)-3-amino-4-methylpyrrolidin-1-yl)prop-2-en-1-one trifluoroacetate (37.3 mg) obtained in Production Example 30 was used instead of 3-N-BOC-aminoazetidine used in Example 46 (step 1), thereby obtaining the title compound (22.2 mg).

Example 56

N-((3S,4R)-1-acryloyl-4-hydroxypyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3S,4R)-3-amino-4-hydroxypyrrolidine-1-carboxylate (18.7 mg) was used instead of 3-N-BOC-aminoazetidine used in Example 46 (step 1), thereby obtaining the title compound (21.8 mg).

Example 57

N-((3S,4R)-1-acryloyl-4-fluoropyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3S,4R)-3-amino-4-fluoropyrrolidine-1-carboxylate (18.9 mg) was used instead of 3-N-BOC-aminoazetidine used in Example 46 (step 1), thereby obtaining the title compound (24.2 mg).

Example 58

N-((3R,4R)-1-acryloyl-4-(hydroxymethyl)pyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3R,4R)-3-amino-4-(hydroxymethyl)pyrrolidine-1-carboxylate (20.0 mg) was used instead of 3-N-BOC-aminoazetidine used in Example 46 (step 1), thereby obtaining the title compound (20.2 mg).

Example 59

N-(trans-1-acryloyl-2-methylazetidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that trans-tert-butyl 3-amino-2-methylazetidine-1-carboxylate (22.6 mg) was used instead of 3-N-BOC-aminoazetidine used in Example 46 (step 1), thereby obtaining the title compound (16.2 mg).

Example 60

N-((3R,4S)-1-acryloyl-4-methylpyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3R,4S)-3-amino-4-methylpyrrolidine-1-carboxylate (28.2 mg) was used instead of 3-N-BOC-aminoazetidine used in Example 46 (step 1), thereby obtaining the title compound (16.3 mg).

Example 61

N-((3S,4R)-1-acryloyl-4-methoxypyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3S,4R)-3-amino-4-methoxypyrrolidine-1-carboxylate (26.9 mg) was used instead of 3-N-BOC-aminoazetidine used in Example 46 (step 1), thereby obtaining the title compound (20.7 mg).

Example 62

N-((3S,4S)-1-acryloyl-4-hydroxypyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3S,4S)-3-amino-4-hydroxypyrrolidine-1-carboxylate (18.7 mg) was used instead of 3-N-BOC-aminoazetidine used in Example 46 (step 1), thereby obtaining the title compound (18.5 mg).

Example 63

N-((3S,4S)-1-acryloyl-4-methoxypyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3S,4S)-3-amino-4-methoxypyrrolidine-1-carboxylate (20.0 mg) was used instead of 3-N-BOC-aminoazetidine used in Example 46 (step 1), and that acrylic anhydride was used instead of acryloyl chloride used in Example 46 (step 2), thereby obtaining the title compound (19.3 mg).

Example 64

N-((3S,4S)-1-acryloyl-4-fluoropyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3S,4S)-3-amino-4-fluoropyrrolidine-1-carboxylate (21.1 mg) was used instead of 3-N-BOC-aminoazetidine used in Example 46 (step 1), thereby obtaining the title compound (6.1 mg).

Example 65

N-((3R,4R)-1-acryloyl-4-(cyanomethyl)pyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3R,4R)-3-amino-4-(cyanomethyl)pyrrolidine-1-carboxylate (20.9 mg) obtained in Production Example 31 was used instead of 3-N-BOC-aminoazetidine used in Example 46 (step 1), thereby obtaining the title compound (12.9 mg).

Example 66

N-((3R,4R)-1-acryloyl-4-(fluoromethyl)pyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3R,4R)-3-amino-4-(fluoromethyl)pyrrolidine-1-carboxylate (17.9 mg) obtained in Production Example 32 was used instead of 3-N-BOC-aminoazetidine used in Example 46 (step 1), thereby obtaining the title compound (11.3 mg).

Example 67

N-((3R,4R)-1-acryloyl-4-(methoxymethyl)pyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3R,4R)-3-amino-4-(methoxymethyl)pyrrolidine-1-carboxylate (16.0 mg) obtained in Production Example 33 was used instead of 3-N-BOC-aminoazetidine used in Example 46 (step 1), thereby obtaining the title compound (18.5 mg).

Example 68

N-((3R,4R)-1-acryloyl-4-((dimethylamino)methyl)pyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3R,4R)-3-amino-4-((dimethylamino)methyl)pyrrolidine-1-carboxylate (10.2 mg) obtained in Production Example 34 was used instead of 3-N-BOC-aminoazetidine used in Example 46 (step 1), thereby obtaining the title compound (7.9 mg).

Example 69

N-((3R,4R)-1-acryloyl-4-ethylpyrrolidin-3-yl)-2-(((5-(tert-butyl)-6-chloro-1H-indazol-3-yl)amino)methyl)-1,4-dimethyl-1H-imidazole-5-carboxamide The procedure of Example 46 (steps 1 and 2) was performed except that tert-butyl (3R,4R)-3-amino-4-ethylpyrrolidine-1-carboxylate (8.6 mg) was used instead of 3-N-BOC-aminoazetidine used in Example 46 (step 1), thereby obtaining the title compound (5.2 mg).

Example 70

N-((3S,4S)-1-acryloyl-4-fluoropyrrolidin-3-yl)-2-(((5-(tert-butyl)-6-chloro-1H-indazol-3-yl)amino)methyl)-4-(difluoromethyl)-1-methyl-1H-imidazole-5-carboxamide Step 1: N,N-diisopropylethylamine (20 μL) and HATU (39 mg) were added to a solution of 2-(((5-(tert-butyl)-6-chloro-1H-indazol-3-yl)amino)methyl)-4-(difluoromethyl)-

1-methyl-1H-imidazole-5-carboxylic acid (30 mg) obtained in Production Example 45 and tert-butyl (3S,4S)-3-amino-4-fluoropyrrolidine-1-carboxylate (20 mg) in DMF (1.2 mL), followed by stirring at room temperature for 30 minutes. Water and ethyl acetate were added to the reaction mixture. The organic layer was separated and washed with a saturated sodium chloride solution. The washed organic layer was dried over sodium sulfate, and the solvent was evaporated under reduced pressure, followed by purifying the obtained residue by column chromatography (ethyl acetate:methanol), thereby obtaining tert-butyl (3S,4S)-3-(2-(((5-(tert-butyl)-6-chloro-1H-indazol-3-yl)amino)methyl)-4-(difluoromethyl)-1-methyl-1H-imidazole-5-carboxamide)-4-fluoropyrrolidine-1-carboxylate (34.1 mg).

Step 2: Trifluoroacetic acid (3.0 mL) was added to tert-butyl (3S,4S)-3-(2-(((5-(tert-butyl)-6-chloro-1H-indazol-3-yl)amino)methyl)-4-(difluoromethyl)-1-methyl-1H-imidazole-5-carboxamide)-4-fluoropyrrolidine-1-carboxylate (34.1 mg) obtained in step 1. After stirring at room temperature for 10 minutes, the reaction mixture was concentrated. THE (2.0 mL) and N,N-diisopropylethylamine (54 μL) were added to the obtained residue, and subsequently, a solution of 1M acryloyl chloride in acetonitrile (63 μL) was added thereto. After stirring at room temperature for 10 minutes, water and ethyl acetate were added thereto. The organic layer was separated and washed with a saturated sodium chloride solution. The washed organic layer was dried over sodium sulfate, and the solvent was evaporated under reduced pressure, followed by purifying the obtained residue by column chromatography (ethyl acetate:methanol), thereby obtaining the title compound (29.7 mg).

Example 71

N-((3R,4R)-1-acryloyl-4-methylpyrrolidin-3-yl)-2-(((5-(tert-butyl)-6-chloro-1H-indazol-3-yl)amino)methyl)-4-(difluoromethyl)-1-methyl-1H-imidazole-5-carboxamide The procedure of Example 46 (step 1) was performed except that 2-(((5-(tert-butyl)-6-chloro-1H-indazol-3-yl)amino)methyl)-4-(difluoromethyl)-1-methyl-1H-imidazole-5-carboxylic acid (20 mg) obtained in Production Example 45 was used instead of 2-(((5-(tert-butyl)-6-chloro-1H-indazol-3-yl)amino)methyl)-1,4-dimethyl-1H-imidazole-5-carboxylic acid used in Example 46 (step 1), and that 1-((3R,4R)-3-amino-4-methylpyrrolidin-1-yl)prop-2-en-1-one trifluoroacetate (39.1 mg) obtained in Production Example 30 was used instead of 3-N-BOC-aminoazetidine used in Example 46 (step 1), thereby obtaining the title compound (20.4 mg).

Example 72

(R)-N-(1-acryloylpyrrolidin-3-yl)-2-(((5-(tert-butyl)-6-chloro-1H-indazol-3-yl)amino)methyl)-4-fluoro-1-methyl-1H-imidazole-5-carboxamide Step 1: Trifluoroacetic acid (209 μL) was added to tert-butyl 2-(((5-(tert-butyl)-6-chloro-1H-indazol-3-yl)amino)methyl)-4-fluoro-1-methyl-1H-imidazole-5-carboxylate (19.4 mg) obtained in Production Example 46. After stirring at room temperature for 30 minutes, the mixture was concentrated under reduced pressure, thereby obtaining 2-(((5-(tert-butyl)-6-chloro-1H-indazol-3-yl)amino)methyl)-4-fluoro-1-methyl-1H-imidazole-5-carboxylic acid.

Step 2: The procedure of Example 70 (steps 1 and 2) was performed except that 2-(((5-(tert-butyl)-6-chloro-1H-indazol-3-yl)amino)methyl)-4-fluoro-1-methyl-1H-imidazole-5-carboxylic acid obtained in step 1 was used instead of 2-(((5-(tert-butyl)-6-chloro-1H-indazol-3-yl)amino)methyl)-4-(difluoromethyl)-1-methyl-1H-imidazole-5-carboxylic acid used in Example 70 (step 1), and that (R)-(+)-1-BOC-3-aminopyrrolidine (10.8 mg) was used instead of tert-butyl (3S,4S)-3-amino-4-fluoropyrrolidine-1-carboxylate used in Example 70 (step 1), thereby obtaining the title compound (10.2 mg).

Example 73

(R)-N-(1-acryloylpyrrolidin-3-yl)-2-(((5-(tert-butyl)-6-chloro-1H-indazol-3-yl)amino)methyl)-4-chloro-1-methyl-1H-imidazole-5-carboxamide The procedure of Example 28 (steps 1 to 3) was performed except that 4-chloro-1-methyl-1H-imidazole-5-carboxylic acid (78.6 mg) obtained in Production Example 13 was used instead of 4-cyano-1-methyl-1H-imidazole-5-carboxylic acid used in Example 28 (step 1), and that (R)-(+)-1-BOC-3-aminopyrrolidine (119 mg) was used instead of 1-Boc-3-aminoazetidine used in Example 28 (step 1), thereby obtaining the title compound (18.0 mg).

Example 74

N-((3R,4R)-1-acryloyl-4-methylpyrrolidin-3-yl)-2-(((5-(tert-butyl)-6-chloro-1H-indazol-3-yl)amino)methyl)-4-fluoro-1-methyl-1H-imidazole-5-carboxamide The procedure of Example 70 (step 1) was performed except that 2-(((5-(tert-butyl)-6-chloro-1H-indazol-3-yl)amino)methyl)-4-fluoro-1-methyl-1H-imidazole-5-carboxylic acid obtained in Example 72 (step 1) was used instead of 2-(((5-(tert-butyl)-6-chloro-1H-indazol-3-yl)amino)methyl)-4-(difluoromethyl)-1-methyl-1H-imidazole-5-carboxylic acid used in Example 70 (step 1), and that 1-((3R,4R)-3-amino-4-methylpyrrolidin-1-yl)prop-2-en-1-one trifluoroacetate (37.2 mg) obtained in Production Example 30 was used instead of tert-butyl (3 S,4S)-3-amino-4-fluoropyrrolidine-1-carboxylate used in Example 70 (step 1), thereby obtaining the title compound (23 mg).

Example 75

N-((3S,4S)-1-acryloyl-4-fluoropyrrolidin-3-yl)-2-(((5-(tert-butyl)-6-chloro-1H-indazol-3-yl)amino)methyl)-4-fluoro-1-methyl-1H-imidazole-5-carboxamide The procedure of Example 70 (steps 1 and 2) was performed except that 2-(((5-(tert-butyl)-6-chloro-1H-indazol-3-yl)amino)methyl)-4-fluoro-1-methyl-1H-imidazole-5-carboxylic acid obtained in Example 72 (step 1) was used instead of 2-(((5-(tert-butyl)-6-chloro-1H-indazol-3-yl)amino)methyl)-4-(difluoromethyl)-1-methyl-1H-imidazole- 5-carboxylic acid used in Example 70 (step 1), thereby obtaining the title compound (12 mg).

Example 76

N-((3S,4S)-1-acryloyl-4-fluoropyrrolidin-3-yl)-2-(((5-(tert-butyl)-6-chloro-1H-indazol-3-yl)amino)methyl)-4-chloro-1-methyl-1H-imidazole-5-carboxamide The procedure of Example 28 (steps 1 to 3) was performed except that 4-chloro-1-methyl-1H-imidazole-5-carboxylic acid (90.0 mg) obtained in Production Example 13 was used instead of 4-cyano-1-methyl-1H-imidazole-5-carboxylic acid used in Example 28 (step 1), and that tert-butyl (3S,4S)-3-amino-4-fluoropyrrolidine-1-carboxylate (126 mg) was used instead of 1-Boc-3-aminoazetidine used in Example 28 (step 1), thereby obtaining the title compound (13.7 mg).

Example 77

(R)-N-(1-acryloylpyrrolidin-3-yl)-2-(((5-(tert-butyl)-6-chloro-1H-indazol-3-yl)amino)methyl)-N,1-dimethyl-1H-imidazole-5-carboxamide The procedure of Example 28 (steps 1 to 3) was performed except that 1-methyl-1H-5-imidazole carboxylic acid (252 mg) was used instead of 4-cyano-1-methyl-1H-imidazole-5-carboxylic acid used in Example 28 (step 1), and that tert-butyl (3R)-3-(methylamino)pyrrolidine-1-carboxylate (450 mg) was used instead of 1-Boc-3-aminoazetidine used in Example 28 (step 1), thereby obtaining the title compound (49.1 mg).

Example 78

N-((3R,4R)-1-acryloyl-4-methylpyrrolidin-3-yl)-2-(((5-(tert-butyl)-6-chloro-1H-indazol-3-yl)amino)methyl)-4-chloro-1-methyl-1H-imidazole-5-carboxamide The procedure of Example 70 (step 1) was performed except that 2-(((5-(tert-butyl)-6-chloro-1H-indazol-3-yl)amino)methyl)-4-chloro-1-methyl-1H-imidazole-5-carboxylic acid (35 mg) obtained in Production Example 47 was used instead of 2-(((5-(tert-butyl)-6-chloro-1H-indazol-3-yl)amino)methyl)-4-(difluoromethyl)-1-methyl-1H-imidazole-5-carboxylic acid used in Example 70 (step 1), and that 1-((3R,4R)-3-amino-4-methylpyrrolidin-1-yl)prop-2-en-1-one trifluoroacetate (37.2 mg) obtained in Production Example 30 was used instead of tert-butyl (3 S,4S)-3-amino-4-fluoropyrrolidine-1-carboxylate used in Example 70 (step 1), thereby obtaining the title compound (22 mg).

Example 79

(E)-2-(((5-(tert-butyl)-6-chloro-1H-indazol-3-yl)amino)methyl)-1-isopropyl-4-methyl-N-(1-(4-(piperidin-1-yl)but-2-enoyl)azetidin-3-yl)-1H-imidazole-5-carboxamide Step 1: Trifluoroacetic acid (1.5 mL) was added to tert-butyl 3-(2-(((5-(tert-butyl)-6-chloro-1H-indazol-3-yl)amino)methyl)-1-isopropyl-4-methyl-1H-imidazole-5-carboxamide)azetidine-1-carboxylate (165 mg) obtained in Production Example 48, followed by stirring at room temperature for 30 minutes. The reaction mixture was concentrated, and toluene was added to the obtained residue, followed by concentrating the residue twice. DMF (1.5 mL), 4-bromocrotonic acid (73.4 mg), N,N-diisopropylethylamine (402 μL), and propylphosphonic anhydride (cyclic trimer, a 50% ethyl acetate solution) (272 mg) were added thereto, followed by stirring at room temperature for 1 hour. Water and ethyl acetate were added to the reaction mixture, and the organic layer was separated. The organic layer was washed with water and a saturated sodium chloride solution and then dried over sodium sulfate. The solvent was evaporated under reduced pressure, followed by purifying the obtained residue by column chromatography (ethyl acetate: methanol), thereby obtaining N-(1-(4-bromobut-2-enoyl)azetidin-3-yl)-2-(((5-(tert-butyl)-6-chloro-1H-indazol-3-yl)amino)methyl)-1-isopropyl-4-methyl-1H-imidazole-5-carboxamide (57.9 mg).

Step 2: Piperidine (17.7 mg), potassium carbonate (42.2 mg), and potassium iodide (17.1 mg) were added to a solution of N-(1-(4-bromobut-2-enoyl)azetidin-3-yl)-2-(((5-(tert-butyl)-6-chloro-1H-indazol-3-yl)amino)methyl)-1-isopropyl-4-methyl-1H-imidazole-5-carboxamide (57.9 mg) obtained in step 1 in DMF (500 μL), followed by stirring at room temperature for 70 minutes. Water and ethyl acetate were added to the reaction mixture, and the organic layer was separated. The organic layer was washed with water and a saturated sodium chloride solution and then dried over sodium sulfate. The solvent was evaporated under reduced pressure, and the obtained residue was purified by column chromatography (basic silica gel, hexane:ethyl acetate), thereby obtaining the title compound (26 mg).

Example 80

(E)-2-(((5-(tert-butyl)-6-chloro-1H-indazol-3-yl)amino)methyl)-N-(1-(4-(dimethylamino)but-2-enoyl)azetidin-3-yl)-1,4-dimethyl-1H-imidazole-5-carboxamide Trifluoroacetic acid (1.5 mL) was added to tert-butyl 3-(2-(((5-(tert-butyl)-6-chloro-1H-indazol-3-yl)amino)methyl)-1,4-dimethyl-1H-imidazole-5-carboxamide)azetidine-1-carboxylate (12.9 mg) obtained in Production Example 49, followed by stirring at room temperature for 15 minutes. The reaction mixture was concentrated, and toluene was added to the obtained residue, followed by concentrating the residue twice. Dichloromethane (2.0 mL), N,N-diisopropylethylamine (83 μL), 1-hydroxybenzotriazole hydrate (6.0 mg), (E)-4-(dimethylamino)but-2-enoic acid hydrochloride (14.0 mg), and WSC hydrochloride (10.8 mg) were added thereto. The mixture was stirred at room temperature for 1 hour, and the reaction mixture was concentrated. Water and ethyl acetate were added thereto, and the organic layer was separated. The organic layer was washed with water and a saturated sodium chloride solution and then dried over sodium sulfate. The solvent was evaporated under reduced pressure, and the obtained residue was purified by column chromatography (basic silica gel, hexane:ethyl acetate), thereby obtaining the title compound (7.6 mg).

Example 81

(E)-N-(1-(but-2-enoyl)azetidin-3-yl)-2-(((5-(tert-butyl)-6-chloro-1H-indazol-3-yl)amino)methyl)-1-isopropyl-4-methyl-1H-imidazole-5-carboxamide Trifluoroacetic acid (1.5 mL) was added to tert-butyl 3-(2-(((5-(tert-butyl)-6-chloro-1H-indazol-3-yl)amino)

methyl)-1-isopropyl-4-methyl-1H-imidazole-5-carboxamide)azetidine-1-carboxylate (165 mg) obtained in Production Example 48, followed by stirring at room temperature for 30 minutes. The reaction mixture was concentrated, and toluene was added to the obtained residue, followed by concentrating the residue twice. THE (2.0 mL), N,N-diisopropylethylamine (130 μL), and crotonoyl chloride (4.1 μL) were added, and the mixture was stirred at room temperature for 20 minutes. The reaction mixture was concentrated under reduced pressure, and the obtained residue was purified by column chromatography (ethyl acetate:methanol), thereby obtaining the title compound (21.6 mg).

Example 82

N-(1-(buty-2-noyl)azetidin-3-yl)-2-(((5-(tert-butyl)-6-chloro-1H-indazol-3-yl)amino)methyl)-1-isopropyl-4-methyl-1H-imidazole-5-carboxamide Trifluoroacetic acid (1.5 mL) was added to tert-butyl 3-(2-(((5-(tert-butyl)-6-chloro-1H-indazol-3-yl)amino)methyl)-1-isopropyl-4-methyl-1H-imidazole-5-carboxamide)azetidine-1-carboxylate (47.6 mg) obtained in Production Example 48, followed by stirring at room temperature for 15 minutes. The reaction mixture was concentrated, and toluene was added to the obtained residue, followed by concentrating the residue twice. Dichloromethane (2.0 mL), N,N-diisopropylethylamine (145 μL), 1-hydroxybenzotriazole hydrate (15.5 mg), 2-butynoic acid (12.0 mg), and WSC hydrochloride (24.9 mg) were added thereto. The mixture was stirred at room temperature for 6 hours, and water and ethyl acetate were added thereto, followed by separating the organic layer. The organic layer was washed with water and a saturated sodium chloride solution and then dried over sodium sulfate. The solvent was evaporated under reduced pressure, and the obtained residue was purified by column chromatography (basic silica gel, hexane:ethyl acetate), thereby obtaining the title compound (16.6 mg).

Example 83

(Z)-2-(((5-(tert-butyl)-6-chloro-1H-indazol-3-yl)amino)methyl)-N-(1-(3-chloroacryloyl)azetidin-3-yl)-1-isopropyl-4-methyl-1H-imidazole-5-carboxamide The procedure of Example 82 was performed except that CIS-3-chloroacrylic acid (14.8 mg) was used instead of 2-butynoic acid used in Example 82, thereby obtaining the title compound (10.0 mg).

Example 84

(E)-2-(((5-(tert-butyl)-6-chloro-1H-indazol-3-yl)amino)methyl)-4-(difluoromethyl)-N-(1-(4-(dimethylamino)but-2-enoyl)azetidin-3-yl)-1-isopropyl-1H-imidazole-5-carboxamide The procedure of Example 80 was performed except that tert-butyl 3-(2-(((5-(tert-butyl)-6-chloro-1H-indazol-3-yl)amino)methyl)-4-(difluoromethyl)-1-isopropyl-1H-imidazole-5-carboxamide)azetidine-1-carboxylate (29.9 mg) obtained in Production Example 50 was used instead of tert-butyl 3-(2-(((5-(tert-butyl)-6-chloro-1H-indazol-3-yl)amino)methyl)-1,4-dimethyl-1H-imidazole-5-carboxamide)azetidine-1-carboxylate used in Example 80, thereby obtaining the title compound (16.4 mg).

Example 85

(E)-2-(((5-(tert-butyl)-6-chloro-1H-indazol-3-yl)amino)methyl)-1-isopropyl-N-(1-(4-methoxybut-2-enoyl)azetidin-3-yl)-4-methyl-1H-imidazole-5-carboxamide The procedure of Example 82 was performed except that (E)-4-methoxybut-2-enoic acid (17.6 mg) was used instead of 2-butynoic acid used in Example 82, thereby obtaining the title compound (1.4 mg).

Example 86

2-(((5-(tert-butyl)-6-chloro-1H-indazol-3-yl)amino)methyl)-1-isopropyl-4-methyl-N-(1-(vinylsulfonyl)azetidin-3-yl)-1H-imidazole-5-carboxamide The procedure of Example 81 was performed except that ethene sulfonyl chloride (3.64 μL) was used instead of crotonoyl chloride used in Example 81, thereby obtaining the title compound (3.2 mg).

Example 87

N-(1-acryloylazetidin-3-yl)-1-butyl-2-(((5-(tert-butyl)-6-chloro-1H-indazol-3-yl)amino)methyl)-4-chloro-1H-imidazole-5-carboxamide Step 1: Potassium carbonate (2.07 g) and 1-iodobutane (1.60 mL) were added to a solution of methyl imidazole-4-carboxylate (1.2 g) in DMF (13 mL), followed by stirring at room temperature for 2 hours and 30 minutes. The reaction mixture was filtered and concentrated, followed by purifying the obtained residue by column chromatography (hexane:ethyl acetate), thereby obtaining methyl 1-butyl-1H-imidazole-5-carboxylate (695 mg).

Step 2: A 5N sodium hydroxide aqueous solution (3.0 mL) was added to a solution of methyl 1-butyl-1H-imidazole-5-carboxylate (390 mg) obtained in step 1 in ethanol (6.0 mL), followed by stirring at room temperature for 1 hour. Water was added to the reaction mixture, and ethanol was evaporated, followed by adding a 10% phosphoric acid aqueous solution. The mixture was extracted with ethyl acetate, and the organic layer was washed with a saturated sodium chloride solution. The washed organic layer was dried over sodium sulfate, and the solvent was evaporated under reduced pressure, thereby obtaining 1-butyl-1H-imidazole-5-carboxylic acid (125 mg).

Step 3: N,N-diisopropylethylamine (250 μL) and HATU (300 mg) were added to a solution of 1-butyl-1H-imidazole-5-carboxylic acid (125 mg) obtained in step 2 and 1-Boc-3-aminoazetidine (200 mg) in DMF (3.0 mL). After stirring at room temperature for 30 minutes, water and ethyl acetate were added thereto, and the organic layer was separated. The organic layer was washed with water and a saturated sodium chloride solution and then dried over sodium sulfate. The solvent was evaporated under reduced pressure, and the obtained residue was purified by column chromatography (hexane:ethyl acetate), thereby obtaining tert-butyl 3-(1-butyl-1H-imidazole-5-carboxamide)azetidine-1-carboxylate (186 mg).

Step 4: THE (7.0 mL) and 2,2,6,6-tetramethylpiperidine (500 μL) were added to tert-butyl 3-(1-butyl-1H-imidazole- 5-carboxamide)azetidine-1-carboxylate (186 mg) obtained in step 3, and the mixture was cooled in a dry ice-acetone bath, followed by adding butyllithium (a 1.55M hexane solution, 2.23 mL). While being cooled in a dry ice-acetone bath, the mixture was stirred for 1 hour and 20 minutes. DMF (500 μL) was added, followed by stirring for another 1 hour. Water and a 10% phosphoric acid aqueous solution were added to the reaction mixture, and the mixture was heated to room temperature. The mixture was extracted with ethyl acetate, and the organic layer was washed with a saturated sodium chloride solution and then dried over sodium sulfate, followed by evaporating the solvent under reduced pressure. The obtained residue was purified by column chromatography (chloroform:ethanol), thereby obtaining tert-butyl 3-(1-butyl-2-formyl-1H-imidazole-5-carboxamide)azetidine-1-carboxylate (200 mg).

Step 5: N-chlorosuccinimide (80 mg) was added to a solution of tert-butyl 3-(1-butyl-2-formyl-1H-imidazole-5-carboxamide)azetidine-1-carboxylate (191 mg) obtained in step 4 in DMF (2.0 mL), followed by stirring at 50° C. for 2 hours and 40 minutes. A saturated sodium hydrogen carbonate aqueous solution and a sodium thiosulfate aqueous solution were added to the reaction mixture, and the mixture was extracted with ethyl acetate. The organic layer was washed with a saturated sodium chloride solution and dried over sodium sulfate, followed by evaporating the solvent under reduced pressure. The obtained residue was purified by column chromatography (hexane:ethyl acetate), thereby obtaining tert-butyl 3-(1-butyl-4-chloro-2-formyl-1H-imidazole-5-carboxamide)azetidine-1-carboxylate (97.5 mg).

Step 6: The procedure of Example 2 (steps 4 and 5) was performed except that tert-butyl 3-(1-butyl-4-chloro-2-formyl-1H-imidazole-5-carboxamide)azetidine-1-carboxylate (96 mg) obtained in step 5 was used instead of tert-butyl 3-(2-formyl-4-methylthiazole-5-carboxamide)azetidine-1-carboxylate used in Example 2 (step 4), thereby obtaining the title compound (61.6 mg).

Example 88

N-(1-acryloylazetidin-3-yl)-2-(((5-(tert-butyl)-6-chloro-1H-indazol-3-yl)amino)methyl)-1-(3,5-dimethoxybenzyl)-1H-imidazole-5-carboxamide Step 1: 3,5-Dimethoxybenzyl alcohol (804 mg) was added to a suspension of methyl imidazole-4-carboxylate (500 mg) and triphenylphosphine (1.57 g) in THE (10 mL). DIAD (1.17 mL) was slowly added thereto, followed by stirring at room temperature for 1 hour. The reaction mixture was concentrated under reduced pressure, and the obtained residue was purified by column chromatography (hexane: ethyl acetate), thereby obtaining crude methyl 1-(3,5-dimethoxybenzyl)-1H-imidazole-5-carboxylate.

Step 2: A 4N sodium hydroxide aqueous solution (2.97 mL) was added to a solution of crude methyl 1-(3,5-dimethoxybenzyl)-1H-imidazole-5-carboxylate obtained in step 1 in methanol (5.0 mL). After stirring at 100° C. for 40 minutes, the mixture was cooled to room temperature, and water and ethyl acetate were added to the reaction mixture. The aqueous layer was separated and washed with ethyl acetate. 6N hydrochloric acid was added, and the precipitated solid was collected, thereby obtaining 1-(3,5-dimethoxybenzyl)-1H-imidazole-5-carboxylic acid (1.04 g).

Step 3: 1-Boc-3-aminoazetidine (685 mg), DMF (3.0 mL), 1-hydroxybenzotriazole hydrate (601 mg), N,N-diisopropylethylamine (2.0 mL), and WSC hydrochloride (1.53 g) were added to 1-(3,5-dimethoxybenzyl)-1H-imidazole-5-carboxylic acid (1.04 g) obtained in step 2. After stirring at room temperature for 2 hours, water and ethyl acetate were added thereto. The organic layer was separated and washed with a saturated sodium chloride solution. The washed organic layer was dried over sodium sulfate, and the solvent was evaporated under reduced pressure, followed by purifying the obtained residue by column chromatography (chloroform:methanol), thereby obtaining tert-butyl 3-(1-(3,5-dimethoxybenzyl)-1H-imidazole-5-carboxamide)azetidine-1-carboxylate (1.13 g).

Step 4: The procedure of Example 28 (steps 2 and 3) was performed except that tert-butyl 3-(1-(3,5-dimethoxybenzyl)-1H-imidazole-5-carboxamide)azetidine-1-carboxylate (1.13 g) obtained in step 3 was used instead of tert-butyl 3-(4-cyano-1-methyl-1H-imidazole-5-carboxamide)azetidine-1-carboxylate used in Example 28 (step 2), thereby obtaining the title compound (31 mg).

Example 89

N-(1-acryloylazetidin-3-yl)-2-(((5-(tert-butyl)-6-chloro-1H-indazol-3-yl)amino)methyl)-4-chloro-1-isobutyl-1H-imidazole-5-carboxamide Step 1: The procedure of Example 88 (steps 1 and 2) was performed except that 2-methyl-1-propanol was used instead of 3,5-dimethoxybenzyl alcohol used in Example 88 (step 1), thereby obtaining 1-isobutyl-1H-imidazole-5-carboxylic acid (277 mg).

Step 2: 1-hydroxybenzotriazole hydrate (258 mg), N,N-diisopropylethylamine (840 μL), and WSC hydrochloride (473 mg) were added to a solution of 1-isobutyl-1H-imidazole-5-carboxylic acid (277 mg) obtained in step 1 and 1-Boc-3-aminoazetidine (285 mg) in dichloromethane (5.0 mL). After stirring at room temperature for 1 hour, water and ethyl acetate were added thereto. The organic layer was separated and washed with a saturated sodium chloride solution. The washed organic layer was dried over sodium sulfate, and the solvent was evaporated under reduced pressure, followed by purifying the obtained residue by column chromatography (ethyl acetate:methanol), thereby obtaining tert-butyl 3-(1-isobutyl-1H-imidazole-5-carboxamide)azetidine-1-carboxylate (388 mg).

Step 3: The procedure of Example 87 (steps 4 to 6) was performed except that tert-butyl 3-(1-isobutyl-1H-imidazole-5-carboxamide)azetidine-1-carboxylate (388 mg) obtained in step 2 was used instead of tert-butyl 3-(1-butyl-1H-imidazole-5-carboxamide)azetidine-1-carboxylate used in Example 87 (step 4), thereby obtaining the title compound (33.1 mg).

Example 90

N-(1-acryloylazetidin-3-yl)-2-(((5-(tert-butyl)-6-chloro-1H-indazol-3-yl)amino)methyl)-4-chloro-1-(2-methoxyethyl)-1H-imidazole-5-carboxamide The procedure of Example 88 (steps 1 to 3), and then the procedure of Example 87 (steps 4 to 6), were performed except that 2-methoxyethanol (227 mg) was used instead of 3,5-dimethoxybenzyl alcohol used in Example 88 (step 1), thereby obtaining the title compound (27.8 mg).

Example 91

N-(1-acryloylazetidin-3-yl)-2-(((5-(tert-butyl)-6-chloro-1H-indazol-3-yl)amino)methyl)-4-(difluoromethyl)-1-(1-methylpyrrolidin-3-yl)-1H-imidazole-5-carboxamide Step 1: DIAD (823 μL) was added to a solution of dimethyl 2-bromo-1H-imidazole-4,5-dicarboxylate (1.0 g), triphenylphosphine (1.10 g), and 1-(tert-butoxycarbonyl)-3-pyrrolidinol (800 mg) in THE (6.0 mL), followed by stirring at 40° C. for 1 hour. Water was added to the reaction mixture, and the reaction mixture was concentrated under reduced pressure, followed by purifying the obtained residue by column chromatography (hexane:ethyl acetate), thereby obtaining crude dimethyl 2-bromo-1-(1-(tert-butoxycarbonyl)pyrrolidin-3-yl)-1H-imidazole-4,5-dicarboxylate (1.88 g).

Step 2: A solution of crude dimethyl 2-bromo-1-(1-(tert-butoxycarbonyl)pyrrolidin-3-yl)-1H-imidazole-4,5-dicarboxylate (1.88 g) obtained in step 1 in THE (16 mL) was cooled in a dry ice-acetone bath, and diisobutylaluminium hydride (a 1M toluene solution) (8.9 mL) was added thereto. While being cooled in a dry ice-acetone bath, the mixture was stirred for 7 hours. A Rochelle salt aqueous solution was added to the reaction mixture, and the mixture was heated to room temperature, followed by stirring overnight. The mixture was extracted with ethyl acetate, followed by washing with a saturated sodium chloride solution, and drying over sodium sulfate. The solvent was evaporated under reduced pressure, and the obtained residue was purified by column chromatography (hexane:ethyl acetate), thereby obtaining methyl 2-bromo-1-(1-(tert-butoxycarbonyl)pyrrolidin-3-yl)-4-formyl-1H-imidazole-5-carboxylate (1.24 g).

Step 3: Bis(2-methoxyethyl)aminosulfur trifluoride (2.3 mL) was added to a solution of methyl 2-bromo-1-(1-(tert-butoxycarbonyl)pyrrolidin-3-yl)-4-formyl-1H-imidazole-5-carboxylate (1.24 g) obtained in step 2 in dichloromethane (15 mL), followed by stirring at room temperature for 2 hours. The mixture was cooled in a water bath, and water was slowly added. The reaction mixture was extracted with dichloromethane, and the extract was dried over sodium sulfate. The solvent was evaporated under reduced pressure, and the obtained residue was purified by column chromatography (hexane:ethyl acetate), thereby obtaining methyl 2-bromo-1-(1-(tert-butoxycarbonyl)pyrrolidin-3-yl)-4-(difluoromethyl)-1H-imidazole-5-carboxylate (902 mg).

Step 4: A solution of methyl 2-bromo-1-(1-(tert-butoxycarbonyl)pyrrolidin-3-yl)-4-(difluoromethyl)-1H-imidazole-5-carboxylate (902 mg) obtained in step 3 in THE (13.5 mL) was cooled in a dry ice-acetone bath, and isopropylmagnesium chloride (a 2M THF solution) (2.52 mL) was added thereto over 5 minutes. While being cooled, the reaction mixture was stirred for 45 minutes, followed by adding DMF (827 μL). The reaction mixture was removed from the dry ice-acetone bath. After 20 minutes, 2N hydrochloric acid (2.5 mL) and a saturated ammonium chloride aqueous solution (30 mL) were added to the reaction mixture at 0° C. The reaction mixture was extracted with ethyl acetate, and the organic layer was washed with a saturated sodium chloride solution and dried over sodium sulfate. The solvent was evaporated under reduced pressure, and the obtained residue was purified by column chromatography (hexane:ethyl acetate), thereby obtaining methyl 1-(1-(tert-butoxycarbonyl)pyrrolidin-3-yl)-4-(difluoromethyl)-2-formyl-1H-imidazole-5-carboxylate (415 mg).

Step 5: Trifluoroacetic acid (19.6 μL) and sodium triacetoxyborohydride (52.0 mg) were added to a solution of methyl 1-(1-(tert-butoxycarbonyl)pyrrolidin-3-yl)-4-(difluoromethyl)-2-formyl-1H-imidazole-5-carboxylate (47.7 mg) obtained in step 4 and 5-(tert-butyl)-6-chloro-1H-indazole-3-amine (30 mg) obtained in Production Example 1 in dichloromethane (4.0 mL). After stirring at room temperature for 2 hours, a sodium hydrogen carbonate aqueous solution was added to the reaction mixture, and the mixture was extracted with ethyl acetate. The organic layer was washed with a saturated sodium chloride solution and dried over sodium sulfate. The solvent was evaporated under reduced pressure, and the obtained residue was purified by column chromatography (ethyl acetate:methanol), thereby obtaining methyl 1-(1-(tert-butoxycarbonyl)pyrrolidin-3-yl)-2-(((5-(tert-butyl)-6-chloro-1H-indazol-3-yl)amino)methyl)-4-(difluoromethyl)-1H-imidazole-5-carboxylate (68 mg).

Step 6: A 1N sodium hydroxide aqueous solution (1 mL) was added to a solution of methyl 1-(1-(tert-butoxycarbonyl)pyrrolidin-3-yl)-2-(((5-(tert-butyl)-6-chloro-1H-indazol-3-yl)amino)methyl)-4-(difluoromethyl)-1H-imidazole-5-carboxylate (68 mg) obtained in step 5 in methanol (3 mL), followed by stirring at room temperature for 30 minutes. After acidification with 1N hydrochloric acid, the reaction mixture was extracted with ethyl acetate. The organic layer was washed with a saturated sodium chloride solution and dried over sodium sulfate. The solvent was evaporated under reduced pressure, thereby obtaining crude 1-(1-(tert-butoxycarbonyl)pyrrolidin-3-yl)-2-(((5-(tert-butyl)-6-chloro-1H-indazol-3-yl)amino)methyl)-4-(difluoromethyl)-1H-imidazole-5-carboxylic acid (68 mg).

Step 7: Crude 1-(1-(tert-butoxycarbonyl)pyrrolidin-3-yl)-2-(((5-(tert-butyl)-6-chloro-1H-indazol-3-yl)amino)methyl)-4-(difluoromethyl)-1H-imidazole-5-carboxylic acid (40 mg) obtained in step 6, 1-(3-aminoazetidin-1-yl)prop-2-en-1-one hydrochloride (13.8 mg) obtained in Production Example 27, and DMF (1.0 mL) were mixed. N,N-diisopropylethylamine (31 μL) and HATU (38 mg) were further added thereto, followed by stirring at room temperature for 30 minutes. Water and ethyl acetate were added to the reaction mixture, and the organic layer was washed with water and a saturated sodium chloride solution and dried over sodium sulfate. The solvent was evaporated under reduced pressure, and the obtained residue was purified by column chromatography (ethyl acetate:methanol), thereby obtaining tert-butyl 3-(5-((1-acryloylazetidin-3-yl)carbamoyl)-2-(((5-(tert-butyl)-6-chloro-1H-indazol-3-yl)amino)methyl)-4-(difluoromethyl)-1H-indazol-1-yl)pyrrolidine-1-carboxylate (32.2 mg).

Step 8: Trifluoroacetic acid (1 mL) was added to tert-butyl 3-(5-((1-acryloylazetidin-3-yl)carbamoyl)-2-(((5-(tert-butyl)-6-chloro-1H-indazol-3-yl)amino)methyl)-4-(difluoromethyl)-1H-indazol-1-yl)pyrrolidine-1-carboxylate (32.2 mg) obtained in step 7, followed by stirring at room temperature for 10 minutes. The reaction mixture was concentrated and purified by preparative reversed-phase HPLC (water:acetonitrile (0.1% formic acid)), thereby obtaining N-(1-acryloylazetidin-3-yl)-2-(((5-(tert-butyl)-6-chloro-1H-indazol-3-yl)amino)methyl)-4-(difluoromethyl)-1-(pyrrolidin-3-yl)-1H-imidazole-5-carboxamide formate (16.1 mg).

Step 9: DMF (300 μL), acetic acid (30 μL) and a formaldehyde solution (37%) (10 L) were added to N-(1-acryloylazetidin-3-yl)-2-(((5-(tert-butyl)-6-chloro-1H-indazol-3-yl)amino)methyl)-4-(difluoromethyl)-1-(pyrrolidin-3-yl)-

1H-imidazole-5-carboxamide formate (5.0 mg) obtained in step 8, and then sodium triacetoxyborohydride (6.9 mg) was added thereto. DMSO (1.0 mL) was added to the reaction mixture, followed by purification by preparative reversed-phase HPLC (water:acetonitrile (0.1% formic acid)). After the residue was concentrated, a 5N sodium hydroxide aqueous solution (1.5 mL) was added, followed by extraction with ethyl acetate. The extract was washed with a saturated sodium chloride solution and dried over sodium sulfate. The solvent was evaporated under reduced pressure, thereby obtaining the title compound (1.35 mg).

Example 92

N-(1-acryloylazetidin-3-yl)-2-(((5-(tert-butyl)-6-chloro-1H-indazol-3-yl)amino)methyl)-4-(difluoromethyl)-1-(1-ethylpyrrolidin-3-yl)-1H-imidazole-5-carboxamide The procedure of Example 91 (step 9) was performed except that acetaldehyde (20 mg) was used instead of the formaldehyde solution used in Example 91 (step 9), thereby obtaining the title compound (3.12 mg).

Example 93

N-(1-acryloylazetidin-3-yl)-2-(((5-(tert-butyl)-6-chloro-1H-indazol-3-yl)amino)methyl)-4-(difluoromethyl)-1-(1-isopropylpyrrolidin-3-yl)-1H-imidazole-5-carboxamide formate The procedure of Example 91 (step 9) was performed except that acetone (20 mg) was used instead of the formaldehyde solution used in Example 91 (step 9). After purification by preparative reversed-phase HPLC (water:acetonitrile (0.1% formic acid)), the solvent was concentrated, thereby obtaining the title compound (8.33 mg).

Example 94

N-(1-acryloylazetidin-3-yl)-2-(((5-(tert-butyl)-6-chloro-1H-indazol-3-yl)amino)methyl)-4-chloro-1-(pyridin-2-yl)-1H-imidazole-5-carboxamide Step 1: Trans-N,N'-dimethylcyclohexane-1,2-diamine (320 μL) was added to a suspension of methyl 4-chloro-1H-imidazole-5-carboxylate (320 mg) obtained in Production Example 12, 2-bromopyridine (650 mg), potassium carbonate (420 mg), and copper(I) iodide (380 mg) in 1,4-dioxane (7.0 mL), followed by stirring at 100° C. overnight.

The reaction mixture was cooled to room temperature, and concentrated ammonia water and ethyl acetate were added thereto. The organic layer was washed with a saturated sodium chloride solution and dried over sodium sulfate. The solvent was evaporated under reduced pressure, and the obtained residue was purified by column chromatography (hexane:ethyl acetate), thereby obtaining methyl 4-chloro-1-(pyridin-2-yl)-1H-imidazole-5-carboxylate (115 mg).

Step 2: The procedure of Production Example 38 (steps 2 to 4) was performed except that methyl 4-chloro-1-(pyridin-2-yl)-1H-imidazole-5-carboxylate (115 mg) obtained in step 1 was used instead of methyl 4-chloro-1-isopropyl-1H-imidazole-5-carboxylate used in Production Example 38 (step 2), thereby obtaining tert-butyl 3-(4-chloro-2-formyl-1-(pyridin-2-yl)-1H-imidazole-5-carboxamide)azetidine-1-carboxylate (48.7 mg).

Step 3: The procedure of Example 2 (steps 4 and 5) was performed except that tert-butyl 3-(4-chloro-2-formyl-1-(pyridin-2-yl)-1H-imidazole-5-carboxamide)azetidine-1-carboxylate (48.7 mg) obtained in step 2 was used instead of tert-butyl 3-(2-formyl-4-methylthiazole-5-carboxamide) azetidine-1-carboxylate used in Example 2 (step 4), thereby obtaining the title compound (11.4 mg).

Example 95

N-(1-acryloylazetidin-3-yl)-2-(((5-(tert-butyl)-6-chloro-1H-indazol-3-yl)amino)methyl)-4-(difluoromethyl)-1-((1-isopropylpyrrolidine-2-yl)methyl)-1H-imidazole-5-carboxamide The procedure of Example 91 (steps 1 to 9) was performed except that N-(tert-butoxycarbonyl)-DL-prolinol was used instead of 1-(tert-butoxycarbonyl)-3-pyrrolidinol used in Example 91 (step 1), and that acetone (20 mg) was used instead of the formaldehyde solution used in Example 91 (step 9), thereby obtaining the title compound (3.5 mg).

Example 96

1-(1-Acetylpyrrolidin-3-yl)-N-(1-acryloylazetidin-3-yl)-2-(((5-(tert-butyl)-6-chloro-1H-indazol-3-yl) amino)methyl)-4-(difluoromethyl)-1H-imidazole-5-carboxamide Acetic anhydride (40 μL) was added to a solution of N-(1-acryloylazetidin-3-yl)-2-(((5-(tert-butyl)-6-chloro-1H-indazol-3-yl)amino)methyl)-4-(difluoromethyl)-1-(pyrrolidin-3-yl)-1H-imidazole-5-carboxamide formate (18.0 mg) obtained in Example 91 (step 8) in pyridine (40 μL), followed by stirring at room temperature for 15 minutes. Methanol (2 mL) and concentrated ammonia water (2 mL) were added to the reaction mixture, followed by stirring at room temperature for 1 hour. The reaction mixture was concentrated and purified by preparative reversed-phase HPLC (water:acetonitrile (0.1% formic acid)), thereby obtaining the title compound (1.08 mg).

Example 97

(S)-N-(1-acryloylazetidin-3-yl)-2-(((5-(tert-butyl)-6-chloro-1H-indazol-3-yl)amino)methyl)-4-chloro-1-(tetrahydrofuran-3-yl)-1H-imidazole-5-carboxamide Step 1: DIAD (1.15 mL) was added to a solution of methyl 4-chloro-1H-imidazole-5-carboxylate (700 mg) obtained in Production Example 12, triphenylphosphine (1.5 g), and (R)-(−)-3-hydroxytetrahydrofuran (500 mg) in THE (12 mL), followed by stirring at room temperature for 30 minutes. The solvent was evaporated under reduced pressure, and the obtained residue was purified by column chromatography (hexane:ethyl acetate), thereby obtaining methyl (S)-4-chloro-1-(tetrahydrofuran-3-yl)-1H-imidazole-5-carboxylate (634 mg).

Step 2: DMF (800 μL) was added to a solution of methyl (S)-4-chloro-1-(tetrahydrofuran-3-yl)-1H-imidazole-5-carboxylate (634 mg) obtained in step 1 in THE (12.0 mL). 2,2,6,6-Tetramethyl piperidinyl magnesium chloride and a lithium chloride complex (a 1M THF/toluene solution, 11 mL) were added thereto at −10° C. After stirring for 20 minutes, water, a 10% phosphoric acid aqueous solution, and ethyl acetate were added thereto, followed by heating to room temperature. The organic layer was separated and washed with a saturated sodium chloride solution, followed by drying over sodium sulfate. The solvent was evaporated under reduced pressure, and the obtained residue was purified by column chromatography (hexane:ethyl acetate), thereby obtaining methyl (S)-4-chloro-2-formyl-1-(tetrahydrofuran-3-yl)-1H-imidazole-5-carboxylate (266 mg).

Step 3: Trifluoroacetic acid (70 μL) and sodium triacetoxyborohydride (142 mg) were added to a solution of methyl (S)-4-chloro-2-formyl-1-(tetrahydrofuran-3-yl)-1H-imidazole-5-carboxylate (266 mg) obtained in step 2 and 5-(tert-butyl)-6-chloro-1H-indazole-3-amine (180 mg) obtained in Production Example 1 in dichloromethane (4.0 mL), followed by stirring at room temperature for 30 minutes. A sodium hydrogen carbonate aqueous solution was added to the reaction mixture, and the mixture was extracted with ethyl acetate. The organic layer was washed with a saturated sodium chloride solution and dried over sodium sulfate. The solvent was evaporated under reduced pressure, and the obtained residue was purified by column chromatography (hexane:ethyl acetate), thereby obtaining methyl (S)-2-(((5-(tert-butyl)-6-chloro-1H-indazol-3-yl)amino) methyl)-4-chloro-1-(tetrahydrofuran-3-yl)-1H-imidazole-5-carboxylate (245 mg).

Step 4: A 5N sodium hydroxide aqueous solution (600 μL) was added to a solution of (S)-2-(((5-(tert-butyl)-6-chloro-1H-indazol-3-yl)amino)methyl)-4-chloro-1-(tetrahydrofuran-3-yl)-1H-imidazole-5-carboxylate (56 mg) obtained in step 3 in ethanol (1.2 mL), followed by stirring at room temperature for 30 minutes. A 10% phosphoric acid aqueous solution was added to the reaction mixture, and the mixture was extracted with ethyl acetate, followed by washing the organic layer with a saturated sodium chloride solution. The washed organic layer was dried over sodium sulfate, and the solvent was evaporated under reduced pressure. 1-(3-Aminoazetidin-1-yl)prop-2-en-1-one hydrochloride (22 mg) obtained in Production Example 27 and DMF (4 mL) were added to the obtained residue, and N,N-diisopropylethylamine (70 μL) and HATU (60 mg) were further added. After stirring at room temperature overnight, a 10% phosphoric acid aqueous solution and ethyl acetate were added thereto. The organic layer was separated and washed with a saturated sodium chloride solution. The washed organic layer was dried over sodium sulfate, and the solvent was evaporated under reduced pressure, followed by purifying the obtained residue by column chromatography (ethyl acetate:ethanol), thereby obtaining the title compound (26.1 mg).

Example 98

N-(1-acryloylazetidin-3-yl)-2-(((5-(tert-butyl)-6-chloro-1H-indazol-3-yl)amino)methyl)-4-chloro-1-(cyclopent-3-en-1-yl)-1H-imidazole-5-carboxamide Step 1: DIAD (600 μL) was added to a solution of methyl 4-chloro-1H-imidazole-5-carboxylate (340 mg) obtained in Production Example 12, triphenylphosphine (750 mg), and 3-cyclopenten-1-ol (240 mg) in THE (12 mL), followed by stirring at room temperature for 30 minutes. The solvent was evaporated under reduced pressure, and the obtained residue was purified by column chromatography (hexane:ethyl acetate), thereby obtaining crude methyl 4-chloro-1-(cyclopent-3-en-1-yl)-1H-imidazole-5-carboxylate (686 mg).

Step 2: A 5N sodium hydroxide aqueous solution (4.0 mL) was added to a solution of crude methyl 4-chloro-1-(cyclopent-3-en-1-yl)-1H-imidazole-5-carboxylate (686 mg) obtained in step 1 in ethanol (6.0 mL), followed by stirring at room temperature for 20 minutes. Water was added to the reaction mixture, and ethanol was evaporated under reduced pressure, followed by adding ethyl acetate to separate the aqueous layer. A 10% phosphoric acid aqueous solution was added to the obtained aqueous layer, and the mixture was extracted with ethyl acetate, followed by washing the organic layer with a saturated sodium chloride solution. The washed organic layer was dried over sodium sulfate, and the solvent was evaporated under reduced pressure. A solution of 1-Boc-3-aminoazetidine (500 mg) in DMF (5.0 mL), N,N-diisopropylethylamine (1.00 mL), and HATU (890 mg) were added to the obtained residue, followed by stirring for 30 minutes. Ethyl acetate, water, and a 10% phosphoric acid aqueous solution were added to the reaction mixture to partition the mixture, and the organic layer was washed with water and a saturated sodium chloride solution. The washed organic layer was dried over sodium sulfate, and the solvent was evaporated under reduced pressure. The obtained residue was purified by column chromatography (hexane:ethyl acetate), thereby obtaining tert-butyl 3-(4-chloro-1-(cyclopent-3-en-1-yl)-1H-imidazole-5-carboxamide)azetidine-1-carboxylate (550 mg).

Step 3: A mixture of tert-butyl 3-(4-chloro-1-(cyclopent-3-en-1-yl)-1H-imidazole-5-carboxamide)azetidine-1-carboxylate (550 mg) obtained in step 2, THE (10.0 mL), and 2,2,6,6-tetramethylpiperidine (1.50 mL) was cooled in a dry ice-acetone bath. Butyllithium (a 1.55M hexane solution, 5.80 mL) was added thereto over 10 minutes. While being cooled in a dry ice-acetone bath, the mixture was stirred for 2 hours, and DMF (1.00 mL) was added, followed by stirring for another 30 minutes. Water and a 10% phosphoric acid aqueous solution were added thereto, and the mixture was heated to room temperature. The mixture was extracted with ethyl acetate, and the organic layer was washed with a saturated sodium chloride solution and dried over sodium sulfate, followed by evaporating the solvent under reduced pressure. The obtained residue was purified by column chromatography (hexane:ethyl acetate), thereby obtaining tert-butyl 3-(4-chloro-1-(cyclopent-3-en-1-yl)-2-formyl-1H-imidazole-5-carboxamide)azetidine-1-carboxylate (539 mg).

Step 4: Trifluoroacetic acid (30 μL) and sodium triacetoxyborohydride (120 mg) were added to a solution of tert-butyl 3-(4-chloro-1-(cyclopent-3-en-1-yl)-2-formyl-1H-imidazole-5-carboxamide)azetidine-1-carboxylate (100 mg) obtained in step 3 and 5-(tert-butyl)-6-chloro-1H-indazole-3-amine (45 mg) obtained in Production Example 1 in dichloromethane (3.0 mL), followed by stirring at room temperature for 20 minutes. A sodium hydrogen carbonate aqueous solution was added to the reaction mixture, and the mixture was extracted with ethyl acetate. The organic layer was washed with a saturated sodium chloride solution and dried over sodium sulfate. The solvent was evaporated under reduced pressure, and the obtained residue was purified by column chromatography (hexane:ethyl acetate), thereby obtaining tert-butyl 3-(2-(((5-(tert-butyl)-6-chloro-1H-indazol-3-yl)amino)methyl)-4-chloro-1-(cyclopent-3-en-1-yl)-1H-imidazole-5-carboxamide)azetidine-1-carboxylate (80 mg).

Step 5: Trifluoroacetic acid (1.00 mL) was added to tert-butyl 3-(2-(((5-(tert-butyl)-6-chloro-1H-indazol-3-yl) amino)methyl)-4-chloro-1-(cyclopent-3-en-1-yl)-1H-imidazole-5-carboxamide)azetidine-1-carboxylate (80 mg) obtained in step 4, followed by stirring. The reaction mixture was concentrated, and THE (3.0 mL) and N,N-diisopropylethylamine (300 μL) were added thereto. A solution of 1M acryloyl chloride in acetonitrile (130 μL) was added, and the mixture was stirred at room temperature for 10 minutes. A sodium hydrogen carbonate aqueous solution was added to the reaction mixture, and the mixture was extracted with ethyl acetate. The organic layer was washed with a saturated sodium chloride solution and dried over sodium sulfate. The solvent was evaporated under reduced pressure, and the obtained residue was purified by column chromatography (chloroform:ethanol), thereby obtaining the title compound (52.8 mg).

Example 99

N-(1-acryloylazetidin-3-yl)-2-(((5-(tert-butyl)-6-chloro-1H-indazol-3-yl)amino)methyl)-4-chloro-1-((3,4-dihydroxycyclopentyl)-1H-imidazole-5-carboxamide Step 1: Acetone (3.0 mL), water (300 μL), 4-methylmorpholine N-oxide (70 mg), and a 1% osmium tetroxide aqueous solution (100 μL) were added to tert-butyl 3-(4-chloro-1-(cyclopent-3-en-1-yl)-2-formyl-1H-imidazole-5-carboxamide)azetidine-1-carboxylate (110 mg) obtained in Example 98 (step 3). After stirring at room temperature overnight, a saturated sodium hydrogen carbonate aqueous solution and sodium bisulfite were added to the reaction mixture. After the mixture was extracted with ethyl acetate, the organic layer was washed with a saturated sodium chloride solution and dried over sodium sulfate, followed by evaporating the solvent under reduced pressure. The obtained residue was purified by column chromatography (chloroform:ethanol), thereby obtaining tert-butyl 3-(4-chloro-1-(3,4-dihydroxycyclopentyl)-2-formyl-1H-imidazole-5-carboxamide)azetidine-1-carboxylate (111 mg).

Step 2: The procedure of Example 98 (steps 4 and 5) was performed except that tert-butyl 3-(4-chloro-1-(3,4-dihydroxycyclopentyl)-2-formyl-1H-imidazole-5-carboxamide) azetidine-1-carboxylate (111 mg) obtained in step 1 was used instead of tert-butyl 3-(4-chloro-1-(cyclopent-3-en-1-yl)-2-formyl-1H-imidazole-5-carboxamide)azetidine-1-carboxylate used in Example 98 (step 4), thereby obtaining the title compound (20.9 mg).

Example 100

N-(1-acryloylazetidin-3-yl)-2-(((5-(tert-butyl)-6-chloro-1H-indazol-3-yl)amino)methyl)-4-chloro-1-(2,2-difluoroethyl)-1H-imidazole-5-carboxamide The procedure of Example 98 (steps 1 to 5) was performed except that 2,2-difluoroethanol was used instead of 3-cyclopenten-1-ol used in Example 98 (step 1), thereby obtaining the title compound (72 mg).

Example 101

N-(1-acryloylazetidin-3-yl)-2-(((5-(tert-butyl)-6-chloro-1H-indazol-3-yl)amino)methyl)-4-chloro-1-(tetrahydro-2H-pyran-4-yl)-1H-imidazole-5-carboxamide The procedure of Example 98 (steps 1 to 5) was performed except that tetrahydro-4H-pyran-4-ol was used instead of 3-cyclopenten-1-ol used in Example 98 (step 1), thereby obtaining the title compound (25.3 mg).

Example 102

(R)-N-(1-acryloylazetidin-3-yl)-2-(((5-(tert-butyl)-6-chloro-1H-indazol-3-yl)amino)methyl)-4-chloro-1-(tetrahydrofuran-3-yl)-1H-imidazole-5-carboxamide The procedure of Example 98 (steps 1 to 5) was performed except that (S)-(+)-3-hydroxytetrahydrofuran was used instead of 3-cyclopenten-1-ol used in Example 98 (step 1), thereby obtaining the title compound (54.1 mg).

Example 103

N-(1-acryloylazetidin-3-yl)-2-(((5-(tert-butyl)-6-chloro-1H-indazol-3-yl)amino)methyl)-4-chloro-1-(1-methylpiperidin-4-yl)-1H-imidazole-5-carboxamide Step 1: The procedure of Example 97 (step 1) was performed except that tert-butyl 4-hydroxypiperidine-1-carboxylate was used instead of (R)-(−)-3-hydroxytetrahydrofuran used in Example 97 (step 1), thereby obtaining tert-butyl 4-(4-chloro-5-methoxycarbonyl-imidazol-1-yl) piperidine-1-carboxylate (661 mg).

Step 2: A 5N sodium hydroxide aqueous solution (5 mL) was added to a solution of tert-butyl 4-(4-chloro-5-methoxycarbonyl-imidazol-1-yl)piperidine-1-carboxylate (661 mg) obtained in step 1 in methanol (10 mL), followed by stirring at 40° C. for 30 minutes. 5N hydrochloric acid was added, and the mixture was extracted with ethyl acetate. The organic layer was washed with a saturated sodium chloride solution and dried over sodium sulfate. The solvent was evaporated under reduced pressure, thereby obtaining 1-(1-tert-butoxycarbonyl-4-piperidyl)-4-chloro-1H-indazole-5-carboxylic acid (514 mg).

Step 3: Ethanol (1 mL), N,N-diisopropylethylamine (619 μL), and HATU (692 mg) were added to a solution of 1-(1-tert-butoxycarbonyl-4-piperidyl)-4-chloro-1H-indazole-5-carboxylic acid (400 mg) obtained in step 2 in DMF (8 mL), followed by stirring at 45° C. for 50 minutes. Ethyl acetate and water were added to the reaction mixture to partition the mixture, and the organic layer was washed with a saturated sodium chloride solution. The washed organic layer was dried over sodium sulfate and the solvent was evaporated under reduced pressure. The obtained residue was purified by column chromatography (hexane/ethyl acetate), thereby obtaining tert-butyl 4-(4-chloro-5-ethoxycarbonyl-imidazol-1-yl)piperidine-1-carboxylate (350 mg).

Step 4: DMF (485 μL) was added to a solution of tert-butyl 4-(4-chloro-5-ethoxycarbonyl-imidazol-1-yl)piperidine-1-carboxylate (350 mg) obtained in step 3 in THE (5 mL). 2,2,6,6-Tetramethyl piperidinyl magnesium chloride and a lithium chloride complex (a 1M THF/toluene solution, 6.12 mL) were added thereto at −8° C. After stirring for 45 minutes, water, 5N hydrochloric acid, and ethyl acetate were added, followed by heating to room temperature. The organic layer was separated and washed with a saturated sodium chloride solution, followed by drying over sodium sulfate. The solvent was evaporated under reduced pressure, and the obtained residue was purified by column chromatography (hexane/ethyl acetate), thereby obtaining tert-butyl 4-(4-chloro-5-ethoxycarbonyl-2-formyl-imidazol-1-yl)piperidine-1-carboxylate (353 mg).

Step 5: Trifluoroacetic acid (50.0 μL) and sodium triacetoxyborohydride (270 mg) were added to a solution of tert-butyl 4-(4-chloro-5-ethoxycarbonyl-2-formyl-imidazol-1-yl)piperidine-1-carboxylate (240 mg) obtained in step 4 and 5-(tert-butyl)-6-chloro-1H-indazole-3-amine (146 mg) obtained in Production Example 1 in THF (2.5 mL), followed by stirring at room temperature. Water was added to the reaction mixture, and the mixture was extracted with ethyl acetate. The organic layer was dried over sodium sulfate. The solvent was evaporated under reduced pressure, and the obtained residue was purified by column chromatography (hexane/ethyl acetate), thereby obtaining tert-butyl 4-(2-(((5-tert-butyl-6-chloro-1H-indazol-3-yl)amino) methyl)-4-chloro-5-ethoxycarbonyl-imidazol-1-yl)piperidine-1-carboxylate (230 mg).

Step 6: A 1N sodium hydroxide aqueous solution (2 mL) was added to a solution of tert-butyl 4-(2-(((5-tert-butyl-6-chloro-1H-indazol-3-yl)amino)methyl)-4-chloro-5-ethoxycarbonyl-imidazol-1-yl)piperidine-1-carboxylate (207 mg) obtained in step 5 in methanol (10 mL), followed by stirring at 40° C. for 3.5 hours. 2.5N hydrochloric acid was added, and the mixture was extracted with ethyl acetate. The organic layer was washed with a saturated sodium chloride solution and dried over sodium sulfate. 1-(3-Aminoazetidin-1-yl)prop-2-en-1-one hydrochloride (73.7 mg) obtained in Production Example 27 and DMF (4.14 mL) were added to the obtained residue, and N,N-diisopropylethylamine (178 μL) and HATU (199 mg) were further added. After stirring at room temperature for 30 minutes, water and ethyl acetate were added thereto. The organic layer was separated and washed with a 0.5N sodium hydroxide aqueous solution, water, 0.5N hydrochloric acid, and a saturated sodium chloride solution. The washed organic layer was dried over sodium sulfate, and the solvent was concentrated under reduced pressure, followed by purifying the obtained residue by column chromatography (ethyl acetate:methanol), thereby obtaining tert-butyl 4-(2-(((5-tert-butyl-6-chloro-1H-indazol-3-yl)amino)methyl)-4-chloro-5-((1-prop-2-enoylazetidin-3-yl)carbonyl)imidazol-1-yl)piperidine-1-carboxylate (166 mg).

Step 7: Acetic anhydride (1 mL) was added to a solution of tert-butyl 4-(2-(((5-tert-butyl-6-chloro-1H-indazol-3-yl) amino)methyl)-4-chloro-5-((1-prop-2-enoylazetidin-3-yl) carbonyl)imidazol-1-yl)piperidine-1-carboxylate (166 mg) obtained in step 6 in pyridine (1 mL), followed by stirring at room temperature for 1 hour. The reaction mixture was concentrated under reduced pressure, and the obtained residue was purified by column chromatography (ethyl acetate/methanol), thereby obtaining tert-butyl 4-(2-(((1-acetyl-5-tert-butyl-6-chloro-1H-indazol-3-yl)amino)methyl)-4-chloro-5-((1-prop-2-enoylazetidin-3-yl)carbonyl)imidazol-1-yl)piperidine-1-carboxylate (105 mg).

Step 8: Trifluoroacetic acid was added to tert-butyl 4-(2-(((1-acetyl-5-tert-butyl-6-chloro-1H-indazol-3-yl)amino) methyl)-4-chloro-5-((1-prop-2-enoylazetidin-3-yl)carbonyl) imidazol-1-yl)piperidine-1-carboxylate (105 mg) obtained in step 7, followed by stirring at room temperature for 20 minutes. The reaction mixture was concentrated under reduced pressure, and ethyl acetate was added to the residue. After concentrating the residue under reduced pressure, heptane was added, and the residue was concentrated, thereby obtaining crude 2-(((1-acetyl-5-tert-butyl-6-chloro-indazol-3-yl)amino)methyl)-4-chloro-1-(4-piperidyl)-N-(1-prop-2-enoylazetidin-3-yl)imidazole-5-carboxamide trifluoroacetate (117 mg).

Step 9: Potassium acetate (10 mg) and a formaldehyde solution (37%) (10 μL) were added to a solution of 2-(((1-acetyl-5-tert-butyl-6-chloro-indazol-3-yl)amino)methyl)-4-chloro-1-(4-piperidyl)-N-(1-prop-2-enoylazetidin-3-yl)imidazole-5-carboxamide trifluoroacetate (20 mg) obtained in step 8 in methanol. Subsequently, sodium triacetoxyborohydride (20 mg) was added thereto. After stirring at room temperature for 30 minutes, water and ethyl acetate were added to partition the reaction mixture, and the organic layer was separated, followed by washing with a 0.5N sodium hydroxide aqueous solution and a saturated sodium chloride solution. The washed organic layer was dried over sodium sulfate, and the solvent was evaporated under reduced pressure, thereby obtaining a residue. Methanol (2 mL) and a 1N sodium hydroxide aqueous solution (29 μL) were added to the obtained residue, followed by stirring at room temperature for 1 hour. Ethyl acetate was added to the reaction mixture, and the reaction mixture was washed with a saturated sodium chloride solution. The washed organic layer was dried over sodium sulfate, and the solvent was evaporated under reduced pressure, thereby obtaining the title compound (12 mg).

Example 104

N-(1-acryloylazetidin-3-yl)-2-(((5-(tert-butyl)-6-chloro-1H-indazol-3-yl)amino)methyl)-4-chloro-1-(tetrahydro-2H-pyran-3-yl)-1H-imidazole-5-carboxamide The procedure of Example 98 (steps 1 to 5) was performed except that tetrahydro-2H-pyran-3-ol was used instead of 3-cyclopenten-1-ol used in Example 98 (step 1), thereby obtaining the title compound (18.5 mg).

Example 105

N-(1-acryloylazetidin-3-yl)-2-(((5-(tert-butyl)-6-chloro-1H-indazol-3-yl)amino)methyl)-4-chloro-1-cyclopentyl-1H-imidazole-5-carboxamide The procedure of Example 98 (steps 1 to 5) was performed except that cyclopentanol was used instead of 3-cyclopenten-1-ol used in Example 98 (step 1), thereby obtaining the title compound (100 mg).

Example 106

Tert-butyl 3-(5-((1-acryloylazetidin-3-yl)carbamoyl)-2-(((5-(tert-butyl)-6-chloro-1H-indazol-3-yl) amino)methyl)-4-chloro-1H-imidazol-1-yl)azetidine-1-carboxylate Step 1: N,N-diisopropylethylamine (1.41 mL) and bis(2-methoxyethyl) azodicarboxylate (2.92 g) were added to a solution of methyl 4-chloro-1H-imidazole-5-carboxylate (1.0 g) obtained in Production Example 12, triphenylphosphine (3.27 g), and tert-butyl 3-hydroxyazetidine-1-carboxylate (1.29 g) in THF (1.5 mL) and toluene (6.0 mL), followed by stirring at 100° C. for 1 hour. The reaction mixture was cooled to room temperature, and water and ethyl acetate were added thereto, followed by separating the organic layer. The organic layer was washed with a saturated sodium chloride solution and dried over sodium sulfate, followed by evaporating the solvent under reduced pressure. The obtained residue was purified by column chromatography (hexane:ethyl acetate), thereby obtaining methyl 1-(1-(tert-butoxycarbonyl)azetidin-3-yl)-4-chloro-1H-imidazole-5-carboxylate (1.30 g).

Step 2: The procedure of Example 97 (steps 2 to 4) was performed except that methyl 1-(1-(tert-butoxycarbonyl) azetidin-3-yl)-4-chloro-1H-imidazole-5-carboxylate obtained in step 1 was used instead of methyl (S)-4-chloro- 1-(tetrahydrofuran-3-yl)-1H-imidazole-5-carboxylate used in Example 97 (step 2), thereby obtaining the title compound (88 mg).

Example 107

N-(1-acryloylazetidin-3-yl)-2-(((5-(tert-butyl)-6-chloro-1H-indazol-3-yl)amino)methyl)-4-chloro-1-(1-isopropylazetidin-3-yl)-1H-imidazole-5-carboxamide Step 1: Acetic anhydride (1.0 mL) was added to a solution of tert-butyl 3-(5-((1-acryloylazetidin-3-yl)carbamoyl)-2-(((5-(tert-butyl)-6-chloro-1H-indazol-3-yl)amino)methyl)-4-chloro-1H-imidazol-1-yl)azetidine-1-carboxylate (88 mg) obtained in Example 106 (step 2) in pyridine (1.0 mL). After stirring at room temperature for 30 minutes, the reaction mixture was concentrated under reduced pressure, and the obtained residue was purified by column chromatography (chloroform:ethanol), thereby obtaining tert-butyl 3-(2-(((1-acetyl-5-(tert-butyl)-6-chloro-1H-indazol-3-yl)amino)methyl)-5-((1-acryloylazetidin-3-yl)carbamoyl)-4-chloro-1H-imidazol-1-yl)azetidine-1-carboxylate (23 mg).

Step 2: Trifluoroacetic acid (1 mL) was added to tert-butyl 3-(2-(((1-acetyl-5-(tert-butyl)-6-chloro-1H-indazol-3-yl)amino)methyl)-5-((1-acryloylazetidin-3-yl)carbamoyl)-4-chloro-1H-imidazol-1-yl)azetidine-1-carboxylate (23 mg) obtained in step 1, and the mixture was stirred and concentrated. THE (0.7 mL), acetone (5.5 μL), and acetic acid (70 L) were added to the obtained residue, and a borane-2-picoline complex (3 mg) was further added. After stirring at room temperature for 40 minutes, a 2N sodium hydroxide aqueous solution (0.7 mL) and methanol (0.3 mL) were added thereto, followed by stirring for 20 minutes. 5N hydrochloric acid (0.2 mL) was then added, and the mixture was extracted with ethyl acetate. The organic layer was separated and washed with a saturated sodium chloride solution. The washed organic layer was dried over sodium sulfate, and the solvent was evaporated under reduced pressure, followed by purifying the obtained residue by column chromatography (ethyl acetate:ethanol), thereby obtaining the title compound (2.2 mg).

Example 108

1-(1-acetylazetidin-3-yl)-N-(1-acryloylazetidin-3-yl)-2-(((5-(tert-butyl)-6-chloro-1H-indazol-3-yl)amino)methyl)-4-chloro-1H-imidazole-5-carboxamide Trifluoroacetic acid (1.0 mL) was added to tert-butyl 3-(5-((1-acryloylazetidin-3-yl)carbamoyl)-2-(((5-(tert-butyl)-6-chloro-1H-indazol-3-yl)amino)methyl)-4-chloro-1H-imidazol-1-yl)azetidine-1-carboxylate (30 mg) obtained in Example 106 (step 2). The mixture was stirred and concentrated, followed by adding THE (1.0 mL), N,N-diisopropylethylamine (56 μL), and acetic anhydride (5 μL) to the obtained residue. After stirring at room temperature for 30 minutes, a saturated sodium hydrogen carbonate aqueous solution and ethyl acetate were added to the reaction mixture. The organic layer was separated and washed with a saturated sodium chloride solution. The washed organic layer was dried over sodium sulfate, and the solvent was evaporated under reduced pressure, followed by purifying the obtained residue by column chromatography (ethyl acetate:ethanol), thereby obtaining the title compound (4.5 mg).

Example 109

N-(1-acryloylazetidin-3-yl)-2-(((5-(tert-butyl)-6-chloro-1H-indazol-3-yl)amino)methyl)-4-chloro-1-cyclohexyl-1H-imidazole-5-carboxamide The procedure of Example 98 (steps 1 to 5) was performed except that cyclohexanol was used instead of 3-cyclopenten-1-ol used in Example 98 (step 1), thereby obtaining the title compound (20.5 mg).

Example 110

N-(1-acryloylazetidin-3-yl)-2-(((5-(tert-butyl)-6-chloro-1H-indazol-3-yl)amino)methyl)-4-chloro-1-(cyclopentylmethyl)-1H-imidazole-5-carboxamide The procedure of Example 97 (steps 1 to 4) was performed except that cyclopentylmethanol was used instead of (R)-(−)-3-hydroxytetrahydrofuran used in Example 97 (step 1), thereby obtaining the title compound (140 mg).

Example 111

N-(1-acryloylazetidin-3-yl)-2-(((5-(tert-butyl)-6-chloro-1H-indazol-3-yl)amino)methyl)-4-chloro-1-((1S,2S,5R)-2-isopropyl-5-methylcyclohexyl)-JH-imidazole-5-carboxamide The procedure of Example 98 (steps 1 to 5) was performed except that (−)-menthol was used instead of 3-cyclopenten-1-ol used in Example 98 (step 1), thereby obtaining the title compound (10.7 mg).

Example 112

N-(1-acryloylazetidin-3-yl)-2-(((5-(tert-butyl)-6-chloro-1H-indazol-3-yl)amino)methyl)-4-chloro-1-(4-methoxycyclohexyl)-1H-imidazole-5-carboxamide The procedure of Example 97 (steps 1 to 4) was performed except that 4-methoxycyclohexanol was used instead of (R)-(−)-3-hydroxytetrahydrofuran used in Example 97 (step 1), thereby obtaining the title compound (140 mg).

Example 113

(R)-N-(1-acryloylazetidin-3-yl)-2-(((5-(tert-butyl)-6-chloro-1H-indazol-3-yl)amino)methyl)-4-chloro-1-(1-(2,2-difluoroethyl)pyrrolidin-3-yl)-1H-imidazole-5-carboxamide Step 1: Trifluoroacetic acid (3.0 mL) was added to methyl (R)-1-(1-(tert-butoxycarbonyl)pyrrolidin-3-yl)-2-(((5-(tert-butyl)-6-chloro-1H-indazol-3-yl)amino)methyl)-4-chloro-1H-imidazole-5-carboxylate (437 mg) obtained in Production Example 51, and the mixture was stirred at room temperature for 5 minutes, followed by concentrating the reaction mixture. Methanol was added to the obtained residue, and a concentration operation was repeated twice under reduced pressure. A solution of potassium acetate (400 mg), difluoroacetaldehyde ethyl hemiacetal (170 μL), and 0.3M sodium cyanoborohydride-1/2 zinc chloride in methanol solution (5.15 mL) was added to the obtained residue, followed by stirring at room temperature overnight. The reaction mixture was concentrated, and a saturated sodium hydrogen carbonate aqueous solution and ethyl acetate were added thereto. The organic layer was separated and washed with a saturated sodium chloride solution, followed by drying over sodium sulfate. The solvent was evaporated under reduced pressure, and the obtained residue was purified by column chromatography (chloroform:ethanol), thereby obtaining methyl (R)-2-(((5-(tert-butyl)-6-chloro-1H-indazol-3-yl)amino)methyl)-4-chloro-1-(1-(2,2-difluoroethyl)pyrrolidin-3-yl)-1H-imidazole-5-carboxylate (261 mg).

Step 2: A 5N sodium hydroxide aqueous solution (1.00 mL) was added to a solution of methyl (R)-2-(((5-(tert-butyl)-6-chloro-1H-indazol-3-yl)amino)methyl)-4-chloro-1-(1-(2,2-difluoroethyl)pyrrolidin-3-yl)-1H-imidazole-5-carboxylate (261 mg) obtained in step 1 in ethanol (3.0 mL). After stirring at room temperature for 30 minutes, 6N hydrochloric acid (820 μL) was added thereto. THE was added to the reaction mixture, and the precipitated solid was filtered off, followed by washing the solid with 2-propanol. The filtrate was concentrated under reduced pressure, and DMF (3.0 mL), 1-(3-aminoazetidin-1-yl)prop-2-en-1-one hydrochloride (120 mg) obtained in Production Example 27, 1-hydroxybenzotriazole hydrate (100 mg), N,N-diisopropylethylamine (420 μL), and WSC hydrochloride (300 mg) were added to the obtained residue, followed by stirring at room temperature overnight. A saturated sodium hydrogen carbonate aqueous solution and ethyl acetate were added to the reaction mixture. The organic layer was separated and washed with water and a saturated sodium chloride solution, followed by drying over sodium sulfate. The solvent was evaporated under reduced pressure, and the obtained residue was purified by column chromatography (chloroform:ethanol), thereby obtaining the title compound (241 mg).

Example 114

(R)-N-(1-acryloylazetidin-3-yl)-2-(((5-(tert-butyl)-6-chloro-1H-indazol-3-yl)amino)methyl)-4-chloro-1-(1-isopropylpyrrolidin-3-yl)-1H-imidazole-5-carboxamide Step 1: Trifluoroacetic acid (1.0 mL) was added to methyl (R)-1-(1-(tert-butoxycarbonyl)pyrrolidin-3-yl)-2-(((5-(tert-butyl)-6-chloro-1H-indazol-3-yl)amino)methyl)-4-chloro-1H-imidazole-5-carboxylate (300 mg) obtained in Production Example 51, and the mixture was stirred at room temperature for 15 minutes, followed by concentrating the reaction mixture. Dichloromethane (5.0 mL), ethanol (0.5 mL), acetone (250 μL), and potassium acetate (150 mg) were added to the obtained residue. Subsequently, sodium triacetoxyborohydride (350 mg) was added thereto, followed by stirring at room temperature for 2 hours. Sodium triacetoxyborohydride (100 mg) was further added to the reaction mixture, followed by stirring at room temperature for 1 hour. A saturated sodium hydrogen carbonate aqueous solution and ethyl acetate were added to the reaction mixture. The organic layer was separated and washed with a saturated sodium chloride solution, followed by drying over sodium sulfate. The solvent was evaporated under reduced pressure. The obtained residue was purified by column chromatography (basic silica gel:hexane:ethyl acetate), thereby obtaining methyl (R)-2-(((5-(tert-butyl)-6-chloro-1H-indazol-3-yl)amino)methyl)-4-chloro-1-(1-isopropylpyrrolidin-3-yl)-1H-imidazole-5-carboxylate (170 mg).

Step 2: The procedure of Example 113 (step 2) was performed except that methyl (R)-2-(((5-(tert-butyl)-6-chloro-1H-indazol-3-yl)amino)methyl)-4-chloro-1-(1-isopropylpyrrolidin-3-yl)-1H-imidazole-5-carboxylate (170 mg) obtained in step 1 was used instead of methyl (R)-2-(((5-(tert-butyl)-6-chloro-1H-indazol-3-yl)amino)methyl)-4-chloro-1-(1-(2,2-difluoroethyl)pyrrolidin-3-yl)-1H-imidazole-5-carboxylate used in Example 113 (step 2), thereby obtaining the title compound (36 mg).

Example 115

(S)-N-(1-acryloylazetidin-3-yl)-2-(((5-(tert-butyl)-6-chloro-1H-indazol-3-yl)amino)methyl)-4-chloro-1-(1-(2,2-difluoroethyl)pyrrolidin-3-yl)-1H-imidazole-5-carboxamide The procedure of Production Example 25, Production Example 51, and Example 113 (steps 1 and 2) was performed except that methyl (S)-1-(1-(tert-butoxycarbonyl)pyrrolidin-3-yl)-4-chloro-1H-imidazole-5-carboxylate obtained in Production Example 24 was used instead of methyl (R)-1-(1-(tert-butoxycarbonyl)pyrrolidin-3-yl)-4-chloro-1H-imidazole-5-carboxylate used in Production Example 25, thereby obtaining the title compound (24 mg).

Example 116

(S)-N-(1-acryloylazetidin-3-yl)-2-(((5-(tert-butyl)-6-chloro-1H-indazol-3-yl)amino)methyl)-4-chloro-1-(1-isopropylpyrrolidin-3-yl)-1H-imidazole-5-carboxamide The procedure of Production Example 25, Production Example 51, and Example 114 (steps 1 and 2) was performed except that methyl (S)-1-(1-(tert-butoxycarbonyl)pyrrolidin-3-yl)-4-chloro-1H-imidazole-5-carboxylate obtained in Production Example 24 was used instead of methyl (R)-1-(1-(tert-butoxycarbonyl)pyrrolidin-3-yl)-4-chloro-1H-imidazole-5-carboxylate used in Production Example 25, thereby obtaining the title compound (12.1 mg).

Example 117

N-(1-acryloylazetidin-3-yl)-2-(((5-(tert-butyl)-6-chloro-1H-indazol-3-yl)amino)methyl)-4-chloro-1-(1-(2,2-difluoroethyl)piperidin-3-yl)-1H-imidazole-5-carboxamide Step 1: The procedure of Example 97 (steps 1 to 4) was performed except that 1-Boc-3-hydroxypiperidine was used instead of (R)-(−)-3-hydroxytetrahydrofuran used in Example 97 (step 1), thereby obtaining tert-butyl 3-(5-((1-acryloylazetidin-3-yl)carbamoyl)-2-(((5-(tert-butyl)-6-chloro-1H-indazol-3-yl)amino)methyl)-4-chloro-1H-imidazol-1-yl)piperidine-1-carboxylate (40.2 mg).

Step 2: Acetic anhydride (0.5 mL) was added to a solution of tert-butyl 3-(5-((1-acryloylazetidin-3-yl)carbamoyl)-2-(((5-(tert-butyl)-6-chloro-1H-indazol-3-yl)amino)methyl)-4-chloro-1H-imidazol-1-yl)piperidine-1-carboxylate (40.2 mg) obtained in step 1 in pyridine (0.5 mL). After stirring at room temperature for 30 minutes, the reaction mixture was concentrated under reduced pressure, and the obtained residue was purified by column chromatography (chloroform:methanol). The purified product was concentrated, and trifluoroacetic acid (0.5 mL) was added thereto, followed by concentrating the reaction mixture, thereby obtaining 2-(((1-acetyl-5-(tert-butyl)-6-chloro-1H-indazol-3-yl)amino)methyl)-N-(1-acryloylazetidin-3-yl)-4-chloro-1-(piperidin-3-yl)-1H-imidazole-5-carboxamide trifluoroacetate (43 mg).

Step 3: A solution of potassium acetate (10 mg), difluoroacetaldehyde ethyl hemiacetal (30 μL), and 0.3M sodium cyanoborohydride-1/2 zinc chloride in methanol solution (1.0 mL) was added to a solution of 2-(((1-acetyl-5-(tert-butyl)-6-chloro-1H-indazol-3-yl)amino)methyl)-N-(1-acryloylazetidin-3-yl)-4-chloro-1-(piperidin-3-yl)-1H-imidazole-5-carboxamide trifluoroacetate (22 mg) obtained in step 2 in methanol (0.2 mL), followed by stirring at 40° C. for 3 days. Water and ethyl acetate were added to the reaction mixture. The organic layer was separated and washed with a 0.5N sodium hydroxide aqueous solution and a saturated sodium chloride solution, followed by drying over sodium sulfate. The solvent was evaporated under reduced pressure, and the obtained residue was purified by column chromatography (chloroform:methanol), thereby obtaining the title compound (3.0 mg).

Example 118

N-(1-acryloylazetidin-3-yl)-2-(((5-(tert-butyl)-6-chloro-1H-indazol-3-yl)amino)methyl)-4-chloro-1-(1-methylpiperidin-3-yl)-1H-imidazole-5-carboxamide The procedure of Example 91 (step 9) was performed except that 2-(((1-acetyl-5-(tert-butyl)-6-chloro-1H-indazol-3-yl)amino)methyl)-N-(1-acryloylazetidin-3-yl)-4-chloro-1-(piperidin-3-yl)-1H-imidazole-5-carboxamide trifluoroacetate (20 mg) obtained in Example 117 (step 2) was used instead of N-(1-acryloylazetidin-3-yl)-2-(((5-(tert-butyl)-6-chloro-1H-indazol-3-yl)amino)methyl)-4-(difluoromethyl)-1-(pyrrolidin-3-yl)-1H-imidazole-5-carboxamide formate used in Example 91 (step 9), thereby obtaining the title compound (8.05 mg).

Example 119

(R)-N-(1-acryloylazetidin-3-yl)-2-(((5-(tert-butyl)-6-chloro-1H-indazol-3-yl)amino)methyl)-4-chloro-1-(1-(2-methoxyethyl)pyrrolidin-3-yl)-1H-imidazole-5-carboxamide Step 1: Trifluoroacetic acid (7.00 mL) was added to methyl (R)-1-(1-(tert-butoxycarbonyl)pyrrolidin-3-yl)-2-(((5-(tert-butyl)-6-chloro-1H-indazol-3-yl)amino)methyl)-4-chloro-1H-imidazole-5-carboxylate (2.95 g) of Production Example 51, followed by stirring at room temperature for 15 minutes and concentrating the reaction mixture. Toluene was added to the obtained residue, and concentration was repeated twice, thereby obtaining a methyl (R)-2-(((5-(tert-butyl)-6-chloro-1H-indazol-3-yl)amino)methyl)-4-chloro-1-(pyrrolidin-3-yl)-1H-imidazole-5-carboxylate trifluoroacetic acid adduct (3.76 g).

Step 2: 1,1,2-Trimethoxyethane (2.5 mL), water (1.94 mL), and trifluoroacetic acid (1.94 mL) were stirred at 50° C. for 25 minutes. The reaction mixture was cooled to room temperature, and a solution of the methyl (R)-2-(((5-(tert-butyl)-6-chloro-1H-indazol-3-yl)amino)methyl)-4-chloro-1-(pyrrolidin-3-yl)-1H-imidazole-5-carboxylate trifluoroacetic acid adduct (3.76 g) obtained in step 1 in ethanol (31 mL) was added to a solution of ethanol (9 mL) and triethylamine (3.53 mL). Sodium triacetoxyborohydride (6.88 g) was added thereto little by little, followed by stirring at room temperature for 1 hour. 1N hydrochloric acid was added to the reaction mixture, and ethanol was concentrated, followed by adding ethyl acetate and a 1N sodium hydroxide aqueous solution. The organic layer was separated and washed with a saturated sodium chloride solution, followed by drying over sodium sulfate. The solvent was evaporated under reduced pressure, and the obtained residue was purified by column chromatography (ethyl acetate:ethanol), thereby obtaining methyl (R)-2-(((5-(tert-butyl)-6-chloro-1H-indazol-3-yl)amino)methyl)-4-chloro-1-(1-(2-methoxyethyl)pyrrolidin-3-yl)-1H-imidazole-5-carboxylate (1.07 g).

Step 3: The procedure of Example 113 (step 2) was performed except that methyl (R)-2-(((5-(tert-butyl)-6-chloro-1H-indazol-3-yl)amino)methyl)-4-chloro-1-(1-(2-methoxyethyl)pyrrolidin-3-yl)-1H-imidazole-5-carboxylate (1.07 g) obtained in step 2 was used instead of methyl (R)-2-(((5-(tert-butyl)-6-chloro-1H-indazol-3-yl)amino)methyl)-4-chloro-1-(1-(2,2-difluoroethyl)pyrrolidin-3-yl)-1H-imidazole-5-carboxylate used in Example 113 (step 2), thereby obtaining the title compound (540 mg).

Example 120

(R)-N-(1-acryloylazetidin-3-yl)-2-(((5-(tert-butyl)-6-chloro-1H-indazol-3-yl)amino)methyl)-4-chloro-1-(1-cyclopropylpyrrolidin-3-yl)-1H-imidazole-5-carboxamide Step 1: Trifluoroacetic acid (500 μL) was added to methyl (R)-1-(1-(tert-butoxycarbonyl)pyrrolidin-3-yl)-4-chloro-1H-imidazole-5-carboxylate (165 mg) obtained in Production Example 23, followed by stirring at room temperature for 15 minutes. The reaction mixture was concentrated, and methanol (3.0 mL), (1-ethoxycyclopropoxy)trimethyl silane (150 μL), acetic acid (200 μL), potassium acetate (100 mg), and sodium cyanoborohydride (200 mg) were added thereto, followed by stirring at 50° C. overnight. The reaction mixture was concentrated, and a saturated sodium hydrogen carbonate aqueous solution and ethyl acetate were added thereto. The organic layer was separated and washed with a saturated sodium chloride solution, followed by drying over sodium sulfate. The solvent was evaporated under reduced pressure. The obtained residue was purified by column chromatography (basic silica gel, hexane:ethyl acetate), thereby obtaining methyl (R)-4-chloro-1-(1-(cyclopropylpyrrolidin-3-yl)-1H-imidazole-5-carboxylate (130 mg).

Step 2: The procedure of Example 97 (steps 2 to 4) was performed except that methyl (R)-4-chloro-1-(1-(cyclopropylpyrrolidin-3-yl)-1H-imidazole-5-carboxylate (130 mg) obtained in step 1 was used instead of methyl (S)-4-chloro-1-(tetrahydrofuran-3-yl)-1H-imidazole-5-carboxylate used in Example 97 (step 2), thereby obtaining the title compound (94.3 mg).

Example 121

(R)-N-(1-acryloylazetidin-3-yl)-2-(((5-(tert-butyl)-6-chloro-1H-indazol-3-yl)amino)methyl)-4-chloro-1-(1-(oxetan-3-yl)pyrrolidin-3-yl)-1H-imidazole-5-carboxamide The procedure of Example 113 (steps 1 and 2) was performed except that oxetane-3-one (11.5 mg) was used instead of difluoroacetaldehyde ethyl hemiacetal used in Example 113 (step 1), thereby obtaining the title compound (29.4 mg).

Example 122

(R)-N-(1-acryloylazetidin-3-yl)-1-(1-benzylpyrrolidin-3-yl)-2-(((5-(tert-butyl)-6-chloro-1H-indazol-3-yl)amino)methyl)-4-chloro-1H-imidazole-5-carboxamide Step 1: Trifluoroacetic acid (3.0 mL) was added to methyl (R)-1-(1-(tert-butoxycarbonyl)pyrrolidin-3-yl)-4-chloro-2- formyl-1H-imidazole-5-carboxylate (90 mg) obtained in Production Example 25, followed by stirring at room temperature for 5 minutes and concentrating the reaction mixture. Benzyl bromide (33 μL), DMF (1.0 mL), and sodium hydrogen carbonate (70 mg) were added to the obtained residue, followed by stirring at room temperature overnight. Water and ethyl acetate were added to the reaction mixture, and the organic layer was separated. The organic layer was washed with a saturated sodium chloride solution and dried over sodium sulfate. The solvent was evaporated under reduced pressure, and the obtained residue was purified by column chromatography (chloroform:ethyl acetate), thereby obtaining methyl (R)-1-(1-benzylpyrrolidin-3-yl)-4-chloro-2-formyl-1H-imidazole-5-carboxylate (28.3 mg).

Step 2: The procedure of Example 97 (steps 3 and 4) was performed except that methyl (R)-1-(1-benzylpyrrolidin-3-yl)-4-chloro-2-formyl-1H-imidazole-5-carboxylate (28.3 mg) obtained in step 1 was used instead of methyl (S)-4-chloro-2-formyl-1-(tetrahydrofuran-3-yl)-1H-imidazole-5-carboxylate used in Example 97 (step 3), thereby obtaining the title compound (9.4 mg).

Example 123

(R)-N-(1-acryloylazetidin-3-yl)-1-(1-allylpyrrolidin-3-yl)-2-(((5-(tert-butyl)-6-chloro-1H-indazol-3-yl)amino)methyl)-4-chloro-1H-imidazole-5-carboxamide The procedure of Example 122 (steps 1 and 2) was performed except that allyl bromide was used instead of benzyl bromide used in Example 122 (step 1), thereby obtaining the title compound (135 mg).

Example 124

(R)-N-(1-acryloylazetidin-3-yl)-2-(((5-(tert-butyl)-6-chloro-1H-indazol-3-yl)amino)methyl)-4-chloro-1-(1-(pyridin-2-yl)pyrrolidin-3-yl)-1H-imidazole-5-carboxamide Step 1: Trifluoroacetic acid (0.5 mL) was added to methyl (R)-1-(1-(tert-butoxycarbonyl)pyrrolidin-3-yl)-4-chloro-1H-imidazole-5-carboxylate (104 mg) obtained in Production Example 23, followed by stirring at room temperature for 5 minutes and concentrating the reaction mixture. Sodium hydrogen carbonate (40 mg) and 2-fluoropyridine (1.0 mL) were added thereto, and the reaction mixture was allowed to react in a microwave reactor at 130° C. for 8 hours. The reaction mixture was purified by column chromatography (ethyl acetate:ethanol), thereby obtaining methyl (R)-4-chloro-1-(1-(pyridin-2-yl)pyrrolidin-3-yl)-1H-imidazole-5-carboxylate (112 mg).

Step 2: The procedure of Example 97 (steps 2 to 4) was performed except that methyl (R)-4-chloro-1-(1-(pyridin-2-yl)pyrrolidin-3-yl)-1H-imidazole-5-carboxylate (112 mg) obtained in step 1 was used instead of methyl (S)-4-chloro-1-(tetrahydrofuran-3-yl)-1H-imidazole-5-carboxylate used in Example 97 (step 2), thereby obtaining the title compound (57.9 mg).

Example 125

N-(1-acryloylazetidin-3-yl)-2-(((5-(tert-butyl)-6-chloro-1H-indazol-3-yl)amino)methyl)-4-chloro-1-((2S,3R)-1-(2,2-difluoroethyl)-2-methylpyrrolidin-3-yl)-1H-imidazole-5-carboxamide Step 1: The procedure of Production Example 13 (step 1) was performed except that tert-butyl (2S,3S)-3-hydroxy-2-methyl-pyrrolidine-1-carboxylate was used instead of methanol used in Production Example 13 (step 1), thereby obtaining methyl 1-((2S,3R)-1-(tert-butoxycarbonyl)-2-methylpyrrolidin-3-yl)-4-chloro-1H-imidazole-5-carboxylate (249 mg).

Step 2: Trifluoroacetic acid (1.5 mL) was added to a solution of methyl 1-((2S,3R)-1-(tert-butoxycarbonyl)-2-methylpyrrolidin-3-yl)-4-chloro-1H-imidazole-5-carboxylate (248 mg) obtained in step 1 in chloroform (3.0 mL), followed by stirring at room temperature for 50 minutes and concentrating the reaction mixture. Heptane was added to the obtained residue, and a concentration operation under reduced pressure was repeated twice. A solution of potassium acetate (106 mg), difluoroacetaldehyde ethyl hemiacetal (111 μL), and 0.3M sodium cyanoborohydride-1/2 zinc chloride in methanol (4.33 mL) was added to the obtained residue, followed by stirring at room temperature overnight. Water, a saturated sodium hydrogen carbonate aqueous solution, and ethyl acetate were added to the reaction mixture, and the insoluble matter was filtered off, followed by separating the organic layer. The organic layer was washed with a saturated sodium chloride solution and dried over sodium sulfate. The solvent was evaporated under reduced pressure, and the obtained residue was purified by column chromatography (hexane:ethyl acetate), thereby obtaining methyl 4-chloro-1-((2S,3R)-1-(2,2-difluoroethyl)-2-methylpyrrolidin-3-yl)-1H-imidazole-5-carboxylate (183 mg).

Step 3: The procedure of Example 97 (steps 2 to 4) was performed except that methyl 4-chloro-1-((2S,3R)-1-(2,2-difluoroethyl)-2-methylpyrrolidin-3-yl)-1H-imidazole-5-carboxylate (183 mg) obtained in step 2 was used instead of methyl (S)-4-chloro-1-(tetrahydrofuran-3-yl)-1H-imidazole-5-carboxylate used in Example 97 (step 2), thereby obtaining the title compound (108 mg).

Example 126

N-(1-acryloylazetidin-3-yl)-2-(((5-(tert-butyl)-6-chloro-1H-indazol-3-yl)amino)methyl)-4-chloro-1-((3R,5R)-1-(2,2-difluoroethyl)-5-methylpyrrolidin-3-yl)-1H-imidazole-5-carboxamide The procedure of Example 125 (steps 1 to 3) was performed except that tert-butyl (2R,4S)-4-hydroxy-2-methyl-pyrrolidine-1-carboxylate (501 mg) was used instead of tert-butyl (2S,3S)-3-hydroxy-2-methyl-pyrrolidine-1-carboxylate used in Example 125 (step 1), thereby obtaining the title compound (71.8 mg).

Reference Example 1

N-(1-acryloylazetidin-3-yl)-2-(((5-bromo-6-chloro-1H-indazol-3-yl)amino)methyl)-1-methyl-1H-imidazole-5-carboxamide The procedure of Example 1 was performed except that 5-bromo-6-chloro-1H-indazole-3-amine obtained in Production Example 5 (step 1) was used instead of 5-(tert-butyl)-6-chloro-1H-indazole-3-amine used in Example 1, thereby obtaining the title compound (4.9 mg).

Reference Example 2

N-(1-acryloylazetidin-3-yl)-5-(((5-(tert-butyl)-6-chloro-1H-indazol-3-yl)amino)methyl)furan-2-carboxamide Step 1: 1-Hydroxybenzotriazole hydrate (333 mg), N,N-diisopropylethylamine (1.00 mL), and WSC hydrochloride (416 mg) were added to a solution of 5-formylfuran-2-carboxylic acid (223 mg) and 1-(3-aminoazetidin-1-yl)prop-2-en-1-one trifluoromethanesulfonate (400 mg) in DMF (4 mL). After the mixture was stirred at room temperature overnight, water and ethyl acetate were added thereto. The organic layer was separated and washed with a saturated sodium chloride solution. The washed organic layer was dried over sodium sulfate, and the solvent was evaporated under reduced pressure, followed by purifying the obtained residue by column chromatography (chloroform:methanol), thereby obtaining N-(1-acryloylazetidin-3-yl)-5-formylfuran-2-carboxamide (235 mg).

Step 2: The procedure of Example 1 was performed except that N-(1-acryloylazetidin-3-yl)-5-formylfuran-2-carboxamide obtained in step 1 was used instead of N-(1-acryloylazetidin-3-yl)-2-formyl-1-methyl-1H-imidazole-5-carboxamide used in Example 1, thereby obtaining the title compound (26.6 mg).

Reference Example 3

N-(1-acryloylazetidin-3-yl)-2-(((5-(tert-butyl)-6-chloro-1H-indazol-3-yl)amino)methyl)-1-methyl-4-phenyl-1H-imidazole-5-carboxamide The procedure of Example 2 (steps 4 and 5) was performed except that tert-butyl 3-(2-formyl-1-methyl-4-phenyl-1H-imidazole-5-carboxamide)azetidine-1-carboxylate (84 mg) obtained in Production Example 39 was used instead of tert-butyl 3-(2-formyl-4-methylthiazole-5-carboxamide)azetidine-1-carboxylate used in Example 2 (step 4), thereby obtaining the title compound (66.0 mg). The following is a list of the compounds of Examples 1 to 126 and Reference Examples 1 to 3.

TABLE 3

| | Structure | NMR | ESI-MS $[M + H]^+$ |
|---|---|---|---|
| 1 | 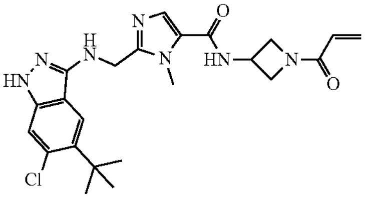 [SMILES: C=CC(=O)N1CC(NC(=O)c2cnc(CNc3n[nH]c4cc(Cl)c(C(C)(C)C)cc34)n2C)C1] | 1H-NMR (CDCl3 + 1 drop of CD3OD) δ: 7.65 (s, 1H), 7.55 (s, 1H), 7.30 (s, 1H), 6.32 (d, J = 17.2 Hz, 1H), 6.17 (dd, J = 16.9, 10.3 Hz, 1H), 5.72 (dd, J = 10.3, 1.5 Hz, 1H), 4.84-4.76 (m, 1H), 4.64-4.55 (m, 1H), 4.62 (s, 2H), 4.39 (t, J = 9.5 Hz, 1H), 4.13 (dd, J = 8.6, 5.3 Hz, 1H), 4.05 (dd, J = 10.8, 5.3 Hz, 1H), 3.94 (s, 3H), 1.51 (s, 9H). | 470 |
| 2 | 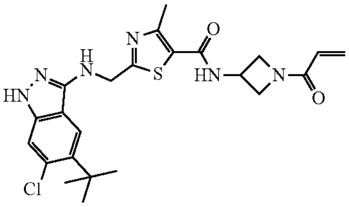 [SMILES: C=CC(=O)N1CC(NC(=O)c2sc(CNc3n[nH]c4cc(Cl)c(C(C)(C)C)cc34)nc2C)C1] | 1H-NMR (CDCl3) δ: 9.36 (br s, 1H), 7.55 (s, 1H), 7.32 (s, 1H), 6.69 (br s, 1H), (6.28 d, J = 16.5 Hz, 1H), 6.10 (dd, J = 16.9, 10.3 Hz, 1H), 5.66 (d, J = 10.3 Hz, 1H), 4.85 (d, J = 5.9 Hz, 2H), 4.81-4.73 (m, 1H), 4.55-4.49 (m, 1H), 4.40-4.34 (m, 1H), 4.05-3.98 (m, 1H), 3.96-3.89 (m, 1H), 2.66 (s, 3H), 1.51 (s, 9H). | 487 |
| 3 | 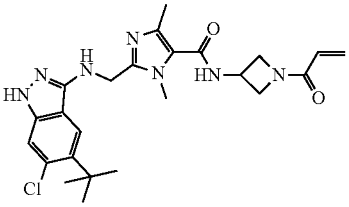 [SMILES: C=CC(=O)N1CC(NC(=O)c2c(C)nc(CNc3n[nH]c4cc(Cl)c(C(C)(C)C)cc34)n2C)C1] | 1H-NMR (DMSO-D6) δ: 11.43 (s, 1H), 8.45 (d, J = 7.3 Hz, 1H), 7.92 (s, 1H), 7.26 (s, 1H), 6.69-6.63 (m, 1H), 6.32 (dd, J = 16.9, 10.3 Hz, 1H), 6.10 (dd, J = 16.9, 2.2 Hz, 1H), 5.67 (dd, J = 10.3, 2.2 Hz, 1H), 4.75-4.66 (m, 1H), 4.54-4.48 (m, 1H), 4.43 (d, J = 5.9 Hz, 2H), 4.23-4.17 (m, 1H), 4.13-4.09 (m, 1H), 3.92-3.86 (m, 1H), 3.68 (s, 3H), 2.25 (s, 3H), 1.45 (s, 9H). | 484 |
| 4 | 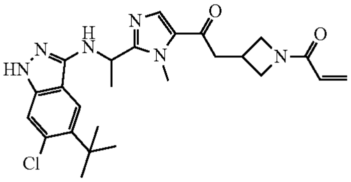 [SMILES: C=CC(=O)N1CC(CC(=O)c2cnc(C(C)Nc3n[nH]c4cc(Cl)c(C(C)(C)C)cc34)n2C)C1] | 1H-NMR (DMSO-D6) δ: 11.38 (s, 1H), 8.73 (d, J = 7.3 Hz, 1H), 7.94 (s, 1H), 7.54 (s, 1H), 7.23 (s, 1H), 6.63 (d, J = 8.8 Hz, 1H), 6.31 (dd, J = 16.9, 10.3 Hz, 1H), 6.10 (dd, J = 16.9, 2.2 Hz, 1H), 5.66 (dd, J = 10.3, 2.2 Hz, 1H), 5.09-5.02 (m, 1H), 4.70-4.61 (m, 1H), 4.51-4.47 (m, 1H), 4.20-4.16 (m, 1H), 4.12-4.07 (m, 1H), 3.91-3.86 (m, 1H), 3.85 (s, 3H), 1.54 (d, J = 6.6 Hz, 3H), 1.45 (s, 9H). | 484 |
| 5 | 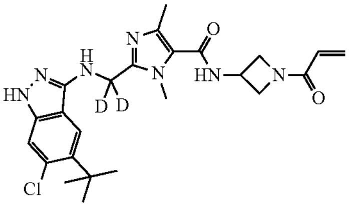 [SMILES: [2H]C([2H])(Nc1n[nH]c2cc(Cl)c(C(C)(C)C)cc12)c1nc(C)c(C(=O)NC2CN(C(=O)C=C)C2)n1C] | NT | 486 |

TABLE 3-continued

| | Structure | NMR | ESI-MS [M + H]+ |
|---|---|---|---|
| 6 | 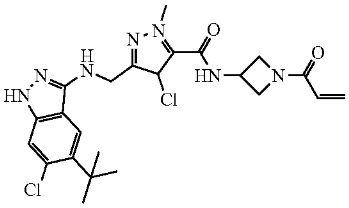 | 1H-NMR (DMSO-D6) δ: 11.38 (s, 1H), 9.14 (d, J = 7.0 Hz, 1H), 7.91 (s, 1H), 7.25 (s, 1H), 6.52 (t, J = 5.7 Hz, 1H), 6.32 (dd, J = 16.9, 10.3 Hz, 1H), 6.10 (dd, J = 16.9, 2.2 Hz, 1H), 5.67 (dd, J = 10.3, 2.2 Hz, 1H), 4.75-4.68 (m, 1H), 4.54 (t, J = 9.2 Hz, 1H), 4.37 (d, J = 5.7 Hz, 2H), 4.22 (t, J = 9.2 Hz, 1H), 4.14 (dd, J = 9.2, 5.7 Hz, 1H), 3.93-3.88 (m, 1H), 3.87 (s, 3H), 1.45 (s, 9H). | 504 |
| 7 | 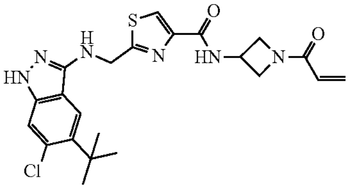 [SMILES: C=CC(=O)N1CC(NC(=O)c2csc(CNc3n[nH]c4cc(Cl)c(C(C)(C)C)cc34)n2)C1] | 1H-NMR (DMSO-D6) δ: 11.53 (s, 1H), 9.13 (d, J = 7.7 Hz, 1H), 8.11 (s, 1H), 7.90 (s, 1H), 7.30 (s, 1H), 7.26 (t, J = 5.9 Hz, 1H), 6.31 (dd, J = 17.0, 10.3 Hz, 1H), 6.10 (dd, J = 17.0, 2.4 Hz, 1H), 5.66 (dd, J = 10.3, 2.2 Hz, 1H), 4.77-4.72 (m, 3H), 4.48 (t, J = 8.8 Hz, 1H), 4.24 (dd, J = 8.8, 5.9 Hz, 1H), 4.17 (dd, J = 9.0, 8.8 Hz, 1H), 4.01-3.98 (m, 1H), 1.48 (s, 9H). | 473 |
| 8 | 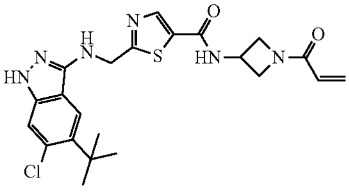 [SMILES: C=CC(=O)N1CC(NC(=O)c2cnc(CNc3n[nH]c4cc(Cl)c(C(C)(C)C)cc34)s2)C1] | 1H-NMR (DMSO-D6) δ: 11.51 (s, 1H), 9.08 (d, J = 7.3 Hz, 1H), 8.26 (s, 1H), 7.90 (s, 1H),7.29 (s, 1H), 7.27 (t, J = 6.0 Hz, 1H), 6.30 (dd, J = 16.9, 10.3 Hz, 1H), 6.09 (dd, J = 16.9, 2.2 Hz, 1H), 5.66 (dd, J = 10.3, 2.2 Hz, 1H), 4.71 (d, J = 6.0 Hz, 2H), 4.68-4.59 (m, 1H), 4.49 (t, J = 8.4 Hz, 1H), 4.18 (dd, J = 9.7, 8.4 Hz, 1H), 4.09 (dd, J = 9.7, 5.1Hz, 1H), 3.88 (dd, J = 9.7, 5.1 Hz, 1H), 1.48 (s, 9H). | 473 |
| 9 | 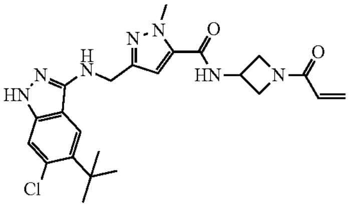 [SMILES: C=CC(=O)N1CC(NC(=O)c2cc(CNc3n[nH]c4cc(Cl)c(C(C)(C)C)cc34)nn2C)C1] | 1H-NMR (DMSO-D6) δ: 11.35 (s, 1H), 8.98 (d, J = 7.0 Hz, 1H), 7.90 (s, 1H), 7.25 (s, 1H), 6.86 (s, 1H), 6.61 (t, J = 5.5 Hz, 1H), 6.29 (dd, J = 16.9, 10.3 Hz, 1H), 6.08 (dd, J = 16.9, 2.2 Hz, 1H), 5.65 (dd, J = 10.3, 2.2 Hz, 1H), 4.69-4.62 (m, 1H), 4.48 (t, J = 8.4 Hz, 1H), 4.37 (d, J = 5.5 Hz, 2H), 4.16 (dd, J = 10.3, 9.0 Hz, 1H), 4.09 (dd, J = 8.8, 5.5 Hz, 1H), 4.00 (s, 3H), 3.87 (dd, J = 10.3, 5.5 Hz, 1H), 1.45 (s, 9H). | 470 |

TABLE 4

| | Structure | NMR | ESI-MS [M + H]+ |
|---|---|---|---|
| 10 | 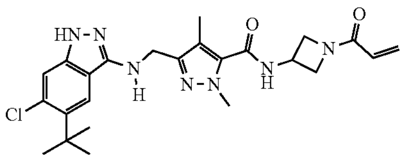 [SMILES: C=CC(=O)N1CC(NC(=O)c2c(C)c(CNc3n[nH]c4cc(Cl)c(C(C)(C)C)cc34)nn2C)C1] | NT | 484 |
| 11 | 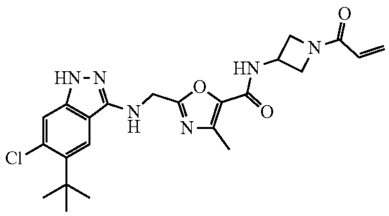 [SMILES: C=CC(=O)N1CC(NC(=O)c2oc(CNc3n[nH]c4cc(Cl)c(C(C)(C)C)cc34)nc2C)C1] | 1H-NMR (CDCl3) δ: 10.42 (s, 1H), 7.81 (d, J = 7.0 Hz, 1H), 7.50 (s, 1H), 7.25 (s, 1H), 6.30 (dd, J = 17.0, 1.6 Hz, 1H), 6.08 (dd, J = 17.0, 10.4 Hz, 1H), 5.67 (dd, J = 10.3, 1.5 Hz, 1H), 5.25 (t, J = 5.9 Hz, 1H), 4.81-4.74 (m, 1H), 4.67-4.61 (m, 2H), 4.50-4.44 (m, 1H), 4.37-4.30 (m, 1H), 4.00-3.92 (m, 2H), 2.40 (s, 3H), 1.44 (s, 9H). | 471 |
| 12 | 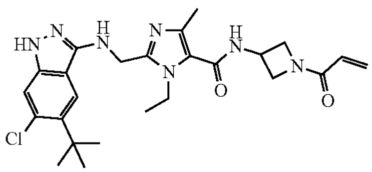 [SMILES: C=CC(=O)N1CC(NC(=O)c2c(C)nc(CNc3n[nH]c4cc(Cl)c(C(C)(C)C)cc34)n2CC)C1] | 1H-NMR (DMSO-$d_6$) δ: 11.42 (s, 1H), 8.48 (d, J = 7.3 Hz, 1H), 7.92 (s, 1H), 7.25 (s, 1H), 6.67 (d, J = 5.9 Hz, 1H), 6.36-6.26 (m, 1H), 6.09 (dd, J = 16.9, 2.2 Hz, 1H), 5.69-5.61 (m, 1H), 4.72-4.62 (m, 1H), 4.51 (t, J = 8.8 Hz, 1H), 4.43 (d, J = 5.9 Hz, 2H), 4.19 (q, J = 7.5 Hz, 3H), 4.09 (dd, J = 9.4, 5.3 Hz, 1H), 3.87 (dd, J = 9.7, 5.3 Hz, 1H), 2.23 (s, 3H), 1.44 (s, 9H), 1.21-1.15 (m, 3H) | 499 |

TABLE 4-continued

| | Structure | NMR | ESI-MS $[M + H]^+$ |
|---|---|---|---|
| 13 | 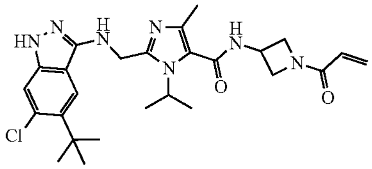 [SMILES: C=CC(=O)N1CC(NC(=O)c2c(C)nc(CNc3n[nH]c4cc(Cl)c(C(C)(C)C)cc34)n2C(C)C)C1] | 1H-NMR (DMSO-$d_6$) δ: 11.43 (s, 1H), 8.82 (brs, 1H), 7.93 (s, 1H), 7.25 (s, 1H), 6.73-6.61 (m, 1H), 6.31 (dd, J = 16.9, 10.3 Hz, 1H), 6.09 (dd, J = 16.9, 2.2 Hz, 1H), 5.68-5.62 (m, 1H), 4.79-4.69 (m, 1H), 4.68-4.59 (m, 1H), 4.56-4.43 (m, 3H), 4.24-4.16 (m, 1H), 4.08 (dd, J = 8.4, 5.5 Hz, 1H), 3.85 (dd, J = 10.3, 5.9 Hz, 1H), 2.16 (s, 3H), 1.48-1.39 (m, 15H) | 512 |
| 14 | 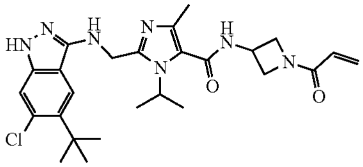 | 1H-NMR (DMSO-$d_6$) δ: 11.42 (s, 1H), 8.53 (d, J = 7.0 Hz, 1H), 7.90 (s, 1H), 7.25 (s, 1H), 6.62 (t, J = 5.9 Hz, 1H), 6.31 (dd, J = 17.0, 10.3 Hz, 1H), 6.09 (dd, J = 17.0, 2.2 Hz, 1H), 5.68-5.63 (m, 1H), 4.69-4.59 (m, 1H), 4.51 (t, J = 8.4 Hz, 1H), 4.43 (d, J = 5.9 Hz, 2H), 4.38 (brt, J = 5.1Hz, 2H), 4.22-4.15 (m, 1H), 4.09 (dd, J = 8.6, 5.7 Hz, 1H), 3.87 (dd, J = 10.1, 5.7 Hz, 1H), 3.49 (t, J = 5.3 Hz, 2H), 3.15 (s, 3H), 2.24 (s, 3H), 1.44 (s, 9H) | 529 |
| 15 | 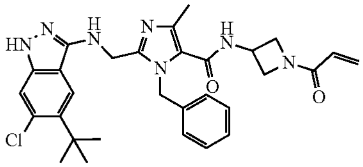 [SMILES: C=CC(=O)N1CC(NC(=O)c2c(C)nc(CNc3n[nH]c4cc(Cl)c(C(C)(C)C)cc34)n2Cc2ccccc2)C1] | 1H-NMR (DMSO-$d_6$) δ: 11.43 (s, 1H), 8.53 (d, J = 7.0 Hz, 1H), 7.88 (s, 1H), 7.29-7.17( m, 4H), 7.08-7.02 (m, 2H), 6.71 (t, J = 5.7 Hz, 1H), 6.26 (dd, J = 17.1, 10.4 Hz, 1H), 6.11-6.03 (m, 1H), 5.65 (dd, J = 10.4, 2.6 Hz, 1H), 5.47 (s, 2H), 4.61-4.50 (m, 1H), 4.47-4.39 (m, 3H), 4.16-4.08 (m, 1H), 3.92 (brdd, J = 8.4, 5.5 Hz, 1H),3.76-3.70 (m, 1H), 2.25 (s, 3H), 1.44 (s, 9H) | 561 |
| 16 | 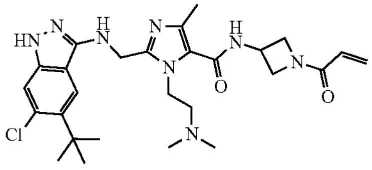 [SMILES: C=CC(=O)N1CC(NC(=O)c2c(C)nc(CNc3n[nH]c4cc(Cl)c(C(C)(C)C)cc34)n2CCN(C)C)C1] | 1H-NMR (DMSO-$d_6$) δ: 11.43 (s, 1H), 8.61 (d, J = 7.0 Hz, 1H), 7.90 (s, 1H), 7.25 (s, 1H), 6.67 (brt, J = 5.3 Hz, 1H), 6.31 (dd, J = 17.1, 10.5 Hz, 1H), 6.13-6.04 (m, 1H), 5.69-5.61 (m, 1H), 4.72-4.61 (m, 1H), 4.51 (t, J = 8.6 Hz, 1H), 4.44 (brd, J = 5.5 Hz, 2H), 4.29-4.15 (m, 3H), 4.09 (dd, J = 8.6, 6.1 Hz, 1H), 3.86 (dd, J = 10.5, 5.7 Hz, 1H), 2.46-2.42 (m, 2H), 2.23 (s, 3H), 2.06 (s, 6H), 1.44 (s, 9H) | 542 |
| 17 | 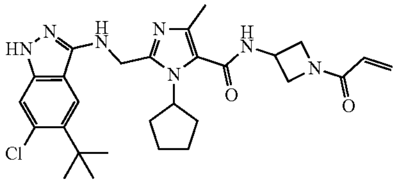 [SMILES: C=CC(=O)N1CC(NC(=O)c2c(C)nc(CNc3n[nH]c4cc(Cl)c(C(C)(C)C)cc34)n2C2CCCC2)C1] | 1H-NMR (DMSO-$d_6$) δ: 11.42 (s, 1H), 8.77 (d, J = 7.0 Hz, 1H), 7.94 (s, 1H), 7.24 (s, 1H), 6.65 (brt, J = 6.1 Hz, 1H), 6.31 (dd, J = 17.0, 10.3 Hz, 1H), 6.09 (dd, J = 17.0, 2.2 Hz, 1H), 5.70-5.63 (m, 1H), 4.92-4.81 (m, 1H), 4.67-4.58 (m, 1H), 4.52 (t, J = 8.3 Hz, 1H), 4.46 (d, J = 5.9 Hz, 2H), 4.24-4.15 (m, 1H), 4.07 (dd, J = 8.8, 5.5 Hz, 1H), 3.84 (dd, J = 9.9, 5.5 Hz, 1H), 2.16 (s, 3H), 2.09-1.86 (m, 4H), 1.78-1.65 (m, 2H), 1.53-1.42 (m, 1 1H) | 539 |
| 18 | 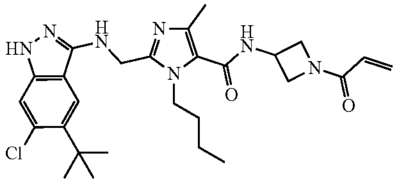 [SMILES: C=CC(=O)N1CC(NC(=O)c2c(C)nc(CNc3n[nH]c4cc(Cl)c(C(C)(C)C)cc34)n2CCCC)C1] | 1H-NMR (DMSO-$d_6$) δ: 11.41 (s, 1H), 8.50 (d, J = 7.3 Hz, 1H), 7.92 (s, 1H), 7.24 (s, 1H), 6.68 (t, J = 5.9 Hz, 1H), 6.31 (dd, J = 17.1, 10.5 Hz, 1H), 6.09 (dd, J = 17.1, 2.4 Hz, 1H), 5.68-5.63 (m, 1H), 4.71-4.61 (m, 1H), 4.51 (t, J = 8.4 Hz, 1H), 4.44 (d, J = 5.9 Hz, 2H), 4.23-4.05 (m, 4H), 3.85 (dd, J = 10.3, 5.5 Hz, 1H), 2.23 (s, 3H), 1.56-1.42 (m, 1 1H), 0.74 (t, J = 7.3 Hz, 3H) | 527 |

TABLE 5

| | Structure | NMR | ESI-MS $[M + H]^+$ |
|---|---|---|---|
| 19 | 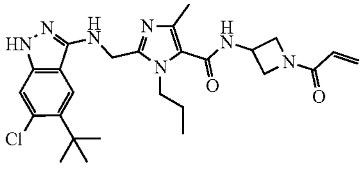 [SMILES: C=CC(=O)N1CC(NC(=O)c2c(C)nc(CNc3n[nH]c4cc(Cl)c(C(C)(C)C)cc34)n2CCC)C1] | 1H-NMR (DMSO-$d_6$) δ: 11.41 (s, 1H), 8.50 (d, J = 7.3 Hz, 1H), 7.92 (s, 1H), 7.24 (s, 1H), 6.68 (t, J = 5.9 Hz, 1H), 6.31 (dd, J = 17.0, 10.3 Hz, 1H), 6.09 (dd, J = 17.0, 2.2 Hz, 1H), 5.69-5.62 (m, 1H), 4.72-4.61 (m, 1H), 4.51 (t, J = 8.3 Hz, 1H), 4.44 (d, J = 6.2 Hz, 2H), 4.23-4.04 (m, 4H), 3.85 (dd, J = 10.3, 5.5 Hz, 1H), 2.23 (s, 3H), 1.63-1.49 (m, 2H), 1.44 (s, 9H), 0.74 (t, J = 7.3 Hz, 3H) | 512 |

TABLE 5-continued

| | Structure | NMR | ESI-MS [M + H]+ |
|---|---|---|---|
| 20 | 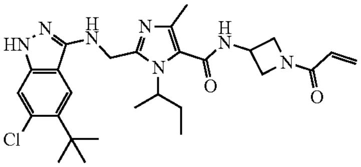 [SMILES: C=CC(=O)N1CC(NC(=O)c2c(C)nc(CNc3n[nH]c4cc(Cl)c(C(C)(C)C)cc34)n2C(C)CC)C1] | 1H-NMR (DMSO-$d_6$) δ: 11.41 (s, 1H), 8.76 (d, J = 7.0 Hz, 1H), 7.94 (s, 1H), 7.24 (s, 1H), 6.68-6.60 (m, 1H), 6.31 (dd, J = 16.9, 10.3 Hz, 1H), 6.09 (dd, J = 16.9, 2.2 Hz, 1H), 5.68-5.63 (m, 1H), 4.67-4.39 (m, 5H), 4.20 (t, J = 9.2 Hz, 1H), 4.11-4.03 (m, 1H), 3.85 (dd, J = 9.7, 5.0 Hz, 1H), 2.17 (s, 3H), 1.92-1.66 (m, 2H), 1.45 (s, 9H), 1.41 (d, J = 6.6 Hz, 3H), 0.70 (t, J = 7.5 Hz, 3H) | 526 |
| 21 | 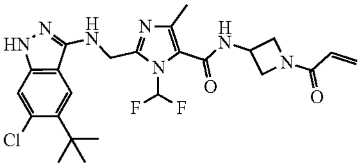 | 1H-NMR (DMSO-$d_6$) δ: 11.48 (s, 1H), 8.75 (d, J = 7.3 Hz, 1H), 7.91 (s, 1H), 7.26 (s, 1H), 6.86 (t, J = 6.1 Hz, 1H), 6.31 (dd, J = 16.9, 10.3 Hz, 1H), 6.09 (dd, J = 16.9, 2.2 Hz, 1H), 5.68-5.63 (m, 1H), 5.38 (q, J = 9.0 Hz, 2H), 4.69-4.59 (m, 1H), 4.55-4.44 (m, 3H), 4.23-4.16 (m, 1H), 4.06 (dd, J = 8.6, 5.3 Hz, 1H), 3.84 (dd, J = 10.1, 5.7 Hz, 1H), 2.26 (s, 3H), 1.45 (s, 9H) | 552 |
| 22 | 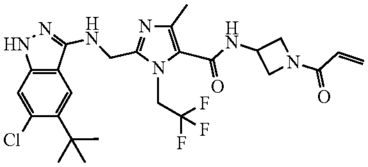 [SMILES: C=CC(=O)N1CC(NC(=O)c2c(C)nc(CNc3n[nH]c4cc(Cl)c(C(C)(C)C)cc34)n2CC(F)(F)F)C1] | 1H-NMR (DMSO-$d_6$) δ: 11.37 (s, 1H), 8.60 (d, J = 7.0 Hz, 1H), 7.95 (s, 1H), 7.24 (s, 1H), 6.60 (t, J = 5.9 Hz, 1H), 6.31 (dd, J = 16.9, 10.3 Hz, 1H), 6.09 (dd, J = 16.9, 2.2 Hz, 1H), 5.68-5.63 (m, 1H), 4.73-4.63 (m, 1H), 4.57-4.48 (m, 3H), 4.21 (t, J = 9.2 Hz, 1H), 4.10 (dd, J = 8.8, 5.1 Hz, 1H), 3.87 (dd, J = 9.9, 5.5 Hz, 1H), 2.13 (s, 3H),1.46 (s, 9H), 1.01-0.94 (m, 2H), 0.86-0.78 (m, 2H) | 510 |
| 23 | 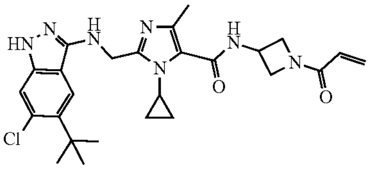 [SMILES: C=CC(=O)N1CC(NC(=O)c2c(C)nc(CNc3n[nH]c4cc(Cl)c(C(C)(C)C)cc34)n2C2CC2)C1] | 1H-NMR (DMSO-$d_6$) δ: 11.44 (s, 1H), 9.16-9.05 (m, 1H), 7.99 (s, 1H), 7.28 (s, 1H),6.65-6.53 (m, 1H), 6.33 (dd, J = 17.0, 10.2 Hz, 1H), 6.11 (dd, J = 17.0, 2.1 Hz, 1H), 5.72-5.64 (m, 1H), 4.71-4.47 (m, 4H), 4.29-4.17 (m, 1H), 4.13-4.06 (m, 1H), 3.92-3.82 (m, 1H), 2.07 (s, 3H), 1.66 (s, 9H), 1.47 (s, 9H) | 526 |
| 24 | 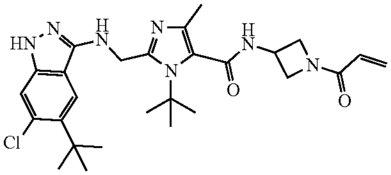 [SMILES: C=CC(=O)N1CC(NC(=O)c2c(C)nc(CNc3n[nH]c4cc(Cl)c(C(C)(C)C)cc34)n2C(C)(C)C)C1] | 1H-NMR (DMSO-$d_6$) δ: 11.40 (s, 1H), 8.81 (d, J = 7.3 Hz, 1H), 7.93 (s, 1H), 7.86 (t, J = 58.3 Hz, 1H), 7.25 (s, 1H), 6.80 (t, J = 6.2 Hz, 1H), 6.31 (dd, J = 17.0, 10.3 Hz, 1H), 6.09 (dd, J = 17.0, 2.2 Hz, 1H), 5.69-5.63 (m, 1H), 4.72-4.58 (m, 3H), 4.51 (t, J = 8.3 Hz, 1H), 4.24-4.09 (m, 2H), 3.90 (dd, J = 10.5, 5.3 Hz, 1H), 2.23 (s, 3H), 1.47 (s, 9H) | 520 |
| 25 | 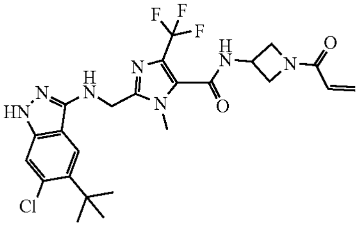 [SMILES: C=CC(=O)N1CC(NC(=O)c2c(C(F)(F)F)nc(CNc3n[nH]c4cc(Cl)c(C(C)(C)C)cc34)n2C)C1] | 1H-NMR (DMSO-D6) δ: 11.48 (s, 1H), 9.44 (d, J = 6.8 Hz, 1H), 7.91 (s, 1H), 7.27 (s, 1H), 6.83 (t, J = 6.8 Hz, 1H), 6.31 (dd, J = 16.9, 10.3 Hz, 1H), 6.09 (dd, J = 16.9, 2.2 Hz, 1H), 5.67 (dd, J = 10.3, 2.2 Hz, 1H), 4.71-4.63 (m, 1H), 4.56-4.52 (m, 3H), 4.22 (dd, J = 9.2, 9.9 Hz, 1H), 4.06 (dd, J = 8.7, 5.5 Hz, 1H), 3.83 (dd, J = 5.5, 9.9 Hz, 1H), 3.69 (s, 3H), 1.46 (s, 9H). | 538 |
| 26 | 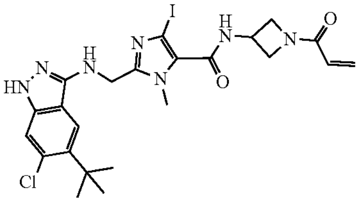 [SMILES: C=CC(=O)N1CC(NC(=O)c2c(I)nc(CNc3n[nH]c4cc(Cl)c(C(C)(C)C)cc34)n2C)C1] | 1H-NMR (DMSO-D6) δ: 11.46 (s, 1H), 8.84 (d, J = 7.3 Hz, 1H), 7.91 (s, 1H), 7.26 (s, 1H), 6.76 (t, J = 6.2 Hz, 1H), 6.32 (dd, J = 17.2, 10.3 Hz, 1H), 6.10 (dd, J = 17.2, 2.2 Hz, 1H), 5.67 (dd, J = 10.3, 2.2 Hz, 1H), 4.77-4.69 (m, 1H), 4.54 (t, J = 8.6 Hz, 1H), 4.46 (d, J = 6.2 Hz, 2H), 4.21 (dd, J = 9.2, 9.9 Hz, 1H), 4.14 (dd, J = 8.6, 5.5 Hz, 1H), 3.93 (dd, J = 9.9, 5.5 Hz, 1H), 3.71 (s, 3H), 1.46 (s, 9H). | 596 |
| 27 | 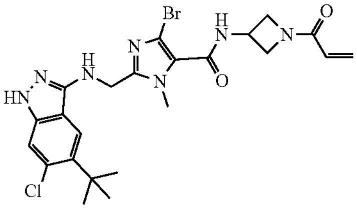 [SMILES: C=CC(=O)N1CC(NC(=O)c2c(Br)nc(CNc3n[nH]c4cc(Cl)c(C(C)(C)C)cc34)n2C)C1] | 1H-NMR (CDCl3) δ: 8.95 (s, 1H), 7.56 (s, 1H), 7.33 (s, 1H), 7.13 (d, J = 7.0 Hz, 1H), 6.36 (dd, J = 16.9, 1.8 Hz, 1H), 6.18 (dd, J = 17.0, 10.4 Hz, 1H), 5.71 (dd, J = 10.4, 1.6 Hz, 1H), 4.86-4.82 (m, 2H), 4.64-4.59 (m, 3H), 4.48 (t, J = 9.5 Hz, 1H), 4.02 (dd, J = 10.8, 5.3 Hz, 1H), 3.98 (s, 3H), 3.72 (q, J = 7.1 Hz, 1H), 1.50 (s, 9H). | 550 |

TABLE 6

| | Structure | NMR | ESI-MS $[M + H]^+$ |
|---|---|---|---|
| 28 | 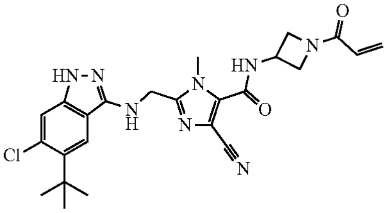 [SMILES: C=CC(=O)N1CC(NC(=O)c2c(C#N)nc(CNc3n[nH]c4cc(Cl)c(C(C)(C)C)cc34)n2C)C1] | 1H-NMR (DMSO-D6) δ: 11.48 (s, 1H), 9.51 (d, J = 7.3 Hz, 1H), 7.90 (s, 1H), 7.27 (s, 1H), 6.83 (t, J = 6.0 Hz, 1H), 6.33 (dd, J = 16.9, 10.3 Hz, 1H), 6.11 (dd, J = 17.0, 2.0 Hz, 1H), 5.68 (dd, J = 10.3, 2.2 Hz, 1H), 4.77-4.69 (m, 1H), 4.59-4.53 (m, 1H), 4.54 (d, J = 5.9 Hz, 2H), 4.24 (t, J = 9.3 Hz, 1H), 4.11 (dd, J = 8.8, 5.1Hz, 1H), 3.89 (dd, J = 10.3, 5.5 Hz, 1H), 3.80 (s, 3H), 1.46 (s, 9H). | 495 |
| 29 | 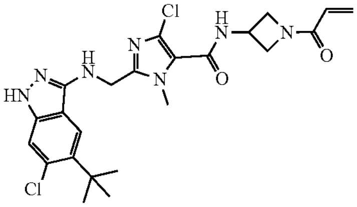 [SMILES: C=CC(=O)N1CC(NC(=O)c2c(Cl)nc(CNc3n[nH]c4cc(Cl)c(C(C)(C)C)cc34)n2C)C1] | 1H-NMR (CDCl3) δ: 9.51 (br s, 1H), 7.55 (s, 1H), 7.30 (s, 1H), 7.10 (d, J = 7.0 Hz, 1H), 6.35 (dd, J = 16.9, 1.8 Hz, 1H), 6.17 (dd, J = 17.0, 10.4 Hz, 1H), 5.70 (dd, J = 10.3, 1.8 Hz, 1H), 5.02 (brs, 1H), 4.85-4.80(m, 1H), 4.61-4.57 (m, 3H), 4.46 (t, J = 9.3 Hz, 1H), 4.12 (dd, J = 7.9, 4.2 Hz, 1H), 4.00 (dd, J = 10.8, 5.3 Hz, 1H), 3.93 (s, 3H), 1.47 (s, 9H). | 504 |
| 30 | 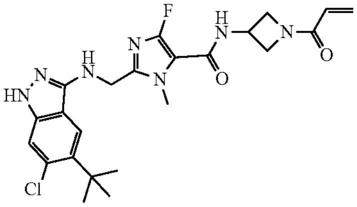 [SMILES: C=CC(=O)N1CC(NC(=O)c2c(F)nc(CNc3n[nH]c4cc(Cl)c(C(C)(C)C)cc34)n2C)C1] | 1H-NMR (CDCl3) δ: 8.89 (br s, 1H), 7.56 (s, 1H), 7.33 (s, 1H), 6.40-6.33 (m, 2H), 6.17 (dd, J = 16.9, 10.3 Hz, 1H), 5.70 (dd, J = 10.3, 1.5 Hz, 1H), 4.85-4.80 (m, 1H), 4.74 (t, J = 5.5 Hz, 1H), 4.61-4.57 (m, 3H), 4.46 (t, J = 9.3 Hz, 1H), 4.10 (t, J = 7.1 Hz, 1H), 3.98 (s, 3H), 1.52 (s, 9H). | 488 |
| 31 | 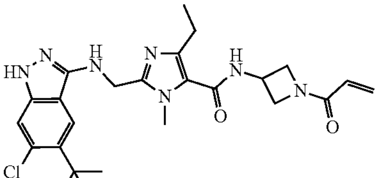 | 1H-NMR (DMSO-$d_6$) δ: 11.43 (s, 1H), 8.51 (d, J = 7.3 Hz, 1H), 7.92 (s, 1H), 7.25 (s, 1H), 6.64 (t, J = 5.9 Hz, 1H), 6.31 (dd, J = 16.9, 10.3 Hz, 1H), 6.09 (dd, J = 16.9, 2.2 Hz, 1H), 5.65 (dd, J = 10.3, 2.2 Hz, 1H), 4.75-4.65 (m, 1H), 4.51 (t, J = 8.5 Hz, 1H), 4.44 (d, J = 5.9 Hz, 2H), 4.19 (t, J = 9.2 Hz, 1H),4.10 (dd, J = 8.5, 5.7 Hz, 1H), 3.88 (dd, J = 10.3, 5.5 Hz, 1H), 3.66 (s, 3H), 2.63 (q, J = 7.5 Hz, 2H), 1.44 (s, 9H), 1.12 (t, J = 7.5 Hz, 3H) | 498 |
| 32 | 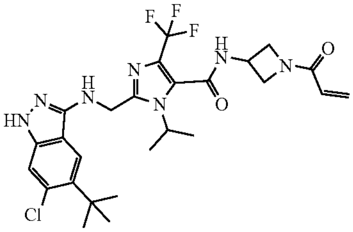 [SMILES: C=CC(=O)N1CC(NC(=O)c2c(C(F)(F)F)nc(CNc3n[nH]c4cc(Cl)c(C(C)(C)C)cc34)n2C(C)C)C1] | 1H-NMR (DMSO-D6) δ: 11.49 (s, 1H), 9.56 (d, J = 6.2 Hz, 1H), 7.93 (s, 1H),7.27 (s, 1H), 6.83 (t, J = 6.2 Hz, 1H), 6.32 (dd, J = 16.9, 10.3 Hz, 1H), 6.09 (dd, J = 16.9, 2.2 Hz, 1H), 5.66 (dd, J = 10.3, 2.2 Hz, 1H), 4.85-4.78 (m, 1H),4.66-4.52 (m, 4H), 4.24-4.19 (m, 1H), 4.05-4.01 (m, 1H), 3.82-3.78 (m, 1H), 1.45 (s, 9H), 1.44 (d, J = 6.8 Hz, 6H). | 566 |
| 33 | 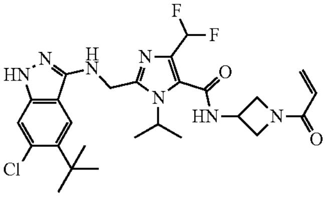 [SMILES: C=CC(=O)N1CC(NC(=O)c2c(C(F)F)nc(CNc3n[nH]c4cc(Cl)c(C(C)(C)C)cc34)n2C(C)C)C1] | 1H-NMR (DMSO-D6) δ: 11.46 (s, 1H), 9.33 (d, J = 6.2 Hz, 1H), 7.94 (s, 1H), 7.26 (s, 1H), 6.88 (t, J = 54.3 Hz, 1H), 6.80 (t, J = 5.9 Hz, 1H), 6.31 (dd, J = 17.2, 10.3 Hz, 1H), 6.09 (d, J = 17.2 Hz, 1H), 5.66 (d, J = 10.3 Hz, 1H), 4.83-4.75 (m, 1H), 4.65-4.60 (m, 1H), 4.56-4.50 (m, 3H), 4.22-4.17 (m, 1H), 4.11-4.07 (m, 1H), 3.88-3.84 (m, 1H), 1.45 (s, 9H), 1.44 (d, J = 6.8 Hz, 6H). | 548 |
| 34 | 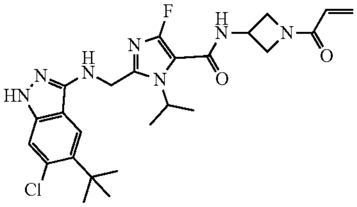 [SMILES: C=CC(=O)N1CC(NC(=O)c2c(F)nc(CNc3n[nH]c4cc(Cl)c(C(C)(C)C)cc34)n2C(C)C)C1] | 1H-NMR (CDCl3) δ: 8.94 (br s, 1H), 7.60 (s, 1H), 7.34 (s, 1H), 6.50 (t, J = 6.8 Hz, 1H), 6.35 (dd, J = 17.0, 1.6 Hz, 1H), 6.17 (dd, J = 17.0, 10.4 Hz, 1H), 5.70 (dd, J = 10.4, 1.6 Hz, 1H), 5.37 (br s, 1H), 4.90 (t, J = 5.5 Hz, 1H),4.82 (q, J = 6.6 Hz, 1H), 4.66 (d, J = 5.5 Hz, 2H), 4.59 (t, J = 8.2 Hz, 1H), 4.47 (t, J = 9.3 Hz, 1H), 4.12 (t, J = 7.1 Hz, 1H) 3.99 (dd, J = 10.8, 5.3 Hz, 1H), 1.58 (d, J = 7.0 Hz, 6H) 1.51 (s, 9H). | 516 |

TABLE 6-continued

| | Structure | NMR | ESI-MS [M + H]+ |
|---|---|---|---|
| 35 | 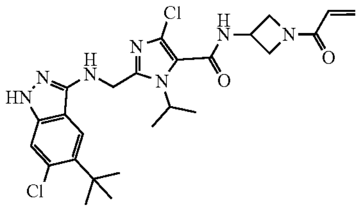 [SMILES: C=CC(=O)N1CC(NC(=O)c2c(Cl)nc(CNc3n[nH]c4cc(Cl)c(C(C)(C)C)cc34)n2C(C)C)C1] | 1H-NMR (CDCl3) δ: 8.86 (s, 1H), 7.61 (s, 1H), 7.33 (s, 1H), 6.93 (d, J = 6.6 Hz, 1H) ,6.36 (dd, J = 17.0, 1.6 Hz, 1H), 6.18 (dd, J = 16.9, 10.3 Hz, 1H), 5.71 (dd, J = 10.3, 1.8 Hz, 1H), 5.27 (sep, J = 7.1 Hz, 1H), 4.95 (d, J = 5.5 Hz, 1H), 4.85 (q, J = 6.1 Hz, 1H), 4.68 (d, J = 5.1 Hz, 2H),4.62 (t, J = 8.2 Hz, 1H), 4.49 (t, J = 9.3 Hz, 1H), 4.13 (t, J = 7.3 Hz, 1H), 4.01 (dd, J = 10.6, 5.1 Hz, 1H), 1.58 (d, J = 7.0 Hz, 6H), 1.51 (s, 9H). | 532 |
| 36 | 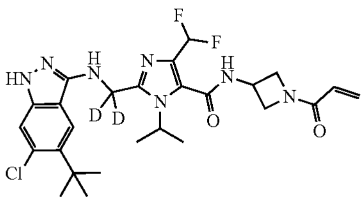 [SMILES: [2H]C([2H])(Nc1n[nH]c2cc(Cl)c(C(C)(C)C)cc12)c1nc(C(F)F)c(C(=O)NC2CN(C(=O)C=C)C2)n1C(C)C] | 1H-NMR (DMSO-D6) δ: 11.46 (s, 1H), 9.33 (d, J = 6.6 Hz, 1H), 7.94 (s, 1H), 7.26 (s, 1H), 6.88 (t, J = 54.3 Hz, 1H), 6.78 (s, 1H), 6.31(dd, J = 16.9, 10.3 Hz, 1H), 6.09 (dd, J = 17.0, 2.4 Hz, 1H), 5.66 (dd, J = 10.3, 2.2 Hz, 1H), 4.83-4.75 (m, 1H), 4.66-4.59 (m, 1H), 4.52 (t, J = 8.2 Hz, 1H), 4.20 (t, J = 9.2 Hz, 1H), 4.09 (dd, J = 8.8, 5.1 Hz, 1H), 3.86 (dd, J = 10.4, 5.3 Hz, 1H), 1.45 (s, 9H), 1.44 (d, J = 7.3 Hz, 6H). | 550 |

TABLE 7

| | Structure | NMR | ESI-MS [M + H]+ |
|---|---|---|---|
| 37 | 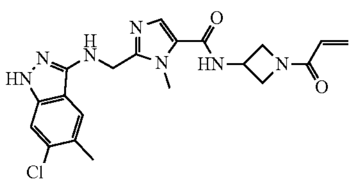 [SMILES: C=CC(=O)N1CC(NC(=O)c2cnc(CNc3n[nH]c4cc(Cl)c(C)cc34)n2C)C1] | 1H-NMR (CD3OD) δ: 7.58 (s, 1H), 7.56 (s, 1H), 7.31 (s, 1H), 6.35 (dd, J = 16.9, 10.3 Hz, 1H), 6.25 (dd, J = 17.0, 2.0 Hz, 1H), 5.75 (dd, J = 10.1, 2.0 Hz, 1H), 4.81-4.75 (m, 1H), 4.66-4.60 (m, 1H), 4.62 (s, 2H), 4.41-4.36 (m, 1H), 4.27-4.22 (m, 1H), 4.09-4.02 (m, 1H), 3.95 (s, 3H), 2.40 (s, 3H). | 428 |
| 38 | 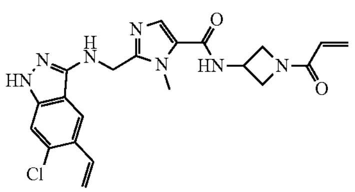 | 1H-NMR (CD3OD) δ: 8.01 (s, 1H), 7.60 (s, 1H), 7.31 (s, 1H), 7.12 (dd, J = 17.6,11.0 Hz, 1H), 6.35 (dd, J = 17.0, 10.1 Hz, 1H), 6.25 (dd, J = 17.0, 2.0 Hz, 1H), 5.75 (dd, J = 9.9, 2.2 Hz, 1H), 5.70 (dd, J = 17.4, 1.3 Hz, 1H), 5.23 (dd, J = 11.0, 1.5 Hz, 1H), 4.80-4.76 (m, 1H), 4.67-4.61 (m, 1H), 4.64 (s, 2H), 4.38 (t, J = 9.5 Hz, 1H), 4.24 (dd, J = 9.3, 5.3 Hz, 1H), 4.05 (dd, J = 11.0, 5.5 Hz, 1H), 3.97 (s, 3H). | 440 |
| 39 | 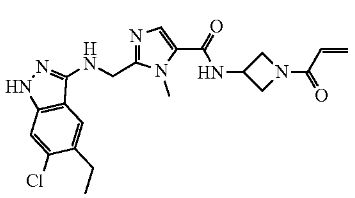 [SMILES: C=CC(=O)N1CC(NC(=O)c2cnc(CNc3n[nH]c4cc(Cl)c(C=C)cc34)n2C)C1] | 1H-NMR (DMSO-D6) δ: 11.50 (s, 1H), 8.78 (d, J = 7.0 Hz, 1H), 7.71 (s, 1H), 7.57 (d, J = 3.7 Hz, 1H), 7.30 (s, 1H), 6.52 (brs, 1H), 6.32 (dd, J = 16.9, 10.3 Hz, 1H), 6.10 (dd, J = 17.2, 2.2 Hz, 1H), 5.67 (dd, J = 10.3, 2.2 Hz, 1H), 4.70-4.64 (m, 1H), 4.53-4.48 (m, 1H), 4.49 (d, J = 5.9 Hz, 2H), 4.19 (t, J = 9.2 Hz, 1H), 4.10 (dd, J = 8.8, 5.1Hz, 1H), 3.89 (dd, J = 10.6, 5.9 Hz, 1H), 3.86 (s, 3H), 2.70 (q, J = 7.5 Hz, 2H), 1.19 (t, J = 7.5 Hz, 3H). | 442 |
| 40 | 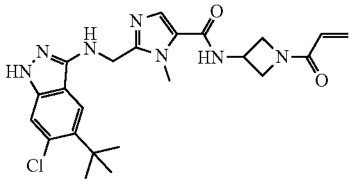 [SMILES: C=CC(=O)N1CC(NC(=O)c2cnc(CNc3n[nH]c4cc(Cl)c(C(C)(C)C)cc34)n2C)C1] | 1H-NMR (CD3OD/CDCl3 = 1/1) δ: 7.69 (s, 1H), 7.58 (s, 1H), 6.29 (d, J = 5.9 Hz, 2H), 5.76 (t, J = 6.0 Hz, 1H), 4.82-4.75 (m, 1H), 4.79 (s, 2H), 4.63 (t, J = 8.6 Hz, 1H), 4.41 (dd, J = 10.8, 8.2 Hz, 1H), 4.26 (dd, J = 9.3, 5.3 Hz, 1H), 4.09 (dd, J = 11.0, 5.5 Hz, 1H), 4.00 (s, 3H), 1.54 (s, 9H). | 471 |

TABLE 7-continued

| | Structure | NMR | ESI-MS [M + H]+ |
|---|---|---|---|
| 41 | 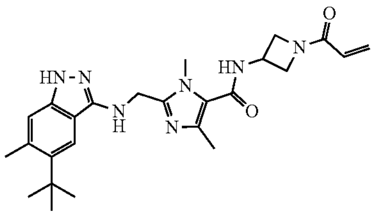 [SMILES: C=CC(=O)N1CC(NC(=O)c2c(C)nc(CNc3n[nH]c4cc(C)c(C(C)(C)C)cc34)n2C)C1] | 1H-NMR (CD3OD) δ: 7.70 (s, 1H), 7.05 (s, 1H), 6.35 (dd, J = 17.0, 10.1 Hz, 1H), 6.25 (dd, J = 17.0, 2.0 Hz, 1H), 5.75 (dd, J = 10.1, 2.0 Hz, 1H), 4.84-4.78 (m, 1H), 4.66 (t, J = 8.6 Hz, 1H), 4.57 (s, 2H), 4.41 (t, J = 9.5 Hz, 1H), 4.26 (dd, J = 9.2, 5.5 Hz, 1H), 4.05 (dd, J = 10.6, 5.5 Hz, 1H), 3.78 (s, 3H), 2.63 (s, 3H), 2.35 (s, 3H), 1.45 (s, 9H). | 464 |
| 42 | 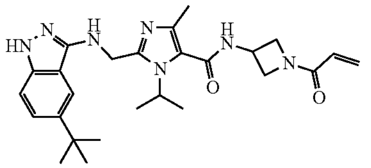 [SMILES: C=CC(=O)N1CC(NC(=O)c2c(C)nc(CNc3n[nH]c4ccc(C(C)(C)C)cc34)n2C(C)C)C1] | 1H-NMR (DMSO-$d_6$) δ: 11.29 (s, 1H), 8.81 (brs, 1H), 7.76 (s, 1H), 7.32 (dd, J = 8.8, 1.8 Hz, 1H), 7.14 (d, J = 8.8 Hz, 1H), 6.40 (brs, 1H), 6.31 (dd, J = 17.0, 10.3 Hz, 1H), 6.09 (dd, J = 17.0, 2.2 Hz, 1H), 5.65 (dd, J = 10.3, 2.2 Hz, 1H), 4.83-4.71 (m, 1H), 4.69-4.59 (m, 1H), 4.56-4.42 (m, 3H),4.24-4.16 (m, 1H), 4.08 (dd, J = 9.0, 5.3 Hz, 1H), 3.85 (dd, J = 9.9, 5.5 Hz, 1H), 2.16 (s, 3H), 1.43 (d, J = 7.0 Hz, 6H), 1.28 (s, 9H) | 478 |
| 43 | 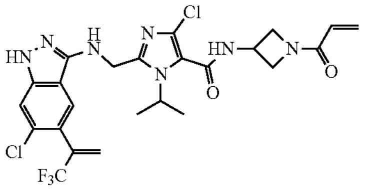 [SMILES: C=CC(=O)N1CC(NC(=O)c2c(Cl)nc(CNc3n[nH]c4cc(Cl)c(C(=C)C(F)(F)F)cc34)n2C(C)C)C1] | 1H-NMR (CDCl3) δ: 9.50 (br s, 1H), 7.53 (s, 1H), 7.39 (s, 1H), 7.01 (d, J = 6.6 Hz, 1H), 6.35 (dd, J = 17.2, 1.8 Hz, 1H), 6.21-6.16 (m, 2H), 5.70 (dd, J = 10.3, 1.8 Hz, 1H), 5.62 (br s, 1H), 5.23 (sep, J = 7.1 Hz, 1H), 5.16 (d, J = 4.8 Hz, 1H), 4.88-4.84 (t, J = 6.0 Hz, 1H), 4.66 (d, J = 5.1 Hz, 2H), 4.61 (t, J = 8.4 Hz, 1H), 4.47 (t, J = 9.3 Hz, 1H), 4.13 (dt, J = 10.9, 3.0 Hz, 1H), 4.01 (dd, J = 10.8, 5.3 Hz, 1H), 1.55 (t, J = 7.5 Hz, 6H). | 570 |
| 44 | 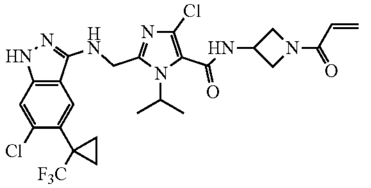 [SMILES: C=CC(=O)N1CC(NC(=O)c2c(Cl)nc(CNc3n[nH]c4cc(Cl)c(C5(C(F)(F)F)CC5)cc34)n2C(C)C)C1] | 1H-NMR (CDCl3) δ: 9.31 (br s, 1H), 7.75 (s, 1H), 7.3 5 (s, 1H), 6.97 (d, J = 7.0 Hz, 1H), 6.36 (dd, J = 17.0, 1.6 Hz, 1H), 6.18 (dd, J = 16.9, 10.3 Hz, 1H), 5.71 (dd, J = 10.3, 1.5 Hz, 1H), 5.25 (t, J = 7.0 Hz, 1H), 5.13 (d, J = 5.5 Hz, 1H), 4.84 (sep, J = 6.0 Hz, 1H), 4.67 (d, J = 5.5 Hz, 2H), 4.61 (t, J = 8.1 Hz, 1H), 4.48 (t, J = 9.2 Hz, 1H), 4.13 (dd, J = 12.6, 5.3 Hz, 1H), 4.02 (dd, J = 10.6, 5.1 Hz, 1H), 1.57 (d, J = 7.0 Hz, 6H), 1.52 (s, 2H), 1.12 (s, 2H). | 584 |
| 45 | 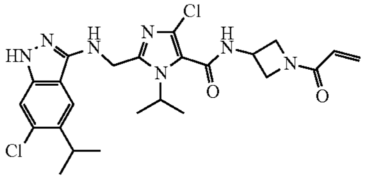 [SMILES: C=CC(=O)N1CC(NC(=O)c2c(Cl)nc(CNc3n[nH]c4cc(Cl)c(C(C)C)cc34)n2C(C)C)C1] | 1H-NMR (DMSO-$d_6$) δ: 11.46 (s, 1H), 9.15 (d, J = 7.0 Hz, 1H), 7.83 (s, 1H), 7.27 (s, 1H), 6.69 (t, J = 6.1 Hz, 1H), 6.31 (dd, J = 17.0, 10.3 Hz, 1H), 6.09 (dd, J = 17.0, 2.2 Hz, 1H), 5.65 (dd, J = 10.3, 2.2 Hz, 1H), 4.87-4.76 (m, 1H), 4.69-4.59 (m, 1H), 4.56-4.46 (m, 3H), 4.24-4.17 (m, 1H), 4.07 (dd, J = 8.8, 5.1 Hz, 1H), 3.84 (dd, J = 10.1, 5.3 Hz, 1H), 3.32-3.23 (m, 1H), 1.43 (d, J = 7.0 Hz, 6H), 1.21 (d, J = 6.6 Hz, 6H) | 518 |

TABLE 8

| | Structure | NMR | ESI-MS [M + H]+ |
|---|---|---|---|
| 46 | 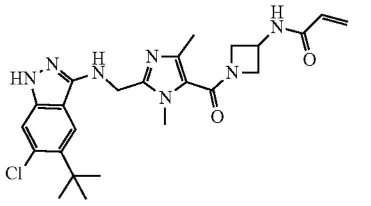 [SMILES: C=CC(=O)NC1CN(C(=O)c2c(C)nc(CNc3n[nH]c4cc(Cl)c(C(C)(C)C)cc34)n2C)C1] | 1H-NMR (DMSO-$d_6$) δ: 11.44 (s, 1H), 8.78 (d, J = 7.0 Hz, 1H), 7.92 (s, 1H), 7.25 (s, 1H), 6.67-6.61 (m, 1H), 6.23-6.05 (m, 2H), 5.66-5.60 (m, 1H), 4.59 (brd, J = 7.7 Hz, 1H), 4.42 (d, J = 5.5 Hz, 2H), 4.27 (t, J = 8.8 Hz, 2H), 3.88 (brdd, J = 9.4, 5.3 Hz, 2H), 3.63 (s, 3H), 2.14 (s, 3H), 1.44 (s, 9H) | 485 |
| 47 | 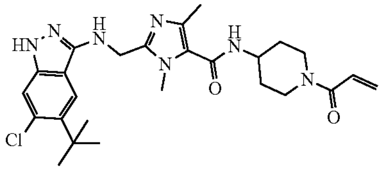 [SMILES: C=CC(=O)N1CCC(NC(=O)c2c(C)nc(CNc3n[nH]c4cc(Cl)c(C(C)(C)C)cc34)n2C)CC1] | 1H-NMR (CDCl3) δ: 9.04-8.95 (brs, 1H), 7.57 (s, 1H), 7.36 (s, 1H), 6.58 (dd, J =16.7, 10.5 Hz, 1H), 6.28 (dd, J = 16.7, 1.9 Hz, 1H), 5.70 (dd, J = 10.5, 1.9 Hz, 1H), 5.62 (d, J = 8.1 Hz, 1H), 4.94-4.88 (brs, 1H), 4.65-4.56 (m, 3H), 4.24-4.13 (m, 1H), 4.04-3.94 (m, 1H), 3.84 (s, 3H), 3.26-3.20 (m, 1H), 2.90-2.84 (m, 1H), 2.39 (s, 3H), 2.18-2.04 (m, 2H), 1.86-1.66 (brs, 2H), 1.49 (s, 9H). | 512 |

TABLE 8-continued

| | Structure | NMR | ESI-MS [M + H]+ |
|---|---|---|---|
| 48 | 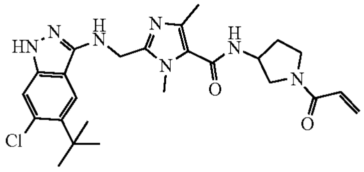 [SMILES: C=CC(=O)N1CCC(NC(=O)c2c(C)nc(CNc3n[nH]c4cc(Cl)c(C(C)(C)C)cc34)n2C)C1] | 1H-NMR (CDCl3) δ: 7.58 (s, 1H), 7.31 (s, 1H), 6.44-6.38 (m, 2H), 5.94 (d, J = 6.0 Hz, 1H), 5.74-5.68 (m, 1H), 5.10-5.00 (brs, 1H), 4.70-4.59 (m, 3H), 3.97-3.67 (m, 6H), 3.59-3.50 (m, 1H), 2.37-1.94 (m, 5H), 1.49 (s, 9H). | 498 |
| 49 | 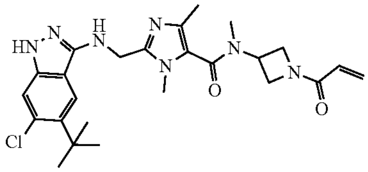 [SMILES: C=CC(=O)N1CC(N(C)C(=O)c2c(C)nc(CNc3n[nH]c4cc(Cl)c(C(C)(C)C)cc34)n2C)C1] | 1H-NMR (CDCl3) δ: 7.59 (s, 1H), 7.33 (s, 1H), 6.38 (dd, J = 16.9, 1.7 Hz, 1H), 6.19 (dd, J = 16.9, 10.3 Hz, 1H), 5.73 (dd, J = 10.3, 1.7 Hz, 1H), 5.06-4.95 (brs, 1H), 4.88-4.80 (brs, 1H), 4.62 (s, 2H), 4.55-4.43 (brs, 1H), 4.37-4.12 (m, 3H), 3.69 (s, 3H), 3.15 (s, 3H), 2.21 (s, 3H), 1.52 (s, 9H). | 498 |
| 50 | 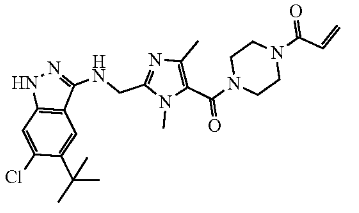 [SMILES: C=CC(=O)N1CCN(C(=O)c2c(C)nc(CNc3n[nH]c4cc(Cl)c(C(C)(C)C)cc34)n2C)CC1] | 1H-NMR (CDCl3) δ: 7.61 (s, 1H), 7.32 (s, 1H), 6.57 (dd, J = 16.7, 10.5 Hz, 1H), 6.35 (dd, J = 16.7, 1.9 Hz, 1H), 5.77 (dd, J = 10.5, 1.9 Hz, 1H), 5.09-4.99 (brs, 1H), 4.63 (s, 2H), 3.75-3.65 (m, 1 1H), 2.23 (s, 3H), 1.51 (s, 9H). | 498 |
| 51 | 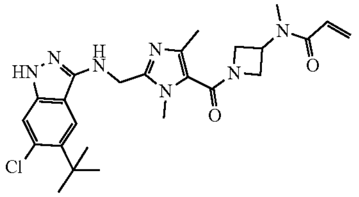 [SMILES: C=CC(=O)N(C)C1CN(C(=O)c2c(C)nc(CNc3n[nH]c4cc(Cl)c(C(C)(C)C)cc34)n2C)C1] | 1H-NMR (CDCl3) δ: 7.59 (s, 1H), 7.30 (s, 1H), 6.60-6.33 (m, 2H), 5.76 (d, J = 10.0 Hz, 1H), 5.32-5.18 (brs, 1H), 5.18-5.02 (brs, 1H), 4.61 (s, 2H), 4.39-4.35 (m, 2H), 4.24-4.10 (brs, 2H), 3.77 (s, 3H), 3.14 (s, 3H), 2.31 (s, 3H), 1.49 (s, 9H). | 498 |
| 52 | 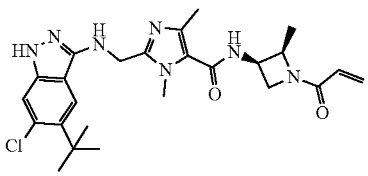 Abs | 1H-NMR (CDCl3) δ: 9.69-9.36 (brs, 1H), 7.57 (s, 1H), 7.28 (s, 1H), 6.43-6.32 (m, 2H), 6.22-6.09 (m, 1H), 5.67 (d, J = 10.6 Hz, 1H), 5.26-5.08 (brs, 1H), 4.99-4.93 (m, 1H), 4.82-4.75 (m, 1H), 4.58-4.51 (m, 2.5H), 4.43-4.38 (m, 0.5H), 4.09-4.05(m, 0.5H), 3.91-3.86 (m, 0.5H), 3.80 (s, 1.5H), 3.79 (s, 1.5H), 2.49 (s, 1.5H), 2.42 (s, 1.5H), 1.46-1.39 (m, 12H). | 498 |
| 53 | 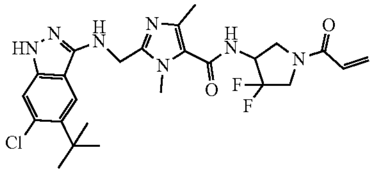 [SMILES: C=CC(=O)N1CC(NC(=O)c2c(C)nc(CNc3n[nH]c4cc(Cl)c(C(C)(C)C)cc34)n2C)C(F)(F)C1] | 1H-NMR (CDCl3) δ: 9.03-8.86 (brs, 1H), 7.63 (s, 1H), 7.32 (s, 1H), 6.48-6.27 (m, 2H), 6.09 (d, J = 8.0 Hz, 0.7H), 5.99 (d, J = 8.0 Hz, 0.3H), 5.82-5.77 (m, 1H), 5.04-4.92 (m, 2H), 4.61 (s, 2H), 4.33-4.27 (m, 1H), 4.10-3.92 (m, 2H), 3.88 (s, 3H), 3.49-3.35 (m, 1H), 2.47 (s, 2.1H), 2.45 (s, 0.9H), 1.50 (s, 9H). | 534 |
| 54 | 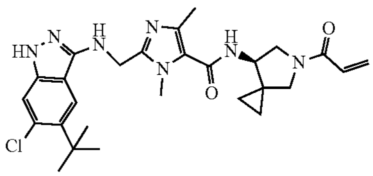 Abs | 1H-NMR (CDCl3) δ: 9.36-9.05 (brs, 1H), 7.56 (s, 1H), 7.30 (s, 1H), 6.42-6.35 (m, 2H), 5.72-5.69 (m, 1H), 5.02-4.90 (brs, 1H), 4.58 (s, 2H), 4.07-3.98 (m, 1H), 3.91-3.79 (m, 6H), 3.44-3.37 (m, 1H), 2.39 (s, 1.8H), 2.37 (s, 1.2H), 1.48 (s, 9H), 0.99-0.64 (m, 4H). | 524 |

TABLE 9

| | Structure | NMR | ESI-MS [M + H]+ |
|---|---|---|---|
| 55 | 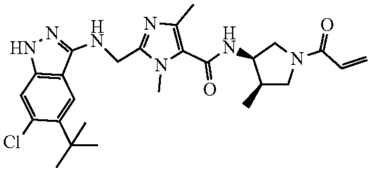 Abs | 1H-NMR (CDCl3) δ: 9.37-9.11 (brs, 1H), 7.57 (s, 1H), 7.30 (s, 1H), 6.41-6.36 (m, 2H), 5.95 (d, J = 7.7 Hz, 1H), 5.72-5.67 (m, 1H), 5.08-4.96 (brs, 1H), 4.27-4.65 (brs, 1H), 4.58 (s, 2H), 3.90-3.76 (m, 5H), 3.66-3.59 (m, 1H), 3.28-3.21 (m, 1H), 2.68-2.60 (m, 0.5H), 2.58-2.50 (m, 0.5H), 2.39 (s, 1.5H), 2.37 (s, 1.5H), 1.48 (s, 9H), 1.12 (d, J = 6.8 Hz, 1.5H), 1.09 (d, J = 6.8 Hz, 1.5H). | 512 |
| 56 | 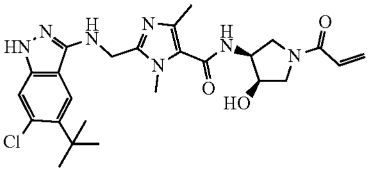 Abs | 1H-NMR (CDCl3) δ: 10.19-9.98 (brs, 0.3H), 9.98-9.71 (brs, 0.7H), 7.60 (s, 0.3H), 7.58 (s, 0.7H), 7.25 (s, 0.7H), 7.22 (s, 0.3H), 6.66-6.57 (1H, m), 6.37-6.25 (2H, m), 5.68-5.64 (1H, m), 5.42-5.29 (brs, 0.3H), 5.25-5.11 (brs, 0.7H), 4.59-4.25 (m, 4H), 4.00-3.96 (m, 1H), 3.76-3.55 (m, 5H), 3.45-3.36 (m, 1H), 2.30 (s, 2.1H), 2.28 (s, 0.9H), 1.44 (s, 6.3H), 1.42 (s, 2.7H). | 514 |
| 57 | 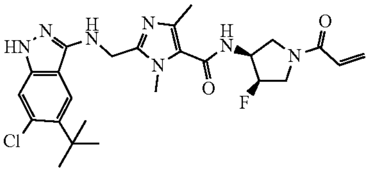 Abs | 1H-NMR (CDCl3) δ: 9.11-8.90 (brs, 1H), 7.58 (s, 1H), 7.31 (s, 0.7H), 7.31 (s, 0.3H), 6.46-6.33 (m, 2H), 6.16 (d, J = 8.0 Hz, 0.7H), 6.05 (d, J = 8.8 Hz, 0.3H), 5.78-5.73 (m, 1H), 5.31-5.13 (m, 1H), 5.03-4.74 (m, 2H), 4.61 (s, 2H), 4.26-4.18 (m, 1H), 4.09-3.74 (m, 5H), 3.44-3.33 (m, 1H), 2.46 (s, 2.1H), 2.44 (s, 0.9H), 1.50 (s, 9H). | 516 |
| 58 | 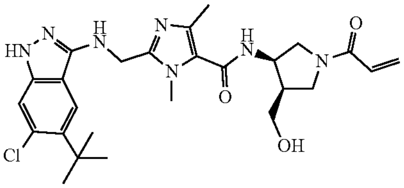 Abs | 1H-NMR (CDCl3) δ: 9.03-8.90 (brs, 1H), 7.57 (s, 1H), 7.31 (s, 1H), 7.01 (d, J = 6.2 Hz, 0.5H), 6.41-6.37 (m, 2H), 6.17 (d, J = 6.0 Hz, 0.5H), 5.75-5.69 (m, 1H), 4.94-4.86 (brs, 1H), 4.73-4.67 (brs, 1H), 4.60 (s, 1H), 4.59 (s, 1H), 3.99-3.95 (m, 0.5H), 3.88-3.67 (m, 7H), 3.57-3.51 (m, 0.5H), 3.45-3.39 (m, 0.5H), 3.23-3.18 (m, 0.5H), 2.81-2.71 (m, 0.5H), 2.67-2.56 (m, 0.5H), 2.36 (s, 1.5H), 2.34 (s, 1.5H), 1.50 (s, 9H). | 528 |
| 59 | 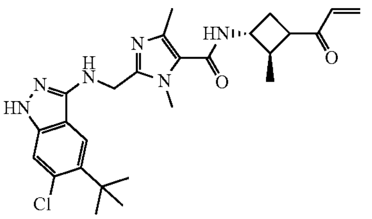 Abs | 1H-NMR (DMSO-D6) δ: 11.43 (s, 1H), 8.42-8.34 (m, 1H), 7.92 (s, 1H), 7.26 (s, 1H), 6.67-6.65 (m, 1H), 6.35-6.24 (m, 1H), 6.15-6.08 (m, 1H), 5.68-5.65 (m, 1H), 4.49-4.38 (m, 3H), 4.28-4.21 (m, 2H), 4.15-3.79 (m, 2H), 3.69 (s, 3H), 2.24 (s, 3H), 1.50-1.42 (m, 12H). | 498 |
| 60 | 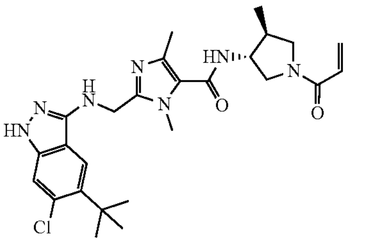 Abs | 1H-NMR (DMSO-D6) δ: 11.43 (s, 1H), 8.07-8.03 (m, 1H), 7.93 (s, 1H), 7.26 (s, 1H), 6.66 (t, J = 5.5 Hz, 1H), 6.59-6.51 (m, 1H), 6.15-6.10 (m, 1H),5.68-5.63 (m, 1H), 4.44-4.42 (m, 2H), 4.12-3.95 (m, 2H), 3.89-3.71 (m, 2H), 3.68 (s, 3H), 3.22-3.15 (m, 1H), 2.30-2.24 (m, 1H), 2.21 (s, 3H), 1.45 (s, 9H), 1.03 (d, J = 6.6 Hz, 3H). | 512 |

TABLE 9-continued

| | Structure | NMR | ESI-MS [M + H]+ |
|---|---|---|---|
| 61 | 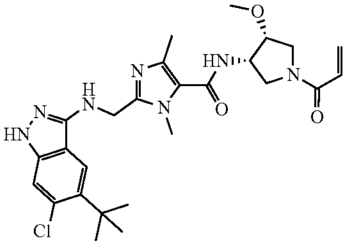 Abs | 1H-NMR (DMSO-D6) δ: 11.43 (s, 1H), 7.93 (s, 1H), 7.86-7.80 (m, 1H), 7.26 (s, 1H), 6.66 (t, J = 5.7 Hz, 1H), 6.60-6.51 (m, 1H), 6.13 (d, J = 16.9 Hz, 1H), 5.67 (d, J = 10.3 Hz, 1H), 4.63-4.51 (m, 1H), 4.44-4.42 (m, 2H), 3.95-3.87 (m, 1H), 3.70 (s, 3H), 3.68-3.60 (m, 1H), 3.49-3.43 (m, 1H), 3.39-3.35 (m, 1H), 3.30-3.29 (m, 3H), 2.24-2.23 (m, 3H), 1.45 (s, 9H). | 528 |
| 62 | 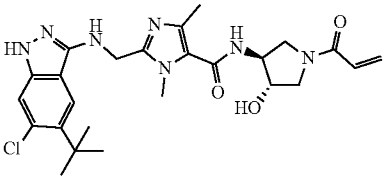 Abs | 1H-NMR (CDCl3) δ: 7.69 (s, 1H), 7.31 (s, 1H), 6.46-6.34 (m, 2H), 5.77-5.73(m, 1H), 4.54 (s, 2H), 4.40-4.33 (m, 1H), 4.31-4.25 (m, 1H), 4.14-4.10 (m, 0.5H), 3.99-3.94 (m, 0.5H), 3.86-3.82 (m, 0.5H), 3.78-3.73 (m, 3.5H), 3.65-3.53 (m, 2.5H), 3.40-3.39 (m, 0.5H), 2.30 (s, 1.5H), 2.30 (s, 1.5H), 1.51 (s, 9H). | 514 |
| 63 | 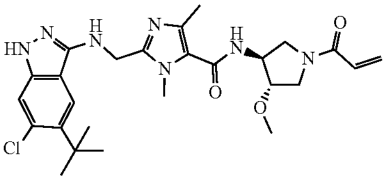 Abs | 1H-NMR (CDCl3) δ: 9.39-9.19 (brs, 1H), 7.55 (s, 1H), 7.29 (s, 1H), 6.38-6.36 (m, 2H), 6.04-6.00 (m, 1H), 5.73-5.68 (m, 1H), 5.02-4.93 (brs, 1H), 4.63-4.53 (m, 3H), 4.03-3.98 (m, 1H), 3.90-3.71 (m, 6H), 3.62-3.54 (m, 1H), 3.49 (s, 1.5H), 3.44 (s, 1.5H), 2.33 (s, 1.5H), 2.30 (s, 1.5H), 1.48 (s, 9H). | 528 |

TABLE 10

| | Structure | NMR | ESI-MS [M + H]+ |
|---|---|---|---|
| 64 | 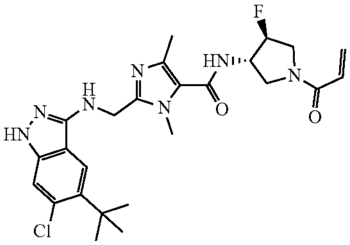 Abs | 1H-NMR (DMSO-D6) δ: 11.43 (s, 1H), 8.30-8.21 (m, 1H), 7.92 (s, 1H), 7.25 (s, 1H), 6.69-6.65 (m, 1H), 6.58 (dd, J = 16.9, 10.3 Hz, 1H), 6.16 (d, J = 16.9 Hz, 1H), 5.70 (d, J = 10.3 Hz, 1H), 5.27-5.10 (m, 1H), 4.55-4.47 (m, 1H), 4.44-4.42 (m, 2H), 3.97-3.91 (m, 1H), 3.89-3.79 (m, 1H), 3.72-3.70 (m, 1H), 3.68 (s, 3H), 3.64-3.59 (m, 1H), 2.17 (s, 3H), 1.45 (s, 9H). | 516 |
| 65 | 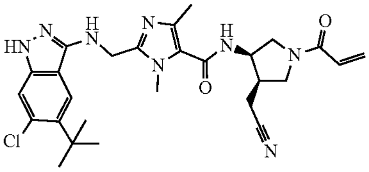 Abs | 1H-NMR (CDCl3) δ: 9.23-9.04 (brs, 1H), 7.58 (s, 1H), 7.30 (s, 1H), 6.42-6.35 (m, 2H), 6.28 (d, J = 7.6 Hz, 0.3H), 6.14 (d, J = 7.2 Hz, 0.7H), 5.78-5.72 (m, 1H), 5.26-5.04 (m, 1H), 4.93-4.86 (brs, 0.3H), 4.80-4.71 (brs, 0.7H), 4.57 (s, 2H), 3.99-3.92 (m, 2H), 3.83 (s, 3H), 3.74-3.64 (m, 1H), 3.54-3.43 (m, 1H), 2.99-2.44 (m, 3H), 2.37 (s, 3H), 1.48 (s, 9H). | 537 |

TABLE 10-continued

| | Structure | NMR | ESI-MS $[M + H]^+$ |
|---|---|---|---|
| 66 | 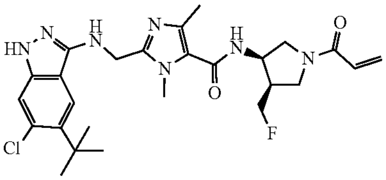 Abs | 1H-NMR (CDCl3) δ: 9.18-8.94 (brs, 1H), 7.57 (s, 1H), 7.31 (s, 1H), 6.44-6.38 (m, 2.6H), 6.14 (d, J = 6.8 Hz, 0.4H), 5.76-5.69 (m, 1H), 5.00-4.90 (brs, 1H), 4.85-4.55 (m, 5H), 4.05-3.84 (m, 5H), 3.71-3.59 (m, 2H), 2.97-2.70 (m, 1H), 2.39 (s, 1.8H), 2.37 (s, 1.2H), 1.49 (s, 9H). | 530 |
| 67 | 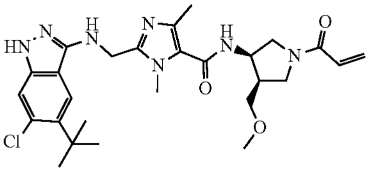 Abs | 1H-NMR (CDCl3) δ: 7.58 (s, 1H), 7.52 (d, J = 4.8 Hz, 0.7H), 7.30 (s, 1H), 7.00 (d, J = 5.0 Hz, 0.3H), 6.46-6.38 (m, 2H), 5.72-5.67 (m, 1H), 5.11-5.00 (brs, 1H), 4.66-4.54 (m, 3H), 4.08-4.03 (m, 1H), 3.94-3.58 (m, 8H), 3.37 (s, 2.1H), 3.35 (s, 0.9H), 2.77-2.70 (m, 0.3H), 2.69-2.62 (s, 0.7H), 2.39 (s, 2.1H), 2.37 (s, 0.9H), 1.49 (s, 9H). | 542 |
| 68 | 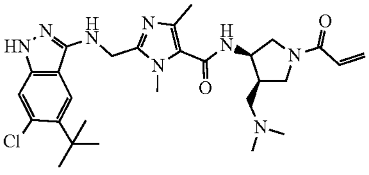 Abs | 1H-NMR (CDCl3) δ: 9.58 (d, J = 5.6 Hz, 1H), 9.01-8.93 (brs, 1H), 7.58 (s, 1H), 7.32 (s, 1H), 6.47-6.36 (m, 2H), 5.72-5.68 (m, 1H), 4.85-4.82 (m, 1H), 4.62-4.60 (m, 2H), 4.38-4.34 (m, 0.6H), 4.30-4.24 (m, 0.4H), 3.86 (s, 1.8H), 3.85 (s, 1.2H), 3.78-3.77 (m, 2H), 3.64-3.62 (m, 2H), 3.35-3.27 (m, 1H), 2.87-2.81 (m, 1H), 2.70-2.61 (m, 1H), 2.40 (s, 1.8H), 2.39 (s, 1.2H), 2.37 (s, 3.6H), 2.25 (s, 2.4H), 1.50 (s, 9H). | 555 |
| 69 | 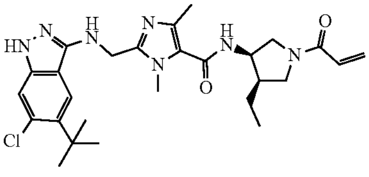 Abs | 1H-NMR (CDCl3) δ: 7.58 (s, 1H), 7.32 (s, 1H), 6.44-6.36 (m, 2H), 5.76-5.68 (m, 2H), 4.94-4.84 (brs, 1H), 4.62-4.58 (brs, 2H), 3.96-3.69 (m, 7H), 3.27-3.18 (m, 1H), 2.40-2.28 (m, 4H), 1.54-1.38 (m, 11H), 1.04-0.99 (m, 3H). | 526 |
| 70 | 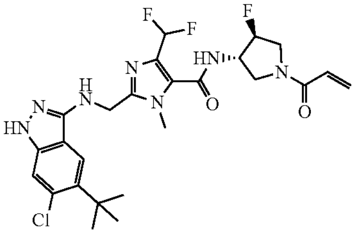 Abs | 1H-NMR (DMSO-D6) δ: 11.46 (s, 1H), 8.92 (dd, J = 34.8, 6.6 Hz, 1H), 7.91 (s, 1H), 7.26 (s, 1H), 6.88 (t, J = 54.3 Hz, 1H), 6.80 (t, J = 5.9 Hz, 1H), 6.61-6.53 (m, 1H), 6.16 (d, J = 16.9 Hz, 1H), 5.70 (d, J = 9.2 Hz, 1H), 5.30-5.12 (m, 1H), 4.59-4.51 (m, 3H), 3.96-3.87 (m, 1H), 3.76-3.61 (m, 3H), 3.71 (s, 3H), 1.45 (s, 9H). | 552 |
| 71 | 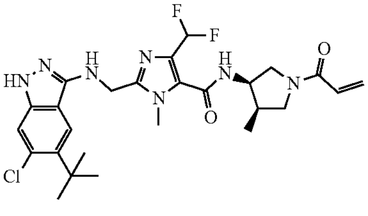 Abs | 1H-NMR (CDCl3) δ: 9.18-8.99 (brs, 1H), 7.55 (s, 1H), 7.32 (s, 1H), 6.88-6.60 (m, 2H), 6.42-6.36 (m, 2H), 5.72-5.67 (m, 1H), 4.89-4.38 (brs, 1H), 4.70-4.58 (brs, 3H), 3.92 (s, 3H), 3.88-3.59 (m, 3H), 3.28-3.23 (m, 1H), 2.63-2.51 (m, 1H), 1.49 (s, 9H), 1.11 (d, J = 7.0 Hz, 3H). | 548 |

TABLE 10-continued

| Structure | NMR | ESI-MS $[M + H]^+$ |
|---|---|---|
| 72 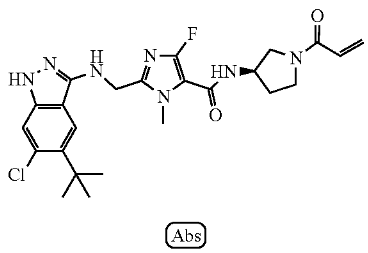 [SMILES: C=CC(=O)N1CC[C@@H](NC(=O)c2c(F)nc(CNc3n[nH]c4cc(Cl)c(C(C)(C)C)cc34)n2C)C1] | 1H-NMR (CDCl3) δ: 8.95 (br s, 1H), 7.56 (s, 1H), 7.33 (s, 1H), 6.45-6.38 (m, 2H), 6.08-6.00 (m, 1H), 5.73-5.66 (m, 1H), 4.76 (t, J = 5.9 Hz, 1H),4.64-4.59 (m, 3H), 3.99 (s, 3H), 3.97-3.85 (m, 1H), 3.71-3.65 (m, 2H), 3.49 (ddd, J = 24.6, 11.7, 4.8 Hz, 1H), 2.35-2.25 (m, 1H), 2.10-1.85 (m, 1H), 1.51 (s, 9H). | 502 |

TABLE 11

| Structure | NMR | ESI-MS $[M + H]^+$ |
|---|---|---|
| 73 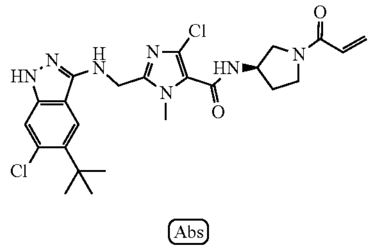 | 1H-NMR (CDCl3) δ: 9.26 (d, J = 14.7 Hz, 1H), 7.55 (s, 1H), 7.31 (s, 1H), 6.72 (dd, J = 33.9, 6.8 Hz, 1H), 6.49-6.38 (m, 2H), 5.74-5.66 (m, 1H), 4.92 (t, J = 4.9 Hz, 1H), 4.68-4.61 (m, 3H), 3.96 (d, J = 3.8 Hz, 3H), 3.89 (dt, J = 26.5, 9.2 Hz, 1H), 3.74-3.68 (m, 2H), 3.55 (ddd, J = 32.2, 11.8, 4.3 Hz, 1H), 2.31 (tt, J = 18.3, 6.2 Hz, 1H), 2.03 (dtd, J = 53.2, 13.6, 7.3 Hz, 2H), 1.49 (s, 9H). | 518 |
| 74 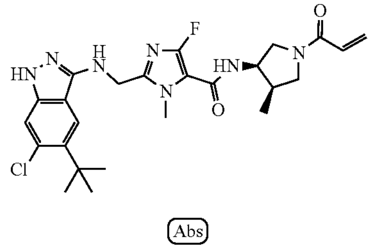 [SMILES: C=CC(=O)N1C[C@@H](C)[C@@H](NC(=O)c2c(F)nc(CNc3n[nH]c4cc(Cl)c(C(C)(C)C)cc34)n2C)C1] | 1H-NMR (CDCl3) δ: 9.26 (br s, 1H), 7.5 5 (s, 1H), 7.31 (s, 1H), 6.42-6.36 (m, 2H), 6.06 (dt, J = 33.8, 7.2 Hz, 1H), 5.70 (td, J = 8.2, 4.0 Hz, 1H), 4.84 (br s, 1H), 4.65 (brs, 1H), 4.59 (d, J = 5.5 Hz, 2H), 3.99 (brs, 3H), 3.89-3.75 (m, 2H), 3.63-3.56 (m, 1H), 3.26 (dt, J = 15.0, 4.7 Hz, 1H), 2.63-2.45 (m, 1H), 1.49 (s, 9H), 1.05 (t, J = 7.0 Hz, 3H). | 516 |
| 75 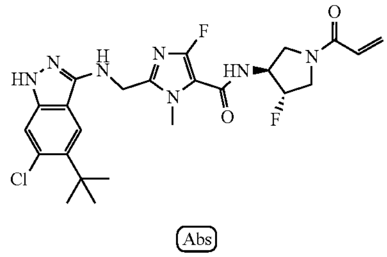 [SMILES: C=CC(=O)N1C[C@H](NC(=O)c2c(F)nc(CNc3n[nH]c4cc(Cl)c(C(C)(C)C)cc34)n2C)[C@@H](F)C1] | 1H-NMR (CDCl3) δ: 8.99 (br s, 1H), 7.56 (s, 1H), 7.33 (s, 1H), 6.40-6.45 (m, 2H), 5.91 (brs, 1H), 5.77 (d, J = 8.4 Hz, 1H), 5.18 (dd, J = 50.8, 39.8 Hz, 1H), 4.77 (s, 1H), 4.59 (d, J = 5.9 Hz, 2H), 3.99 (s, 3H), 3.97-3.63 (m, 5H), 1.50 (s, 9H). | 520 |
| 76 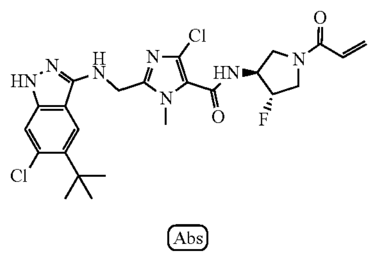 [SMILES: C=CC(=O)N1C[C@H](NC(=O)c2c(Cl)nc(CNc3n[nH]c4cc(Cl)c(C(C)(C)C)cc34)n2C)[C@@H](F)C1] | 1H-NMR (CDCl3) δ: 8.87 (s, 1H), 7.56 (s, 1H), 7.33 (s, 1H), 6.57 (dd, J = 31.0, 6.8 Hz, 1H), 6.44-6.42 (m, 1H), 5.79-5.75 (m, 1H), 5.20 (dd, J = 49.3, 41.6 Hz, 1H), 4.78 (brs, 1H), 4.62 (d, J = 5.9 Hz, 2H), 3.99 (s, 3H), 3.97-3.69 (m, 5H), 1.51 (s, 9H). | 536 |

TABLE 11-continued

| | Structure | NMR | ESI-MS [M + H]$^+$ |
|---|---|---|---|
| 77 | 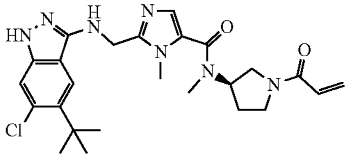 | 1H-NMR (CDCl3) δ: 9.10 (d, J = 32.3 Hz, 1H), 7.58 (s, 1H), 7.32 (d, J = 4.8 Hz, 1H), 7.22 (d, J = 13.6 Hz, 1H), 6.46-6.38 (m, 2H), 5.76-5.70 (m, 1H), 5.21-5.03 (m, 1H), 4.98-4.87 (m, 1H), 4.67 (s, 2H), 4.06-3.84 (m, 2H), 3.82 (d, J = 4.4 Hz, 3H), 3.63-3.45 (m, 2H), 3.10 (d, J = 17.2 Hz, 3H), 2.28-2.09 (m, 2H). | 498 |
| 78 | 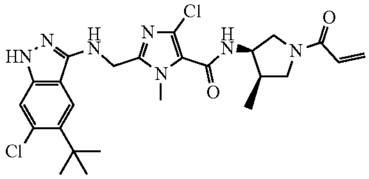 | 1H-NMR (CDCl3) δ: 9.11 (d, J = 21.3 Hz, 1H), 7.55 (s, 1H), 7.32 (s, 1H), 6.68 (dd, J = 59.2, 7.9 Hz, 1H), 6.43-6.37 (m, 2H), 5.73-5.68 (m, 1H), 4.86 (t, J = 5.5 Hz, 1H), 4.67 (brs, 1H), 4.62 (d, J = 5.5 Hz, 2H), 3.98 (d, J = 4.0 Hz, 3H), 3.90-3.78 (m, 2H), 3.69-3.59 (m, 1H), 3.31-3.25 (m, 1H), 2.63-2.50 (m, 1H), 1.49 (s, 9H), 1.12 (dd, J = 9.7, 6.8 Hz, 3H). | 532 |
| 79 | 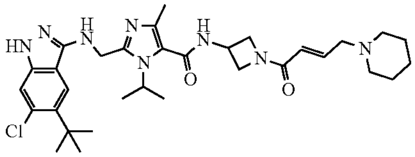 | 1H-NMR (DMSO-$d_6$) δ: 11.43 (s, 1H), 8.77 (d, J = 6.6 Hz, 1H), 7.96 (s, 1H), 7.26 (s, 1H), 6.72-6.51 (m, 2H), 6.10 (d, J = 15.4 Hz, 1H), 4.88-4.42 (m, 5H), 4.23-4.17 (m,1H), 4.12-4.00 (m, 1H), 3.88-3.80 (m, 1H), 3.03 (brd, J = 5.4 Hz, 2H),2.58-2.43 (brs, 4H), 2.17 (s, 3H), 1.55-1.31 (m, 21H) | 610 |
| 80 | 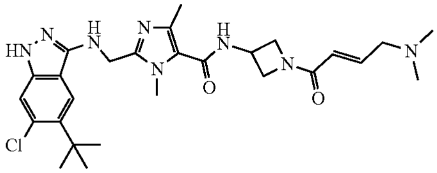 | 1H-NMR ($CDCl_3$) δ: 9.00 (brs, 1H), 7.58 (s, 1H), 7.33 (s, 1H), 6.88 (dt, J = 15.4, 6.1 Hz, 1H), 6.22 (brd, J = 7.0 Hz, 1H), 6.05-5.98 (m, 1H), 4.90-4.81 (m, 2H), 4.66-4.55 (m, 3H), 4.47 (brt, J = 9.4 Hz, 1H), 4.11-4.03 (m, 1H), 3.96 (dd, J = 10.8, 4.6 Hz, 1H), 3.85 (s, 3H), 3.07 (dd, J = 5.9, 1.5 Hz, 2H), 2.46 (s, 3H), 2.25 (s, 6H), 1.51 (s, 9H) | 542 |
| 81 | 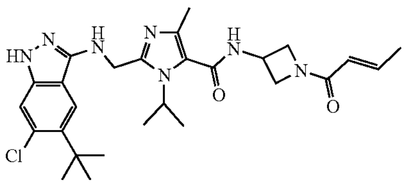 [SMILES: C/C=C/C(=O)N1CC(NC(=O)c2c(C)nc(CNc3n[nH]c4cc(Cl)c(C(C)(C)C)cc34)n2C(C)C)C1] | 1H-NMR (DMSO-$d_6$) δ: 11.42 (s, 1H), 8.77 (brd, J = 6.2 Hz, 1H), 7.94 (s, 1H), 7.24 (s, 1H), 6.68-6.58 (m, 2H), 5.99 (dd, J = 15.0, 1.7 Hz, 1H), 4.77-4.68 (m, 1H), 4.67-4.56 (m, 1H), 4.50-4.42 (m, 3H), 4.20-4.11 (m, 1H), 4.06-3.99 (m, 1H), 3.81 (dd, J = 9.9, 5.9 Hz, 1H), 2.15 (s, 3H), 1.80 (dd, J = 6.8, 1.7 Hz, 3H), 1.44 (s, 9H), 1.41 (d, J = 7.0 Hz, 6H) | 526 |

TABLE 12

| | Structure | NMR | ESI-MS [M + H]$^+$ |
|---|---|---|---|
| 82 | 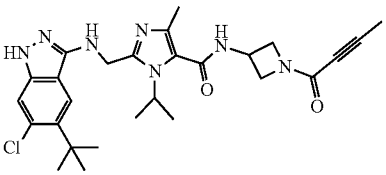 [SMILES: CC#CC(=O)N1CC(NC(=O)c2c(C)nc(CNc3n[nH]c4cc(Cl)c(C(C)(C)C)cc34)n2C(C)C)C1] | 1H-NMR (DMSO-$d_6$) δ: 11.42 (s, 1H), 8.77 (brs, 1H), 7.94 (s, 1H),7.25 (s, 1H), 6.70-6.60 (m, 1H), 4.79-4.59 (m, 2H), 4.51-4.37 (m, 3H), 4.21-4.13 (m, 1H), 4.05-3.99 (m, 1H), 3.79 (dd, J = 10.1, 5.3 Hz, 1H), 2.16 (s, 3H), 1.98 (s, 3H), 1.45 (s, 9H), 1.42 (d, J = 7.0 Hz, 6H) | 524 |

TABLE 12-continued

| | Structure | NMR | ESI-MS $[M + H]^+$ |
|---|---|---|---|
| 83 | 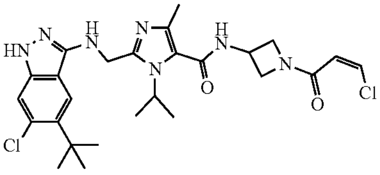 [SMILES: Cc1nc(CNc2n[nH]c3cc(Cl)c(C(C)(C)C)cc23)n(C(C)C)c1C(=O)NC1CN(C(=O)/C=C\Cl)C1] | 1H-NMR (DMSO-$d_6$) δ: 11.42 (s, 1H), 8.80 (d, J = 6.6 Hz, 1H), 7.94 (s, 1H), 7.25 (s, 1H), 6.77 (d, J = 8.1 Hz, 1H), 6.69-6.60 (m, 1H), 6.39 (d, J = 8.1 Hz, 1H), 4.78-4.55 (m, 2H), 4.52-4.37 (m, 3H), 4.24-4.15(m, 1H), 4.00 (dd, J = 8.4, 5.9 Hz, 1H), 3.84 (dd, J = 10.5, 5.3 Hz, 1H), 2.16 (s, 3H), 1.45 (s, 9H), 1.41 (d, J = 7.0 Hz, 6H) | 546 |
| 84 | 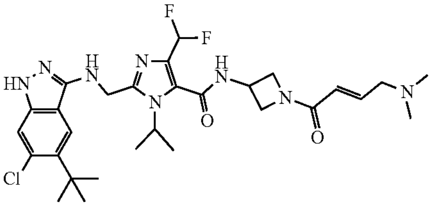 [SMILES: CC(C)n1c(CNc2n[nH]c3cc(Cl)c(C(C)(C)C)cc23)nc(C(F)F)c1C(=O)NC1CN(C(=O)/C=C/CN(C)C)C1] | 1H-NMR (DMSO-$d_6$) δ: 11.45 (s, 1H), 9.31 (d, J = 6.6 Hz, 1H), 7.93(s, 1H), 7.25 (s, 1H), 6.87 (t, J = 53.9 Hz, 1H), 6.78 (t, J = 6.1 Hz, 1H), 6.56 (dt, J = 15.4, 6.1 Hz, 1H), 6.12-6.05 (m, 1H), 4.82-4.74(m, 1H), 4.64-4.45 (m, 4H), 4.17 (t, J = 9.0 Hz, 1H), 4.06 (dd, J = 8.3, 5.3 Hz, 1H), 3.83 (dd, J = 9.7, 5.0 Hz, 1H), 3.02-2.95 (m, 2H), 2.11 (s, 6H), 1.51-1.38 (m, 15H) | 605 |
| 85 | 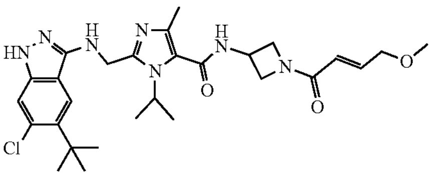 [SMILES: COC/C=C/C(=O)N1CC(NC(=O)c2c(C)nc(CNc3n[nH]c4cc(Cl)c(C(C)(C)C)cc34)n2C(C)C)C1] | 1H-NMR (DMSO-$d_6$) δ: 11.42 (s, 1H), 8.77 (d, J = 6.2 Hz, 1H), 7.94 (s, 1H), 7.24 (s, 1H), 6.68-6.59 (m, 2H), 6.11 (td, J = 15.4, 1.8 Hz, 1H), 4.78-4.56 (m, 2H), 4.54-4.43 (m, 3H), 4.22-4.15 (m, 1H), 4.09-4.01 (m, 3H), 3.83 (dd, J = 10.1, 5.3 Hz, 1H), 3.26 (s, 3H), 2.16 (s, 3H), 1.44 (s, 9H), 1.42 (d, J = 6.6 Hz, 6H) | 557 |
| 86 | 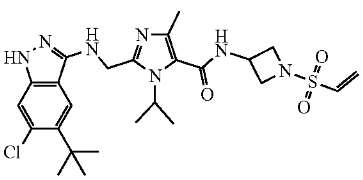 [SMILES: C=CS(=O)(=O)N1CC(NC(=O)c2c(C)nc(CNc3n[nH]c4cc(Cl)c(C(C)(C)C)cc34)n2C(C)C)C1] | 1H-NMR ($CDCl_3$) δ: 8.91 (brs, 1H), 7.61 (s, 1H), 7.33 (s, 1H), 6.56 (dd, J = 16.7, 10.1 Hz, 1H), 6.37 (d, J = 16.7 Hz, 1H), 6.28 (brd, J = 7.3 Hz, 1H), 6.16 (d, J = 10.1 Hz, 1H), 5.10-5.00 (m, 1H), 4.98-4.87 (m, 1H), 4.85-4.75 (m, 1H), 4.64 (d, J = 5.1 Hz, 2H), 4.21 (t, J = 8.4 Hz, 2H), 3.89 (dd, J = 9.2, 5.9 Hz, 2H), 2.40 (s, 3H), 1.54 (d, J = 7.0 Hz, 6H), 1.52 (s, 9H) | 548 |
| 87 | 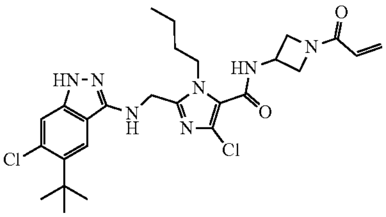 [SMILES: C=CC(=O)N1CC(NC(=O)c2c(Cl)nc(CNc3n[nH]c4cc(Cl)c(C(C)(C)C)cc34)n2CCCC)C1] | 1H-NMR (DMSO-D6) δ: 11.45 (s, 1H), 8.81 (d, J = 7.3 Hz, 1H), 7.91(s, 1H), 7.26 (s, 1H), 6.82 (t, J = 6.0 Hz, 1H), 6.31 (dd, J = 16.9, 10.3 Hz, 1H), 6.09 (dd, J = 17.0, 2.0 Hz, 1H), 5.66 (dd, J = 10.3, 2.2 Hz, 1H), 4.71-4.63 (m, 1H), 4.55-4.47 (m, 3H), 4.24-4.16 (m, 3H), 4.12-4.07 (m, 1H), 3.87 (dd, J = 10.3, 5.9 Hz, 1H), 1.59-1.52 (m, 2H), 1.46 (s, 9H), 1.21-1.11 (m, 2H), 0.76 (t, J = 7.3 Hz, 3H). | 546 |
| 88 | 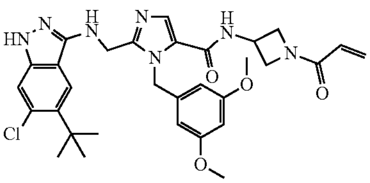 [SMILES: C=CC(=O)N1CC(NC(=O)c2cnc(CNc3n[nH]c4cc(Cl)c(C(C)(C)C)cc34)n2Cc2cc(OC)cc(OC)c2)C1] | 1H-NMR (DMSO-$d_6$) δ: 11.42 (s, 1H), 8.87 (d, J = 7.0 Hz, 1H), 7.83 (s, 1H), 7.64 (s, 1H), 7.24 (s, 1H), 6.66 (t, J = 5.9 Hz, 1H), 6.35-6.25 (m, 2H), 6.17-6.05 (m, 3H), 5.68-5.61 (m, 3H), 4.67-4.55 (m, 1H), 4.51-4.39 (m, 3H), 4.16 (t, J = 9.0 Hz, 1H), 4.05 (dd, J = 8.6, 5.3 Hz, 1H), 3.85 (dd, J = 10.3, 5.5 Hz, 1H), 3.62 (s, 6H), 1.44 (s, 9H) | 606 |
| 89 | 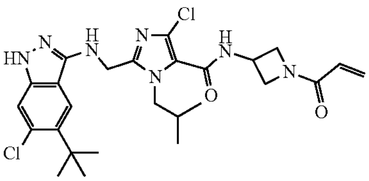 [SMILES: C=CC(=O)N1CC(NC(=O)c2c(Cl)nc(CNc3n[nH]c4cc(Cl)c(C(C)(C)C)cc34)n2CC(C)C)C1] | 1H-NMR (DMSO-$d_6$) δ: 11.45 (s, 1H), 8.88 (d, J = 7.0 Hz, 1H), 7.90 (s, 1H), 7.25 (s, 1H), 6.81 (t, J = 6.1 Hz, 1H), 6.31 (dd, J = 17.0, 10.3 Hz, 1H), 6.09 (dd, J = 17.0, 2.2 Hz, 1H), 5.65 (dd, J = 10.3, 2.2 Hz, 1H), 4.70-4.60 (m, 1H), 4.54-4.44 (m, 3H), 4.22-4.05 (m, 4H), 3.84 (dd, J = 9.9, 5.5 Hz, 1H), 1.94-1.82 (m, 1H), 1.45 (s, 9H), 0.79 (d,J = 6.6 Hz, 6H) | 546 |

TABLE 12-continued

| | Structure | NMR | ESI-MS [M + H]+ |
|---|---|---|---|
| 90 | 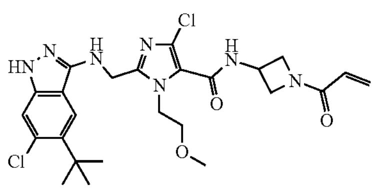 [SMILES: C=CC(=O)N1CC(NC(=O)c2c(Cl)nc(CNc3n[nH]c4cc(Cl)c(C(C)(C)C)cc34)n2CCOC)C1] | 1H-NMR (DMSO-$d_6$) δ: 11.44 (s, 1H), 8.80 (d, J = 7.3 Hz, 1H), 7.90(s, 1H), 7.25 (s, 1H), 6.76 (t, J = 5.9 Hz, 1H), 6.31 (dd, J = 17.0, 10.3 Hz, 1H), 6.09 (dd, J = 17.0, 2.2 Hz, 1H), 5.65 (dd, J = 10.3, 2.2 Hz, 1H), 4.71-4.60 (m, 1H), 4.55-4.40 (m, 5H) ,4.18 (t, J = 9.4 Hz, 1H), 4.11 (dd, J = 8.8, 5.5 Hz, 1H), 3.88 (dd, J = 10.3, 5.1 Hz, 1H),3.53 (t, J = 5.1 Hz, 2H), 3.17 (s, 3H), 1.45 (s, 9H) | 548 |

TABLE 13

| | Structure | NMR | ESI-MS [M + H]+ |
|---|---|---|---|
| 91 | 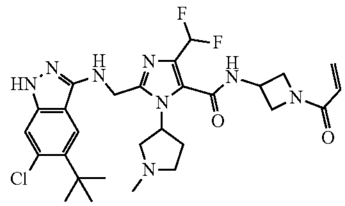 [SMILES: C=CC(=O)N1CC(NC(=O)c2c(C(F)F)nc(CNc3n[nH]c4cc(Cl)c(C(C)(C)C)cc34)n2C2CCN(C)C2)C1] | 1H-NMR (DMSO-D6) δ: 11.45 (s, 1H), 9.42 (d, J = 6.6 Hz, 1H), 7.93 (s, 1H), 7.25 (s, 1H), 6.88 (t, J = 54.3 Hz, 1H), 6.85-6.80 (m, 1H), 6.31 (dd, J = 17.0, 10.4 Hz, 1H), 6.09 (d, J = 17.0 Hz, 1H), 5.66 (d, J = 10.3 Hz, 1H), 5.14-5.06 (m, 1H), 4.66 (s, 2H), 4.63-4.57 (m, 1H), 4.51 (t, J = 8.2 Hz, 1H), 4.21-4.17 (m, 1H), 4.14-4.09 (m, 1H), 3.90-3.85 (m, 1H), 3.02-2.97 (m, 1H), 2.82-2.77(m, 1H), 2.70-2.66 (m, 1H), 2.46-2.43 (m, 1H), 2.28-2.22 (m, 2H), 2.18 (s, 3H), 1.46 (s, 9H). | 589 |
| 92 | 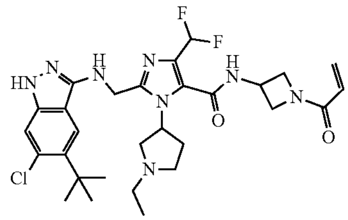 [SMILES: C=CC(=O)N1CC(NC(=O)c2c(C(F)F)nc(CNc3n[nH]c4cc(Cl)c(C(C)(C)C)cc34)n2C2CCN(CC)C2)C1] | 1H-NMR (DMSO-D6) δ: 11.45 (s, 1H), 9.42 (d, J = 6.6 Hz, 1H), 7.93 (s, 1H), 7.25 (s, 1H), 6.88 (t, J = 54.3 Hz, 1H), 6.85-6.80 (m, 1H), 6.31 (dd, J = 17.0, 10.4 Hz, 1H), 6.09 (d, J = 17.0 Hz, 1H), 5.66 (d, J = 10.3 Hz, 1H), 5.14-5.06 (m, 1H), 4.66 (s, 2H), 4.63-4.57 (m, 1H), 4.51 (t, J = 8.2 Hz, 1H), 4.21-4.17 (m, 1H), 4.14-4.09 (m, 1H), 3.90-3.85 (m, 1H), 3.02-2.97 (m, 1H), 2.82-2.77 (m, 1H), 2.70-2.66 (m, 1H), 2.46-2.43 (m, 1H), 2.36-2.22 (m, 4H), 1.46 (s, 9H), 0.94 (t, J = 7.1 Hz, 3H). | 603 |
| 93 | 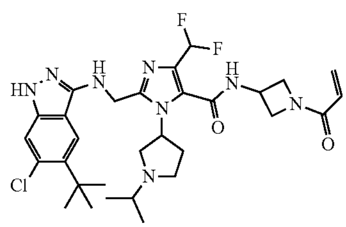 [SMILES: C=CC(=O)N1CC(NC(=O)c2c(C(F)F)nc(CNc3n[nH]c4cc(Cl)c(C(C)(C)C)cc34)n2C2CCN(C(C)C)C2)C1] 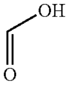 | 1H-NMR (DMSO-D6) δ: 11.45 (s, 1H), 9.38 (d, J = 6.6 Hz,1H), 8.13 (s, 1H), 7.93 (s, 1H), 7.25 (s, 1H), 6.89 (t, J = 54.3 Hz, 1H), 6.84-6.79 (m, 1H), 6.31(dd, J = 17.2, 10.3 Hz, 1H), 6.09 (d, J = 17.0 Hz, 1H), 5.66 (d, J = 10.3 Hz, 1H), 5.12-5.03 (m, 1H), 4.66-4.59 (m, 3H), 4.52 (t, J = 8.4 Hz, 1H), 4.21-4.08 (m, 2H), 3.91-3.85 (m, 1H), 3.10-3.04 (m, 1H), 2.95-2.91 (m, 1H), 2.78-2.74 (m, 1H), 2.56-2.53 (m, 1H), 2.41-2.37 (m, 1H), 2.27-2.17 (m, 2H), 1.46 (s, 9H), 0.97-0.93 (m, 6H). | 617 |
| 94 | 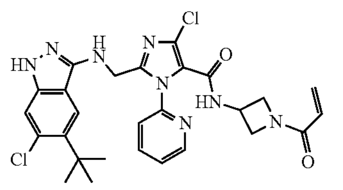 [SMILES: C=CC(=O)N1CC(NC(=O)c2c(Cl)nc(CNc3n[nH]c4cc(Cl)c(C(C)(C)C)cc34)n2-c2ccccn2)C1] | 1H-NMR (CDCl3) δ: 8.74 (brs, 1H), 8.57 (d, J = 4.8 Hz, 1H) , 7.90-7.85 (m, 1H), 7.55 (s, 1H), 7.46-7.41 (m, 2H), 7.30 (s, 1H), 7.03 (d, J = 7.0 Hz, 1H), 6.35 (dd, J = 17.0, 1.6 Hz, 1H), 6.14 (dd, J = 16.9, 10.3 Hz, 1H), 5.69 (dd, J = 10.4, 1.6 Hz, 1H), 4.91-4.84 (m, 1H), 4.76-4.69 (m, 1H), 4.54-4.48 (m, 1H), 4.45 (d, J = 5.1 Hz, 2H), 4.45-4.38 (m, 1H), 4.07-4.02 (m, 1H), 3.98-3.92 (m, 1H), 1.52 (s, 9H). | 567 |
| 95 | 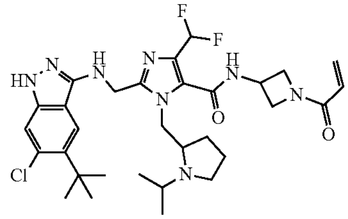 [SMILES: C=CC(=O)N1CC(NC(=O)c2c(C(F)F)nc(CNc3n[nH]c4cc(Cl)c(C(C)(C)C)cc34)n2CC2CCCN2C(C)C)C1] | 1H-NMR (DMSO-D6) δ: 11.47 (s, 1H), 9.83 (d, J = 7.0 Hz, 1H), 7.92 (s, 1H), 7.26 (s, 1H), 6.99 (t, J = 53.9 Hz, 1H), 6.86-6.84 (m, 1H), 6.32 (dd, J = 17.0, 10.4 Hz, 1H), 6.09 (d, J = 17.0 Hz, 1H), 5.67 (d, J = 10.4 Hz, 1H), 4.72-4.66 (m, 2H), 4.55-4.49 (m, 2H), 4.22 (t, J = 8.2 Hz, 1H), 4.12-4.09 (m, 3H), 3.87-3.83 (m, 1H), 3.23-3.22 (m, 1H), 2.75-2.73 (m, 1H), 2.56-2.52 (m, 1H), 2.40-2.34 (m, 1H), 1.64-1.57 (m, 4H), 1.45 (s, 9H), 0.77 (d, J = 6.6 Hz, 3H), 0.71 (d, J = 6.2 Hz, 3H). | 631 |

TABLE 13-continued

| | Structure | NMR | ESI-MS [M + H]$^+$ |
|---|---|---|---|
| 96 | 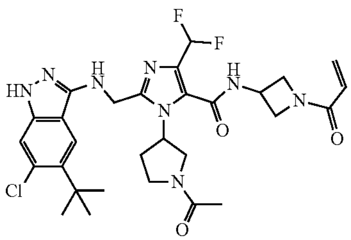 | 1H-NMR (DMSO-D6) δ: 11.50-11.48 (m, 1H), 9.43-9.40 (m, 1H), 7.94-7.92 (m, 1H), 7.27-7.26 (m, 1H), 7.06-6.78 (m, 2H), 6.33-6.27 (m, 1H), 6.11-6.07 (m, 1H), 5.67-5.65 (m, 1H), 5.37-5.23 (m, 1H), 4.64-4.48 (m, 4H), 4.21-4.15 (m, 1H), 4.10-4.06 (m, 1H), 3.92-3.80 (m, 2H), 3.40-3.13 (m, 4H), 2.30-2.25 (m, 1H), 1.90-1.76 (m, 3H), 1.46 (s, 9H). | 617 |
| 97 | 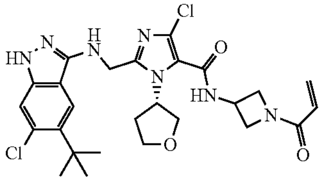 | 1H-NMR (DMSO-D6) δ: 11.46 (s, 1H), 9.15 (d, J = 7.0 Hz, 1H), 7.92 (s, 1H), 7.25 (s, 1H), 6.83 (t, J = 6.2 Hz, 1H), 6.31 (dd, J = 17.2, 10.3 Hz, 1H), 6.09 (dd, J = 17.0, 2.4 Hz, 1H), 5.66 (dd, J = 10.3, 2.2 Hz, 1H), 5.40-5.29 (m, 1H), 4.66-4.59 (m, 1H), 4.57-4.48 (m, 3H), 4.24-4.17 (m, 1H), 4.12-4.07 (m, 1H), 4.06-4.02 (m, 1H), 3.99-3.84 (m, 3H), 3.68-3.62 (m, 1H), 2.41-2.25 (m, 1H), 1.46 (s, 9H). | 560 |
| 98 | 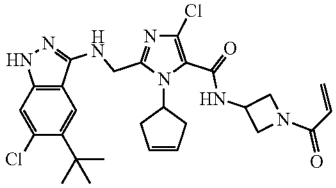 [SMILES: C=CC(=O)N1CC(NC(=O)c2c(Cl)nc(CNc3n[nH]c4cc(Cl)c(C(C)(C)C)cc34)n2C2CC=CC2)C1] | 1H-NMR (CDCl3) δ: 9.18 (s, 1H), 7.57 (s, 1H), 7.29 (t, J = 7.9 Hz, 1H), 7.07 (d, J = 6.6 Hz, 1H), 6.36 (d, J = 16.9 Hz, 1H), 6.18 (dd, J = 16.9, 10.3 Hz, 1H), 5.95-5.86 (m, 1H), 5.78 (s, 2H), 5.71 (d, J = 10.3 Hz, 1H), 5.00-4.94 (m, 1H), 4.90-4.81 (m, 1H), 4.63-4.54 (m, 1H), 4.57 (d, J = 5.5 Hz, 2H), 4.51-4.45 (m, 1H), 4.15-4.09 (m, 1H), 4.04-3.96 (m, 1H), 2.99-2.88 (m, 2H), 2.87-2.77 (m, 2H), 1.50 (s, 9H). | 556 |
| 99 | 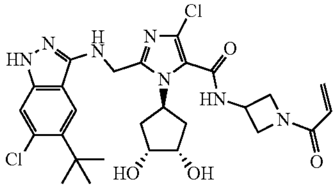 | 1H-NMR (CD30D) δ: 7.82 (s, 1H), 7.30 (s, 1H), 6.34 (dd, J = 17.0, 10.1 Hz, 1H), 6.26 (dd, J = 17.0, 2.4 Hz, 1H), 5.75 (dd, J = 9.9, 2.2 Hz, 1H), 5.47-5.37 (m, 1H), 4.81-4.75 (m, 1H), 4.69-4.63 (m, 1H), 4.60 (s, 2H), 4.45-4.39 (m, 1H), 4.32-4.23 (m, 3H), 4.13-4.03 (m, 2H), 2.44-2.33 (m, 2H), 2.23-2.14 (m, 2H), 1.52 (s, 9H). | 590 |

TABLE 14

| | Structure | NMR | ESI-MS [M + H]$^+$ |
|---|---|---|---|
| 100 | 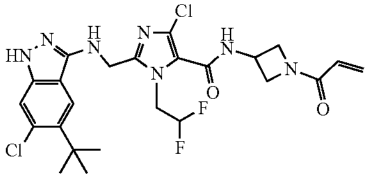 [SMILES: C=CC(=O)N1CC(NC(=O)c2c(Cl)nc(CNc3n[nH]c4cc(Cl)c(C(C)(C)C)cc34)n2CC(F)F)C1] | 1H-NMR (CDCl3) δ: 9.01 (br s, 1H), 7.5 3 (s, 1H), 7.31 (s, 1H), 7.08 (d, J = 6.6 Hz, 1H), 6.36 (dd, J = 17.0, 1.6 Hz, 1H), 6.30-6.02 (m, 2H), 5.71 (dd, J = 10.3, 1.8 Hz,1H), 4.99 (td, J = 13.5, 3.9 Hz, 2H), 4.88 (brs, 1H), 4.83-4.78 (m, 1H), 4.64 (d, J = 5.9 Hz, 2H), 4.59 (t, J = 8.2 Hz, 1H), 4.47 (t, J = 9.5 Hz, 1H), 4.10 (t, J = 7.1Hz, 1H), 3.99 (dd, J = 10.8, 5.3 Hz, 1H), 1.49 (s, 9H). | 554 |
| 101 | 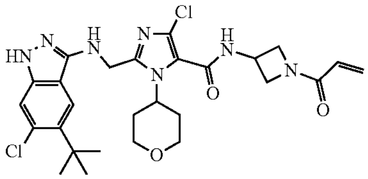 | 1H-NMR (DMSO-$d_6$) δ: 11.48 (s, 1H), 9.21 (d, J = 7.0 Hz, 1H), 7.89 (s, 1H), 7.26 (s, 1H), 6.88-6.79 (m, 1H), 6.31 (dd, J = 16.9, 10.3 Hz, 1H), 6.09 (dd, J = 16.9, 2.2 Hz, 1H), 5.65 (dd, J = 10.3, 2.2 Hz, 1H), 4.77-4.61 (m, 2H), 4.59-4.50 (m,3H), 4.25-4.17 (m, 1H), 4.10-4.04 (m, 1H), 3.87-3.78 (m, 3H), 3.26-3.17 (m, 2H), 2.31-2.16 (m, 2H), 1.74-1.64 (m, 2H), 1.46 (s, 9H) | 574 |

TABLE 14-continued

| | Structure | NMR | ESI-MS $[M + H]^+$ |
|---|---|---|---|
| 102 | 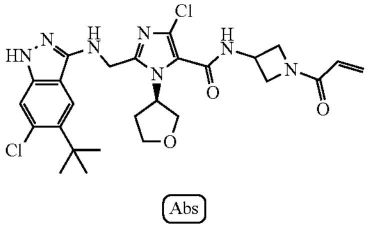 [SMILES: C=CC(=O)N1CC(NC(=O)c2c(Cl)nc(CNc3n[nH]c4cc(Cl)c(C(C)(C)C)cc34)n2[C@@H]2CCOC2)C1] | 1H-NMR (DMSO-$d_6$) δ: 11.46 (s, 1H), 9.15 (d, J = 6.6 Hz, 1H), 7.93 (s, 1H),7.27 (s, 1H), 6.82 (t, J = 6.1Hz, 1H), 6.38-6.26 (m, 1H), 6.10 (dd, J = 17.0, 2.3 Hz, 1H), 5.73-5.61 (m, 1H), 5.42-5.30 (m, 1H), 4.73-4.44 (m, 4H), 4.27-4.16 (m, 1H), 4.16-3.80 (m, 5H), 3.65 (q, J = 7.9 Hz, 1H), 2.43-2.23 (m, 2H), 1.47 (s, 9H) | 560 |
| 103 | 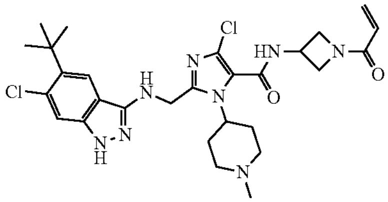 [SMILES: C=CC(=O)N1CC(NC(=O)c2c(Cl)nc(CNc3n[nH]c4cc(Cl)c(C(C)(C)C)cc34)n2C2CCN(C)CC2)C1] | 1H-NMR (DMSO-D6) δ: 11.48 (s, 1H), 9.20 (d, J = 6.6 Hz, 1H), 7.91 (s, 1H), 7.26 (s, 1H), 6.80 (t, J = 6.0 Hz, 1H), 6.32 (dd, J = 10.3, 16.9 Hz, 1H), 6.09 (dd, J = 16.9, 1.8 Hz, 1H), 5.66 (dd, J = 10.3, 1.8 Hz, 1H), 4.67-4.62 (m, 1H), 4.56-4.52 (m, 3H), 4.45-4.39 (m, 1H), 4.22 (t, J = 8.9 Hz, 1H), 4.09-4.06 (m, 1H), 3.86-3.82 (m, 1H), 2.76-2.71 (m, 2H), 2.26-2.20 (m, 2H), 2.10 (s, 3H), 1.84-1.81 (m, 2H), 1.72-1.69 (m, 2H), 1.45 (s, 9H). | 587 |
| 104 | 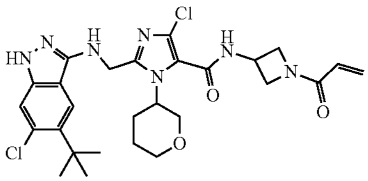 | 1H-NMR (DMSO-$d_6$) δ: 11.49 (s, 1H), 9.24 (d, J = 7.0 Hz, 1H), 7.91 (s, 1H), 7.25 (s, 1H), 6.86-6.74 (m, 1H), 6.31 (dd, J = 17.0, 10.4 Hz, 1H), 6.09 (dd, J = 17.0, 2.4 Hz, 1H), 5.66 (dd, J = 10.4, 2.4 Hz, 1H), 4.70-4.45 (m, 5H), 4.22 (t, J = 9.0 Hz, 1H), 4.08 (dd, J = 8.8, 5.1Hz, 1H), 3.92-3.81 (m, 3H), 3.79-3.71 (m, 1H), 3.20-3.10 (m, 1H), 2.22-2.07 (m, 1H), 1.98-1.89 (m, 1H), 1.67-1.49 (m, 2H), 1.45 (s, 9H) | 574 |
| 105 | 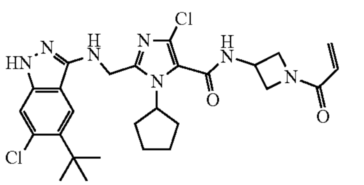 [SMILES: C=CC(=O)N1CC(NC(=O)c2c(Cl)nc(CNc3n[nH]c4cc(Cl)c(C(C)(C)C)cc34)n2C2CCCC2)C1] | 1H-NMR (DMSO-D6) δ: 11.46 (s, 1H), 9.16 (d, J = 6.6 Hz, 1H), 7.93 (s, 1H), 7.26 (s, 1H), 6.79 (t, J = 6.0 Hz, 1H), 6.31 (dd, J = 16.9, 10.3 Hz, 1H), 6.09 (d, J = 17.2 Hz, 1H), 5.66 (d, J = 10.6 Hz, 1H), 4.99-4.91 (m, 1H), 4.66-4.61 (m, 1H), 4.55-4.51 (m, 3H), 4.21 (t, J = 9.0 Hz, 1H), 4.09-4.04 (m, 1H), 3.86-3.82 (m, 1H), 2.04-1.99 (m, 4H), 1.74-1.69 (m, 2H), 1.52-1.49 (m, 2H), 1.46 (s, 9H). | 558 |
| 106 | 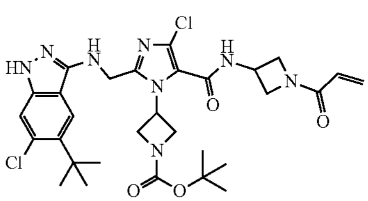 [SMILES: C=CC(=O)N1CC(NC(=O)c2c(Cl)nc(CNc3n[nH]c4cc(Cl)c(C(C)(C)C)cc34)n2C2CN(C(=O)OC(C)(C)C)C2)C1] | 1H-NMR (CDCl3) δ: 9.39 (br s, 1H), 7.57 (s, 1H), 7.35 (s, 1H), 6.33 (dd, J = 16.9, 1.8 Hz, 1H), 6.14 (dd, J = 16.9, 10.3 Hz, 1H), 5.76 (brs, 1H), 5.68 (dd, J = 10.4, 1.6 Hz, 1H), 4.88-4.81 (m, 2H), 4.73 (br s, 2H), 4.50 (br s, 1H), 4.38 (s, 3H), 4.28 (br s, 2H), 4.10 (brs, 2H), 3.98 (brs, 1H), 1.51 (s, 9H), 1.42 (s, 9H). | 645 |
| 107 | 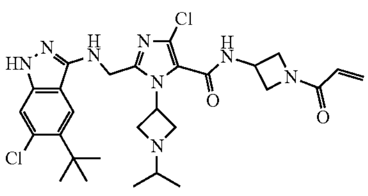 [SMILES: C=CC(=O)N1CC(NC(=O)c2c(Cl)nc(CNc3n[nH]c4cc(Cl)c(C(C)(C)C)cc34)n2C2CN(C(C)C)C2)C1] | 1H-NMR (CDCl3) δ: 9.11 (s, 1H), 7.56 (s, 1H), 7.33 (s, 1H), 6.91 (d, J = 7.3 Hz, 1H), 6.36 (dd, J = 16.9, 1.8 Hz, 1H), 6.17 (dd, J = 17.0, 10.4 Hz, 1H), 5.71 (dd, J = 10.4, 1.6 Hz, 1H), 5.37 (t, J = 7.3 Hz, 1H), 4.91 (brs, 1H), 4.85-4.80 (m, 1H), 4.63-4.59 (m, 3H), 4.48 (t, J = 9.5 Hz, 1H), 4.10 (t, J = 7.0 Hz, 1H), 4.02-3.96 (m, 3H), 3.33 (t, J = 7.1 Hz, 2H), 2.49-2.40 (m, 1H), 1.51 (s, 9H), 0.95 (d, J = 6.2 Hz, 6H). | 587 |
| 108 | 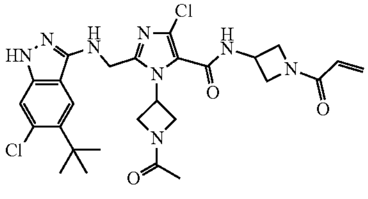 [SMILES: C=CC(=O)N1CC(NC(=O)c2c(Cl)nc(CNc3n[nH]c4cc(Cl)c(C(C)(C)C)cc34)n2C2CN(C(C)=O)C2)C1] | 1H-NMR (CDCl3) δ: 9.60 (br s, 1H), 7.56 (d, J = 7.0 Hz, 1H), 7.34 (d, J = 5.1 Hz, 1H), 6.97 (s, 1H), 6.33 (dd, J = 17.2, 7.7 Hz, 1H), 6.14 (dd, J = 16.9, 10.3 Hz, 1H), 5.91-5.83 (m, 1H), 5.67 (dd, J = 15.6, 10.4 Hz, 1H), 4.99-4.92 (m, 1H), 4.82-4.67 (m, 4H), 4.56-4.47 (m, 2H) 4.35-4.30 (m, 2H), 4.20-4.08 (m, 2H), 4.05-3.96 (m, 1H), 1.85 (s, 3H), 1.51 (s, 9H). | 587 |

TABLE 15

| | Structure | NMR | ESI-MS [M + H]$^+$ |
|---|---|---|---|
| 109 | 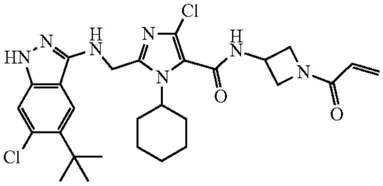 [SMILES: C=CC(=O)N1CC(NC(=O)c2c(Cl)nc(CNc3n[nH]c4cc(Cl)c(C(C)(C)C)cc34)n2C2CCCCC2)C1] | 1H-NMR (DMSO-$d_6$) δ: 11.45 (s, 1H), 9.17 (d, J = 7.0 Hz, 1H), 7.91 (s, 1H), 7.25 (s, 1H), 6.78 (t, J = 6.1 Hz, 1H), 6.31 (dd, J = 17.0, 10.3 Hz, 1H), 6.08 (dd, J = 17.0, 2.2 Hz, 1H), 5.65 (dd, J = 10.3, 2.2 Hz, 1H), 4.68-4.57 (m, 1H), 4.56-4.48 (m, 3H), 4.45-4.34 (m, 1H), 4.24-4.17 (m, 1H), 4.06 (dd, J = 8.6, 5.0 Hz, 1H), 3.83 (dd, J = 10.5, 5.0 Hz, 1H), 2.03-1.87 (m, 2H), 1.83-1.74 (m, 2H), 1.71-1.61 (m, 2H), 1.57-1.49 (m, 1H), 1.45 (s, 9H), 1.29-1.10 (m, 2H), 1.07-0.93 (m, 1H) | 572 |
| 110 | 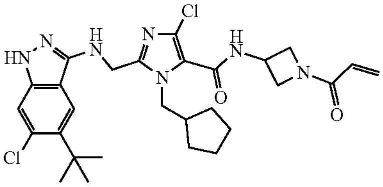 [SMILES: C=CC(=O)N1CC(NC(=O)c2c(Cl)nc(CNc3n[nH]c4cc(Cl)c(C(C)(C)C)cc34)n2CC2CCCC2)C1] | 1H-NMR (CDCl3) δ: 9.16 (s, 1H), 7.57 (s, 1H), 7.31 (s, 1H), 7.07 (d, J = 6.6 Hz, 1H), 6.36 (dd, J = 16.9, 1.8 Hz, 1H), 6.18 (dd, J = 16.9, 10.3 Hz, 1H), 5.70 (dd, J = 10.3, 1.8 Hz, 1H), 5.01 (t, J = 5.5 Hz, 1H), 4.83 (d, J = 7.0 Hz, 1H), 4.63 (d, J = 5.9 Hz, 2H), 4.59 (d, J = 8.4 Hz, 1H), 4.49-4.40 (m, 3H), 4.10 (t, J = 7.1Hz, 1H), 4.00 (t, J = 5.5 Hz, 1H),2.24 (s, 1H), 1.75 (s, 2H), 1.64 (brs, 4H), 1.51 (s, 9H), 1.22-1.17 (m, 2H). | 572 |
| 111 | 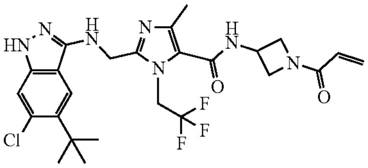 [SMILES: C=CC(=O)N1CC(NC(=O)c2c(C)nc(CNc3n[nH]c4cc(Cl)c(C(C)(C)C)cc34)n2CC(F)(F)F)C1] | 1H-NMR (CDCl3) δ: 8.71 (s, 1H), 7.66 (s, 1H), 7.35 (s, 1H), 7.01 (s, 1H),6.38 (dd, J = 16.9, 1.4 Hz, 1H), 6.20 (dd, J = 16.8, 10.4 Hz, 1H), 5.85-5.76 (m, 1H), 5.72 (dd, J = 10.4, 1.5 Hz, 1H), 5.27-5.22 (m, 1H), 4.92-4.86 (m, 1H), 4.83-4.69 (m, 2H), 4.67-4.61 (m, 1H), 4.55-4.48 (m, 1H), 4.16-4.10 (m, 1H), 4.06-3.98 (m, 1H), 2.66-2.58 (m, 1H), 2.37-2.24 (m, 1H), 2.02-1.96 (m, 1H), 1.91-1.88 (m, 1H), 1.82-1.21 (m, 5H), 1.11(d, J = 7.0 Hz, 3H), 0.92 (d, J = 6.7 Hz, 3H),0.45-0.38 (m, 3H). | 628 |
| 112 | 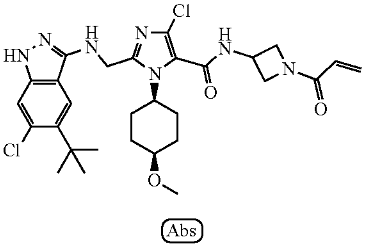 [SMILES: C=CC(=O)N1CC(NC(=O)c2c(Cl)nc(CNc3n[nH]c4cc(Cl)c(C(C)(C)C)cc34)n2[C@H]2CC[C@@H](OC)CC2)C1] | 1H-NMR (DMSO-$d_6$) δ: 11.44 (s, 1H), 9.19 (d, J = 6.6 Hz, 1H), 7.91 (s, 1H), 7.25 (s, 1H), 6.77 (t, J = 6.2 Hz, 1H), 6.29 (dd, J = 17.0, 10.3 Hz, 1H), 6.08 (dd, J = 17.0, 2.3 Hz, 1H), 5.65 (dd, J = 10.3, 2.3 Hz, 1H), 4.62-4.40 (m, 5H), 4.22-4.15 (m, 1H), 4.10 (dd, J = 8.4, 4.8 Hz, 1H), 3.87 (dd, J = 10.5, 5.3 Hz, 1H), 3.29-3.33 (m, 1H), 3.14 (s, 3H), 2.24-2.11 (m, 2H), 1.90-1.80 (m, 2H), 1.62-1.49 (m, 2H), 1.45 (s, 9H), 1.36-1.25 (m, 2H) | 603 |
| 113 | 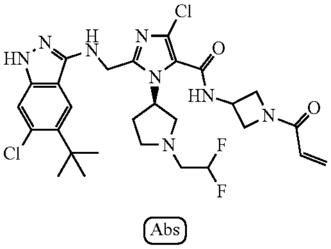 [SMILES: C=CC(=O)N1CC(NC(=O)c2c(Cl)nc(CNc3n[nH]c4cc(Cl)c(C(C)(C)C)cc34)n2[C@@H]2CCN(CC(F)F)C2)C1] | 1H-NMR (CDCl3) δ: 8.88 (br s, 1H), 7.59 (s, 1H), 7.32 (s, 1H), 7.02 (d, J = 6.6 Hz, 1H), 6.37 (dd, J = 17.0, 1.6 Hz, 1H), 6.22-6.14 (m, 1H), 6.03-5.85 (m, 2H), 5.72 (dd, J = 10.3, 1.8 Hz, 1H), 5.06 (dd, J = 15.0, 6.2 Hz, 1H), 4.96-4.91 (m, 1H), 4.88-4.79 (m, 1H), 4.65-4.57 (m, 1H), 4.53-4.46 (m, 1H), 4.16-4.10 (m, 2H), 4.06-3.98 (m, 1H), 3.46-3.40 (m, 1H), 3.31-3.24 (m, 1H), 3.04-2.89 (m, 1H), 2.87-2.74 (m, | 623 |
| 114 | 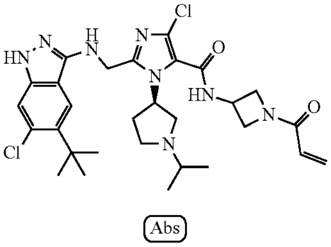 [SMILES: C=CC(=O)N1CC(NC(=O)c2c(Cl)nc(CNc3n[nH]c4cc(Cl)c(C(C)(C)C)cc34)n2[C@@H]2CCN(C(C)C)C2)C1] | 1H-NMR (CDCl3) δ: 9.16-9.00 (m, 1H), 7.58 (s, 1H), 7.32 (s, 1H), 7.12-7.03 (m, 1H), 6.36 (dd, J = 17.0, 1.6 Hz, 1H), 6.18 (dd, J = 16.9, 10.3 Hz, 1H), 5.83 (brs, 1H), 5.71 (dd, J = 10.4, 1.6 Hz, 1H), 5.33 (brs, 1H), 5.00 (d, J = 15.4 Hz, 1H), 4.90-4.79 (m, 2H), 4.64-4.58 (m, 1H), 4.51-4.45 (m, 1H), 4.16-4.10 (m, 1H), 4.04-3.99 (m, 1H), 3.31-3.25 (m, 1H), 3.22-3.16 (m, 1H), 2.86-2.79 (m, 1H), 2.52-2.40 (m, 3H), 2.22-2.12 (m, 1H), 1.51 (s, 9H), 1.13 (d, J = 6.2 Hz, 3H), 1.08 (d, J = 6.6 Hz, 3H). | 601 |

TABLE 15-continued

| | Structure | NMR | ESI-MS [M + H]$^+$ |
|---|---|---|---|
| 115 | 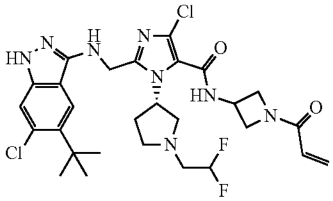 | Identical to Example 113 | 623 |
| 116 | 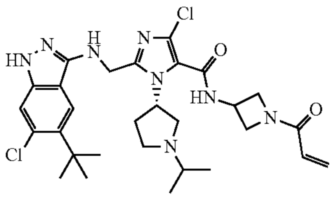 | Identical to Example 114 | 601 |
| 117 | 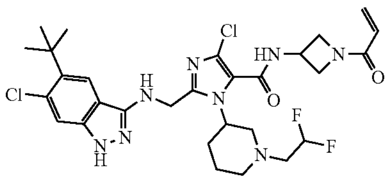 [SMILES: C=CC(=O)N1CC(NC(=O)c2c(Cl)nc(CNc3n[nH]c4cc(Cl)c(C(C)(C)C)cc34)n2C2CCCN(CC(F)F)C2)C1] | 1H-NMR (DMSO-D6) δ: 11.47 (s, 1H), 9.23 (d, J = 6.6 Hz, 1H), 7.92 (s, 1H), 7.26 (s, 1H), 6.79 (t, J = 6.0 Hz, 1H), 6.32 (dd, J = 16.9, 10.3 Hz, 1H), 6.09 (d, J = 16.9 Hz, 1H), 5.89 (tt, J = 55.7, 4.0 Hz, 1H), 5.66 (d, J = 10.3 Hz, 1H), 4.66-4.61 (m, 1H), 4.59-4.47 (m, 3H), 4.22 (t, J = 9.0 Hz, 1H), 4.10-4.07 (m, 1H), 3.88-3.84 (m, 1H), 3.31-3.27 (m, 1H), 3.05-3.02 (m, 1H), 2.89-2.83 (m, 1H), 2.78-2.74 (m, 1H), 2.72-2.61 (m, 2H), 2.08-2.02 (m, 1H), 1.93-1.81 (m, 2H), 1.62-1.58 (m, 1H), 1.45 (s, 9H). | 637 |

TABLE 16

| | Structure | NMR | ESI-MS [M + H]$^+$ |
|---|---|---|---|
| 118 | 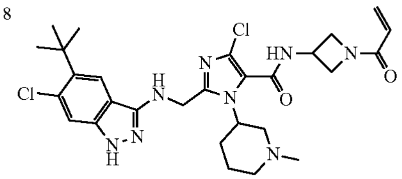 | 1H-NMR (DMSO-D6) δ: 11.47 (s, 1H), 9.23 (d, J = 6.6 Hz, 1H), 7.91 (s, 1H), 7.26 (s, 1H), 6.78 (t, J = 5.7 Hz, 1H), 6.32 (dd, J = 16.9, 10.3 Hz, 1H), 6.09 (d, J = 16.9 Hz, 1H), 5.66 (d, J = 10.3 Hz, 1H), 4.64-4.62 (m, 1H), 4.57-4.47 (m, 5H), 4.22 (t, J = 8.6 Hz, 1H), 4.10-4.06 (m, 1H), 3.87-3.84 (m, 1H), 2.89-2.86 (m, 1H), 2.64-2.62 (m, 1H), 2.44-2.47 (m, 1H), 2.10 (s, 3H), 1.91-1.88 (m, 1H), 1.83-1.80 (m, 1H),1.74-1.68 (m, 1H), 1.61-1.57 (m, 1H), 1.45 (s, 9H). | 587 |
| 119 | 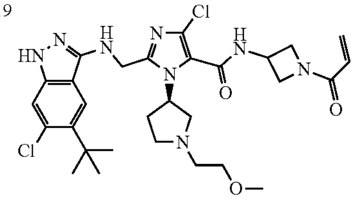 | 1H-NMR (CDCl3) δ: 7.62 (s, 1H), 7.32 (s, 1H), 7.16-7.10 (m, 1H), 6.36 (dd, J = 17.2, 1.5 Hz, 1H), 6.18 (dd, J = 17.2, 10.3 Hz, 1H), 5.95-5.83 (m, 1H), 5.71 (t, J = 5.9 Hz, 1H), 4.95 (d, J = 15.4 Hz, 1H), 4.86-4.77 (m, 2H), 4.63-4.56 (m, 1H), 4.52-4.44 (m ,1H), 4.16-4.09 (m, 1H), 4.06-3.98 (m, 1H), 3.54 (t, J = 5.5 Hz, 2H), 3.38-3.31 (m, 1H), 3.27 (s, 3H), 3.23-3.17 (m, 1H), 2.88-2.77 (m, 2H), 2.72-2.64 (m, 1H), 2.61-2.51 (m, 1H), 2.50-2.41 (m, 1H), 2.24-2.12 (m, 1H), 1.52 (s, 9H). | 617 |

TABLE 16-continued

| | Structure | NMR | ESI-MS $[M + H]^+$ |
|---|---|---|---|
| 120 | 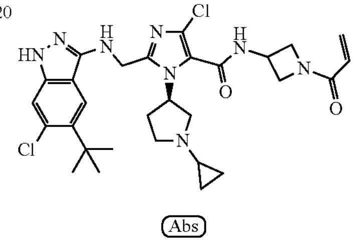 | 1H-NMR (CDCl3) δ: 8.86 (s, 1H), 7.58 (s, 1H), 7.32 (s, 1H), 7.00 (d, J = 6.6 Hz, 1H), 6.37 (dd, J = 17.0, 1.6 Hz, 1H), 6.19 (dd, J = 17.2, 10.3 Hz, 1H), 5.94-5.84 (m, 1H), 5.72 (dd, J = 10.4, 1.6 Hz, 1H), 5.04-4.74 (m, 4H), 4.65-4.58 (m, 1H), 4.54-4.45 (m, 1H), 4.17-4.10 (m, 1H), 4.05-3.99 (m, 1H), 3.32-3.27 (m, 1H), 3.25-3.19 (m, 1H), 3.01-2.91 (m, 1H), 2.61-2.52 (m, 1H), 2.49-2.40 (m, 1H), 2.17-2.07 (m, 1H), 1.52 (s, 9H), 0.58-0.34 (m, 4H). | 599 |
| 121 | 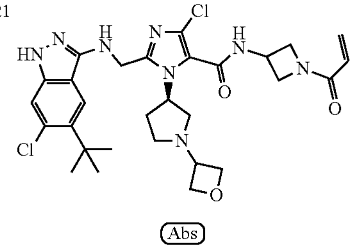 | 1H-NMR (DMSO-D6) δ: 11.45 (s, 1H), 9.13 (d, J = 6.4 Hz, 1H), 7.93 (s, 1H), 7.25 (s, 1H), 6.83 (t, J = 6.1 Hz, 1H), 6.31 (dd, J = 16.9, 10.3 Hz, 1H), 6.09 (dd, J = 16.9, 2.1 Hz, 1H), 5.66 (dd, J = 10.3, 2.1 Hz, 1H), 5.21 (s, 1H), 4.72-4.60 (m, 3H), 4.54-4.47 (m, 3H), 4.42-4.38 (m, 2H), 4.20 (t, J = 9.2 Hz, 1H), 4.13-4.08 (m, 1H), 3.89-3.84 (m, 1H), 3.58-3.55 (m, 1H), 3.06-3.04 (m, 1H), 2.82-2.79 (m, 1H), 2.73-2.68 (m, 1H), 2.46-2.42 (m, 1H), 2.30-2.27 (m, 1H), 2.21-2.16 (m, 1H), 1.46 (s, 9H). | 615 |
| 122 | 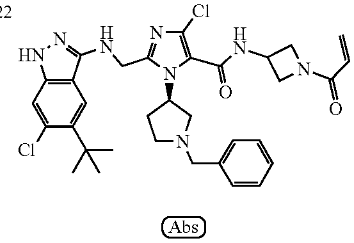 | 1H-NMR (CDCl3) δ: 8.79 (br s, 1H), 7.5 8 (s, 1H), 7.41-7.36 (m, 2H), 7.33 (s, 1H), 7.22-7.17 (m, 3H), 6.99 (d, J = 6.2 Hz, 1H), 6.37 (dd, J = 16.9, 1.8 Hz, 1H), 6.18 (dd, J = 17.0, 10.4 Hz, 1H), 5.99-5.89 (m, 1H), 5.71 (dd, J = 10.3, 1.8 Hz, 1H), 5.11-4.90 (m, 3H), 4.87-4.79 (m, 1H), 4.64-4.57 (m, 1H), 4.52-4.44 (m, 1H), 4.15-4.08 (m, 1H), 4.04-3.97 (m, 1H), 3.73 (d, J = 12.8 Hz, 1H), 3.58 (d, J = 12.8 Hz, 1H), 3.23-3.12 (m, 2H), 2.75-2.67 (m, 1H), 2.53-2.34 (m, 2H), 2.29-2.18 (m, 1H), 1.52 (s, 9H). | 649 |
| 123 | 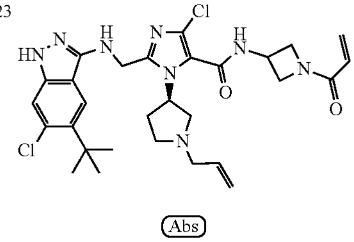 | 1H-NMR (DMSO-D6) δ: 11.44 (s, 1H), 9.13 (d, J = 6.6 Hz, 1H), 7.92 (s, 1H), 7.25 (s, 1H), 6.78 (t, J = 6.0 Hz, 1H), 6.31 (dd, J = 16.9, 10.3 Hz, 1H), 6.09 (dd, J = 16.9, 2.2 Hz, 1H), 5.82-5.72 (m, 1H), 5.66 (dd, J = 10.3, 2.2 Hz, 1H), 5.21-5.10 (m, 2H), 4.99 (d, J = 10.6 Hz, 1H), 4.67-4.57 (m, 3H), 4.55-4.50 (m, 1H), 4.23-4.17 (m, 1H), 4.12-4.08 (m, 1H), 3.90-3.84 (m, 1H), 3.08-3.03 (m, 1H), 2.98-2.92 (m, 2H), 2.80 (t, J = 9.0 Hz, 1H), 2.74-2.66 (m, 2H), 2.29-2.17 (m, 2H), 1.46 (s, 9H). | 599 |
| 124 | 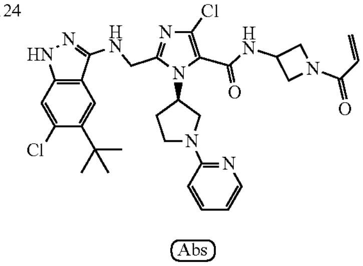 | 1H-NMR (CDCl3) δ: 8.92 (br s, 1H), 8.15-8.13 (m, 1H), 7.56 (s, 1H), 7.46-7.42 (m, 1H), 7.00 (d, J = 6.7 Hz, 1H), 6.59 (dd, J = 6.9, 5.3 Hz, 1H), 6.39-6.34 (m, 2H), 6.20-6.14 (m, 1H), 5.88-5.80 (m, 1H), 5.70 (dd, J = 10.4, 1.5 Hz, 1H), 4.86-4.78 (m, 2H), 4.75-4.67 (m, 2 H), 4.61-4.53 (m, 1H), 4.49-4.43 (m, 1H), 4.10-4.05 (m, 1H), 4.01-3.86 (m, 4H), 3.48-3.42 (m, 1H), 2.85-2.80 (m, 1H), 2.53-2.46 (m, 1H), 1.51 (s, 9H). | 636 |
| 125 | 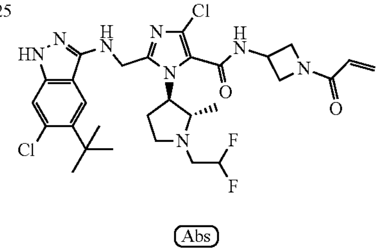 | 1H-NMR (CDCl3) δ: 8.85 (s, 1H), 7.58 (s, 1H), 7.34 (s, 1H), 6.97(d, J = 6.7 Hz, 1H), 6.37 (dd, J = 17.0, 1.7 Hz, 1H), 6.19 (dd, J = 17.0, 10.4 Hz, 1H), 5.89 (tt, J = 56.0, 4.5 Hz, 1H), 5.72 (dd, J = 10.4, 1.5 Hz, 1H), 5.08-5.01 (brs, 1H), 4.86-4.74 (m, 3H), 4.69-4.60 (m, 2H), 4.51-4.48 (m, 1H), 4.13-4.10 (m, 1H), 4.01-3.99 (m, 1H), 3.29-3.22 (m, 2H), 3.08-2.98 (m, 2H), 2.79-2.75 (m, 1H), 2.41-2.36 (m, 1H), 2.28-2.21 (m, 1H), 1.52 (s, 9H), 1.08 (d, J = 6.1Hz, 3H). | 637 |

TABLE 16-continued

| | Structure | NMR | ESI-MS $[M+H]^+$ |
|---|---|---|---|
| 126 | 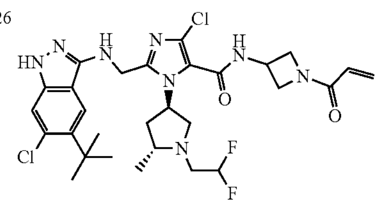 | 1H-NMR (CDCl3) δ: 8.78 (s, 1H), 7.58 (s, 1H), 7.33 (s, 1H), 6.95 (d, J = 6.2 Hz, 1H), 6.36 (dd, J = 16.9, 1.5 Hz, 1H), 6.18 (dd, J = 16.9, 10.3 Hz, 1H), 6.02-5.70 (m, 3H), 4.86-4.72 (m, 4H), 4.63-4.59 (m, 1H), 4.51-4.47 (m, 1H), 4.15-4.09 (m, 1H), 4.04-3.97 (m, 1H), 3.37-3.33 (m, 2H), 3.19-3.11 (m, 1H), 3.02-2.95 (m, 1H), 2.85-2.76 (m, 1H),2.45-2.34 (m, 1H), 2.07-2.00 (m, 1H), 1.52 (s, 9H), 1.08 (d, J = 6.2 Hz, 3H). | 637 |

TABLE 17

| | | | |
|---|---|---|---|
| ref. 1 | 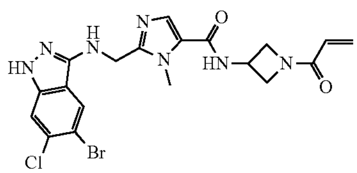 | 1H-NMR (CDCl3) δ: 8.86 (s, 1H), 7.87 (s, 1H), 7.47 (s, 1H), 7.45 (s, 1H), 7.21 (s, 1H), 6.36 (dd, J = 16.7, 1.6 Hz, 1H), 6.31 (d, J = 6.2 Hz, 1H), 6.18 (dd, J = 16.9, 10.3 Hz, 1H), 5.71 (dd, J = 10.4, 1.6 Hz, 1H), 4.92-4.79 (m, 2H), 4.66-4.57 (m, 1H), 4.64 (d, J = 5.5 Hz, 2H), 4.52-4.44 (m, 1H), 4.15-4.09 (m, 1H), 4.04-3.98 (m, 1H), 3.95 (s, 3H). | 494 |
| ref. 2 | 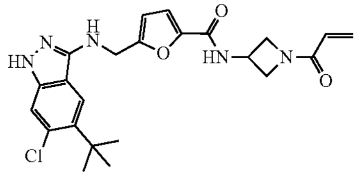 | 1H-NMR (CDCl3) δ: 9.26 (br s, 1H), 7.53 (s, 1H), 7.34 (s, 1H), 7.21 (br s, 1H), 7.08 (d, J = 3.3 Hz, 1H), 6.43 (d, J = 3.7 Hz, 1H), 6.34 (dd, J = 16.7, 1.3 Hz, 1H), 6.15 (dd, J = 16.9, 10.3 Hz, 1H), 5.69 (dd, J = 10.4, 1.3 Hz, 1H), 4.90-4.83 (m, 1H), 4.64 (s, 2H), 4.55 (t, J = 8.2 Hz, 1H), 4.49 (br s, 1H), 4.42 (t, J = 9.3 Hz, 1H), 4.07-3.97 (m, 2H), 1.51 (s, 9H). | 456 |
| ref. 3 | 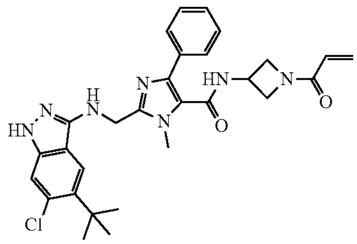 | 1H-NMR (CDCl3) δ: 8.79 (br s, 1H), 7.58-7.54 (m, 3H), 7.47-7.43 (m, 3H), 7.33 (s, 1H), 6.31 (d, J = 16.9 Hz, 1H), 6.09 (dd, J = 16.9, 10.3 Hz, 1H), 5.97 (d, J = 7.3 Hz, 1H), 5.67 (d, J = 10.6 Hz, 1H), 4.89 (d, J = 5.1Hz, 1H), 4.77 (d, J = 7.0 Hz, 1H), 4.71 (d, J = 5.9 Hz, 2H), 4.46 (t, J = 8.6 Hz, 1H), 4.30 (t, J = 9.3 Hz, 1H), 3.97 (s, 3H), 3.77 (brs, 1H), 3.54 (brs, 1H), 1.50 (s, 9H). | 546 |

Test Example 1: A Test of Compounds to Determine Whether they Bind to KRASG12C Test compounds were prepared in the form of a 10 mM DMSO solution.

Wt K-Ras4B (1-169) and G12C K-Ras4B (1-169) proteins were mixed and diluted with a buffer (1×TBS, 0.1 mM TCEP) to prepare individual 1 μM protein solutions. A 10 mM test compound was diluted tenfold with DMSO to make a 1 mM solution, and then diluted fivefold with DMSO to make a 200 μM solution. The 200 μM solution was further diluted fivefold to make a 40 μM solution. When the final compound concentration was 10 μM, 1 μL of a 200 μM test compound was added to 19 μL of a 1 μM protein solution. When the final compound concentration was 2 μM, 1 μL of a 40 μM test compound was added to 19 μL of a 1 μM protein solution. The mixtures were stored in an incubator at 25° C. for 2 hours, and 80 μL of a 1×TBS solution containing 0.2% formic acid was added thereto to end the reaction, followed by LC-MS measurement. LC-MS measurement was performed using Xevo G2-S Q-Tof manufactured by Waters, and reverse-phase chromatography was performed with a desalting column. A mass spectrum of positive ions was obtained by electrospray. For a mass spectrum, a spectrum of a polyvalent ion was collectively converted to a molecular weight by using OpenLynx software by the MaxEnt technique, and a compound binding rate was obtained from the ratio of a signal intensity that corresponds to the molecular weight of a protein to a signal intensity that corresponds to the molecular weight of a compound binding to the protein.

By obtaining the compound binding rate for wt K-Ras4B (1-169) and the compound binding rate for G12C K-Ras4B (1-169) at the same time, information of the selectivity for G12C K-Ras4B (1-169) was obtained at the same time.

The test compounds were measured at their final compound concentration of 2 μM. For G12C K-Ras4B (1-169), a binding rate of 80% or more is rated "A," a binding rate of 60% or more and less than 80% is rated "B," a binding rate of 40% or more and less than 60% is rated "C," a binding rate of 20% or more and less than 40% is rated "D," and a binding rate of less than 20% is rated "E." The following table shows the results. Almost none of the compounds of the disclosure bound to wt K-Ras4B (1-169). The "binding rate" (%) for each of wt K-Ras4B (1-169) and G12C K-Ras4B (1-169) refers to the ratio of the signal intensity of bound forms to the sum of the signal intensity of non-bound forms and the signal intensity of bound forms.

The test results shown below in Table 18 reveal that the compound of the disclosure has an excellent capability of binding to G12C K-Ras4B mutant protein.

TABLE 18

| Example | |
|---|---|
| 1 | A |
| 2 | B |
| 3 | A |
| 4 | C |
| 5 | A |
| 6 | B |
| 7 | D |
| 8 | B |
| 9 | D |
| 10 | B |
| 11 | B |
| 12 | B |
| 13 | A |
| 14 | B |
| 15 | A |
| 16 | B |
| 17 | B |
| 18 | B |
| 19 | A |
| 20 | A |
| 21 | B |
| 22 | B |
| 23 | A |
| 24 | C |
| 25 | A |
| 26 | A |
| 27 | A |
| 28 | B |
| 29 | B |
| 30 | C |
| 31 | D |
| 32 | B |
| 33 | A |
| 34 | A |
| 35 | B |
| 36 | B |
| 37 | C |
| 38 | C |
| 39 | C |
| 40 | A |
| 41 | A |
| 42 | B |
| 43 | C |
| 44 | B |
| 45 | A |
| 46 | B |
| 47 | C |
| 48 | B |
| 49 | C |
| 50 | C |
| 51 | B |
| 52 | B |
| 53 | B |
| 54 | B |
| 55 | A |
| 56 | C |

TABLE 18-continued

| Example | |
|---|---|
| 57 | C |
| 58 | B |
| 59 | B |
| 60 | C |
| 61 | B |
| 62 | A |
| 63 | B |
| 64 | A |
| 65 | B |
| 66 | A |
| 67 | A |
| 68 | C |
| 69 | E |
| 70 | A |
| 71 | C |
| 72 | B |
| 73 | B |
| 74 | A |
| 75 | A |
| 76 | A |
| 77 | C |
| 78 | B |
| 79 | E |
| 80 | C |
| 81 | E |
| 82 | D |
| 83 | D |
| 84 | C |
| 85 | C |
| 86 | A |
| 87 | A |
| 88 | B |
| 89 | A |
| 90 | A |
| 91 | A |
| 92 | B |
| 93 | A |
| 94 | B |
| 95 | A |
| 96 | A |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | B |
| 110 | A |
| 111 | B |
| 112 | A |
| 113 | A |
| 114 | A |
| 115 | A |
| 116 | B |
| 117 | A |
| 118 | A |
| 119 | B |
| 120 | A |
| 121 | A |
| 122 | A |
| 123 | A |
| 124 | A |
| 125 | A |
| 126 | A |
| Reference Example 1 | E |
| Reference Example 2 | E |
| Reference Example 3 | E |

Test Example 2: Evaluation of Inhibitory Activity of Compounds on the KRAS G12C Nucleotide (GDP-GTP) Exchange Reaction The inhibitory activity of compounds on the exchange reaction of GDP into GppNHp in Bodipy (trademark) FL-bound KRAS G12C was examined by fluorescence measurement using human recombinant KRAS G12C and SOS1 proteins.

For the preparation of KRAS G12C to which Bodipy FL GDP was bound, first, 50 μM KRAS G12C (amino acid region: 1-169) and 1 mM Bodipy FL GDP (Invitrogen, G22360) were incubated for 1 hour in a buffer (20 mM Tris-HCl (pH 7.5), 50 mM NaCl, 1 mM DTT) in ice in the presence of 2.5 mM EDTA. Thereafter, $MgCl_2$ with a final concentration of 10 mM was added, and the mixture was incubated at room temperature for 30 minutes. The protein was allowed to pass through a NAP-5 column to remove free nucleotides and was used for compound evaluation.

For the measurement of the inhibitory activity of compounds on nucleotide exchange reaction, first, the compound of the disclosure was diluted stepwise with dimethyl sulfoxide (DMSO). Subsequently, a solution of the gradually diluted compound of the disclosure in DMSO (the final concentration of DMSO: 5%) and KRAS G12C (25 nM) bound to Bodipy FL GDP were added to a reaction buffer (20 mM Tris-HCl (pH 7.5), 100 mM NaCl, 1 mM $MgCl_2$, 2 mM DTT, 0.1% Tween20), followed by preincubation at 25° C. for 4 hours. Thereafter, Son of Sevenless Homolog 1 (SOS1, amino acid region: 564-1049) and GppNHp (GMPPNP, Jena Bioscience GmbH, NU-401-50) were added such that their final concentration was 100 nM and 1 μM respectively, followed by reaction for 30 minutes. The change in fluorescence intensity of Bodipy FL (excitation wavelength: 485 nm, fluorescence wavelength: 520 nm) immediately after the start of reaction and after 30 minutes from the start of reaction was standardized. The signal value for only DMSO was determined to be 0% inhibition, and the signal value for no addition of GppNHp was determined to be 100% inhibition. The compound concentration at which 50% inhibition is achieved was determined to be the IC50 (nM) and was calculated. The following table shows the inhibitory activity IC50 (nM) of the test compounds.

The test results in Table 19 below reveal that the compound of the disclosure has an excellent inhibitory capability against the activity of KRAS G12C mutant protein.

TABLE 19

| Ex. | IC50 (nM) |
|---|---|
| 1 | 16 |
| 2 | 365 |
| 3 | 9 |
| 4 | 1560 |
| 5 | 10 |
| 6 | 791 |
| 7 | 4257 |
| 8 | 783 |
| 9 | 3143 |
| 10 | 129 |
| 11 | 1064 |
| 12 | 16 |
| 13 | 15 |
| 14 | 24 |
| 15 | 84 |
| 16 | 25 |
| 17 | 17 |
| 18 | 12 |
| 19 | 9 |
| 20 | 31 |
| 21 | 58 |
| 22 | 55 |
| 23 | 7 |
| 24 | 35 |
| 25 | 163 |
| 26 | 69 |
| 27 | 8 |
| 28 | 70 |
| 29 | 6 |
| 30 | 11 |
| 31 | 642 |
| 32 | 50 |
| 33 | 13 |
| 34 | 13 |
| 35 | 8 |
| 36 | 19 |
| 37 | 5479 |
| 38 | 2168 |
| 39 | 870 |
| 40 | 27 |
| 41 | 14 |
| 42 | 68 |
| 43 | 809 |
| 44 | 180 |
| 45 | 24 |
| 46 | 92 |
| 47 | 1729 |
| 48 | 126 |
| 49 | 208 |
| 50 | 4276 |
| 51 | 42 |
| 52 | 38 |
| 53 | 42 |
| 54 | 301 |
| 55 | 24 |
| 56 | 198 |
| 57 | 324 |
| 58 | 28 |
| 59 | 85 |
| 60 | 1502 |
| 61 | 210 |
| 62 | 96 |
| 63 | 84 |
| 64 | 13 |
| 65 | 19 |
| 66 | 20 |
| 67 | 24 |
| 68 | 99 |
| 69 | 6650 |
| 70 | 79 |
| 71 | 117 |
| 72 | 71 |
| 73 | 52 |
| 74 | 36 |
| 75 | 16 |
| 76 | 13 |
| 77 | 142 |
| 78 | 20 |
| 79 | 122 |
| 80 | 63 |
| 81 | 2634 |
| 82 | 209 |
| 83 | 2347 |
| 84 | 63 |
| 85 | 196 |
| 86 | 58 |
| 87 | 14 |
| 88 | 158 |
| 89 | 7 |
| 90 | 6 |
| 91 | 7 |
| 92 | 10 |
| 93 | 6 |
| 94 | 118 |
| 95 | 44 |

TABLE 19-continued

| Ex. | IC50 (nM) |
|---|---|
| 96 | 4 |
| 97 | 4 |
| 98 | 7 |
| 99 | 7 |
| 100 | 14 |
| 101 | 7 |
| 102 | 5 |
| 103 | 5 |
| 104 | 9 |
| 105 | 8 |
| 106 | 8 |
| 107 | 4 |
| 108 | 9 |
| 109 | 23 |
| 110 | 9 |
| 111 | 15 |
| 112 | 5 |
| 113 | 5 |
| 114 | 7 |
| 115 | 7 |
| 116 | 8 |
| 117 | 9 |
| 118 | 5 |
| 119 | 11 |
| 120 | 6 |
| 121 | 5 |
| 122 | 6 |
| 123 | 9 |
| 124 | 6 |
| 125 | 13 |
| 126 | 4 |
| Reference Example 1 | >10000 |
| Reference Example 2 | >10000 |
| Reference Example 3 | >10000 |

Test Example 3: A Measurement Test of Growth Inhibition Activity on KRAS-G12C Mutant Cell Line (NCI-H358) (In Vitro)

NCI-H358 cells (ATCC, Cat #: CRL-5807), which are a KRAS-G12C mutant human lung cancer cell line, were suspended in a 10% fetal bovine serum-containing RPMI1640 medium (manufactured by Fujifilm Wako Pure Chemical Corporation.). The cell suspension was seeded into each well of a 384-well flat-bottom microplate and cultured in an incubator containing 5% $CO_2$ gas at 37° C. for 1 day. The test compound was dissolved in DMSO and diluted with DMSO to give a concentration 500 times the final concentration. The solution of the test compound in DMSO was diluted with the medium used for suspending cells and added to each well of the cell-culture plate to give a DMSO final concentration of 0.2%, followed by culture in an incubator containing 5% $CO_2$ gas at 37° C. for another 3 days. The cell count after 3-day culture in the presence of the compound was measured using CellTiter-Glo2.0 (manufactured by Promega Corporation) in accordance with the protocol recommended by Promega Corporation. The growth inhibition rate was calculated from the following equation, and the concentration of the test compound at which 50% inhibition was achieved (IC50 (nM)) was determined. The following table shows the results.

$$\text{Growth Inhibition Rate (\%)}=(C-T)/(C)\times 100$$

T: the emission intensity in a well into which a test compound was added.

C: the emission intensity in a well into which a test compound was not added.

The test results reveal that the compound of the disclosure has excellent cell growth inhibition activity on KRAS-G12C mutant cell line NCI-H358.

TABLE 20

| Ex. | IC50 (nM) |
|---|---|
| 3 | 114 |
| 13 | 135 |
| 29 | 34 |
| 33 | 153 |
| 35 | 67 |
| 64 | 241 |
| 75 | 142 |
| 76 | 232 |
| 78 | 350 |
| 93 | 40 |
| 97 | 52 |
| 101 | 54 |
| 102 | 69 |
| 103 | 29 |
| 104 | 91 |
| 105 | 76 |
| 106 | 42 |
| 107 | 78 |
| 112 | 52 |
| 113 | 22 |
| 114 | 32 |
| 115 | 56 |
| 123 | 21 |
| 124 | 19 |
| 126 | 35 |
| Reference Example 1 | >10000 |

Test Example 4: Anti-Tumor Activity of Combinations of a Compound of Formula (I) and an Additional Anti-Cancer Agent The effect of a compound of Formula (I) in combination with an additional anti-cancer agent can be assessed using the following technique, with appropriate optimization of experimental conditions well within the skill of one of ordinary skill in the art.

Anti-Proliferation Assay

Available cancer cell lines (e.g., available from commercial sources such as ATCC or ECCAC or Health Science Research Resources Bank) are used for the assay.

A 384-well culture plate (781086 from Greiner Bio-One International, Kremsmunster, Austria or 3830 from Corning, Corning, NY) is used for a cell survival rate measurement assay. Each cell line is collected by a conventional method, then suspended in a medium which has appropriate components corresponding to growth condition of each cell type. The appropriate number of cells seeded per well is set for each cell line between 100 and 500 cells/20 μL. After incubation at 37° C. for 24 hours under 5% $CO_2$, a compound of Formula (I) and an additional anti-cancer agent having an antitumor effect or a vehicle (DMSO) is added to each well using a D300e Digital Dispenser (Tecan, Mannedorf, Switzerland). The concentration of a compound of Formula (I) is set to 7 concentrations. The concentration of each additional anti-cancer agent is set to 9 concentrations including 0 nM. After adding the compounds to the cells, the cells are further incubated at 37° C. for 5 days under 5% $CO_2$. Cell survival rates are calculated by adding 20 μL of CellTiter-GloR (Promega, Madison, WI) solution to each well, incubating the cells at room temperature for 10 minutes, and then measuring the chemiluminescence intensity of each well using a plate reader (EnVision, PerkinElmer, Waltham, MA).

A combination index (CI) value at each combined concentration of the compound of Formula (I) and the additional anti-cancer agent is determined. The combinatory effect of the compound of Formula (I) and the additional anti-cancer agent is assessed as shown in Table 21 (Trends Pharmacol. Sci. 4, 450-454, 1983; Pharmacol Rev. 2006, 58(3), 621-81).

TABLE 21

| CI Range (upper limit) | Description |
|---|---|
| <0.1 | Very strong synergy |
| 0.1-0.3 | Strong synergy |
| 0.3-0.7 | Synergy |
| 0.7-0.85 | Moderate synergy |
| 0.85-0.9 | Slight synergy |
| 0.9-1 | Almost additive |
| 1-1.2 | Slight antagonism |
| 1.2-1.45 | Moderate antagonism |
| 1.45-3.3 | Antagonism |
| 3.3-10 | Strong antagonism |
| >10 | Very strong antagonism |

Alternatively, anti-tumor activity of combinations of a compound of Formula (I) and an additional anti-cancer agent is determined as follows. Synergy is determined when the GI50 or IC50 shifted down in the presence of sub-effective doses of a compound of Formula (I). Additivity is determined when the response to an additional anti-cancer agent compound and a compound of Formula (I) together resulted in an effect equivalent to the sum of the two compounds individually. Antagonistic effects are defined as those causing the GI50 or IC50 to shift upward, i.e., those where the response to the two compounds is less than the sum of the effect of the two compounds.

Text Example 5: Anti-Tumor Activity of Combinations of a Compound of Formula (I) and an SHP2 Inhibitor An anti-proliferation assay was conducted as described in Test Example 4. As a compound of Formula (I), Compound A was used. As an additional anti-tumor agent, the SHP2 inhibitor Compound I was used.

Cell lines and culture medium were used as shown in Table 22.

TABLE 22

| Cell line (origin) | Culture medium | Cell number (Cells/20 μL/well) |
|---|---|---|
| NCI-H358(NSCLC) | ATCC formulated RPMI-1640 (10% fetal bovine serum) | 100 |
| NCI-H2122(NSCLC) | RPMI-1640 (10% FBS) | 250 |
| MIAPaCa-2(Pancreatic ductal adenocarcinoma) | RPMI-1640 (10% FBS) | 250 |
| NCI-H1373 (NSCLC) | RPMI-1640 (10% FBS) | 250 |
| LU99 (NSCLC) | RPMI-1640 (10% FBS) | 500 |
| SW837 (Colorectal cancer) | RPMI-1640 (10% FBS) | 500 |
| SW1463 (Colorectal cancer) | RPMI-1640 (10% FBS) | 250 |
| Calu-1 (NSCLC) | RPMI-1640 (10% FBS) | 250 |
| HCC44 (NSCLC) | RPMI-1640 (10% FBS) | 250 |
| NCI-H1792 (NSCLC) | RPMI-1640 (10% FBS) | 250 |
| NCI-H2030 (NSCLC) | RPMI-1640 (10% FBS) | 500 |

TABLE 22-continued

| Cell line (origin) | Culture medium | Cell number (Cells/20 μL/well) |
|---|---|---|
| SW1573 (NSCLC) | RPMI-1640 (10% FBS) | 250 |
| UM-UC-3 (Bladder cancer) | RPMI-1640 (10% FBS) | 250 |
| KYSE-410 (Esophagus cancer) | RPMI-1640 (10% FBS) | 250 |
| LU65 (NSCLC) | RPMI-1640 (10% FBS) | 250 |
| NCI-H23 (NSCLC) | RPMI-1640 (10% FBS) | 250 |

The CI value was calculated, and combination effect was determined based on it.

Result: Synergistically enhanced anti-proliferation activity was observed for the combination of Example Compound A and STIP2 inhibitor Compound I.

Test Example 6: Anti-Tumor Activity of Combinations of a Compound of Formula (I) and an ERK Inhibitor An anti-proliferation assay was conducted as described in Test Example 4. As a compound of Formula (I), Compound A was used. As an additional anti-tumor agent, the ERK inhibitor SCH772984 and Compound II were used.

Cell lines and culture medium were used as shown in Table 23.

TABLE 23

| Cell line (origin) | Culture medium | Cell number (Cells/20 μL/well) |
|---|---|---|
| NCI-H358(NSCLC) | ATCC formulated RPMI-1640 (10% fetal bovine serum) | 500 |
| NCI-H2122(NSCLC) | | 500 |
| MIAPaCa-2(Pancreatic ductal adenocarcinoma) | | 500 |
| NCI-H1373 (NSCLC) | RPMI-1640 (10% FBS) | 250 |
| LU99 (NSCLC) | RPMI-1640 (10% FBS) | 500 |
| SW837 (Colorectal cancer) | RPMI-1640 (10% FBS) | 500 |
| SW1463 (Colorectal cancer) | RPMI-1640 (10% FBS) | 250 |
| Calu-1 (NSCLC) | RPMI-1640 (10% FBS) | 250 |
| HCC44 (NSCLC) | RPMI-1640 (10% FBS) | 250 |
| NCI-H1792 (NSCLC) | RPMI-1640 (10% FBS) | 250 |
| NCI-H2030 (NSCLC) | RPMI-1640 (10% FBS) | 500 |
| SW1573 (NSCLC) | RPMI-1640 (10% FBS) | 250 |
| UM-UC-3 (Bladder cancer) | RPMI-1640 (10% FBS) | 250 |
| KYSE-410 (Esophagus cancer) | RPMI-1640 (10% FBS) | 250 |
| LU65 (NSCLC) | RPMI-1640 (10% FBS) | 250 |
| NCI-H23 (NSCLC) | RPMI-1640 (10% FBS) | 250 |

The CI value was calculated, and combination effect was determined based on it.

Result: Synergistically or additively enhanced anti-proliferation activity was observed for the combination of Compound A and the ERK inhibitor SCH772984 or Compound II.

Test Example 7: Anti-Tumor Activity of Combinations of a Compound of Formula (I) and an MEK Inhibitor An anti-proliferation assay was conducted as described in Test Example 4. As a compound of Formula (I), Compound A was used. As an additional anti-tumor agent, the MEK inhibitor PD0325901 was used.

Cell lines and culture medium were used as shown in Table 24.

TABLE 24

| Cell line (origin) | Culture medium | Cell number (Cells/20 μL/well) |
|---|---|---|
| NCI-H358(NSCLC) | ATCC formulated RPMI-1640 (10% fetal bovine serum) | 500 |
| NCI-H2122(NSCLC) | RPMI-1640 (10% FBS) | 500 |
| MIAPaCa-2(Pancreatic ductal adenocarcinoma) | RPMI-1640 (10% FBS) | 500 |

The CI value was calculated, and combination effect was determined based on it.

Result: Synergistically or additively enhanced anti-proliferation activity was observed for the combination of Compound A and the MEK inhibitor PD0325901.

Test Example 8: Anti-Tumor Activity of Combinations of a Compound of Formula (I) and an AKT Inhibitor An anti-proliferation assay was conducted as described in Test Example 4. As a compound of Formula (I), Compound A was used. As an additional anti-tumor agent, the AKT inhibitor trans-3-amino-1-methyl-3-[4-(3-phenyl-5H-imidazo[1,2-c]pyrido[3,4-e][1,3]oxazin-2-yl)phenyl]-cyclobutanol hydrochloride was used.

Cell lines and culture medium were used as shown in Table 25.

TABLE 25

| Cell line (origin) | Culture medium | Cell number (Cells/20 μL/well) |
|---|---|---|
| NCI-H358(NSCLC) | ATCC formulated RPMI-1640 (10% fetal bovine serum) | 500 |
| NCI-H2122(NSCLC) | RPMI-1640 (10% FBS) | 500 |
| MIAPaCa-2(Pancreatic ductal adenocarcinoma) | RPMI-1640 (10% FBS) | 500 |

The CI value was calculated, and combination effect was determined based on it.

Result: Synergistically or additively enhanced anti-proliferation activity was observed for the combination of Compound A and the AKT inhibitor trans-3-amino-1-methyl-3-[4-(3-phenyl-5H-imidazo[1,2-c]pyrido[3,4-e][1,3]oxazin-2-yl)phenyl]-cyclobutanol hydrochloride.

Test Example 9: Measurement of Anti-Tumor Effect of Concomitant Use of a Compound of Formula (I) and an Additional Anti-Tumor Agent on Tumor from a Human Cancer Cell Line Implanted to SCID-Beige Mouse The effect of a compound of Formula (I) in combination with an additional anti-cancer agent can be assessed using the following technique, with appropriate optimization of experimental conditions well within the skill of one of ordinary skill in the art.

Available cancer cell lines (e.g., available from commercial sources such as ATCC or ECCAC or Health Science Research Resources Bank) are used for the assay. Cells are cultured by a conventional method for subsequent implantation.

A human cancer call line is subcutaneously implanted to 6-week-old male SCID-Beige mice (Charles River Japan, Inc.) at 1×107 cells/mouse for MIAPaCa-2 cells, LU65 cells and NCI-H358 cells, and 1×106 cells/mouse for SW837 cells. For grouping (n=5/group), after the cell suspension implantation, tumor volumes (TV) are calculated according to the expression given below, and mice having TV of 100 to 200 $mm^3$ are selected and assigned such that an average TV is equal among groups. The day at which the grouping is carried out is defined as Day 0.

TV ($mm^3$)=(Major axis×Minor $axis^2$)/2 (units for the major axis and the minor axis were mm)

A compound of Formula (I) at 100 or 300 mg/kg/day is orally administered once a day for 3 or 4 weeks, and a specific amount of an additional anti-cancer agent (mg/kg/day) is orally administered once a day or twice a day for 3 or 4 weeks. The dose of a compound of Formula (I) is set to 100-300 mg/kg which corresponds to an effective dose for these mouse subcutaneous implantation models.

Anti-tumor effects are evaluated by using the difference between the average values of tumor volumes (TV) in two groups to be compared at the day of assessment, as an index. TV is calculated according to the expression given below from TV values on the day of measurement and on the day of grouping. Also, T/C (%) is calculated from the average RTV values in medicine administration groups and a control group.

RTV=(TV on the day of measurement)/(TV on the day of grouping)

*T/C* (%)=(Average RTV in each medicine administration group on the day of assessment)/(Average RTV in the control group on the day of assessment)×100

Example 10: Measurement of Anti-Tumor Effect of Concomitant Use of a Compound of Formula (I) and an SHP2 Inhibitor on Tumor from a Human Cancer Cell Line Implanted to SCID-Beige Mouse An assay was conducted as described in Test Example 9. As a compound of Formula (I), Compound A was used. As an additional anti-tumor agent, the SHP2 inhibitor Compound I was used.

Cell lines and culture medium were used as shown in Table 26.

TABLE 26

| Cell line (origin) |
|---|
| MIAPaCa-2(Pancreatic ductal adenocarcinoma) |
| LU65(NSCLC) |
| NCI-H358(NSCLC) |
| SW837 (Colorectal cancer) |

As a result, in MIAPaCa-2 xenograft model, each of the treatments, i.e, treatment with Compound A (100 mg/kg, q.d.) and treatment with Compound I (25 mg/kg, b.i.d.), alone inhibited the growth of subcutaneously implanted cancer cells, with respective T/C (%) on the day of assessment being 30.9% and 20.3%. By contrast, the concomitant treatment with 100 mg/kg Compound A and 25 mg/kg Compound I, i.e., in combination, inhibited tumor growth more than treatment with either Compound A or Compound I alone, with respective T/C (%) being 9.9%.

Figure 1B:
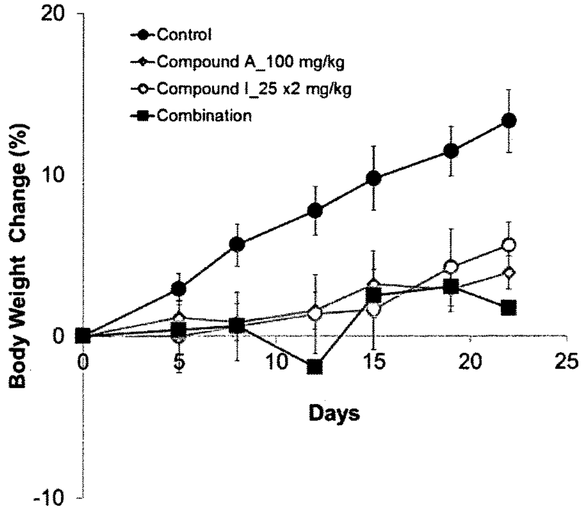
FIG. 1B shows the effects of Compound A of the present disclosure and SHP2 inhibitor Compound I used alone or concomitantly on mouse body weight in an MIAPaCa-2 xenograft model.

The combination effect was significantly stronger than that of each monotherapy (P<0.01, Student's t test). The results are shown in FIGS. 1A and 1B. FIG. 1A shows the anti-tumor effects of Compound A and Compound I used alone or concomitantly. The relative tumor volumes (RTV) for the combination treatment, Compound A treatment, Compound I treatment, and a control group are shown. FIG. 1B shows the effects of Compound A and Compound I used alone or concomitantly on mouse body weight. The rates of mouse body weight change for the combination treatment, Compound A treatment, Compound I treatment, and a control group are shown. The average rate of body weight change in the Compound A/Compound I concomitant use group exhibited no significant difference from the rate of body weight change for Compound A or Compound I alone.

In the LU65 xenograft model, each of the treatments, i.e., treatment with Compound A (100 mg/kg, q.d.) and treatment with Compound 1 (25 mg/kg, b.i.d.), alone inhibited the growth of subcutaneously implanted cancer cells, with respective T/C (%) on the day of assessment being 71.4% and 26.2%. By contrast, the concomitant treatment with 100 mg/kg Compound A and 25 mg/kg Compound I, i.e., in combination, inhibited tumor growth more than treatment with either Compound A or Compound I alone, with respective T/C (%) being 13.9%.

Figure 2A:
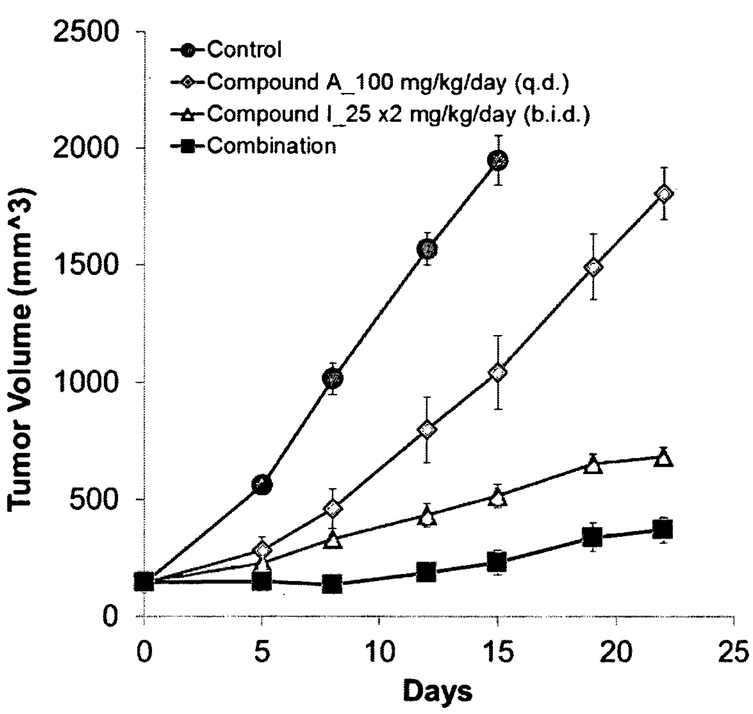
FIG. 2A shows the anti-tumor effects of Compound A of the present disclosure and SHP2 inhibitor Compound I used alone or concomitantly in a LU65 xenograft model.
Figure 2B:
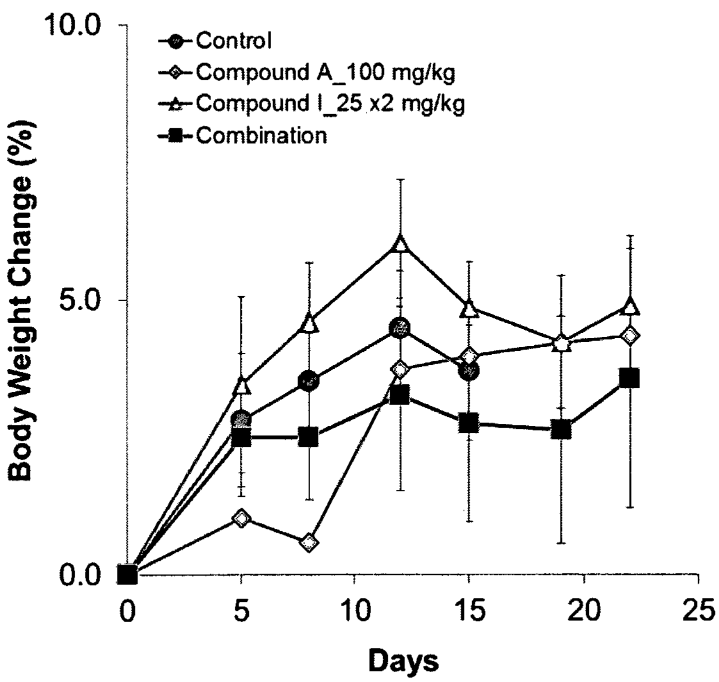
FIG. 2B shows the effects of Compound A of the present disclosure and SHP2 inhibitor Compound I used alone or concomitantly on mouse body weight in a LU65 xenograft model.

The combination effect was significantly stronger than that of each monotherapy ($P<0.01$, Student's t test). The results are shown in FIGS. 2A and 2B. FIG. 2A shows the anti-tumor effects of Compound A and Compound I used alone or concomitantly. The relative tumor volumes (RTV) for the combination treatment, Compound A treatment, Compound I treatment, and a control group are shown. FIG. 2B shows the effects of Compound A and Compound I used alone or concomitantly on mouse body weight. The rates of mouse body weight change for the combination treatment, Compound A treatment, Compound I treatment, and a control group are shown. The average rate of body weight change in the Compound A/Compound I concomitant use group exhibited no significant difference from the rate of body weight change for Compound A or Compound I alone.

In H358 xenograft model, Compound A and Compound I are orally administered once a day (q.d.) or twice a day (b.i.d.) by 5 days on 2 days off schedule for 3 weeks, respectively. Each of the treatments, i.e., treatment with Compound A (100 mg/kg, q.d.) and treatment with Compound I (25 mg/kg, b.i.d.), alone inhibited the growth of subcutaneously implanted cancer cells, with respective T/C (%) on the day of assessment being 42.6% and 28.2%. By contrast, the concomitant treatment with 100 mg/kg Compound A and 25 mg/kg Compound I, i.e., in combination, inhibited tumor growth more than treatment with either Compound A or Compound I alone, with respective T/C (%) being 11.7%.

Figure 3A:
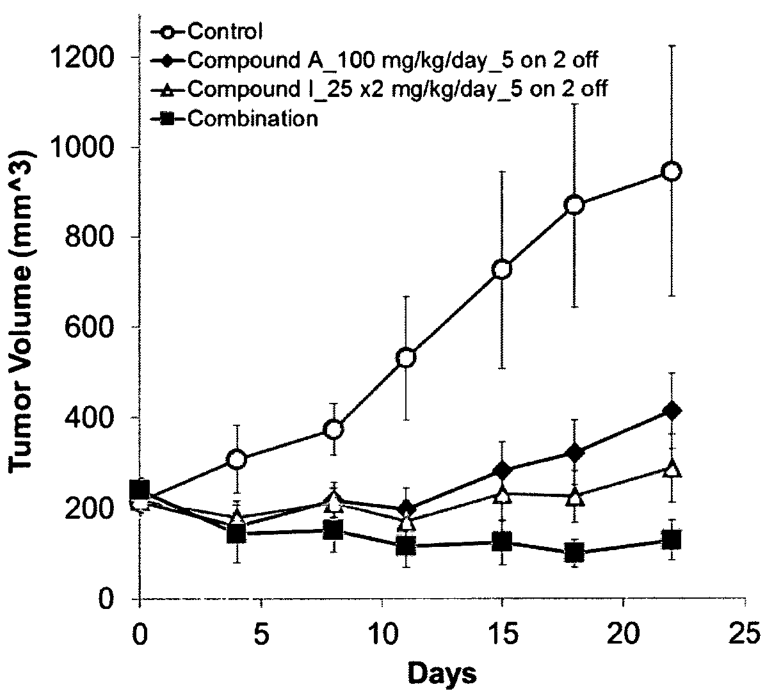
FIG. 3A shows the anti-tumor effects of Compound A of the present disclosure and SHP2 inhibitor Compound I used alone or concomitantly in an H358 xenograft model.
Figure 3B:
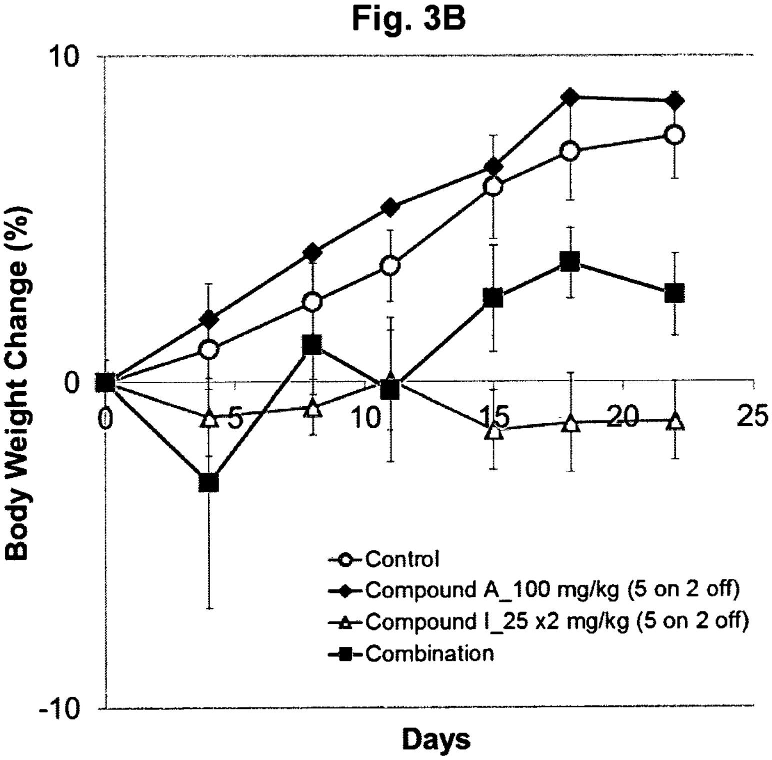
FIG. 3B shows the effects of Compound A of the present disclosure and SHP2 inhibitor Compound I used alone or concomitantly on mouse body weight in an H358 xenograft model.

The combination effect was significantly stronger than that of each monotherapy ($P<0.01$, Student's t test). The results are shown in FIGS. 3A and 3B. FIG. 3A shows the anti-tumor effects of Compound A and Compound I used alone or concomitantly. The relative tumor volumes (RTV) for the combination treatment, Compound A treatment, Compound I treatment, and a control group are shown. FIG. 3B shows the effects of Compound A and Compound I used alone or concomitantly on mouse body weight. The rates of mouse body weight change for the combination treatment, Compound A treatment, Compound I treatment, and a control group are shown. The average rate of body weight change in the Compound A/Compound I concomitant use group exhibited no significant difference from the rate of body weight change for Compound A or Compound I alone.

In SW837 xenograft model, each of the treatments, i.e., treatment with Compound A (300 mg/kg, q.d.) and treatment with Compound I (25 mg/kg, q.d.), alone inhibited the growth of subcutaneously implanted cancer cells, with respective T/C (%) on the day of assessment being 39.5% and 65.0%. By contrast, the concomitant treatment with 300 mg/kg Compound A and 25 mg/kg Compound I, i.e., in combination, inhibited tumor growth more than treatment with either Compound A or Compound I alone, with respective T/C (%) being 13.2%.

Figure 4A:
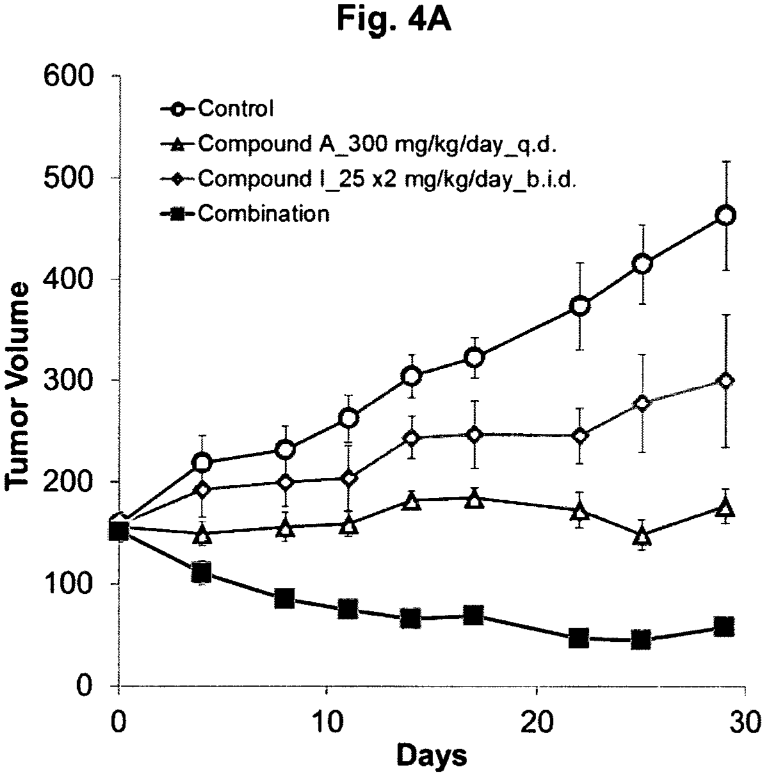
FIG. 4A shows the anti-tumor effects of Compound A of the present disclosure and SHP2 inhibitor Compound I used alone or concomitantly in an SW837 xenograft model.
Figure 4B:
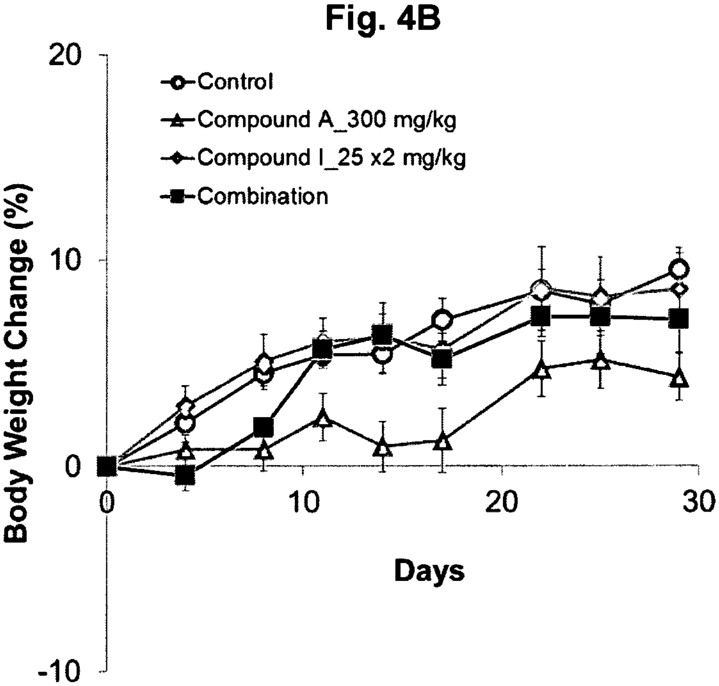
FIG. 4B shows the effects of Compound A of the present disclosure and SHP2 inhibitor Compound I used alone or concomitantly on mouse body weight in an SW837 xenograft model.

The combination effect was significantly stronger than that of each monotherapy ($P<0.01$, Student's t test). The results are shown in FIGS. 4A and 4B. FIG. 4A shows the anti-tumor effects of Compound A and Compound I used alone or concomitantly. The relative tumor volumes (RTV) for the combination treatment, Compound A treatment, Compound I treatment, and a control group are shown. FIG. 4B shows the effects of Compound A and Compound I used alone or concomitantly on mouse body weight. The rates of mouse body weight change for the combination treatment, Compound A treatment, Compound I treatment, and a control group are shown. The average rate of body weight change in the Compound A/Compound I concomitant use group exhibited no significant difference from the rate of body weight change for Compound A or Compound I alone.

What is claimed is:

1. A method of treating cancer comprising administering:

(a) a compound of Formula (I) or a pharmaceutically acceptable salt thereof; and (b) an additional anti-cancer agent, to a subject in need of such treatment, the compound of Formula (I) being:

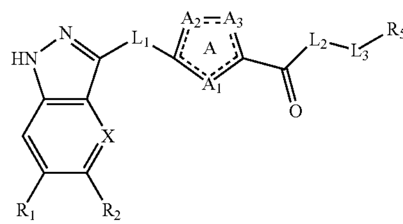

wherein

X is nitrogen or CH, $R_1$ is selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_4$-$C_{10}$ cycloalkyl, $C_6$-$C_{10}$ aromatic hydrocarbon, a 5- to 10-membered saturated heterocyclic group, and a 5- to 10-membered unsaturated heterocyclic group, $R_2$ is selected from the group consisting of hydrogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ cycloalkyl, $C_6$-$C_{10}$ aromatic hydrocarbon, a 5- to 10-membered saturated heterocyclic group, and a 5- to 10-membered unsaturated heterocyclic group, $L_1$ is —NH—$C(R_a)_2$—, wherein $R_a$s are identical or different, and each is a hydrogen atom, a deuterium atom, or $C_1$-$C_6$ alkyl, ring A is a substituted or unsubstituted 5-membered unsaturated heterocyclic group, one of $A_1$, $A_2$, and $A_3$ is substituted or unsubstituted nitrogen or sulfur, and the rest of $A_1$, $A_2$, and $A_3$ are identical or different, and are substituted or unsubstituted carbon, substituted or unsubstituted nitrogen, sulfur, or oxygen, when $A_1$ is substituted carbon or substituted nitrogen, the substituent is at least one member selected from the group consisting of hydrogen, halogen, cyano, nitro, amino, hydroxy, carboxy, $C_1$-$C_6$ alkyl that may be substituted with $R_b$, $C_2$-$C_6$ alkenyl that may be substituted with $R_b$, $C_2$-$C_6$ alkynyl that may be substituted with $R_b$, $C_3$-$C_{10}$ cycloalkyl that may be substituted with $R_c$, $C_4$-$C_{10}$ cycloalkenyl that may be substituted with $R_c$, $C_6$-$C_{10}$ aromatic hydrocarbon that may be substituted with $R_c$, a 4- to 10-membered saturated heterocyclic group that may be substituted with $R_c$, and a 5- to 10-membered unsaturated heterocyclic group that may be substituted with $R_c$, $R_b$ is selected from the group consisting of halogen, cyano, nitro, amino, hydroxy, carboxy, $C_1$-$C_6$ alkoxy, $C_1$-$C_6$ alkylamino, $C_3$-$C_6$ cycloalkyl, substituted or unsubstituted $C_6$-$C_{10}$ aromatic hydrocarbon, and a substituted or unsubstituted 5- to 10-membered saturated heterocyclic group, $R_c$ is selected from the group consisting of halogen, cyano, nitro, amino, hydroxy, carboxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkylamino, $C_1$-$C_6$ alkylcarbonyl, $C_1$-$C_6$ alkoxy-$C_1$-$C_6$ alkyl, $C_7$-$C_{20}$ aralkyl, $C_1$-$C_6$ alkoxycarbonyl, $C_3$-$C_6$ cycloalkyl, $C_6$-$C_{10}$ aromatic hydrocarbon, a 5- to 10-membered saturated heterocyclic group, and a 5- to 10-membered unsaturated heterocyclic group, when two or more $R_b$s are present, the plurality of $R_b$s may be identical or different, when two or more $R_c$s are present, the plurality of $R_c$s may be identical or different, when $A_2$ is substituted carbon or substituted nitrogen, the substituent is at least one member selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, and substituted or unsubstituted $C_2$-$C_6$ alkynyl, when $A_3$ represents substituted carbon or substituted nitrogen, the substituent is at least one member selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, and substituted or unsubstituted $C_2$-$C_6$ alkynyl, $L_2$ is

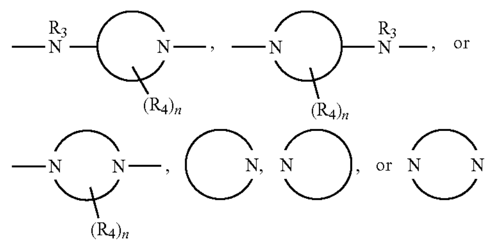

is a 4- to 8-membered saturated heterocyclic group that contains at least one nitrogen atom, and that may contain 1 or 2 heteroatoms selected from sulfur and oxygen, in which N represents nitrogen, $R_3$ is hydrogen or $C_1$-$C_6$ alkyl, $R_4$ is selected from the group consisting of halogen, cyano, nitro, amino, hydroxy, carboxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkylamino-$C_1$-$C_6$ alkyl, cyano-$C_1$-$C_6$ alkyl, $C_1$-$C_6$ alkoxy-$C_1$-$C_6$ alkyl, and $C_1$-$C_6$ hydroxyalkyl, when two or more $R_4$s are present, the plurality of $R_4$s may be identical or different, when two $R_4$s are attached to the same carbon atom, and these two $R_4$s each represent $C_1$-$C_6$ alkyl, then these two $R_4$s, taken together with the carbon atom to which these two $R_4$s are attached, may form a ring, and n is 0, 1, 2, or 3, $L_3$ is —C(=O)— or —S(=O)$_2$—, and $R_5$ is substituted or unsubstituted $C_2$-$C_6$ alkenyl or substituted or unsubstituted $C_2$-$C_6$ alkynyl.

2. The method according to claim 1, wherein the compound of Formula (I) is selected from the group consisting of:

N-(1-acryloylazetidin-3-yl)-2-(((5-(tert-butyl)-6-chloro-1H-indazol-3-yl)amino)methyl)-1,4-dimethyl-1H-imidazole-5-carboxamide;

N-(1-acryloylazetidin-3-yl)-2-(((5-(tert-butyl)-6-chloro-1H-indazol-3-yl)amino)methyl)-1-isopropyl-4-methyl-1H-imidazole-5-carboxamide;

N-(1-acryloylazetidin-3-yl)-2-(((5-(tert-butyl)-6-chloro-1H-indazol-3-yl)amino)methyl)-4-chloro-1-methyl-1H-imidazole-5-carboxamide;

N-(1-acryloylazetidin-3-yl)-2-(((5-(tert-butyl)-6-chloro-1H-indazol-3-yl)amino)methyl)-4-(difluoromethyl)-1-isopropyl-1H-imidazole-5-carboxamide;

N-(1-acryloylazetidin-3-yl)-2-(((5-(tert-butyl)-6-chloro-1H-indazol-3-yl)amino)methyl)-4-chloro-1-isopropyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-1,4-dimethyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-4-fluoro-1-methyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-4-chloro-1-methyl-1H-imidazole-5-carboxamide;

N-((3R,4R)-1-acryloyl-4-methylpyrrolidin-3-yl)-2-(((5-(tert-butyl)-6-chloro-1H-indazol-3-yl)amino)methyl)-4-chloro-1-methyl-1H-imidazole-5-carboxamide;

N-(1-acryloylazetidin-3-yl)-2-(((5-(tert-butyl)-6-chloro-1H-indazol-3-yl)amino)methyl)-4-(difluoromethyl)-1-(1-isopropylpyrrolidin-3-yl)-1H-imidazole-5-carboxamide;

(S)-N-(1-acryloylazetidin-3-yl)-2-(((5-(tert-butyl)-6-chloro-1H-indazol-3-yl)amino)methyl)-4-chloro-1-(tetrahydrofuran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(tetrahydro-2H-pyran-4-yl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(tetrahydrofuran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(1-methylpiperidin-4-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(tetrahydro-2H-pyran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-cyclopentyl-1H-imidazole-5-carboxamide;

tert-butyl 3-(5-((1-acryloylazetidin-3-yl) carbamoyl)-2-(((5-(tert-butyl)-6-chloro-1H-indazol-3-yl)amino) methyl)-4-chloro-1H-imidazol-1-yl) azetidine-1-carboxylate;

N-(1-acryloylazetidin-3-yl)-2-(((5-(tert-butyl)-6-chloro-1H-indazol-3-yl)amino)methyl)-4-chloro-1-(1-isopropylazetidin-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(4-methoxycyclohexyl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-(2,2-difluoroethyl) pyrrolidin-3-yl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-isopropylpyrrolidin-3-yl)-1H-imidazole-5-carboxamide;

(S)-N-(1-acryloylazetidin-3-yl)-2-(((5-(tert-butyl)-6-chloro-1H-indazol-3-yl)amino)methyl)-4-chloro-1-(1-(2,2-difluoroethyl) pyrrolidin-3-yl)-1H-imidazole-5-carboxamide;

(R)-N-(1-acryloylazetidin-3-yl)-1-(1-allylpyrrolidin-3-yl)-2-(((5-(tert-butyl)-6-chloro-1H-indazol-3-yl) amino)methyl)-4-chloro-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-(pyridin-2-yl) pyrrolidin-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-((3R,5R)-1-(2,2-difluoroethyl)-5-methylpyrrolidin-3-yl)-1H-imidazole-5-carboxamide; and the pharmaceutically acceptable salts thereof.

3. The method according to claim 1, wherein the additional anti-cancer agent is selected from the group consisting of a chemotherapeutic agent, an immunotherapeutic agent, a hormonal agent, an anti-hormonal agent, a targeted therapy agent, or an anti-angiogenesis agent.

4. The method according to claim 1, wherein the additional anti-cancer agent is selected from the group consisting of a MEK inhibitor, an ERK inhibitor, an AKT inhibitor, and an SHP2 inhibitor.

5. The method according to claim 2, wherein the additional anti-cancer agent is selected from the group consisting of a MEK inhibitor, an ERK inhibitor, an AKT inhibitor, and an SHP2 inhibitor.

6. The method according to claim 1, wherein the compound of Formula (I) or the pharmaceutically acceptable salt thereof is administered in a therapeutically effective amount.

7. The method according to claim 1, wherein the additional anti-cancer agent is administered in a therapeutically effective amount.

8. The method according to claim 1, wherein (a) and (b) are administered simultaneously.

9. The method according to claim 8, wherein (a) and (b) are administered via a single pharmaceutical preparation further comprising at least one pharmaceutical acceptable carrier.

10. The method according to claim 1, wherein (a) and (b) are administered separately.

11. The method according to claim 1, wherein (a) and (b) are administered sequentially.

12. The method according to claim 11, wherein (a) is administered and then (b) is administered.

13. The method according to claim 11, wherein (b) is administered and then (a) is administered.

14. The method according to claim 1, wherein the subject is a human.

15. The method according to claim 1, wherein the cancer is selected from the group consisting of glandular tumors, carcinoid tumors, undifferentiated carcinomas, angiosarcoma, adenocarcinoma, gastrointestinal cancers, lung cancers, urological cancers, head and neck cancers, endocrine cancers, breast cancers, male and female reproductive cancers, brain and nervous system cancers, skin cancers, tissue and bone cancers, cardiovascular cancers, appendix cancers, childhood and adolescent cancers, viral-induced cancers, multiple myeloma, leukemias, lymphomas, myelodysplastic syndromes and myeloproliferative disorders.

16. A method of treating cancer comprising administering:

a compound of Formula (I) or a pharmaceutically acceptable salt thereof; and radiation therapy, to a subject in need of such treatment, the compound of Formula (I) being:

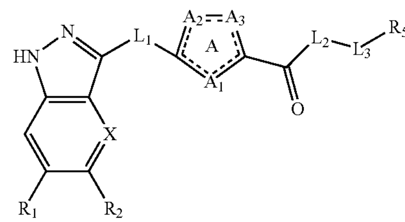

wherein

X is nitrogen or CH, $R_1$ is selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_4$-$C_{10}$ cycloalkyl, $C_6$-$C_{10}$ aromatic hydrocarbon, a 5- to 10-membered saturated heterocyclic group, and a 5- to 10-membered unsaturated heterocyclic group, $R_2$ is selected from the group consisting of hydrogen, cyano, nitro, amino, hydroxy, carboxy, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ cycloalkyl, $C_6$-$C_{10}$ aromatic hydrocarbon, a 5- to 10-membered saturated heterocyclic group, and a 5- to 10-membered unsaturated heterocyclic group, $L_1$ is —NH—C$(R_a)_2$—, wherein $R_a$s are identical or different, and each is a hydrogen atom, a deuterium atom, or $C_1$-$C_6$ alkyl, ring A is a substituted or unsubstituted 5-membered unsaturated heterocyclic group, one of $A_1$, $A_2$, and $A_3$ is substituted or unsubstituted nitrogen or sulfur, and the rest of $A_1$, $A_2$, and $A_3$ are identical or different, and are substituted or unsubstituted carbon, substituted or unsubstituted nitrogen, sulfur, or oxygen, when $A_1$ is substituted carbon or substituted nitrogen, the substituent is at least one member selected from the group consisting of hydrogen, halogen, cyano, nitro, amino, hydroxy, carboxy, $C_1$-$C_6$ alkyl that may be substituted with $R_b$, $C_2$-$C_6$ alkenyl that may be substituted with $R_b$, $C_2$-$C_6$ alkynyl that may be substituted with $R_b$, $C_3$-$C_{10}$ cycloalkyl that may be substituted with $R_c$, $C_4$-$C_{10}$ cycloalkenyl that may be substituted with $R_c$, $C_6$-$C_{10}$ aromatic hydrocarbon that may be substituted with $R_c$, a 4- to 10-membered saturated heterocyclic group that may be substituted with $R_c$, and a 5- to 10-membered unsaturated heterocyclic group that may be substituted with $R_c$, $R_b$ is selected from the group consisting of halogen, cyano, nitro, amino, hydroxy, carboxy, $C_1$-$C_6$ alkoxy, $C_1$-$C_6$ alkylamino, $C_3$-$C_6$ cycloalkyl, substituted or unsubstituted $C_6$-$C_{10}$ aromatic hydrocarbon, and a substituted or unsubstituted 5- to 10-membered saturated heterocyclic group, $R_c$ is selected from the group consisting of halogen, cyano, nitro, amino, hydroxy, carboxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkylamino, $C_1$-$C_6$ alkylcarbonyl, $C_1$-$C_6$ alkoxy-$C_1$-$C_6$ alkyl, $C_7$-$C_{20}$ aralkyl, $C_1$-$C_6$ alkoxycarbonyl, $C_3$-$C_6$ cycloalkyl, $C_6$-$C_{10}$ aromatic hydrocarbon, a 5- to 10-membered saturated heterocyclic group, and a 5- to 10-membered unsaturated heterocyclic group, when two or more $R_b$s are present, the plurality of $R_b$s may be identical or different, when two or more $R_c$s are present, the plurality of $R_c$s may be identical or different, when $A_2$ is substituted carbon or substituted nitrogen, the substituent is at least one member selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, and substituted or unsubstituted $C_2$-$C_6$ alkynyl, when $A_3$ represents substituted carbon or substituted nitrogen, the substituent is at least one member selected from the group consisting of hydrogen, halogen, cyano, nitro, amino, hydroxy, carboxy, substituted or unsubstituted $C_1$-$C_6$ alkyl, substituted or unsubstituted $C_2$-$C_6$ alkenyl, and substituted or unsubstituted $C_2$-$C_6$ alkynyl, $L_2$ is

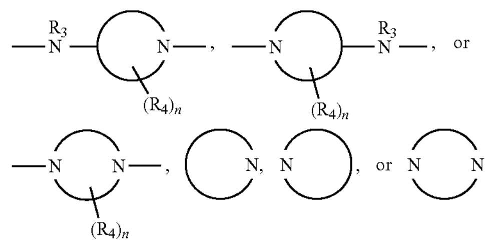

is a 4- to 8-membered saturated heterocyclic group that contains at least one nitrogen atom, and that may contain 1 or 2 heteroatoms selected from sulfur and oxygen, in which N represents nitrogen, $R_3$ is hydrogen or $C_1$-$C_6$ alkyl, $R_4$ is selected from the group consisting of halogen, cyano, nitro, amino, hydroxy, carboxy, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkylamino-$C_1$-$C_6$ alkyl, cyano-$C_1$-$C_6$ alkyl, $C_1$-$C_6$ alkoxy-$C_1$-$C_6$ alkyl, and $C_1$-$C_6$ hydroxyalkyl, when two or more $R_4$s are present, the plurality of $R_4$s may be identical or different, when two $R_4$s are attached to the same carbon atom, and these two $R_4$s each represent $C_1$-$C_6$ alkyl, then these two $R_4$s, taken together with the carbon atom to which these two $R_4$s are attached, may form a ring, and n is 0, 1, 2, or 3, $L_3$ is —C(═O)— or —S(═O)$_2$—, and $R_5$ is substituted or unsubstituted $C_2$-$C_6$ alkenyl or substituted or unsubstituted $C_2$-$C_6$ alkynyl.

17. The method according to claim 16, wherein the compound of Formula (I) is selected from the group consisting of:

N-(1-acryloylazetidin-3-yl)-2-(((5-(tert-butyl)-6-chloro-1H-indazol-3-yl)amino)methyl)-1,4-dimethyl-1H-imidazole-5-carboxamide;

N-(1-acryloylazetidin-3-yl)-2-(((5-(tert-butyl)-6-chloro-1H-indazol-3-yl)amino)methyl)-1-isopropyl-4-methyl-1H-imidazole-5-carboxamide;

N-(1-acryloylazetidin-3-yl)-2-(((5-(tert-butyl)-6-chloro-1H-indazol-3-yl)amino)methyl)-4-chloro-1-methyl-1H-imidazole-5-carboxamide;

N-(1-acryloylazetidin-3-yl)-2-(((5-(tert-butyl)-6-chloro-1H-indazol-3-yl)amino)methyl)-4-(difluoromethyl)-1-isopropyl-1H-imidazole-5-carboxamide;

N-(1-acryloylazetidin-3-yl)-2-(((5-(tert-butyl)-6-chloro-1H-indazol-3-yl)amino)methyl)-4-chloro-1-isopropyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-1,4-dimethyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-4-fluoro-1-methyl-1H-imidazole-5-carboxamide;

N-((3S,4S)-1-acryloyl-4-fluoropyrrolidin-3-yl)-2-(((5-(tert-butyl)-6-chloro-1H-indazol-3-yl)amino)methyl)-4-chloro-1-methyl-1H-imidazole-5-carboxamide;

N-((3R,4R)-1-acryloyl-4-methylpyrrolidin-3-yl)-2-(((5-(tert-butyl)-6-chloro-1H-indazol-3-yl)amino)methyl)-4-chloro-1-methyl-1H-imidazole-5-carboxamide;

N-(1-acryloylazetidin-3-yl)-2-(((5-(tert-butyl)-6-chloro-1H-indazol-3-yl)amino)methyl)-4-(difluoromethyl)-1-(1-isopropylpyrrolidin-3-yl)-1H-imidazole-5-carboxamide;

(S)-N-(1-acryloylazetidin-3-yl)-2-(((5-(tert-butyl)-6-chloro-1H-indazol-3-yl)amino)methyl)-4-chloro-1-(tetrahydrofuran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(tetrahydro-2H-pyran-4-yl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(tetrahydrofuran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(1-methylpiperidin-4-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(tetrahydro-2H-pyran-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-cyclopentyl-1H-imidazole-5-carboxamide;

tert-butyl 3-(5-((1-acryloylazetidin-3-yl) carbamoyl)-2-(((5-(tert-butyl)-6-chloro-1H-indazol-3-yl)amino)methyl)-4-chloro-1H-imidazol-1-yl) azetidine-1-carboxylate;

N-(1-acryloylazetidin-3-yl)-2-(((5-(tert-butyl)-6-chloro-1H-indazol-3-yl)amino)methyl)-4-chloro-1-(1-isopropylazetidin-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-(4-methoxycyclohexyl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-(2,2-difluoroethyl) pyrrolidin-3-yl)-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-isopropylpyrrolidin-3-yl)-1H-imidazole-5-carboxamide;

(S)-N-(1-acryloylazetidin-3-yl)-2-(((5-(tert-butyl)-6-chloro-1H-indazol-3-yl)amino)methyl)-4-chloro-1-(1-(2,2-difluoroethyl) pyrrolidin-3-yl)-1H-imidazole-5-carboxamide;

(R)-N-(1-acryloylazetidin-3-yl)-1-(1-allylpyrrolidin-3-yl)-2-(((5-(tert-butyl)-6-chloro-1H-indazol-3-yl) amino)methyl)-4-chloro-1H-imidazole-5-carboxamide;

(R)-N-(1-acryloylazetidin-3-yl)-2-(((5-(tert-butyl)-6-chloro-1H-indazol-3-yl)amino)methyl)-4-chloro-1-(1-(pyridin-2-yl) pyrrolidin-3-yl)-1H-imidazole-5-carboxamide;

N-(1-acryloylazetidin-3-yl)-2-(((5-(tert-butyl)-6-chloro-1H-indazol-3-yl)amino)methyl)-4-chloro-1-((3R,5R)-1-(2,2-difluoroethyl)-5-methylpyrrolidin-3-yl)-1H-imidazole-5-carboxamide; and the pharmaceutically acceptable salts thereof.

18. The method according to claim 16, wherein the compound of Formula (I) or the pharmaceutically acceptable salt thereof is administered in a therapeutically effective amount.

19. The method according to claim 16, wherein the subject is a human.

20. The method according to claim 16, wherein the cancer is selected from the group consisting of glandular tumors, carcinoid tumors, undifferentiated carcinomas, angiosarcoma, adenocarcinoma, gastrointestinal cancers, lung cancers, urological cancers, head and neck cancers, endocrine cancers, breast cancers, male and female reproductive cancers, brain and nervous system cancers, skin cancers, tissue and bone cancers, cardiovascular cancers, appendix cancers, childhood and adolescent cancers, viral-induced cancers, multiple myeloma, leukemias, lymphomas, myelodysplastic syndromes and myeloproliferative disorders.

* * * * *